(12) United States Patent
Schaab et al.

(10) Patent No.: US 8,772,495 B2
(45) Date of Patent: Jul. 8, 2014

(54) 5-LIPOXYGENASE-ACTIVATING PROTEIN INHIBITOR

(75) Inventors: Kevin Murray Schaab, Spring Valley, CA (US); Nicholas Simon Stock, San Diego, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 640 days.

(21) Appl. No.: 12/471,106

(22) Filed: May 22, 2009

(65) Prior Publication Data

US 2009/0291981 A1 Nov. 26, 2009

Related U.S. Application Data

(60) Provisional application No. 61/055,887, filed on May 23, 2008, provisional application No. 61/055,899, filed on May 23, 2008.

(51) Int. Cl.
*C07D 401/14* (2006.01)
*A61K 31/444* (2006.01)

(52) U.S. Cl.
CPC ............ *C07D 401/14* (2013.01); *A61K 31/444* (2013.01)
USPC ........................................................ 546/256

(58) Field of Classification Search
USPC .......................................... 546/256; 514/333
See application file for complete search history.

(56) References Cited

U.S. PATENT DOCUMENTS

| | | | |
|---|---|---|---|
| 4,273,782 A | 6/1981 | Cross et al. | |
| 4,616,009 A | 10/1986 | Tahara et al. | |
| 4,826,987 A | 5/1989 | Nielsen et al. | |
| 5,081,138 A | 1/1992 | Gillard et al. | |
| 5,081,145 A | 1/1992 | Guindon et al. | |
| 5,093,356 A | 3/1992 | Girard et al. | |
| 5,095,031 A | 3/1992 | Brooks et al. | |
| 5,109,009 A | 4/1992 | Nielsen et al. | |
| 5,157,039 A | 10/1992 | Nielsen et al. | |
| 5,182,367 A | 1/1993 | Gillard et al. | |
| 5,190,968 A | 3/1993 | Gillard et al. | |
| 5,202,321 A | 4/1993 | Hutchinson et al. | |
| 5,204,344 A | 4/1993 | Prasit et al. | |
| 5,225,421 A | 7/1993 | Gillard et al. | |
| 5,229,516 A | 7/1993 | Musser et al. | |
| 5,232,916 A | 8/1993 | Zamboni et al. | |
| 5,252,585 A | 10/1993 | Frenette et al. | |
| 5,254,567 A | 10/1993 | Down et al. | |
| 5,272,145 A | 12/1993 | Prasit et al. | |
| 5,273,980 A | 12/1993 | Frenette et al. | |
| 5,288,743 A | 2/1994 | Brooks et al. | |
| 5,290,788 A | 3/1994 | Stevens et al. | |
| 5,290,798 A | 3/1994 | Gillard et al. | |
| 5,308,850 A | 5/1994 | Gillard et al. | |
| 5,314,898 A | 5/1994 | Chung et al. | |
| 5,334,719 A | 8/1994 | Frenette | |
| 5,374,635 A | 12/1994 | Leger et al. | |
| 5,380,850 A | 1/1995 | Prasit et al. | |
| 5,389,650 A | 2/1995 | Frenette et al. | |
| 5,399,699 A | 3/1995 | Kolasa et al. | |
| 5,420,282 A | 5/1995 | Brooks et al. | |
| 5,420,289 A | 5/1995 | Musser et al. | |
| 5,459,150 A | 10/1995 | Brooks et al. | |
| 5,635,516 A | 6/1997 | Caubere et al. | |
| 5,750,558 A | 5/1998 | Brooks et al. | |
| 5,877,329 A | 3/1999 | Chen et al. | |
| 5,972,241 A | 10/1999 | Johnson et al. | |
| 6,246,452 B1 | 6/2001 | Sekine et al. | |
| 6,500,853 B1 | 12/2002 | Seehra et al. | |
| 6,627,646 B2 * | 9/2003 | Bakale et al. | 514/322 |
| 6,699,883 B1 | 3/2004 | Doemling et al. | |
| 6,867,209 B1 | 3/2005 | Mavunkel et al. | |
| 7,118,869 B2 | 10/2006 | Blumenfeld et al. | |
| 7,405,302 B2 | 7/2008 | Hutchinson et al. | |
| 7,795,274 B2 | 9/2010 | Hutchinson et al. | |
| 7,834,037 B2 | 11/2010 | Hutchinson et al. | |
| 7,977,359 B2 * | 7/2011 | Hutchinson et al. | 514/333 |
| 8,399,666 B2 | 3/2013 | Hutchinson et al. | |
| 8,546,431 B2 | 10/2013 | Hutchinson et al. | |
| 2001/0039037 A1 | 11/2001 | Harland | |
| 2003/0203833 A1 | 10/2003 | Ignar et al. | |
| 2004/0014759 A1 | 1/2004 | Picard et al. | |

(Continued)

FOREIGN PATENT DOCUMENTS

| | | |
|---|---|---|
| CA | 2032253 | 6/1991 |
| CA | 1337427 | 10/1995 |

(Continued)

OTHER PUBLICATIONS

Chemical & Engineering News, Feb. 2003, 32-35.*
Brittain ed., "Polymorphism in Pharmaceutical Science.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*

(Continued)

*Primary Examiner* — Patricia L Morris
(74) *Attorney, Agent, or Firm* — Wilson, Sonsini, Goodrich & Rosati

(57) ABSTRACT

Described herein is the FLAP inhibitor 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, or a pharmaceutically acceptable salt thereof. Also described are methods of preparing the FLAP inhibitor, or a pharmaceutically acceptable salt thereof, including solvates, and polymorphs thereof. Also described herein are pharmaceutical compositions suitable for administration to a mammal that include the FLAP inhibitor, or a pharmaceutically acceptable salt thereof, and methods of using such pharmaceutical compositions for treating respiratory conditions or diseases, as well as other leukotriene-dependent or leukotriene mediated conditions or diseases.

7 Claims, 25 Drawing Sheets

(56) References Cited

U.S. PATENT DOCUMENTS

| | | |
|---|---|---|
| 2004/0086952 A1 | 5/2004 | Gentz et al. |
| 2004/0198800 A1 | 10/2004 | Allan et al. |
| 2005/0245515 A1 | 11/2005 | Dehmlow et al. |
| 2006/0211677 A1 | 9/2006 | Chu et al. |
| 2007/0003971 A1 | 1/2007 | Blumenfeld et al. |
| 2007/0105866 A1 | 5/2007 | Hutchinson et al. |
| 2007/0123522 A1 | 5/2007 | Hutchinson et al. |
| 2007/0219206 A1 | 9/2007 | Hutchinson et al. |
| 2007/0225285 A1 | 9/2007 | Hutchinson et al. |
| 2007/0244128 A1 | 10/2007 | Hutchinson et al. |
| 2008/0227807 A1 | 9/2008 | Hutchinson et al. |
| 2008/0293739 A1 | 11/2008 | Trede |
| 2009/0018170 A1 | 1/2009 | Hutchinson et al. |
| 2009/0221574 A1 | 9/2009 | Hutchinson et al. |
| 2009/0291981 A1 | 11/2009 | Schaab et al. |
| 2011/0160249 A1 | 6/2011 | Schaab et al. |
| 2012/0220779 A1 | 8/2012 | Crawford et al. |
| 2013/0102636 A1 | 4/2013 | Hutchinson et al. |

FOREIGN PATENT DOCUMENTS

| | | |
|---|---|---|
| DE | 4338770 A1 | 5/1995 |
| EP | 0419049 A1 | 3/1991 |
| EP | 0510398 A2 | 10/1992 |
| EP | 0535924 A1 | 4/1993 |
| EP | 0540051 B1 | 5/1993 |
| EP | 0597112 A1 | 5/1994 |
| EP | 0937459 A2 | 8/1999 |
| EP | 1749829 A1 | 2/2007 |
| FR | 2431491 A1 | 2/1980 |
| GB | 2280181 A | 1/1995 |
| JP | 6058881 A | 3/1994 |
| JP | 6100551 A | 4/1994 |
| JP | 3457694 B2 | 8/1994 |
| JP | 7005651 A | 1/1995 |
| JP | 08020532 A2 | 1/1996 |
| JP | 09002977 A2 | 1/1997 |
| JP | 11080032 A2 | 3/1999 |
| JP | 11189531 A2 | 7/1999 |
| JP | 11193265 A2 | 7/1999 |
| JP | 2000007590 A | 1/2000 |
| JP | 2000302671 A2 | 10/2000 |
| JP | 2001139462 A2 | 5/2001 |
| JP | 2002226429 A | 8/2002 |
| JP | 2004262933 A | 9/2004 |
| JP | 2005002346 A | 1/2005 |
| JP | 2005082701 A | 3/2005 |
| JP | 2005170939 A2 | 6/2005 |
| JP | 2005194250 A | 7/2005 |
| JP | 2009023986 A | 2/2009 |
| WO | 88/02364 A2 | 4/1988 |
| WO | WO-91-06537 A2 | 5/1991 |
| WO | 92/03132 A1 | 3/1992 |
| WO | WO-93-16069 | 8/1993 |
| WO | WO-93-20065 A1 | 10/1993 |
| WO | 93/23391 A | 11/1993 |
| WO | WO-93-25546 | 12/1993 |
| WO | 94/00446 A1 | 1/1994 |
| WO | 94/11378 A1 | 5/1994 |
| WO | 94/12179 A1 | 6/1994 |
| WO | 94/13293 A2 | 6/1994 |
| WO | 94/13662 A1 | 6/1994 |
| WO | 94/14434 A1 | 7/1994 |
| WO | 94/29290 A1 | 12/1994 |
| WO | 95/06637 A | 3/1995 |
| WO | 95/35372 A1 | 12/1995 |
| WO | 96/03377 A1 | 2/1996 |
| WO | 96/15118 A1 | 5/1996 |
| WO | WO-96-18393 A1 | 6/1996 |
| WO | WO-96-32379 A1 | 10/1996 |
| WO | 96/35670 A1 | 11/1996 |
| WO | 97/28105 A1 | 8/1997 |
| WO | WO-97-41100 A1 | 11/1997 |
| WO | 97/49703 A1 | 12/1997 |
| WO | 98/03202 A1 | 1/1998 |
| WO | 98/21184 A1 | 5/1998 |
| WO | 98/52943 A1 | 11/1998 |
| WO | 98/56757 A1 | 12/1998 |
| WO | 99/33458 A1 | 7/1999 |
| WO | WO-99-33800 A1 | 7/1999 |
| WO | 99/43651 A1 | 9/1999 |
| WO | 99/43672 A1 | 9/1999 |
| WO | 99/52942 A2 | 10/1999 |
| WO | 00/29574 A2 | 5/2000 |
| WO | 00/43384 A1 | 7/2000 |
| WO | 01/21594 A1 | 3/2001 |
| WO | 01/32621 A1 | 5/2001 |
| WO | 01/36403 A1 | 5/2001 |
| WO | 01/41807 A1 | 6/2001 |
| WO | 01/44184 A1 | 6/2001 |
| WO | 01/59105 A1 | 8/2001 |
| WO | WO-01-58869 A3 | 8/2001 |
| WO | 01/64639 A2 | 9/2001 |
| WO | 01/66520 A1 | 9/2001 |
| WO | 01/70211 A2 | 9/2001 |
| WO | 01/77149 A1 | 10/2001 |
| WO | 02/00621 A1 | 1/2002 |
| WO | 02/10152 A2 | 2/2002 |
| WO | 02/28835 A2 | 4/2002 |
| WO | 02/51397 A1 | 7/2002 |
| WO | 02/51837 A2 | 7/2002 |
| WO | 03/22813 A1 | 3/2003 |
| WO | 03/22814 A1 | 3/2003 |
| WO | 03/28719 A1 | 4/2003 |
| WO | 03/35625 A1 | 5/2003 |
| WO | WO 03-044014 A1 | 5/2003 |
| WO | 03/50174 A1 | 6/2003 |
| WO | 03/094889 A1 | 11/2003 |
| WO | 03/099771 A2 | 12/2003 |
| WO | 04/000795 A1 | 12/2003 |
| WO | WO-2004-000831 A1 | 12/2003 |
| WO | 2004/017917 A2 | 3/2004 |
| WO | 2004/017920 A1 | 3/2004 |
| WO | 2004/020409 A1 | 3/2004 |
| WO | 2004/043392 A1 | 5/2004 |
| WO | 2004/048331 A1 | 6/2004 |
| WO | 2004/050643 A2 | 6/2004 |
| WO | 2004/065388 A1 | 8/2004 |
| WO | 2004/078719 A1 | 9/2004 |
| WO | 2004/101554 | 11/2004 |
| WO | 2004/108671 A1 | 12/2004 |
| WO | 2005/009951 A2 | 2/2005 |
| WO | 2005/019381 A1 | 3/2005 |
| WO | 2005/023246 A1 | 3/2005 |
| WO | 2005/023806 A1 | 3/2005 |
| WO | WO-2005-030717 A1 | 4/2005 |
| WO | 2005/054176 A1 | 6/2005 |
| WO | 2005/054193 A1 | 6/2005 |
| WO | 2005/054213 A1 | 6/2005 |
| WO | 2005/065266 A2 | 7/2005 |
| WO | 2005/066151 A2 | 7/2005 |
| WO | 2005/066157 A1 | 7/2005 |
| WO | 2005/082346 A1 | 9/2005 |
| WO | 2005/097203 A2 | 10/2005 |
| WO | 2005/112921 A2 | 12/2005 |
| WO | 2005/123674 A1 | 12/2005 |
| WO | WO-2006-014262 A3 | 2/2006 |
| WO | 2006/023843 A1 | 3/2006 |
| WO | 2006/030031 A1 | 3/2006 |
| WO | 2006/041961 A1 | 4/2006 |
| WO | 2006/044602 A2 | 4/2006 |
| WO | 2006/074984 A1 | 7/2006 |
| WO | 2006/077364 A1 | 7/2006 |
| WO | 2006/077365 A1 | 7/2006 |
| WO | 2006/077366 A1 | 7/2006 |
| WO | 2006/077367 A1 | 7/2006 |
| WO | 2006/098912 A1 | 9/2006 |
| WO | 2006/105439 A2 | 10/2006 |
| WO | WO-2006-111560 A2 | 10/2006 |
| WO | 2006/131737 A2 | 12/2006 |
| WO | 2007/022427 A2 | 2/2007 |
| WO | 2007/048042 A2 | 4/2007 |
| WO | WO-2007-047204 | 4/2007 |

(56) References Cited

FOREIGN PATENT DOCUMENTS

| | | |
|---|---|---|
| WO | WO-2007-047207 A2 | 4/2007 |
| WO | 2007/052123 A2 | 5/2007 |
| WO | 2007/053094 A1 | 5/2007 |
| WO | 2007/053095 A1 | 5/2007 |
| WO | WO-2007-056021 A2 | 5/2007 |
| WO | WO-2007-056220 A2 | 5/2007 |
| WO | WO-2007-056228 A2 | 5/2007 |
| WO | 2007064719 A2 | 6/2007 |
| WO | 2007/109279 A1 | 9/2007 |
| WO | 2007/123225 A1 | 11/2007 |
| WO | 2008/058341 A1 | 5/2008 |
| WO | 2008/067566 A1 | 6/2008 |
| WO | 2008/097930 A1 | 8/2008 |
| WO | 2008/127728 A1 | 10/2008 |
| WO | WO-2008-137609 | 11/2008 |
| WO | WO-2008-137805 | 11/2008 |
| WO | WO-2008-141011 | 11/2008 |
| WO | 2009/002746 A1 | 12/2008 |
| WO | 2009/009041 A1 | 1/2009 |
| WO | 2009/045700 A2 | 4/2009 |
| WO | 2009/055721 A2 | 4/2009 |
| WO | 2009/114865 A2 | 9/2009 |
| WO | 2010/068311 A2 | 6/2010 |

OTHER PUBLICATIONS

Rowland & Tozer, "Clinical Pharmacokinetics, etc.," 1995, p. 123.*
Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, english translation of Ann. Pharm. Fr., 2002, 60: 161-176, pp. 1-39.*
Doelker, english translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
Bernstein et al., "Polymorphism in Moleular Crystals", Oxford: Clarendon Press, 2002, pp. 117, 118, 272 and 273.*
Davidovich et al., "Detection of Polymorphism, etc.," American Pharmaceutical Review, IN: Russell Pub., 2004, 7(1), pp. 10, 12, 14, 16 and 100.*
Brideau, C., et al., (1992) "Pharmacology of MK-0591 (3-[1-(4-chlorobenzyl)-3-(t-butylthio)-5-(quinolin-2-ylmethoxy)-indol-2-yl]-2,2-dimethylpropanoic acid), a Potent, Orally Active Leukotriene Biosynthesis Inhibito,". Can. J. Physiol. Pharmacol., 70, 799-807.
Chapman, K. R., et al., (1994) "The efficacy of an oral inhibitor of leukotriene synthesis (MK-0591) in asthmatics treated with inhaled steroids," Am. J. Respir. Crit. Care Med., 149, A215.
Depre, M., et al., (1994) "Pharmakokinetics and pharmacodynamics of multiple oral doses of MK-0591, a 5-lipoxygenase-activating protein inhibitor," Clin. Pharmacol. Ther., 56, 22-30.
Diamant, Z., et al., (1995) "The effect of MK-0591, a novel 5-lipoxygenase activating protein inhibitor, on leukotriene biosynthesis and allegen-induced airway response in asthmatic subjects in vivo," J Allergy Clin Immunol., 95, 42-51.
Drazen, J. (1998) "Clinical pharmacology of leukotriene receptor antagonists and 5-lipoxygenase inhibitors," Am. J. Respire. Crit. Care Med., 157, S233-S237.
Friedman et al., "Oral Leukotriene Inhibitor (MK-886) Blocks Allergen-Induced Airway Responses," ARRD 147:839 (1994).
Hakonarson H., et al., (2005) "Effects of a 5-lipoxygenase-activating protein inhibitor on biomarkers associated with risk of myocardial infarction: a randomized trial," J.A.M.A, 293, 2277-2279.
Hamilton et al., "Attenuation of early and late phase allergen-induced bronchoconstriction in asthmatic subjects by a 5-lipoxygenase activating protein antagonist, BAYx 1005," Thorax 52:348-354 (1997).
Hui et al., "Effect if a 5-lipoxygenase inhibitor on leukotriene generation and airway responses after allergen challenge in asthmatic patients," Thorax 46:184-189 (1991).
Jawien, J. et al., (2006) "Inhibition of five lipoxygenase activating protein (FLAP) by MK-886 decreases atherosclerosis in apoE/LDLR-double knockout mice," European Journal of Clinical Investigation 36 (3), 141-146.
Kemp JP., "Leukotriene receptor antagonists for the treatment of asthma", IDrugs. Apr. 2000;3(4):430-441.
Leff, A.R. et al., "Discovery of leukotrienes and development of antileukotriene agents,"Ann. Allergy Asthma Immunol. 86 (Suppl. 1):4-8 (2001).
Nasser et al., "Effect of the 5-lipoxygenase inhibitor ZD2138 on allergen-induced early and late asthmatic responses," Thorax 49:743-748 (1994).
O'Byrne, P.M., "Leukotrines in the Pathogenesis of Asthma," Chest 111 (Supp.2):27S-34S (1997).
Riccioni, G. et al., "Brief Review. Advances in Therapy with Antileukotriene Drugs," Ann. Clin. Lab Sci. 34(4):379-387 (2004).
SCIENCEIP Search Report Jun. 2, 2006.
SCIENCEIP Search Report Jun. 15, 2007.
Uematsu, et al., (1995) "Pharmacokinetics and pharmacodynamic analysis of a novel leukotriene biosynthesis inhibitor," MK-0591, in healthy volunteers. Br. J. Clin. Pharmacol., 40, 59-66.
Brooks,C.D.W. and Summers, J.B., "Modulators of Leukotriene Biosynthesis and Receptor Activation," J. Med. Chem. 39(14): 2629-2654 (1996).
Ford-Hutchinson, A.W. et al., "5-Lipoxygenase," Annu. Rev. Biochem. 63:383-417 (1994).
Frenett, R. et al., "Substituted Indoles as Potent and Orally Active 5-Lipoxygenase Activating Protein (FLAP) Inhibitors," Biorg. & Medicinal Chem. Ltrs. 9:2391-2396 (1996).
Miller, D.K. et al., "Identification and isolation of a membrane protein necessary for leukotriene production," Nature 343:278-281 (1990).
Rouzert, C.A. et al., "MK886, a Potent and Specific Leukotriene Biosynthesis Inhibitor Blocks and Reverses the Membrane Association of 5-Lipoxygenase in Ionophore-challenged Leukocytes," J. Biol. Chem. 265(1):1436-1442 (1990).
Woods, K.W. et al., "O-Alkylcarboxylate Oxime and N-Hydroxyurea Analogs of Substituted Indole Leukotriene Biosynthesis Inhibitors," Biorg. & Medicinal Chem. Ltrs. 6(13):1547-1552 (1996).
Young, R.N., "Inhibitors of 5-lipoxygenase: a therapeutic potential yet to be fully realized?" Eur. J. Med. Chem. 34:671-685 (1999).
U.S. Appl. No. 12/089,706, filed Apr. 9, 2008.
U.S. Appl. No. 12/092,570, filed May 2, 2008.
U.S. Appl. No. 11/925,841, filed Oct. 27, 2007.
U.S. Appl. No. 12/089,7007, filed Oct. 1, 2008.
Hutchinson, et al., "Development of L-689,065: The Prototype of a New Class of Potent 5-Lipoxygenase Inhibitors" Bioorganic & Medicinal Chemistry Letters; 1992 2(12); pp. 1699-1702.
Prasit, et al., "A New Class of Leukotriene Biosynthesis Inhibitors: The Discovery of MK0591"; Bioorganic & Medicinal Chemistry Letters; Nov. 1, 1992; 2(11)); pp. 1395-1398.
Gillard, et al., "L-663,536 (MK-886) (3-[1-(4-chlorobenzyl)-3-t-butyl-thio=5=isopropylindol-2-yl]-2,2-dimethylpropanoic acid), a novel, orally active leukotriene biosynthesis inhibitor"; Canadian Journal of Physiol. Pharmac.; 1989; 67; pp. 456-464.
Larraya, et al., "Preparation of 4-Azaindoel and 7-Azaindole Dimers with a Bisalkoxyalkyl Spacer in order to Preferentially Target Melatonin MT1 Receptors over Melatonin MT2 receptors" European Journal of Medicinal Chemistry; 2004; 39(6); pp. 515-526.
Gardiner, et al., Inhibition of antigen-included contraction of guinea pig airways by a leukotriene synthesis inhibitor, Bay x1005; European Journal of Pharmacology; 1994; 258(1/2); pp. 95-102.
Whittle, et al., "Gastrointestinal Effects of Non-steroidal Anti-inflammatory Drugs'" Fundamental and Clinical Pharmacology; 2003; 17(3); pp. 301-313.
Guillard, et al.,"Synthesis of New Melatonin Analogues from dimers of Azaindole and indole by use of Suzuki Homocoupling"; Heterocycles; 2003; 60(4); pp. 865-877.

(56) References Cited

OTHER PUBLICATIONS

Vaananen, et al., "Pharmacological Investigation of the Role of Leukotrienes in the Pathogenesis of Experimental NSAID Gastropathy"; Inflammation; 1992; 16(3); pp. 227-240.

Brinberg, et al., "The Synthesis of 5-Arylpyrrolo[3, 2-b]pyridines and 7-Aryl-pyrrolo[3, 2-b] pyridines: Addition of 3-Aminopyrroles to Aryl Enaminones" Journal of Heterocyclic Chemistry; 1995; 32(4); pp. 1293-1298.

Valasinas, et al., "Synthesis of Porphobilinogen-9-14C" Journal of Labelled Compounds and Radiopharmaceuticals; 1978; 15(Suppl. vol.) pp. 549-554.

Hutchinson, et al., "Substituted Thiopyranol [2,3,4-c,d] indoles as Potent, Selective, and Orally Active Inhibitors of 5-Lipoxygenase. Synthesis and Biological Evaluation of L-691, 816" J. Med. Chem; 1993; 36; pp. 2771-2787.

Hutchinson, et al., "5-Lipoxygenase-Activating Protein Inhibitors: Development of 3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic Acid (AM103)" J. Med. Chem; 2009; 52; pp. 5803-5815.

Frydman, et al., "Synthesis of Substituted 4- and 6-Azaindoles" Journal of Organic Chemistry; 1968; 33(10); pp. 3762-3766.

Suzuki, et al., "Sodium Telluride in N-Methyl-2-pyrrolidone. Reduction of Aromatic carbonyl Compounds to Alcohols and Formation of Pyrrolo[2, 3-d] pyrimidines (7-deaza-9H-purines) from Aromatic Nitriles" Journal of Organic Chemistry; 1993; 58(1); pp. 241-244.

Rainsford, "Inhibition of Leukotrience Inhibitors, and Calcium and Platelet-activating Factor Antagonists, of acute gastric and intestinal damage in arthritic rats and in cholinomimetic-treated mice" Journal of Pharmacy and Pharmacology; 1999; 51(3); pp. 331-339.

Frydman, et al., "Pyroles from Azaindoles. A Synthesis of Porphobilinogen and Related Pyrroles" Journal of the American Chemical Society; 1969; 91(9); pp. 2338-2342.

Battersby, et al., "Biosynthesis of Porphyrins and Related Macrocycles. Part I. Synthesis of 14C-Labelled Pyrromethanes" Journal of the Chemical Society, Perkins Trans I; 1973; pp. 1546-1556.

Guasch, et al., "MK-591 acutely restores glomerular size selectivity and reduces proteinuria in human glomerulonephritis" Kidney International; 1999; 56; pp. 261-267.

Lorrain, et al., "Pharmacological Characterization of 3-[3-ter-Butylsulfanyl-1-[4-(6-methoxy-pyridin-3-yl)-benzyl]-5-(pyridin-2-ylmethoxy)-1Hindol-2-yl]-2,2-dimethyl-propionic Acid (AM103), a Novel Selective 5-Lipoxygenase-Activating Protein Inhibitor That Reduces Acute and Chronic Inflammation" The Journal of Pharmacology and Experimental Therapeutics; 2009; 331(3); pp. 1042-1050.

Gadaginamath, et al., Chemoselective reactiion of bisheterocycle dicarboxylate towards hydrazine hydrate: Synthesis and antimicrobial activity of some new trisheterocycles:5-pyrrolyalaminocrbonyl/oxadiazolyl/mercaptooxadiazolylmethoxy-1-furfuryl-2 methylindoles Indian J. Chem; 2003; vol. 42B; pp. 3108-3012.

Evans, et al., "What's all the FLAP about?: 5-lipoxygenase-activating protein inhibitors for inflammatory diseases" Trends in Pharmaceutical Science; 2008; 29(2); pp. 72-78.

Bhovi, et al., "Synthesis and Antimicrobial Activity of Some 1,5-Dioxadiazolyl/Ditriazolyl and Dipyrrolylindole Derivatives" Asian Journal of Chemistry; 2005; vol. 17(1); pp. 518-524.

Dunitz, "Are crystal structures predictable?" 2003; The Royal Society of Chemistry; Chem. Comm.; pp. 545-548.

Gadaginamath, et al., "Chemoselective reaction of bisheterocycle dicarboxylate towards hydrazine hydrate: Synthesis and antimicrobial activity of some new trisheterocycles: 5-Pyrrolylaminocarbonyl/oxadiazolyl/mercaptooxadiazolymethoxy-1-furfuryl-2-methylindoles"; 2003; Indian Journal of Chemistry; vol. 42B; pp. 3108-3112.

U.S. Appl. No. 13/942,934, filed Jul. 16, 2013.

Bain, et al., "Pharmacodynamics and Pharmacokinetics of AM103, a Novel Inhibitor of 5-Lipoxygenase-Activating Protein (FLAP)." Clinical Pharmacology & Therapeutics 87, (Apr. 2010), p. 437-444.

Lorrain, et al., "Pharmacology of AM803, a novel selective five-lipoxygenase-activating protein(FLAP) inhibitor in rodent models of acute inflammation." European Journal of Pharmacology, 640 (2010), p. 211-218.

Musiyenko, et al. "A Novel 5-Lipoxygenase-Activating Protein Inhibitor, AM679, Reduces Inflammation in the Respiratory Syncytial Virus-Infected Mouse Eye." Clinical and Vaccine Immunology, Nov. 2009, p. 1654-1659.

Stock, et al. "5-Lipoxygenase-Activating Protein (FLAP) Inhibitors. Part 4: Development of 3-[3-tert-Butylsulfanyl-1-[4-(6-ethoxypyridin-3-yl)benzyl]-5-(5-methylpyridin-2-ylmethoxy)-1H-indol-2-yl]-2,2-dimethylpropionic Acid (AM803), a Potent, Oral, Once Daily FLAP Inhibitor." J. Med. Chem., 2011, 54 (23), p. 8013-8029 (additional supplement).

Stock, et al., "5-Lipoxygenase-activating protein inhibitors. Part 2: 3-{5-((S)-1-Acetyl-2,3-dihydro-1H-indol-2-ylmethoxy)-3-tert-butylsulfanyl-1[4-(5-methoxy-pyrimidin-2-yl)-benzyl]-1H-indol-2-yl}-2,2-dimethyl-propionic acid (AM679)—A potent FLAP inhibitor." Bioorganic & Medicinal Chemistry Letters, vol. 20, Issue 1, Jan. 1, 2010, p. 213-217.

Stock, et al. "5-Lipoxygenase-activating protein inhibitors. Part 3: 3-{3-tert-Butylsulfanyl-1[4-(5-methoxy-pyrimidin-2-yl)-benzyl]-5-(5-methyl-pyridin-2-ylmethoxy)-1H-indol-2-yl]-2,2-dimethyl-propionic acid (AM643)—A potent FLAP inhibitor suitable for topical adminstration." Biooraganic & Medicinal Chemistry Letters, vol. 20, Issue 15, Aug. 1, 2010, p. 4598-4601.

* cited by examiner

Figure 1. Polymorph Form C

Figure 2. Polymorph Form B

Figure 3. Amorphous Phase A

Figure 4. XRPD of solids from various Solvents

Figure 12. TGA (top) and DSC (bottom) for Amorphous Phase A

TGA (top) and DSC (bottom) for Polymorph Form B

TGA (top) and DSC (bottom) for Polymorph Form C

US 8,772,495 B2

5-LIPOXYGENASE-ACTIVATING PROTEIN INHIBITOR

RELATED APPLICATIONS

This application claims benefit of U.S. Provisional Application No. 61/055,887, entitled "ORAL FORMULATIONS OF A FLAP INHIBITOR" filed on May 23, 2008; and U.S. Provisional Application No. 61/055,899, entitled "MANUFACTURING PROCESS AND POLYMORPHS OF A 5-LIPOXYGENASE ACTIVATING PROTEIN INHIBITOR" filed on May 23, 2008; each of which is herein incorporated by reference in their entirety.

FIELD OF THE INVENTION

Described herein are pharmaceutical compositions that comprise 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionic acid, pharmaceutically acceptable salts, pharmaceutically acceptable solvates (including hydrates), amorphous phases, partially crystalline and crystalline forms, prodrugs, metabolites and N-oxides thereof and methods of use thereof in the treatment or prevention of diseases or conditions associated with 5-lipoxygenase-activating protein (FLAP) activity.

BACKGROUND OF THE INVENTION

Leukotrienes are biological compounds formed from arachidonic acid in the leukotriene synthesis pathway. Leukotrienes are synthesized primarily by eosinophils, neutrophils, mast cells, basophils, dendritic cells, macrophages and monocytes. Leukotrienes have been implicated in biological actions including, by way of example only, smooth muscle contraction, leukocyte activation, cytokine secretion, mucous secretion, and vascular function. FLAP is a member of the MAPEG (membrane associated proteins involved in eicosanoid and glutathione metabolism) family of proteins. FLAP is responsible for binding arachidonic acid and transferring it to 5-lipoxygenase. 5-Lipoxygenase can then catalyze the two-step oxygenation and dehydration of arachidonic acid, converting it into the intermediate compound 5-HPETE (5-hydroperoxyeicosatetraenoic acid), and in the presence of FLAP convert the 5-HPETE to Leukotriene $A_4$ ($LTA_4$). $LTA_4$ is acted on by $LTC_4$ synthase, which conjugates $LTA_4$ with reduced glutathione (GSH) to form the intracellular product leukotriene $C_4$ ($LTC_4$). $LTC_4$ is transformed to leukotriene $D_4$ ($LTD_4$) and leukotrine $E_4$ ($LTE_4$) by the action of gamma-glutamyl-transpeptidase and dipeptidases. $LTC_4$ synthase plays a pivotal role as the only committed enzyme in the formation of cysteinyl leukotrienes.

SUMMARY OF THE INVENTION

Described herein is 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionic acid including all pharmaceutically acceptable solvates (including hydrates), amorphous phases, partially crystalline and crystalline forms (including all polymorphs), prodrugs, metabolites and N-oxides thereof (Compound 1) or a pharmaceutically acceptable salt of Compound 1 including all pharmaceutically acceptable solvates (including hydrates), amorphous phases, partially crystalline and crystalline forms (including all polymorphs), prodrugs, metabolites and N-oxides thereof, and methods of uses thereof in the manufacture of medicaments for the treatment of leukotriene mediated diseases, disorders, or conditions. Also described are pharmacokinetic and pharmacodynamic properties of such formulations in mammals, including humans.

Included within the scope of the term "Compound 1" are all pharmaceutically acceptable solvates (including hydrates), amorphous phases, partially crystalline and crystalline forms (including all polymorphs), prodrugs, metabolites and N-oxides. Included within the scope of the term "pharmaceutically acceptable salt of Compound 1" are all pharmaceutically acceptable solvates (including hydrates), amorphous phases, partially crystalline and crystalline forms (including all polymorphs), prodrugs, metabolites and N-oxides of said pharmaceutically acceptable salt.

Included within the scope of the term "Compound 2" are all pharmaceutically acceptable solvates (including hydrates), amorphous phases, partially crystalline and crystalline forms (including all polymorphs), prodrugs, metabolites and N-oxides.

In one aspect, described is a pharmaceutically acceptable salt of Compound 1. In some embodiments, the pharmaceutically acceptable salt of Compound 1 is Compound 2. In another aspect, described herein is Compound 1.

Described herein are pharmaceutical compositions comprising Compound 1, or a pharmaceutically acceptable salt thereof as the active ingredient in the pharmaceutical composition; and at least one pharmaceutically acceptable inactive ingredient selected from among excipients, diluents, and carriers.

In one aspect, described is a pharmaceutically acceptable salt comprising 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionate as the anion and a cation selected from $Na^+$, $K^+$, $Li^+$, $Ca^{2+}$, $NH_4^+$, the protonated form of dicyclohexylamine, the protonated form of N-methyl-D-glucamine, the protonated form of tris(hydroxymethyl)methylamine, the protonated form of arginine, and the protonated form of lysine. In some embodiments, the cation is selected from $Na^+$, $K^+$, $Li^+$, $Ca^{2+}$, and $NH_4^+$. In some embodiments, the cation is selected from $Na^+$, $K^+$, and $Li^+$. In some embodiments, the cation is $Na^+$.

In some embodiments, the pharmaceutically acceptable salt is solvated or desolvated. In some embodiments, the pharmaceutically acceptable salt is desolvated. In some embodiments, the pharmaceutically acceptable salt is solvated. In a specific embodiment, the pharmaceutically acceptable salt is solvated with a Class 3 solvent. In some embodiments, the pharmaceutically acceptable salt is solvated with a Class 3 solvent and water. In a specific embodiment, the Class 3 solvent selected from ethyl acetate, isopropyl acetate, methyl tert-butylether, heptane, isopropanol, and ethanol. In some embodiments, the pharmaceutically acceptable salt is solvated with methyl tert-butylether. In some embodiments, the pharmaceutically acceptable salt comprises a detectable amount of water. In some embodiments, the pharmaceutically acceptable salt comprises a detectable amount of palladium that is less than 20 ppm. In some other embodiments, the pharmaceutically acceptable salt comprises a detectable amount of palladium that is less than 10 ppm. In yet other embodiments, the pharmaceutically acceptable salt comprises a detectable amount of palladium that is less than 5 ppm. In yet other embodiments, the pharmaceutically acceptable salt comprises less than 20 ppm of palladium.

In one aspect, Compound 1 or a pharmaceutically acceptable salt thereof is in an amorphous phase, a partially crystalline form, or a crystalline form.

In some embodiments, Compound 1 or a pharmaceutically acceptable salt thereof is in an amorphous phase.

In other embodiments, Compound 1 or a pharmaceutically acceptable salt thereof is in a crystalline form.

In some embodiments, the pharmaceutically acceptable salt undergoes a crystal formation (whether by a crystallization, solid-to-solid transformation or crystalline inter-conversion) from methyl tert-butylether.

In one aspect, described herein is the compound sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate (Compound 2):

Compound 2

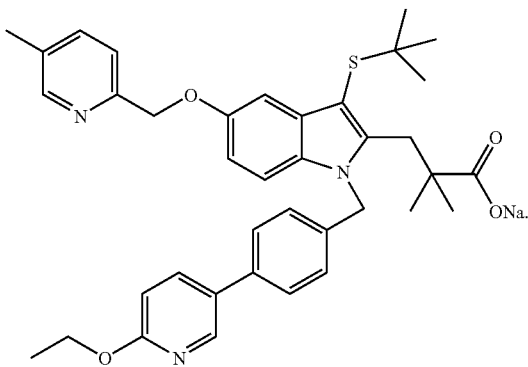

In one aspect provided is a composition comprising Compound 2. In some embodiments, Compound 2 is in an amorphous phase, a partially crystalline form, a crystalline form, milled form, or nano-particulate form. In some embodiments, the composition comprises a detectable amount of palladium that is less than 20 ppm. In some other embodiments, the composition comprises a detectable amount of palladium that is less than 10 ppm. In yet other embodiments, the composition comprises a detectable amount of palladium that is less than 5 ppm.

In some embodiments, the composition comprises less than 20 ppm of palladium. In some other embodiments, the composition comprises less than 10 ppm of palladium. In yet other embodiments, the composition comprises less than 5 ppm of palladium.

In some embodiments, the composition comprises crystalline Compound 2. In some embodiments, crystalline Compound 2 is Polymorph Form B. In some embodiments, crystalline Compound 2 is Polymorph Form C. In some embodiments, the composition comprises amorphous Compound 2.

In some embodiments, the composition comprises crystalline polymorph Form C of Compound 2. In some embodiments, the composition comprises crystalline polymorph Form B of Compound 2. In some embodiments, the composition comprises amorphous Compound 2.

In some embodiments, the composition comprises crystalline Compound 2 and a detectable amount of amorphous Compound 2.

In some embodiments, the composition comprises a detectable amount of water.

In some embodiments, Compound 2 is crystalline and was crystallized from methyl tert-butyl ether.

In some embodiments, the composition of Compound 2 comprises a detectable amount of solvent selected from 1,2-dimethoxyethane, ethyl acetate, methanol, ethanol, tetrahydrofuran, and methyl tert-butyl ether; wherein the solvents are detected at levels less than about 5000 ppm. In some embodiments, the composition comprises a detectable amount of solvent selected from 1,2-dimethoxyethane, ethyl acetate, methanol, ethanol, tetrahydrofuran, and methyl tert-butyl ether; wherein the solvents are detected at levels less than about 4000 ppm. In some embodiments, the composition comprises a detectable amount of solvent selected from 1,2-dimethoxyethane, ethyl acetate, methanol, ethanol, tetrahydrofuran, and methyl tert-butyl ether; wherein the solvents are detected at levels less than about 3000 ppm. In some embodiments, the composition comprises a detectable amount of solvent selected from 1,2-dimethoxyethane, ethyl acetate, methanol, ethanol, tetrahydrofuran, and methyl tert-butyl ether; wherein the solvents are detected at levels less than about 2000 ppm. In some embodiments, the composition comprises a detectable amount of solvent selected from 1,2-dimethoxyethane, ethyl acetate, methanol, ethanol, tetrahydrofuran, and methyl tert-butyl ether; wherein the solvents are detected at levels less than about 1000 ppm.

In some embodiments, Compound 2 has a solubility in water at about pH 10 and at about 25° C. that is greater than about 10 mg/mL.

In some embodiments, the composition described herein comprises Compound 2 which was crystallized or precipitated from methyl tert-butyl ether. In some embodiments, the composition comprises Compound 2 that underwent a crystal formation (whether by a crystallization, solid-to-solid transformation or crystalline inter-conversion) from methyl tert-butyl ether.

In some embodiments, the composition of Compound 2 comprises a detectable amount of a compound selected from:

Compound 3

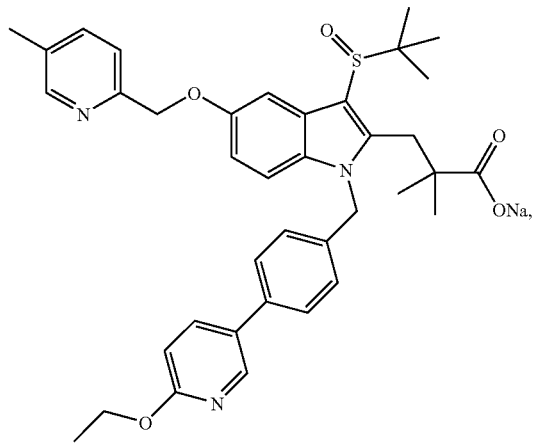

Compound 4

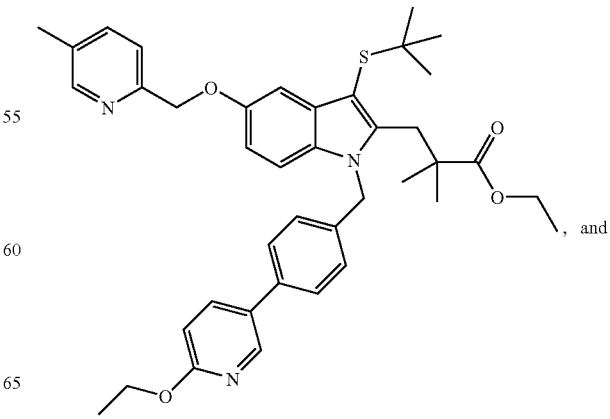

, and

-continued

Compound 5

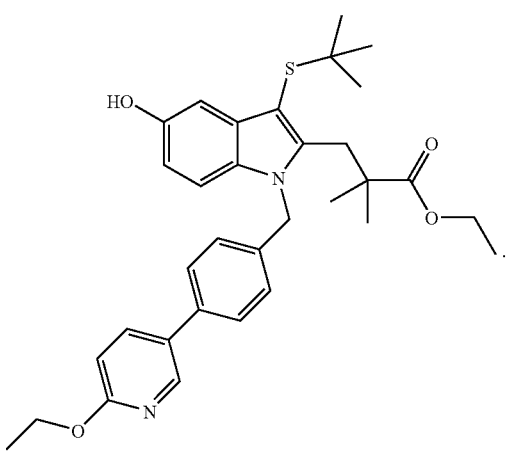

In some embodiments, Compound 2 is greater than 97% pure. In further embodiments, Compound 2 is greater than 98% pure. In yet further embodiments, Compound 2 is greater than 99% pure.

In one aspect, described herein is an amorphous form of Compound 2. In some embodiments, described herein is an amorphous form of Compound 2 that has at least one property selected from:
(1a) an XRPD pattern showing a lack of crystallinity;
(2a) at least one endotherm and at least one exotherm observed by differential scanning calorimetry (DSC);
(3a) a glass transition temperature of about 127° C.;
(4a) a melting point at about 155° C. followed by a re-crystallization event at about 200° C. followed by a second melting point at about 288° C. to about 295° C.;
(5a) a phase change to a crystalline form when heated above about 200° C., wherein the crystalline form that is formed above about 200° C. is characterized by an XRPD pattern substantially similar to any one of the XRPD patterns set forth in FIG. 9;
(6a) a DSC or a TGA substantially similar to the ones set forth in FIG. 12;
(7a) hygroscopicity; and/or
(8a) chemical stability.

In one aspect is a crystalline form of Compound 2. In some embodiments, the crystalline form of Compound 2 has at least one property selected from:
(1c) an X-ray powder diffraction (XRPD) pattern substantially similar to the one set forth in FIG. 1;
(2c) an XRPD pattern with peaks at about 17.2°2-Theta, at about 18.4°2-Theta, at about 19.1°2-Theta, at about 20.8°2-Theta, and at about 23.8°2-Theta;
(3c) a single melting point at about 290° C. to about 295° C. as measured by differential scanning calorimetry (DSC);
(4c) a DSC or a thermo-gravimetric analysis (TGA) substantially similar to the ones set forth in FIG. 15;
(5c) physical and chemical stability (at 5° C., 25° C./60% relative humidity (RH), and/or 40° C./75% RH for at least one month in a humidity chamber);
(6c) non-hygroscopicity;
(7c) IR spectrum substantially similar to the one set forth in FIG. 19; and/or
(8c) an X-ray powder diffraction (XRPD) pattern substantially similar to an XRPD pattern obtained for crystals of Compound 2 obtained from methyl tert-butyl ether or acetonitrile.

In some embodiments, the crystalline form of Compound 2 has at least one property selected from: (1c) an X-ray powder diffraction (XRPD) pattern substantially similar to the one set forth in FIG. 1; and (2c) an XRPD pattern with peaks at about 17.2°2-Theta, at about 18.4°2-Theta, at about 19.1°2-Theta, at about 20.8°2-Theta, and at about 23.8°2-Theta.

In some embodiments, Compound 2 is crystalline polymorph Form B.

In some embodiments, Compound 2 is crystalline and has at least one of the following properties: (1b) an X-ray powder diffraction (XRPD) pattern substantially similar to the one set forth in FIG. 2; (2b) an XRPD pattern with peaks at about 6.6° 2-Theta, at about 8.1°2-Theta, at about 19.7°2-Theta, at about 21.0°2-Theta, at about 21.9°2-Theta, and at about 22.1°2-Theta.

In one aspect there is provided Compound 1 and/or a pharmaceutically acceptable salt thereof is used in the treatment of asthma, treatment or prevention of exercise-induced bronchoconstriction, treatment and/or prevention of rhinitis (allergic and non-allergic), treatment of chronic obstructive pulmonary disease, treatment of cardiovascular disease, treatment of NSAID-induced gastric lesions, treatment of ocular disease, treatment of pain, or treatment of skin disease, in a human. In some embodiments the pharmaceutically acceptable salt is Compound 2.

In one aspect, Compound 1 is used for treating asthma, preventing exercise-induced bronchoconstriction, treating or preventing rhinitis (allergic and non-allergic), treating chronic obstructive pulmonary disease, treating cardiovascular disease, treating NSAID-induced gastric lesions, treating pain, treating or preventing ocular disease or treating skin disease in a human. In some embodiments, Compound 1 is crystalline. In some embodiments, Compound 1 is amorphous.

In one aspect, a pharmaceutically acceptable salt of Compound 1 is used for treating asthma, preventing exercise-induced bronchoconstriction, treating or preventing rhinitis (allergic and non-allergic), treating chronic obstructive pulmonary disease, treating cardiovascular disease, treating NSAID-induced gastric lesions, treating pain, treating or preventing ocular disease or treating skin disease in a human. In some embodiments, the pharmaceutically acceptable salt of Compound 1 is Compound 2.

In one aspect, crystalline Compound 2 is used for treating asthma, preventing exercise-induced bronchoconstriction, treating or preventing rhinitis (allergic and non-allergic), treating chronic obstructive pulmonary disease, treating cardiovascular disease, treating NSAID-induced gastric lesions, treating pain, treating or preventing ocular disease or treating skin disease in a human. In some embodiments, crystalline Compound 2 is Form C.

In one aspect, amorphous Compound 2 is used for treating asthma, preventing exercise-induced bronchoconstriction, treating or preventing rhinitis (allergic and non-allergic), treating chronic obstructive pulmonary disease, treating cardiovascular disease, treating NSAID-induced gastric lesions, treating pain, treating or preventing ocular disease or treating skin disease in a human.

Described herein are pharmaceutical compositions comprising Compound 1 and/or pharmaceutically acceptable salts thereof. In some embodiments, the pharmaceutical compositions comprise Compound 1. In other embodiments, the pharmaceutical compositions comprise a pharmaceutically acceptable salt of Compound 1. In some embodiments, the pharmaceutically acceptable salt of Compound 1 is Compound 2. In some embodiments, the pharmaceutical compositions further comprise at least one pharmaceutically acceptable inactive ingredient selected from among excipients, diluents, and carriers. In some embodiments, the pharmaceutically acceptable salt of Compound 1 comprises 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionate as the anion, and the cation is a metal cation or an ammonium cation. In specific embodiments, the cation is selected from Li$^+$, Na$^+$, K$^+$, and NH$_4^+$. In more specific embodiments, the cation is selected from Li$^+$, Na$^+$, and K$^+$. In even more specific embodiments, the cation is Na$^+$.

In some embodiments, pharmaceutical compositions described herein comprise a detectable amount of Compound 3, Compound 4 and/or Compound 5.

In some embodiments, pharmaceutical compositions described herein are in a form suitable for oral administration to a mammal. In specific embodiments, the composition is in the form of a pill, capsule, tablet, aqueous solution, or aqueous suspension.

In various embodiments the pharmaceutical compositions described herein comprise less than about 10 ppm of palladium.

In some embodiments, the pharmaceutically acceptable salt of Compound 1 is sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionate (Compound 2) and Compound 2 is in an amorphous phase, a partially crystalline form, or a crystalline form. In specific embodiments, the pharmaceutical composition described herein is formulated as a tablet and Compound 2 is in crystalline form.

In some embodiments, Compound 1 is in an amorphous phase, a partially crystalline form, or a crystalline form. In specific embodiments, the pharmaceutical composition described herein is formulated as a tablet and Compound 1 is in crystalline form. In specific embodiments, the pharmaceutical composition described herein is formulated as a tablet and Compound 1 is in amorphous phase.

In specific embodiments, any of the pharmaceutical compositions described herein comprise the crystalline form of Compound 2 that has an X-ray diffraction pattern with characteristic deg 2-theta values at about 17.2°2-Theta, at about 18.4°2-Theta, at about 19.1°2-Theta, at about 20.8°2-Theta, and at about 23.8°2-Theta. In some embodiments, Compound 2 described herein is in a crystalline form having an X-ray diffraction pattern substantially similar to the one set forth in FIG. 1. In other specific embodiments, any of the pharmaceutical compositions described herein comprise Compound 2 in amorphous phase. In another specific embodiment, any of the pharmaceutical compositions described herein comprise Compound 2 in a crystalline form having an X-ray diffraction pattern with characteristic deg 2-theta values at about 6.6° 2-Theta, at about 8.1°2-Theta, at about 19.7° 2-Theta, at about 21.0°2-Theta, at about 21.9°2-Theta, and at about 22.1°2-Theta. In further embodiments, Compound 2 described herein is in a crystalline form having an X-ray diffraction pattern substantially similar to the one set forth in FIG. 2.

In some embodiments, pharmaceutical compositions disclosed herein comprise crystalline Compound 2 and a detectable amount of amorphous Compound 2.

In some embodiments, Compound 2 is in a form/phase that has a solubility in water at a pH of about 9 to about 10 and about 25° C. of greater than about 10 mg/mL.

In one aspect, provided herein is an oral pharmaceutical composition comprising: (a) an alkali metal salt of Compound 1; (b) optional sorbitol or ethanol; and (c) an aqueous buffer solution. In specific embodiments, the alkali metal is sodium. In one aspect, provided is an oral pharmaceutical composition comprising: (a) a pharmaceutically acceptable salt comprising 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionate as the anion, and the cation selected from Na$^+$, K$^+$, and Li$^+$; (b) an aqueous buffer solution; and optionally (c) ethanol or Poloxamer 124. In some embodiments, the cation is Na$^+$. In some embodiments, the aqueous buffer solution is an aqueous sodium carbonate buffer solution. In some embodiments, the oral pharmaceutical composition further comprises a pharmaceutically acceptable sweetener. In specific embodiments, the pharmaceutically acceptable sweetener is selected from sucrose, sucralose, simple syrup, and syrpalta. In more specific embodiments, the pharmaceutically acceptable sweetener is sucralose. In other specific embodiments, the pharmaceutically acceptable sweetener is aspartame. In certain embodiments, any of the oral pharmaceutical compositions described herein comprise less than about 10 ppm palladium. In some embodiments, the oral pharmaceutical composition has a concentration of up to about 60 mg/mL, about 0.1 mg/mL to about 60 mg/mL, about 1 mg/mL to about 50 mg/mL, about 10 mg/mL to about 50 mg/mL, about 1 mg/mL to about 20 mg/mL, or about 10 mg/mL of Compound 2.

In some embodiments, provided herein is an oral pharmaceutical composition comprising: a. about 1 g of the sodium salt of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionic acid (Compound 2); and b. about 100 mL of a solution of 1% (w/w) Poloxamer 124 and 99% (w/w) aqueous sodium carbonate buffer (0.010M, pH9-10), sweetened with sucralose.

In some embodiments, provided herein is an oral pharmaceutical composition comprising (a) about 1 gram or about 10 mg/mL of the sodium salt of Compound 1 (Compound 2); and (b) about 100 mL of about 10 mM aqueous sodium carbonate buffer solution with a pH of about 9-10 comprising about 10% w/w absolute ethanol and about 0.003% w/w aspartame. In a specific embodiment, provided herein is an oral pharmaceutical composition comprising (a) about 10 mg/mL of Compound 2; (b) a solution comprising about 1% w/w poloxamer 124 and about 99% w/w aqueous sodium carbonate buffer (about 0.010M, pH about 9-10); and (c) sucralose (about 5 mg/100 mL).

In some embodiments, any pharmaceutical composition (e.g. any oral pharmaceutical composition) described herein comprises or is formulated in a single dose comprising from about 10 mg to about 1000 mg of a pharmaceutically active salt of Compound 1. In specific embodiments, the single dose comprises about 10 mg to about 600 mg, about 20 mg to about 600 mg, about 40 mg to about 600 mg or about 50 mg to about 600 mg of a pharmaceutically acceptable salt of Compound 1. In specific embodiments, the single dose, when administered to healthy adult human subjects in the fasted state provides a $C_{max}$ of about 0.1 µM to about 30 µM, about 0.2 µM to about 30 µM, or about 0.1 µM to about 5 µM. In some embodiments, the single dose, when administered to healthy human subjects in the fasted state provides a $t_{max}$ of about 1 hour to about 4 hours, or about 2 hours to about 3 hours. In some embodiments, the single dose, when administered to healthy human subjects in the fasted state provides an $AUC_{0-24}$ of about 4 hr·µM to about 160 hr·µM, about 5 hr·µM to about 110 hr·µM, about 5 hr·µM to about 90 hr·µM, about 5 hr·µM to about 50 hr·µM, about 5 hr·µM to about 25 hr·µM. In some embodiments, the single dose of the pharmaceutical composition when administered to healthy adult human subjects in the fasted state provides a $C_{max}$ that is less than about 5 µM, less than about 9 µM, or less than about 12 µM. In some embodiments, the single dose of the oral pharmaceutical composition when administered to healthy adult human subjects in the fasted state provides after about 8 hours at least 25%, at least 50%, at least 60%, at least 70%, at least 80% or at least 90% reduction in blood $LTB_4$ levels. In some embodiments, the single dose provides after about 24 hours at least 5%, at least 10%, at least 20%, at least 30%, at least 40%, or at least 50% reduction in blood $LTB_4$ levels. In some embodiments, the single dose provides at least 25%, at least 50%, at least 60%, at least 70%, at least 80%, or at least 90% reduction in urinary $LTE_4$ levels. In some embodiments, the pharmaceutically active salt of Compound 1 is Compound 2. In some embodiments, the single dose of the oral pharmaceutical composition comprises about 10 mg to about 1 g, about 10 mg to about 600 mg, about 10 mg, about 50 mg, about 150 mg, about 300 mg, about 600 mg, or about 1000 mg of Compound 2.

In some embodiments, any oral pharmaceutical composition described herein comprises or is formulated in a single dose comprising from about 10 mg to about 1000 mg of Compound 1. In further embodiments, the single dose comprises about 50 mg to about 1 g, about 10 mg to about 600 mg, or about 50 mg to about 600 mg of Compound 1. In further or alternative embodiments, the single dose of the oral pharmaceutical composition comprises about 10 mg to about 1 g, about 10 mg to about 600 mg, about 10 mg, about 50 mg, about 150 mg, about 300 mg, about 600 mg, or about 1000 mg of Compound 1.

An oral solid dosage form pharmaceutical composition comprising: (a) about 10 mg to about 1 g, or about 50 mg to about 1 g, or about 50 mg to about 600 mg of Compound 2; and (b) at least one inactive pharmaceutical ingredient. In specific embodiments, the oral solid dosage form comprises about 10 mg, about 50 mg, about 100 mg, about 150 mg, about 200 mg, about 250 mg, about 300 mg, about 450 mg or about 600 mg of Compound 2. In specific embodiments, the oral solid dosage form comprises about 10 mg, about 50 mg, about 100 mg, about 150 mg, about 200 mg, about 250 mg, or about 300 mg of Compound 2. In certain embodiments, the oral solid dosage form pharmaceutical composition comprises less than about 10 ppm palladium. In some embodiments, the oral solid dosage form pharmaceutical composition comprises less than about 5000 ppm ethyl acetate. In some embodiments, the oral solid dosage form comprises less than about 5000 ppm ethanol. In some embodiments, the oral solid dosage form pharmaceutical composition comprises a crystalline form of Compound 2. In some embodiments, Compound 2 is in a crystalline form having an X-ray diffraction pattern with characteristic deg 2-theta values at about 17.2°2-Theta, at about 18.4°2-Theta, at about 19.1°2-Theta, at about 20.8°2-Theta, and at about 23.8°2-Theta. In some embodiments, Compound 2 is in a crystalline form having an X-ray diffraction spectrum substantially similar to the one set forth in FIG. 1. In some embodiments, Compound 2 is in a crystalline form having an X-ray diffraction pattern with characteristic deg 2-theta values at about 6.6°2-Theta, at about 8.1°2-Theta, at about 19.7°2-Theta, at about 21.0°2-Theta, at about 21.9°2-Theta, and at about 22.1°2-Theta. In some embodiments, Compound 2 is in a crystalline form having an X-ray diffraction spectrum substantially similar to the one set forth in FIG. 2. In some embodiments, the oral solid dosage form comprises an amorphous phase (Phase A) of Compound 2. An oral solid dosage form pharmaceutical composition comprising: (a) about 10 mg to about 1 g, or about 50 mg to about 1 g, or about 50 mg to about 600 mg of Compound 1; and (b) at least one inactive pharmaceutical ingredient. In specific embodiments, the oral solid dosage form comprises about 10 mg, about 50 mg, about 100 mg, about 150 mg, about 200 mg, about 250 mg, about 300 mg, about 450 mg or about 600 mg of Compound 1. In certain embodiments, the oral solid dosage form pharmaceutical composition comprises less than about 10 ppm palladium. In some embodiments, the oral solid dosage form pharmaceutical composition comprises less than about 5000 ppm ethyl acetate. In some embodiments, the oral solid dosage form comprises less than about 5000 ppm ethanol. In some embodiments, the oral solid dosage form pharmaceutical composition comprises a crystalline form of Compound 1. In some embodiments, Compound 1 is in amorphous phase.

In one aspect, any of the oral solid dosage form pharmaceutical composition described herein allows for rapid absorption of the active ingredient in the stomach and upper gastrointestinal tract. In specific embodiments, provided herein is an oral solid dosage form that is in the form of a tablet or capsule. In specific embodiments, provided herein is an oral solid dosage form that is in the form of a tablet. In more specific embodiments, the tablet is an immediate release tablet.

In some embodiments, the oral solid dosage form that comprises Compound 2 exhibits an in vitro release of Compound 2 in about 1% sodium lauryl sulfate solution at pH of about 7 and about 37° C. of more than about 90% after about 10 minutes. In specific embodiments, the in vitro release is measured by a drug release test using the United States Pharmacopea (USP) Type 1, basket at about 100 rpm with about 500 mL of about 1% sodium lauryl sulfate solution at pH of about 7 and about 37° C.

In some embodiments, provided herein is a pharmaceutical composition comprising Compound 2, e.g., an oral solid dosage form, wherein administration of a single dose of the pharmaceutical composition to a healthy adult human subject in the fasted state provides a $C_{max}$ less of than about 5 µM, and provides after about 8 hours at least an 80% reduction in blood $LTB_4$ levels. In some embodiments, provided herein is a pharmaceutical composition, e.g., an oral solid dosage form pharmaceutical composition, wherein administration of a single dose of the pharmaceutical composition to a healthy adult human subject in the fasted state provides after about 24 hours at least 30% reduction in blood $LTB_4$ levels. In some embodiments, provided herein is a pharmaceutical composition, e.g., an oral solid dosage form pharmaceutical composition, wherein administration of a single dose of the pharmaceutical composition to a healthy adult human subject in the fasted state provides after about 24 hours at least 50% reduction of urinary $LTE_4$ levels.

In some embodiments, any oral solid dosage form described herein comprises a binding agent, a disintegrant, and a glidant as inactive pharmaceutical ingredients. In specific embodiments, the inactive pharmaceutical ingredients comprise silicified microcrystalline cellulose (SMCC), mannitol, crospovidone, and magnesium stearate.

In some embodiments oral solid dosage form pharmaceutical compositions provided herein comprise from about 1% to about 99%, about 1% to about 30%, about 1% to about 20%, or about 10% by weight to about 20% by weight of Compound 2.

Described herein are pharmaceutical compositions that provide at least one metabolite of Compound 1 to a mammal after administration to the mammal. In specific embodiments, the at least one metabolite is selected from among: 3-[3-tert-butylsulfinyl-1-[4-(6-ethoxy-pyridin-3-yl)-benzyl]-5-(5-methyl-pyridin-2-ylmethoxy)-1H-indol-2-yl]-2,2-dimethyl-propionic acid; 3-[3-tert-butylsulfanyl-1-[4-(6-hydroxy-pyridin-3-yl)-benzyl]-5-(5-methyl-pyridin-2-ylmethoxy)-

1H-indol-2-yl]-2,2-dimethyl-propionic acid; 3-[3-tert-butylsulfanyl-1-[4-(6-ethoxy-pyridin-3-yl)-benzyl]-5-(5-methyl-N-oxy-pyridin-2-ylmethoxy)-1H-indol-2-yl]-2,2-dimethyl-propionic acid; the acyl gluconuride of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid; and combinations thereof. In specific embodiments, the at least one metabolite is the acyl gluconuride of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid. In some embodiments, the pharmaceutical composition comprises a pharmaceutically acceptable (e.g., sodium) salt of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionic acid.

Described in certain embodiments herein is a pharmaceutical composition comprising an active ingredient that inhibits 5-lipoxygenase-activating protein (FLAP) and does not substantially inhibit at least one Cytochrome P450 enzyme selected from CYP 3A4, CYP 1A2, CYP 2A6, CYP 2B6, CYP 2C8, CYP 2C9, CYP 2C19, CYP 2D6, and CYP 2E1 at doses up to 40 µM or 50 µM. In some embodiments, the pharmaceutical composition comprising an active FLAP inhibitor has an $IC_{50}$ greater than about 40 µM, or 50 µM for at least one Cytochrome P450 enzyme selected from CYP 3A4, CYP 1A2, CYP 2A6, CYP 2B6, CYP 2C8, CYP 2C9, CYP 2C19, CYP 2D6, and CYP 2E1. In some embodiments, the pharmaceutical composition does not substantially induce Cytochrome P450 CYP 3A4, CYP 2C9, CYP 1A2, CYP 2C19, or CYP 2D6 at doses up to 40 µM, or up to 50 µM. In some embodiments, the pharmaceutical composition comprising an active FLAP inhibitor has an $IC_{50}$ greater than about 40 µM, or 50 µM for at least one Cytochrome P450 enzyme selected from CYP 3A4, CYP 2C9, CYP 1A2, CYP 2C19, and CYP 2D6. In certain embodiments, the FLAP inhibitor is Compound 1, or a pharmaceutically acceptable salt thereof. In a specific embodiment, the FLAP inhibitor is Compound 1. In another specific embodiment, the FLAP inhibitor is Compound 2. Described in certain embodiments herein is an oral solid dosage form pharmaceutical composition comprising: (a) Compound 2; and (b) optionally at least one inactive pharmaceutical ingredient. In specific embodiments, the oral solid dosage form pharmaceutical composition is in the form of a capsule. In more specific embodiments, the capsule is a hard gelatine capsule. In various embodiments, the capsules described herein comprise at least one excipient or no excipients. In some embodiments, Compound 2 of the oral dosage form is amorphous, partially crystalline, or crystalline. In specific embodiments, Compound 2 is crystalline.

Described in certain embodiments provided herein is an article of manufacture comprising multiple unit doses of any of the oral solid dosage form pharmaceutical compositions described herein in a high-density polyethylene (HDPE) bottle equipped with a high-density polyethylene (HDPE) cap. In certain embodiments, the article of manufacture further comprises an aluminum foil induction seal and an optional silica gel desiccant.

In certain embodiments, provided herein are methods of treating asthma in a human comprising administering to the human one or more of the pharmaceutical compositions described herein.

In certain embodiments, provided herein are methods of preventing exercise-induced bronchoconstriction in a human comprising administering to the human one or more of the pharmaceutical compositions described herein.

In certain embodiments, provided herein are methods of treating allergic rhinitis in a human comprising administering to the human one or more of the pharmaceutical compositions described herein. In certain embodiments, provided herein are methods of treating allergic rhinitis in a human comprising administering to the human one or more of the oral pharmaceutical compositions described herein.

In certain embodiments, the methods further comprise administering at least one additional pharmaceutical agent selected from inhaled corticosteroids, non-steroidal glucocorticoid receptor (GR) agonists, short acting beta-agonists, long acting beta-agonists, and antihistamines.

In certain embodiments, provided herein are methods of treating chronic obstructive pulmonary disease in a human comprising administering to the human one or more of the pharmaceutical compositions described herein.

In certain embodiments, provided herein are methods of treating cardiovascular disease in a human comprising administering to a human any of the pharmaceutical compositions described herein.

In certain embodiments, provided herein are methods of treating NSAID-induced gastric lesions in a human comprising administering to a human any of the pharmaceutical compositions described herein.

In certain embodiments, provided herein are methods of treating pain in a human comprising administering to a human any of the pharmaceutical compositions described herein.

In certain embodiments, provided herein are methods of treating skin disease in a human comprising administering to a human any of the pharmaceutical compositions described herein.

In certain embodiments, provided herein are methods of treating ocular disease in a human comprising administering to a human any of the pharmaceutical compositions described herein.

In one aspect, described herein are pharmaceutical compositions for oral administration to a mammal that comprises an active ingredient that inhibits FLAP and does not substantially cause increases in liver weight of the mammal. In some embodiments, the active ingredient is Compound 1 or a pharmaceutically acceptable salt thereof. In one specific embodiment, the active ingredient is Compound 1. In another specific embodiment, the active ingredient is Compound 2.

In one aspect, described herein is a method of treating asthma in a human comprising administering to the human an oral pharmaceutical composition comprising Compound 1 or a pharmaceutically acceptable salt thereof.

In one aspect, described herein is a method of treating allergic rhinitis in a human comprising administering to the human an oral pharmaceutical composition comprising Compound 1 or a pharmaceutically acceptable salt thereof.

In any of the method of treatments described herein, the methods further comprise administering at least one additional pharmaceutical agent selected from inhaled corticosteroids, short acting beta-agonists, long acting beta-agonists, antihistamines, anticholinergics, non-steroidal GR agonists, antiinfectives and antivirals.

In one aspect, provided herein is a method of treating chronic obstructive pulmonary disease in a human comprising administering to the human a pharmaceutical composition comprising Compound 1 or a pharmaceutically acceptable salt thereof.

In one aspect, provided herein is a method of treating cardiovascular disease in a human comprising administering to the human a pharmaceutical composition comprising Compound 1 or a pharmaceutically acceptable salt thereof.

In one aspect, provided herein is a method of treating pain in a human comprising administering to the human a pharmaceutical composition comprising Compound 1 or a pharmaceutically acceptable salt thereof.

In one aspect, provided herein is a method of treating NSAID-induced gastric lesions in a human comprising administering to the human a pharmaceutical composition comprising Compound 1 or a pharmaceutically acceptable salt thereof.

In one aspect, provided herein is a method of treating ocular disease in a human comprising administering to the human a pharmaceutical composition comprising Compound 1 or a pharmaceutically acceptable salt thereof.

In one aspect, Compound 1, or a pharmaceutically acceptable salt thereof (e.g. Compound 2) is used to treat patients suffering from leukotriene-dependent conditions or diseases, including, but not limited to, asthma, chronic obstructive pulmonary disease, pulmonary hypertension, interstitial lung fibrosis, allergic rhinitis, adult respiratory distress syndrome, and inflammatory conditions.

In one aspect provided are methods for modulating, including reducing and/or inhibiting the activity of 5-lipoxygenase activating protein, directly or indirectly, in a mammal comprising administering to the mammal at least once an effective amount of Compound 1, or a pharmaceutically acceptable salt thereof (e.g. Compound 2).

In one aspect provided are methods for modulating, including reducing and/or inhibiting, the activity of leukotrienes in a mammal, directly or indirectly, comprising administering to the mammal at least once an effective amount of Compound 1, or a pharmaceutically acceptable salt thereof (e.g. Compound 2).

In one aspect provided are methods for treating leukotriene-dependent or leukotriene mediated conditions or diseases, comprising administering to the mammal at least once an effective amount of Compound 1, or a pharmaceutically acceptable salt thereof (e.g. Compound 2).

In one aspect provided are methods for treating mammals with an inflammatory and/or allergic condition comprising administering to the mammal at least once an effective amount of Compound 1, or a pharmaceutically acceptable salt thereof (e.g. Compound 2).

In one aspect, provided herein is an oral pharmaceutical composition as described herein comprising Compound 1 or a pharmaceutically acceptable salt thereof as the active ingredient for use in the treatment or prevention of an inflammatory and/or allergic condition in a mammal. In some embodiments, the active ingredient is Compound 1. In other embodiments, the active ingredient is Compound 2.

In one aspect are methods for treating inflammation in a mammal comprising administering to the mammal at least once an effective amount of Compound 1, or a pharmaceutically acceptable salt thereof (e.g. Compound 2).

In one aspect are methods for treating respiratory diseases in a mammal comprising administering to the mammal at least once an effective amount of Compound 1, or a pharmaceutically acceptable salt thereof (e.g. Compound 2). In a specific embodiment of this aspect, the respiratory disease is asthma.

Respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vasomotor rhinitis, vascular responses, endotoxin shock, fibrogenesis, pulmonary fibrosis, allergic diseases, chronic inflammation, and adult respiratory distress syndrome.

In one aspect are methods for treating chronic obstructive pulmonary disease in a mammal comprising administering to the mammal at least once an effective amount of Compound 1, or a pharmaceutically acceptable salt thereof (e.g. Compound 2).

Chronic obstructive pulmonary disease includes, but is not limited to, chronic bronchitis or emphysema, pulmonary hypertension, interstitial lung fibrosis and/or airway inflammation and cystic fibrosis.

In one aspect are methods for preventing increased mucosal secretion and/or edema in a mammal comprising administering to the mammal at least once an effective amount of Compound 1, or a pharmaceutically acceptable salt thereof (e.g. Compound 2).

In one aspect are methods for preventing eosinophil and/or basophil and/or dendritic cell and/or neutrophil and/or monocyte recruitment in a mammal comprising administering to the mammal at least once an effective amount of Compound 1, or a pharmaceutically acceptable salt thereof (e.g. Compound 2).

In another aspect are methods for preventing ocular disease (for example, ocular inflammation, allergic conjunctivitis, vernal keratoconjunctivitis and papillary conjunctivitis) in a mammal comprising administering to the mammal at least once an effective amount of Compound 1, or a pharmaceutically acceptable salt thereof (e.g. Compound 2).

In another aspect are methods for preventing or treating acute or chronic disorders involving recruitment or activation of eosinophils in a mammal comprising administering to the mammal at least once an effective amount of Compound 1, or a pharmaceutically acceptable salt thereof (e.g. Compound 2).

In another aspect are methods for preventing or treating NSAID-induced gastric lesions in a mammal comprising administering to the mammal at least once an effective amount of Compound 1, or a pharmaceutically acceptable salt thereof (e.g. Compound 2).

In any of the aforementioned aspects, the mammal is a human. In any of the aforementioned aspects, the mammal is a human, including embodiments wherein (a) the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned aspects are further embodiments in which the mammal is an animal model for pulmonary inflammation, examples of which are provided herein.

In any of the aforementioned aspects are further embodiments comprising single administrations of the effective amount of Compound 1, or a pharmaceutically acceptable salt thereof (e.g. Compound 2), including further embodiments in which Compound 1, or a pharmaceutically acceptable salt thereof (e.g. Compound 2) is (i) administered once-a-day; (ii) is administered twice-a-day; or (iii) is administered multiple times over the span of one day.

In any of the aforementioned aspects are further embodiments comprising multiple administrations of the effective amount of the compound, including further embodiments in which (i) the compound is administered in a single dose; (ii) the time between multiple administrations is every 6 hours; (iii) the time between multiple administrations is every 8 hours; (iv) the time between multiple administrations is every 12 hours.

In some embodiments, the methods of treatment or prevention disclosed herein comprise a drug holiday, wherein the administration of Compound 1, or a pharmaceutically acceptable salt thereof (e.g. Compound 2) is temporarily suspended or the dose being administered is temporarily reduced; at the end of the drug holiday dosing is resumed. In some embodiments, the length of the drug holiday varies from 2 days to 1 year.

In one aspect, Compound 1, or a pharmaceutically acceptable salt thereof (e.g. Compound 2) is used in the manufacture of medicaments for the treatment of leukotriene dependent conditions, disorders, or diseases in a human that is a non-responder to montelukast. In some embodiments, the leukotriene dependent condition, disorder, or disease is a respiratory disease or condition. In a specific embodiment, the respiratory disease or condition is asthma.

Compound 1, or a pharmaceutically acceptable salt thereof (e.g. Compound 2) for treating any of the diseases or conditions disclosed herein.

A pharmaceutical composition comprising Compound 1, or a pharmaceutically acceptable salt thereof (e.g. Compound 2) for use in any of the uses and methods disclosed herein.

Use of Compound 1, or a pharmaceutically acceptable salt thereof (e.g. Compound 2) in the manufacture of a medicament for treating or preventing any of the diseases disclosed herein in a mammal.

In one aspect, described herein is the treatment of leukotriene dependent conditions, diseases, or disorders in a human that is a non-responder to montelukast. In some embodiments, the leukotriene dependent condition, disorder, or disease is a respiratory disease or condition. In a specific embodiment, the respiratory disease or condition is asthma. In a specific embodiment, the non-responder to montelukast is administered Compound 1, or a pharmaceutically acceptable salt thereof (e.g. Compound 2).

In one aspect, the dose of Compound 1, or a pharmaceutically acceptable salt thereof (e.g. Compound 2) that is administered to healthy human patients is reduced in human patients that lack or have a defect in a UDP-glucuronosyltransferase enzyme normally present in the human.

In one aspect, described herein is a method of increasing the bioavailability of an orally administered dose of Compound 1, or a pharmaceutically acceptable salt thereof (e.g. Compound 2) in healthy human patients comprising orally administering to a mammal: (1) a dose of Compound 1, or a pharmaceutically acceptable salt thereof (e.g. Compound 2); and (2) an inhibitor of a UDP-glucuronosyltransferase enzyme normally present in the mammal. In some embodiments, the UDP-glucuronosyltransferase enzyme is selected from UGT1A1, UGT1A3, UGT1A6, UGT1A9, and UGT2B7.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; (e) measuring levels of $LTB_4$ in the calcium ionophore-challenged blood of a mammal; (f) measuring levels of $LTE_4$ in the urinary excretion of a mammal; or (g) identifying a patient by measuring leukotriene-driven inflammatory biomarkers such as $LTB_4$, $LTC_4$, Il-6, CRP, SAA, MPO, EPO, MCP-1, MIP-$\alpha$, sICAMs, Il-4, Il-13.

In any of the aforementioned aspects involving the prevention or treatment of leukotriene-dependent or leukotriene mediated diseases or conditions are further embodiments comprising identifying patients by screening for a leukotriene gene haplotype. In some embodiments the leukotriene gene haplotype is a leukotriene pathway gene. In a specific embodiment, the leukotriene gene haplotype is a FLAP haplotype.

In any of the aforementioned aspects involving the prevention or treatment of leukotriene-dependent or leukotriene mediated diseases or conditions are further embodiments comprising identifying patients by monitoring the patient for either:
  i) at least one leukotriene related inflammatory biomarker; or
  ii) at least one functional marker response to a leukotriene modifying agent; or
  iii) at least one leukotriene related inflammatory biomarker and at least one functional marker response to a leukotriene modifying agent.

In some embodiments, the leukotriene-related inflammatory biomarkers are selected from the group consisting of $LTB_4$, cysteinyl leukotrienes, CRP, SAA, MPO, EPO, MCP-1, MIP-$\alpha$, sICAM, IL-6, IL-4, and IL-13. In some embodiments, the functional marker response is significant lung volume (FEV1).

In any of the aforementioned aspects involving the prevention or treatment of leukotriene-dependent or leukotriene mediated diseases or conditions are further embodiments comprising identifying patients by either:
  i) screening the patient for at least one leukotriene gene SNP and/or haplotype including SNP's in intronic or exonic locations; or
  ii) monitoring the patient for at least one leukotriene related inflammatory biomarker; or
  iii) monitoring the patient for at least one functional marker response to a leukotriene modifying agent In some embodiments, the leukotriene gene SNP or haplotype is a leukotriene pathway gene. In specific embodiments, the leukotriene gene SNP or haplotype is a FLAP SNP or haplotype. In some embodiments, the leukotriene-related inflammatory biomarkers are selected from the group consisting of $LTB_4$, cysteinyl leukotrienes, CRP, SAA, MPO, EPO, MCP-1, MIP-$\alpha$, sICAM, IL-6, IL-4, and IL-13. In some embodiments, the functional marker response is significant lung volume (FEV1).

In any of the aforementioned aspects involving the prevention or treatment of leukotriene-dependent or leukotriene mediated diseases or conditions are further embodiments comprising identifying patients by at least two of the following:
  i) screening the patient for at least one leukotriene gene SNP or haplotype;
  ii) monitoring the patient for at least one leukotriene related inflammatory biomarker;
  iii) monitoring the patient for at least one functional marker response to a leukotriene modifying agent.

In some embodiments, the leukotriene gene SNP or haplotype is a leukotriene pathway gene. In some embodiments, the leukotriene gene SNP or haplotype is a FLAP SNP or haplotype. In some embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13. In some embodiments, the functional marker response is significant lung volume (FEV1).

In any of the aforementioned aspects involving the prevention or treatment of leukotriene-dependent or leukotriene mediated diseases or conditions are further embodiments comprising identifying patients by:
i) screening the patient for at least one leukotriene gene SNP or haplotype;
ii) monitoring the patient for at least one leukotriene related inflammatory biomarker; and
iii) monitoring the patient for at least one functional marker response to a leukotriene modifying agent.

In some embodiments, the leukotriene gene SNP or haplotype is a leukotriene pathway gene. In some embodiments, the leukotriene gene SNP or haplotype is a FLAP SNP or haplotype. In some embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13. In some embodiments, the functional marker response is significant lung volume (FEV1).

In another aspect is the prevention or treatment of leukotriene-dependent or leukotriene mediated diseases or conditions comprising administering to a patient an effective amount of Compound 1, or pharmaceutically acceptable salt and/or solvate thereof, wherein the patients has been identified using information obtained by:
i) screening the patient for at least one leukotriene gene SNP or haplotype; and
ii) monitoring the patient for at least one leukotriene related inflammatory biomarker; and
iii) monitoring the patient for at least one functional marker response to a leukotriene modifying agent.

In some embodiments, the leukotriene gene SNP or haplotype is a leukotriene pathway gene. In some embodiments, the leukotriene gene SNP or haplotype is a FLAP SNP or haplotype. In some embodiments, the leukotriene-related inflammatory biomarkers are selected from the group consisting of $LTB_4$, cysteinyl leukotrienes, CRP, SAA, MPO, EPO, MCP-1, MIP-α, sICAM, IL-6, IL-4, and IL-13. In some embodiments, the functional marker response is significant lung volume (FEV1). In some embodiments, the information obtained from the three diagnostic methods are used in an algorithm in which the information is analyzed to identify patients in need of treatment Compound 1 or a pharmaceutically acceptable salt thereof and the treatment regimen.

In any of the aforementioned aspects the leukotriene-dependent or leukotriene mediated diseases or conditions include, but are not limited to, asthma, chronic obstructive pulmonary disease, pulmonary hypertension, interstitial lung fibrosis, rhinitis, allergy, adult respiratory distress syndrome.

Also described herein are process for the preparation of Compound 1 and pharmaceutically acceptable salts thereof. In one aspect, the pharmaceutically acceptable salt of Compound 1 is Compound 2.

In one aspect, described is a process for the preparation of a crystalline form of sodium 3-[3-(tert-butylsulfanyl)-1-[4-(6-ethoxy-pyridin-3-yl)benzyl]-5-(5-methyl-pyridin-2-ylmethoxy)-1H-indol-2-yl]-2,2-dimethylpropionate (Compound 2) comprising the steps of:
(1) adding Compound 2 to methyl tert-butylether to form a mixture;
(2) heating the mixture from step (1) and then cooling the solution; and
(3) isolating the solids that are formed from step (2) to provide a crystalline form of Compound 2.

In some embodiments, the crystalline form of Compound 2 has an X-ray diffraction pattern with characteristic deg 2-theta values at about 6.6°2-Theta, at about 8.1°2-Theta, at about 19.7°2-Theta, at about 21.0°2-Theta, at about 21.9°2-Theta, and at about 22.1°2-Theta.

In some embodiments, the crystalline form of Compound 2 has an X-ray diffraction pattern that correlates with the X-ray diffraction pattern displayed in FIG. 2.

In some embodiments, the crystalline form of Compound 2 has an X-ray diffraction pattern with characteristic deg 2-theta values at about 17.2°2-Theta, at about 18.4°2-Theta, at about 19.1°2-Theta, at about 20.8°2-Theta, and at about 23.8°2-Theta.

In some embodiments, the crystalline form of Compound 2 has an X-ray diffraction pattern that correlates with the X-ray diffraction pattern displayed in FIG. 1.

In one aspect, described is a process for the preparation of Compound 2 comprising the steps of:
(a) reacting 4-methoxyphenylhydrazine hydrochloride with 4-bromobenzyl bromide in the presence of triethylamine and toluene to provide N-(4-bromo-benzyl)-N-(4-methoxy-phenyl)-hydrazine hydrochloride;
(b) treating the product of step (a) with HCl to provide N-(4-bromo-benzyl)-N-(4-methoxy-phenyl)-hydrazine hydrochloride;
(c) reacting N-(4-bromo-benzyl)-N-(4-methoxy-phenyl)-hydrazine hydrochloride with acetic acid, 5-tert-butylsulfanyl-2,2-dimethyl-4-oxo-pentanoic acid ethyl ester, and sodium acetate in toluene to provide 3-[1-(4-bromo-benzyl)-3-tert-butylsulfanyl-5-methoxy-1H-indol-2-yl]-2,2-dimethyl-propionic acid ethyl ester;
(d) reacting 3-[1-(4-bromo-benzyl)-3-tert-butylsulfanyl-5-methoxy-1H-indol-2-yl]-2,2-dimethyl-propionic acid ethyl ester with 2-methyl-2-propanethiol and aluminum chloride in dichloromethane to provide 3-[1-(4-bromo-benzyl)-3-tert-butylsulfanyl-5-hydroxy-1H-indol-2-yl]-2,2-dimethyl-propionic acid ethyl ester;
(e) reacting 3-[1-(4-bromo-benzyl)-3-tert-butylsulfanyl-5-hydroxy-1H-indol-2-yl]-2,2-dimethyl-propionic acid ethyl ester with bis(pinacolato)diboron using palladium mediated reaction conditions to provide 3-{3-tert-butylsulfanyl-5-hydroxy-1-[4-(4,4,5,5-tetramethyl-[1,3,2]dioxaborolan-2-yl)-benzyl]-1H-indol-2-yl}-2,2-dimethyl-propionic acid ethyl ester;
(f) reacting 3-{3-tert-butylsulfanyl-5-hydroxy-1-[4-(4,4,5,5-tetramethyl-[1,3,2]dioxaborolan-2-yl)-benzyl]-1H-indol-2-yl}-2,2-dimethyl-propionic acid ethyl ester with 5-bromo-2-ethoxypyridine using palladium mediated reaction conditions to provide 3-{3-tert-butylsulfanyl-1-[4-(6-ethoxy-pyridin-3-yl)-benzyl]-5-hydroxy-1H-indol-2-yl}-2,2-dimethyl-propionic acid ethyl ester;
(g) reacting 3-{3-tert-butylsulfanyl-1-[4-(6-ethoxy-pyridin-3-yl)-benzyl]-5-hydroxy-1H-indol-2-yl}-2,2-dimethyl-propionic acid ethyl ester with 2-chloro-5-methylpyridine hydrochloride in the presence of a base and solvent to provide 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester;
(h) reducing the amount of residual palladium from 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester; and
(i) forming Compound 2 from 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester.

In some embodiments, step (h) comprises treating 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with thiol derivatized silica gel.

In some embodiments, step (h) comprises treating 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with thiol derivatized silica gel or activated carbon. In some embodiments, step (h) comprises treating 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with thiol derivatized silica gel and activated carbon. In some embodiments, step (h) comprises treating 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with thiol derivatized silica gel. In some embodiments, step (h) comprises treating 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with activated carbon.

In some embodiments, step (i) comprises reacting 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester with sodium hydroxide in a suitable solvent.

In some embodiments, step (i) further comprises crystal formation (whether by a crystallization, solid-to-solid transformation or crystalline inter-conversion) or precipitating Compound 2 from methyl tert-butyl ether.

In some embodiments, a sample of Compound 2 comprises a detectable amount of palladium that is less than 20 ppm. In one aspect, a sample of Compound 2 comprises less than 20 ppm of palladium.

In one aspect, described herein is a process for the preparation of sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate (Compound 2) comprising the steps of:

(A) reacting a compound of Formula (III)

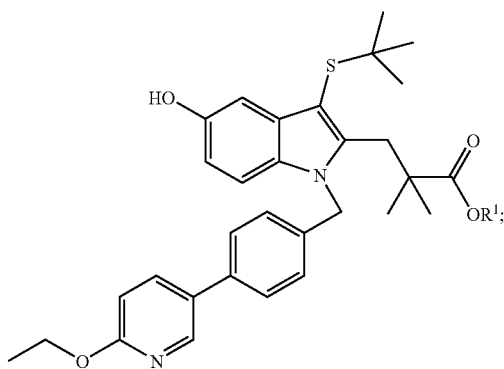

Formula (III)

wherein $R^1$ is $C_1$-$C_6$ alkyl; with a compound of Formula (II)

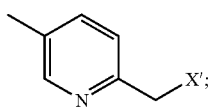

Formula (II)

wherein X' is a leaving group; in the presence of a base and solvent to form a compound of Formula (I)

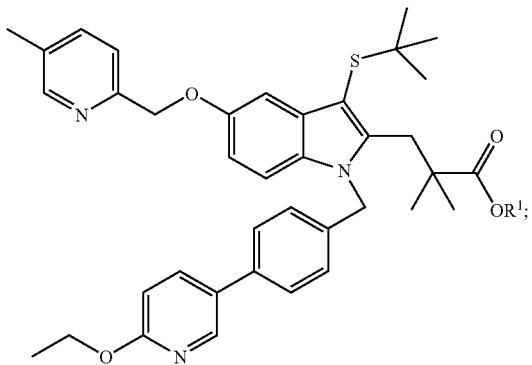

Formula (I)

and (B) forming Compound 2 from the compound of Formula (I) of step (A).

In some embodiments, step (A) further comprises isolating the compound of Formula (I) prior to step (B).

In some embodiments, step (A) further comprises reducing the amount of palladium to less than about 20 ppm. In one aspect, reducing the amount of palladium comprises treatment of compound of Formula (I) with thiol derivatized silica gel.

In some embodiments, the product from step (A) is isolated. In some embodiments, the product from step (A) is not isolated. In some embodiments, the compound of Formula (III) is prepared using palladium coupling reactions and contains residual palladium. In some embodiments, isolating the product from step (A) comprises reducing residual palladium.

In some embodiments, activated carbon is used to reduce residual palladium. In a specific embodiment, the activated carbon is DARCO® KB-G, DARCO® KB-WJ. In some embodiments, reducing residual palladium comprises derivatized silica gel. In some embodiments, reducing residual palladium comprises thiol derivatized silica gel.

In some embodiments, the reaction of step (A) is heated to a temperature of about 50° C. to about 90° C.

In some embodiments, step (B) comprises hydrolysis of the ester moiety of the product of step (A).

In some embodiments, step (B) comprises treatment of the compound of Formula (I) from step (A) with:

a) LiOH, KOH, or Ca(OH)$_2$, followed by pH adjustment to form the carboxylic acid, followed by NaOH; or b) NaOH.

In some embodiments, step (B) comprises treatment of the compound of Formula (I) from step (i) with LiOH followed by NaOH. In some other embodiments, step (B) comprises treatment of the compound of Formula (I) from step (i) with NaOH.

In some embodiments, step (B) is carried out in a solvent system comprising tetrahydrofuran, water and an alcohol selected from methanol and ethanol. In some embodiments, step (B) is carried out in a solvent system comprising tetrahydrofuran, water and ethanol.

In one aspect, the process for the preparation of Compound 2 further comprises forming crystals of Compound 2 with methyl tert-butyl ether. The crystal formation may occur by a crystallization, solid-to-solid transformation or crystalline inter-conversion.

In some embodiments, $R^1$ is —CH$_3$ or —CH$_2$CH$_3$. In a specific embodiment, $R^1$ is —CH$_2$CH$_3$.

In some embodiments, the base in step (A) is a cesium base, potassium base or sodium base. In some embodiments, the base is a cesium base. In a specific embodiment, the base is cesium carbonate.

In some embodiments, X' is selected from Cl, Br, I, —OSO$_2$CF$_3$, —OSO$_2$(4-methylphenyl), —OSO$_2$(phenyl) and —OSO$_2$CH$_3$. In specific embodiments, X' is Cl.

In one aspect, the compound of Formula (III) is prepared by:
reacting a compound of formula (IV):

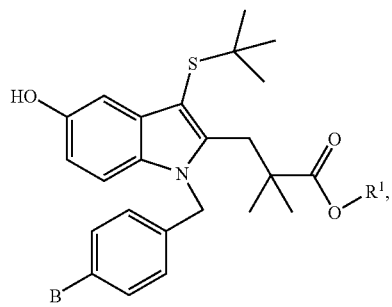

Formula (IV)

wherein R$^1$ is C$_1$-C$_6$ alkyl and B is a boronic acid or boronate ester;
with a compound of Formula (V) in the presence of a first coupling catalyst;

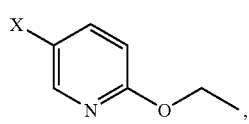

Formula (V)

wherein X is a leaving group,
to provide a compound of Formula (III)

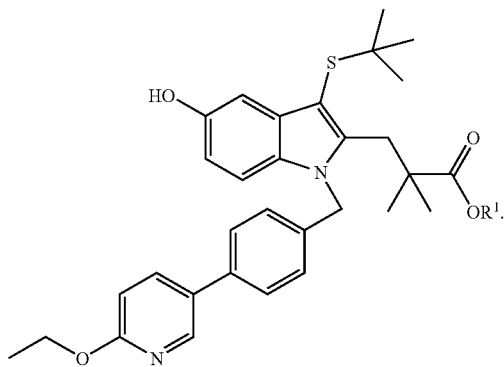

Formula (III)

In some embodiments, X is a halide or triflate. In some embodiments, X is selected from Cl, Br, I, —OSO$_2$CF$_3$, —OSO$_2$(4-methylphenyl), —OSO$_2$(phenyl) and —OSO$_2$CH$_3$. In some embodiments, X is selected from Cl, Br, I, and —OSO$_2$CF$_3$. In some embodiments, X is Br.

In some embodiments, B is selected from

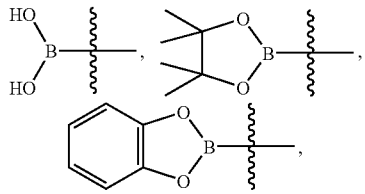

In some embodiments, B is

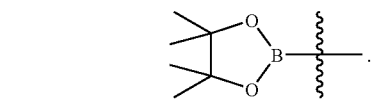 [SMILES: *B1OC(C)(C)C(C)(C)O1 ; "."]

In one aspect, the first coupling catalyst is a palladium catalyst. In some embodiments, the palladium catalyst is tetrakis(triphenylphosphine)palladium (Pd(PPh$_3$)$_4$). In some embodiments, the reaction for the synthesis of compounds of Formula (III) further comprises heating to a temperature of from about 60° C. to about 95° C.

In one aspect, the compound of Formula (IV) is prepared by reacting a compound of Formula (VI):

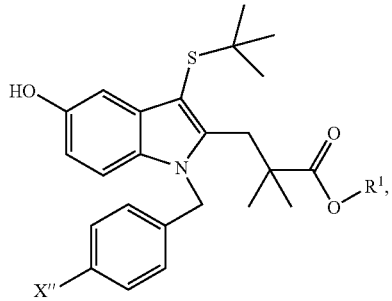

Formula (VI)

wherein X" is a leaving group; R$^1$ is C$_1$-C$_6$ alkyl;
with a borylation reagent, in the presence of a second coupling catalyst to provide a compound of Formula (IV):

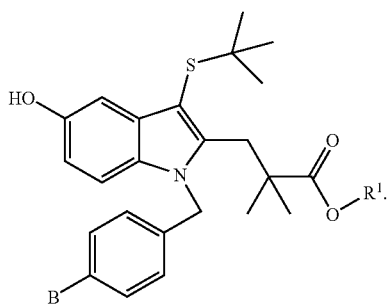

Formula (IV)

In some embodiments, X" is selected from Cl, Br, I, and —OSO$_2$CF$_3$.

In some embodiments, the borylation reagent is selected from pinacolborane, catecholborane, bis(neopentylglycolato)diboron, bis(pinacolato)diboron, bis(hexyleneglycolato) diboron, and bis(catecholato)diboron. In specific embodiments, the borylation reagent is bis(pinacolato)diboron.

In one aspect, the second coupling catalyst is a second palladium catalyst. In a specific embodiment, the second palladium catalyst is dichloro[1,1'-bis(diphenylphosphino)ferrocene]palladium (Pd(dppf)Cl$_2$). In some embodiments, the reaction further comprises heating to a temperature of from about 60° C. to about 95° C.

In one aspect, Formula (VI) is prepared by:

(C) reacting a compound of Formula (VII):

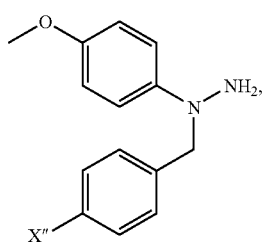

Formula (VII)

wherein X" is a halide;

with a compound of Formula (VIII):

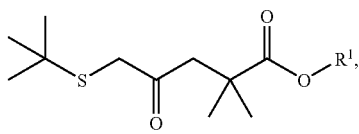

Formula (VIII)

wherein R$^1$ is C$_1$-C$_6$ alkyl; and (D) demethylating the product of step (i) to provide the corresponding phenol of Formula (VI)

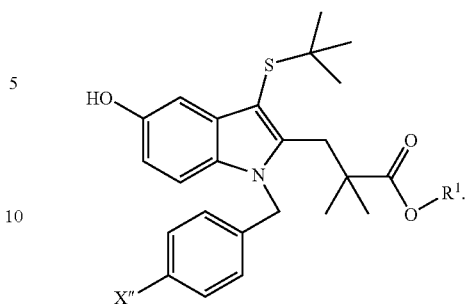

Formula (VI)

In some embodiments, step (C) is performed at a temperature of about from 110° C. to about 35° C.

In some embodiments, X" is selected from Br, Cl, and I. In a specific embodiment, R$^1$ is —CH$_2$CH$_3$.

In some embodiments, step (D) comprises reacting the product of step (i) with 2-methyl-2-propanethiol and AlCl$_3$ in a solvent.

In some embodiments, step (D) comprises reacting the product of step (i) with a Lewis Acid reagent in a solvent. In some embodiments, the Lewis Acid reagent is selected from aluminum trichloride (AlCl$_3$), Fe (III) chloride, boron trifluoride, niobium pentachloride, and lanthanide triflates (such as by way of example only, ytterbium (III) triflate). In a further embodiment, the solvent of step (D) is dichloromethane. In one embodiment, step (D) comprises reacting the product of step (i) with 2-methyl-2-propanethiol and AlCl$_3$ in a solvent.

The disclosed processes provide for the synthesis of Compound 1 and pharmaceutically acceptable salts thereof. The processes disclosed herein are particularly applicable to large scale chemical production of Compound 1 and pharmaceutically acceptable salts thereof. Also described herein are processes for the preparation of Compound 2, in good yield that have good solubility and good oral bioavailability.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

DETAILED DESCRIPTION OF THE INVENTION

Figure 1:
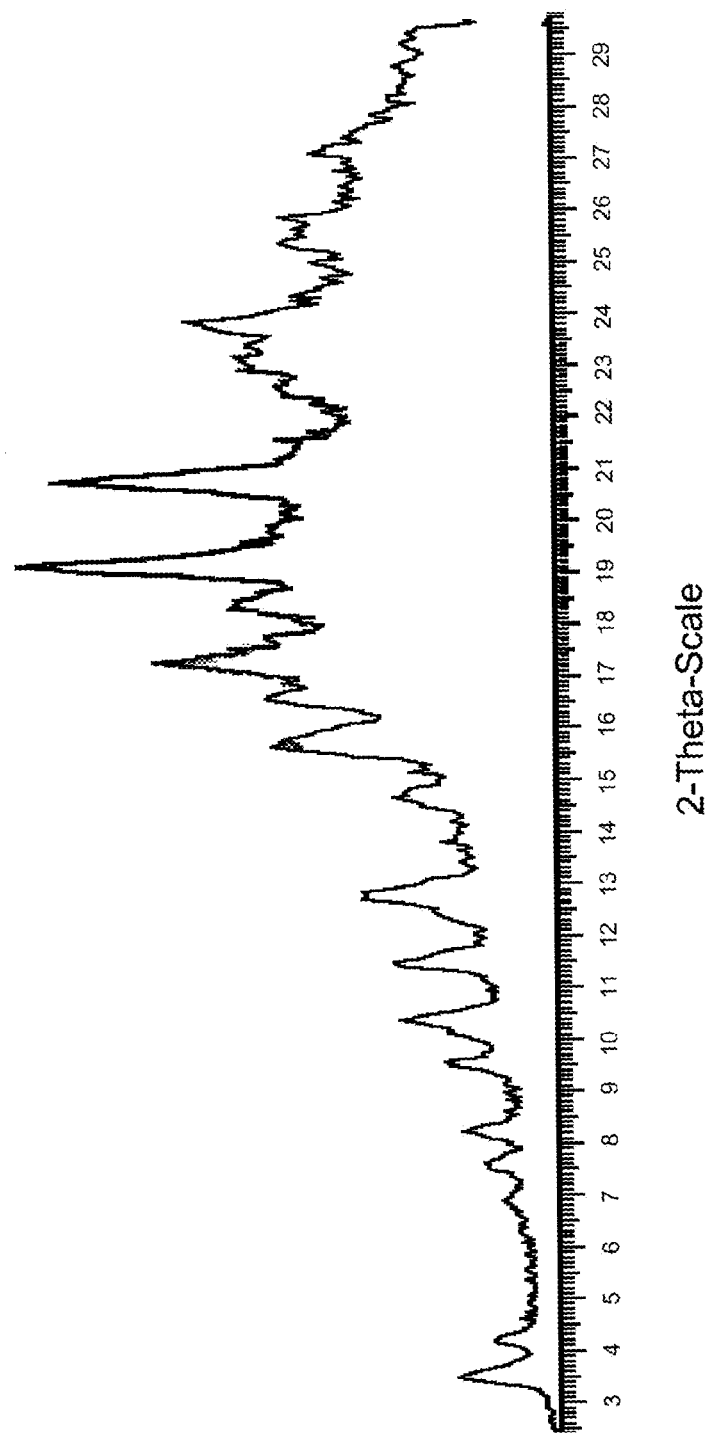
FIG. 1 illustrates an XRPD pattern of Polymorph Form C of Compound 2.

Leukotrienes (LTs) are a class of pro-inflammatory lipid mediators derived from arachidonic acid that play important roles in a number of biological processes. Arachidonic acid is converted to leukotriene $A_4$ ($LTA_4$) in a two-step process mediated by the enzyme 5-lipoxygenase (5-LO). The initial step is the oxygenation of arachidonic acid to form 5(S)-hydroperoxy-6,8,11,14(E,Z,Z,Z)-eicosatetraenoic acid (5-HPETE) followed by dehydration to produce the unstable epoxide $LTA_4$. $LTA_4$ is converted either to $LTB_4$ via $LTA_4$ hydrolase or to $LTC_4$ through conjugation with glutathione mediated by $LTC_4$ synthase. Amide bond cleavage converts $LTC_4$ to $LTD_4$ and then subsequently to $LTE_4$. The initial oxidation step is a process that requires the intimate involvement of both 5-LO and the membrane bound 5-lipoxygenase-activating protein (FLAP). Inhibition of either FLAP or 5-LO results in the inhibition of all leukotriene production. $LTB_4$ is the ligand for the G protein-coupled receptors (GPCRs) $BLT_1$ and $BLT_2$ and both receptors are involved in chemotaxis and cell stimulation in the inflammatory response. Bronchoconstriction, airway edema and hypersecretion of mucus are a result of the actions of the cysteinyl leukotrienes (cysLTs) $LTC_4$, $LTD_4$ and LTE4. Both $LTD_4$ and $LTE_4$ are ligands for the $cysLT_1$ receptor.

Leukotrienes are lipid mediators of inflammation that are involved in the pathogenesis of respiratory and cardiovascular diseases. Cellular activation by immune complexes and other inflammatory stimuli results in an increase of intracellular calcium and the translocation of cytosolic phospholipase $A_2$ ($cPLA_2$) and 5-lipoxygenase (5-LO) from the cytosol to the nuclear membrane. In the presence of the 5-lipoxygenase-activating protein (FLAP), arachidonic acid (AA) released from the nuclear membrane by $cPLA_2$ is delivered to 5-LO for conversion to 5-(S)-hydroperoxy-6,8,11,14-eicosatetraenoic acid (5-HpETE) and then leukotriene $A_4$ ($LTA_4$). Membrane interaction of 5-LO with FLAP is essential for leukotriene biosynthesis. FLAP is an integral membrane protein that belongs to the MAPEG (membrane-associated proteins in eicosanoid and glutathione metabolism) superfamily. In contrast to other MAPEGs, FLAP has not been shown to have enzymatic activity or to be functionally modulated by glutathione.

Leukotrienes are potent mediators of inflammation and bronchospasm. Leukotrienes are produced mainly by mast cells, eosinophils, monocytes/macrophages, and neutrophils in response to allergic or inflammatory stimuli. For cellular synthesis of leukotrienes, 5-lipoxygenase translocates from a nonmembrane compartment (cytosol or nucleosol) to membranes (nuclear or endoplasmic reticulum) and interacts with FLAP. FLAP transfers arachidonic acid, released from membrane phospholipids by phospholipases, to 5-LO. Then, a two step reaction occurs to convert arachidonic acid to $LTA_4$. $LTA_4$ can be exported from the cell for transcellular metabolism or converted to either $LTB_4$ or $LTC_4$. $LTC_4$ is exported from cells and converted to $LTD_4$ and then $LTE_4$ in blood. $LTB_4$ activates $BLT_1$ and $BLT_2$ receptors, and the cysteinyl leukotrienes activate $cysLT_1$ and $cysLT_2$ receptors (and possibly a $cysLT_3$ receptor).

While cysteinyl leukotriene-mediated human bronchoconstriction occurs by means of $cysLT_1$ receptor activation, both $cysLT_1$ and $cysLT_2$ receptors are present on cells involved in allergic inflammation, including mast cells, eosinophils, and monocytes.

A number of orally active drugs affect the leukotriene pathway. Montelukast is a leukotriene receptor antagonist. Pranlukast and zafirlukast are leukotriene receptor antagonists used in the treatment of asthma and allergic rhinitis. These drugs antagonize $cysLT_1$ receptors but not $cysLT_2$ or $LTB_4$ receptors. Clinical studies with these $cysLT_1$ receptor antagonists demonstrate that cysteinyl leukotrienes are important mediators of allergen-induced lung volume decline (early and late phases) as well as chronic asthma. One 5-lipoxygenase inhibitor, zileuton, exhibits clinical efficacy in chronic asthma although it is not effective in allergen-challenge studies.

Three FLAP inhibitors in clinical trials (MK-0591, MK-866, and BAYX-1005) show efficacy against allergen-induced early and late phases of lung-volume decline. MK-0591 also shows efficacy in chronic asthma studies.

Inhaled medications, such as beta-agonists and corticosteroids, can be effective and minimize systemic exposure, but patient compliance with such drug-delivery devices is less than optimal. Furthermore, among patients who use inhaled steroids, for example, growth may be retarded in children or cataracts may be induced in adults.

Compound 1 is a potent FLAP inhibitor that blocks an early step in the leukotriene pathway, i.e., 5-lipoxygenase activation. Compound 1 is pharmacologically active in vitro and after oral administration and well tolerated in nonclinical studies. Furthermore, because it inhibits the formation of $LTB_4$ and the cysteinyl leukotrienes, Compound 1 offers additional clinical benefits over leukotriene receptor antagonists such as montelukast.

The role of FLAP in the leukotriene synthesis pathway is significant because FLAP in concert with 5-lipoxygenase performs the first step in the pathway for the synthesis of leukotrienes. Therefore FLAP inhibition provides a target for compounds useful in the treatment of leukotriene-dependent or leukotriene mediated diseases or conditions, including, by way of example, vascular and inflammatory disorders, proliferative diseases, respiratory and non-cancerous disorders. FLAP inhibitors are useful in the treatment of leukotriene-dependent or leukotriene mediated diseases or conditions.

Described herein are compositions, pharmaceutical compositions, methods for treating, methods for formulating, methods for producing, methods for manufacturing, treatment strategies, pharmacokinetic strategies using Compound 1, or salts thereof.

"Compound 1" or "3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropanoic acid" refers to the compound with the following structure:

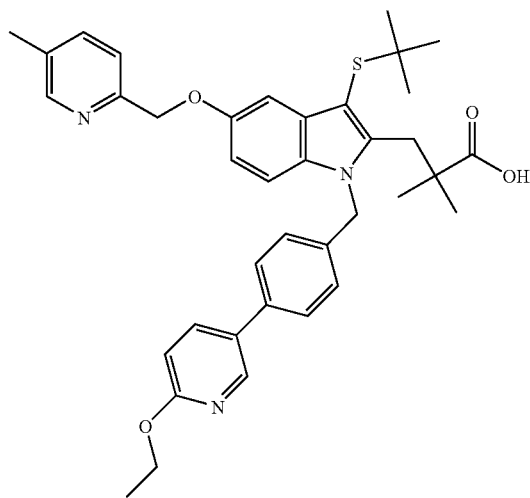 [SMILES: CCOc1ccc(-c2ccc(Cn3c(CC(C)(C)C(=O)O)c(SC(C)(C)C)c4cc(OCc5ccc(C)cn5)ccc43)cc2)cn1]

including pharmaceutically acceptable solvates (including hydrates), amorphous phases, partially crystalline and crystalline forms (including all polymorphs), prodrugs, metabolites and N-oxides thereof.

"Compound 2" or "sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate" refers to the sodium salt of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropanoic acid including pharmaceutically acceptables solvates (including hydrates), amorphous phases, partially crystalline and crystalline forms (including all polymorphs), prodrugs, metabolites and N-oxides thereof.

Sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate (also known as Compound 2) has the following structure:

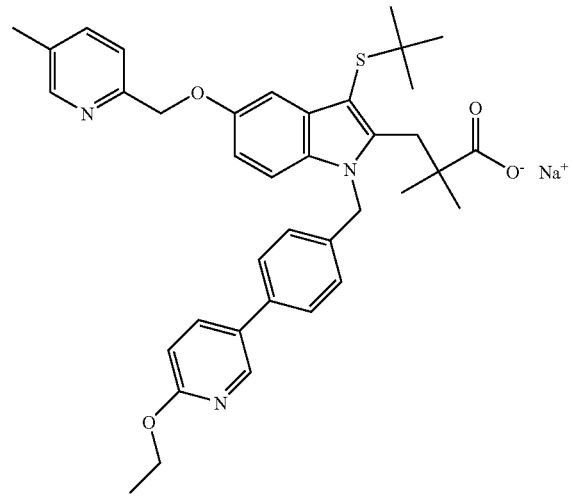 [SMILES: CCOc1ccc(-c2ccc(Cn3c(CC(C)(C)C(=O)[O-])c(SC(C)(C)C)c4cc(OCc5ccc(C)cn5)ccc43)cc2)cn1 ; [Na+]]

Compound 1 contains two basic sites (pyridinyl groups) and one acidic site (carboxylic acid). A wide variety of salts are formed. Salts of Compound 1 include:

A) salts formed when the acidic proton of the carboxylic acid of Compound 1 is replaced by a metal ion, such as for example, an alkali metal ion (e.g. lithium, sodium, potassium), an alkaline earth ion (e.g. magnesium, or calcium), or an aluminum ion, or is replaced by an ammonium cation ($NH_4^+$);

B) salts formed by reacting Compound 1 with a pharmaceutically acceptable organic base, which includes alkylamines, such as choline, ethanolamine, diethanolamine, triethanolamine, tromethamine, N-methylglucamine, dicyclohexylamine, tris(hydroxymethyl)methylamine, and salts with amino acids such as arginine, lysine, and the like;

C) salts formed by reacting Compound 1 with a pharmaceutically acceptable acid, which provides acid addition salts. Pharmaceutically acceptable acids include hydrochloric acid, hydrobromic acid, sulfuric acid, nitric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is Compound 1. In some embodiments, an API is Compound 2.

The term "pharmaceutically acceptable salt" in reference to Compound 1 refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of crystal formation (whether by a crystallization, solid-to-solid transformation or crystalline inter-conversion) with pharmaceutically acceptable solvents such as water, ethanol, methyl tert-butyl ether, isopropanol, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound 1, or salts thereof, are conveniently prepared or formed during the processes described herein. In addition, Compound 1, or salts thereof, exist in unsolvated form.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of Compound 1, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

Forms and Phases

Polymorphism, the ability of a substance to exist in two or more crystalline phases enables a different arrangement and/or conformation of molecules in the crystal lattice. This arrangement can significantly affect the physiochemical, formulation and processing parameters as well as the shelf life or stability of the substance and excipients. Generally, polymorphs also provide and improved solubility and give improved dissolution rates. Thermodynamic properties such as heat capacity, free energy and chemical potential, vapor pressure, solubility, and thermodynamic activity as well as kinetic properties such as dissolution rates and stability differ among polymorphs. Provided herein are compositions comprising polymorphs of Compound 2.

Provided herein is an active pharmaceutical ingredient (API), Compound 1, or pharmaceutically acceptable salt thereof, with a purity of greater than 80%, greater than 85%, greater than 90%, greater than 95%, greater than 96%, greater than 97%, greater than 98%, greater than 98%, or greater than 99%. In specific embodiments, provided herein is an active pharmaceutical ingredient (API), Compound 2, with a purity of greater than 80%, greater than 85%, greater than 90%, greater than 95%, greater than 96%, greater than 97%, greater than 98%, or greater than 99%.

Various forms of Compound 1 and pharmaceutically acceptable salts thereof are provided herein. In certain embodiments, any of the forms described herein is utilized in the preparation of a pharmaceutical composition. In certain embodiments, forms of Compound 1, including pharmaceutically acceptable salts thereof, and pharmaceutically acceptable solvates disclosed herein include but are not limited to, an amorphous form, partially crystalline forms, crystalline forms, milled forms, and nano-particulate forms. Various crystalline forms are known as polymorphs. Polymorphs include the different crystal packing arrangements of the same elemental composition of a compound. In certain embodiments, polymorphs usually have different X-ray diffraction patterns, infrared spectra, melting points, density, hardness, crystal shape, optical and electrical properties, stability, and/or solubility. Various factors such as the crystal formation solvent, rate of crystal formation (whether by a crystallization, solid-to-solid transformation or crystalline inter-conversion), and/or storage temperature cause a particular polymorph to be prepared.

In some embodiments, Compound 2 is precipitated from methyl-t-butyl-ether.

In some embodiments, Compound 2 undergoes a crystal formation from methyl-t-butyl-ether.

In some embodiments, Compound 2 undergoes a crystal formation from acetonitrile.

In some embodiments, Compound 2 undergoes a crystal formation from isopropanol.

In some embodiments, Compound 2 undergoes a crystal formation from dimethylsulfoxide.

In some embodiments, Compound 2 undergoes a crystal formation from methyl-t-butyl-ether/water.

In some embodiments, Compound 2 undergoes a crystal formation and is solvated. In specific embodiments, the solvate comprises water, MTBE or a combination thereof.

In some embodiments, Compound 2 is desolvated.

In some embodiments, Compound 2 is crystalline.

Presented herein are polymorphs of Compound 2. In one aspect, described herein are polymorphs of Compound 2, wherein the polymorph is amorphous or crystalline. In one embodiment, the polymorph of Compound 2 is amorphous. In another embodiment, the polymorph of Compound 2 is crystalline form. In another embodiment, the polymorph of Compound 2 is crystalline form and is solvated. In another embodiment, the polymorph of Compound 2 is crystalline form and is desolvated.

Amorphous Phase A

Figure 3:
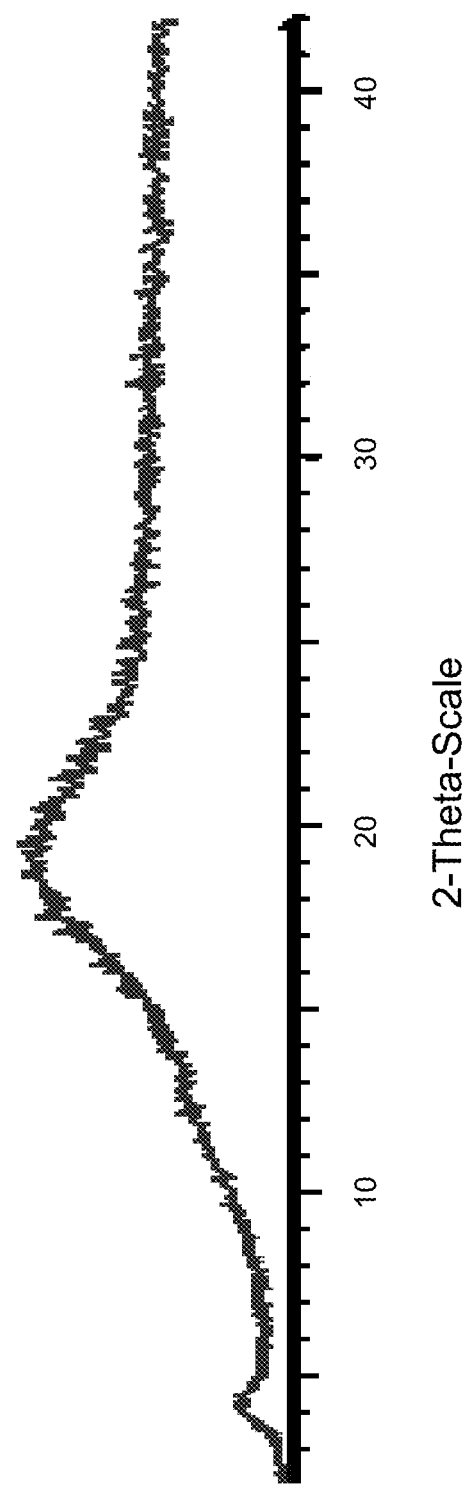
FIG. 3 illustrates an XRPD pattern of Amorphous Phase A of Compound 2.

In some embodiments, Compound 2 is Amorphous Phase A. FIG. 3 illustrates the XRPD pattern of amorphous Compound 2. In certain embodiments, Amorphous Phase A of Compound 2 has at least one property selected from:

(1a) an XRPD pattern showing a lack of crystallinity;
(2a) at least one endotherm and at least one exotherm observed by differential scanning calorimetry (DSC);
(3a) a glass transition temperature of about 127° C.;
(4a) a melting point at about 155° C. followed by a re-crystallisation event at about 200° C. followed by a second melting point at about 288° C. to about 295° C.;
(5a) a phase change to a crystalline form when heated above about 200° C., wherein the crystalline form that is formed above about 200° C. is characterized by an XRPD pattern substantially similar to any one of the XRPD patterns set forth in FIG. 9;
(6a) a DSC or a TGA substantially similar to the ones set forth in FIG. 12;
(7a) hygroscopicity; and/or
(8a) chemical stability (at 5° C., 25° C./60% RH, and/or 40° C./75% RH for at least one month).

In some embodiments, Amorphous Phase A of Compound 2 has at least two properties selected from (1a) through (6a). In some embodiments, Amorphous Phase A of Compound 2 has at least three properties selected from (1a) through (6a). In some embodiments, Amorphous Phase A of Compound 2 has at least four properties selected from (1a) through (6a).

In some embodiments, Amorphous Phase A of Compound 2 is defined as having (1a) an XRPD pattern showing a lack of crystallinity.

In some embodiments, Amorphous Phase A of Compound 2 is defined as having (2a) at least one endotherm and at least one exotherm observed by differential scanning calorimetry (DSC).

In some embodiments, Amorphous Phase A of Compound 2 is defined as having (3a) a glass transition temperature of about 127° C.

In some embodiments, Amorphous Phase A of Compound 2 is defined as having (4a) a melting point at about 155° C. followed by a re-crystallisation event at about 200° C. followed by a second melting point at about 288° C. to about 295° C.

Figure 9:
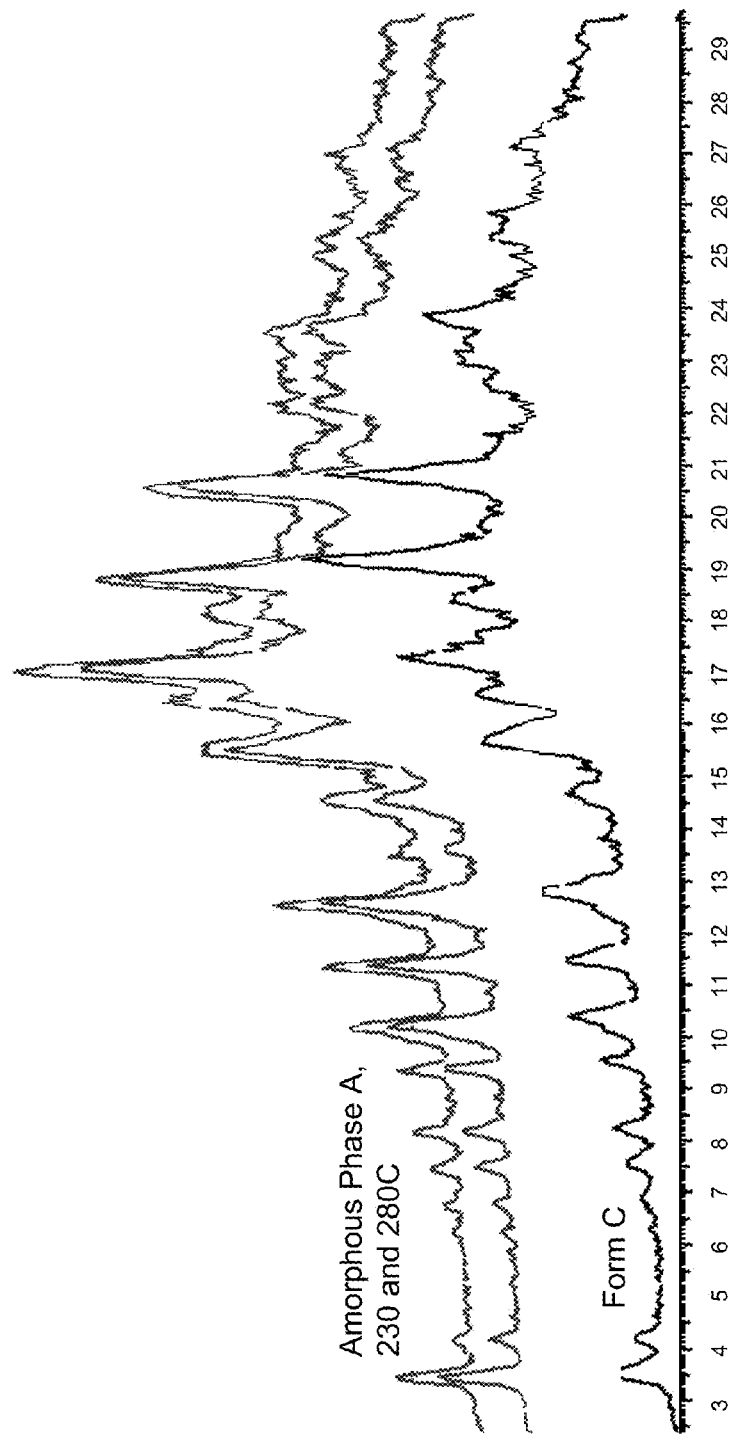
FIG. 9 illustrates a comparison of the XRPD patterns of Amorphous Phase A of Compound 2 at 230° C. and 280° C. with the XRPD pattern of Polymorph Form C.

In some embodiments, Amorphous Phase A of Compound 2 is defined as having (5a) a phase change to a crystalline form when heated above about 200° C., wherein the crystalline form that is formed above about 200° C. is characterized by an XRPD pattern substantially similar to any one of the XRPD patterns set forth in FIG. 9.

Figure 12:
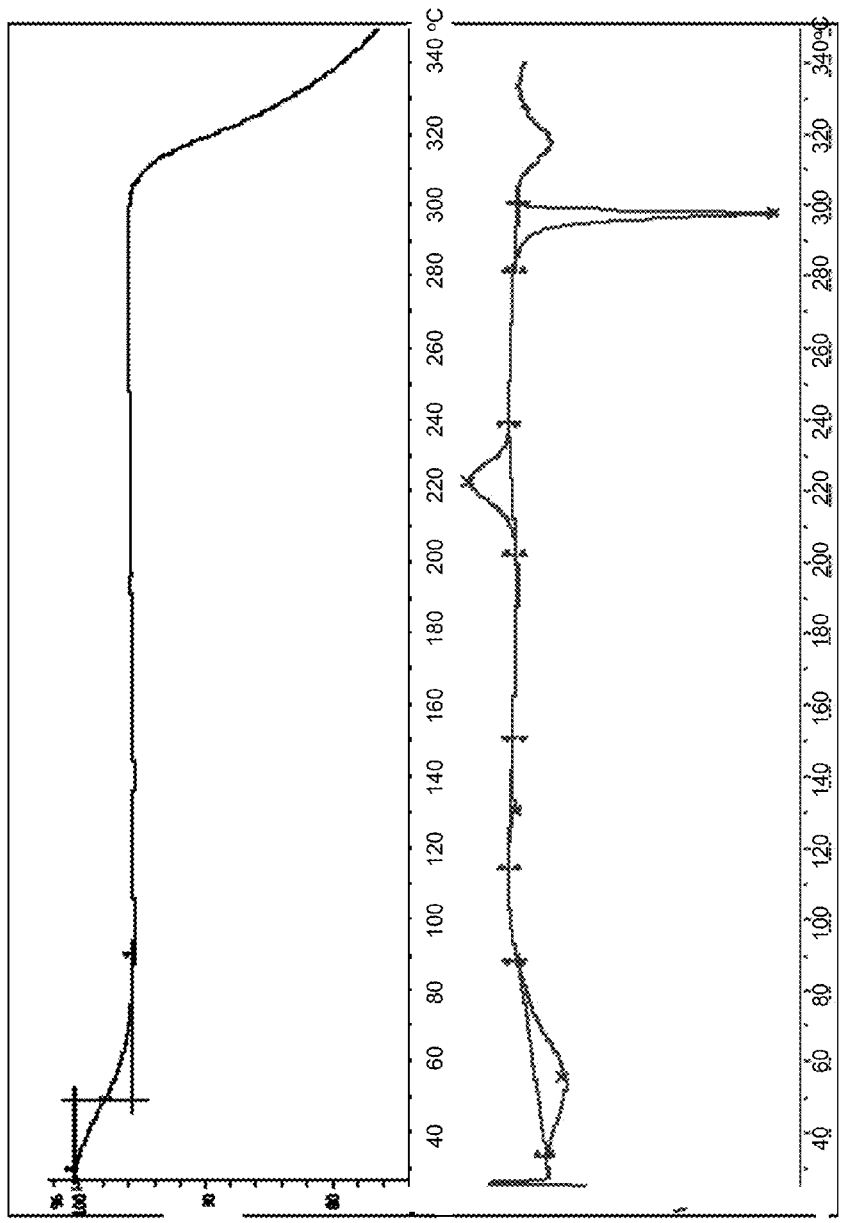
FIG. 12 illustrates a DSC (bottom) and TGA (top) trace for Amorphous Phase A of Compound 2.

In some embodiments, Amorphous Phase A of Compound 2 is defined as having (6a) a DSC or a TGA substantially similar to the ones set forth in FIG. 12.

In some embodiments, Amorphous Phase A of Compound 2 is defined as having (7a) hygroscopicity.

In some embodiments, Amorphous Phase A of Compound 2 is defined as having (8a) chemical stability.

Polymorph Form B

In one aspect, provided herein is a crystalline Form B of Compound 2 having at least one property selected from:
(1b) an XRPD pattern substantially similar to the one set forth in FIG. 2;
(2b) an XRPD pattern with peaks at about 6.6°2-Theta, at about 8.1°2-Theta, at about 19.7°2-Theta, at about 21.0°2-Theta, at about 21.9°2-Theta, and at about 22.1°2-Theta;
(3b) an X-ray powder diffraction (XRPD) pattern substantially similar to an XRPD pattern for crystals of Compound 2 obtained from methyl tert-butyl ether (MTBE) or isopropanol;
(4b) at least one endotherm and at least one exotherm observed by differential scanning calorimetry (DSC);
(5b) a phase change to a second crystalline form when heated above about 180° C., wherein the second crystalline form that is formed above about 180° C. is characterized by an XRPD pattern substantially similar to any one of the XRPD patterns set forth in FIG. 11;
(6b) hygroscopicity; and/or
(7b) loss of crystallinity after a full sorption/desorption cycle of a GVS experiment.

In some embodiments, provided herein is a crystalline Form B of Compound 2 having at least two properties selected from (1b) through (7b). In some embodiments, provided herein is a crystalline Form B of Compound 2 having at least three properties selected from (1b) through (7b). In some embodiments, provided herein is a crystalline Form B of Compound 2 having at least four properties selected from (1b) through (7b).

Figure 2:
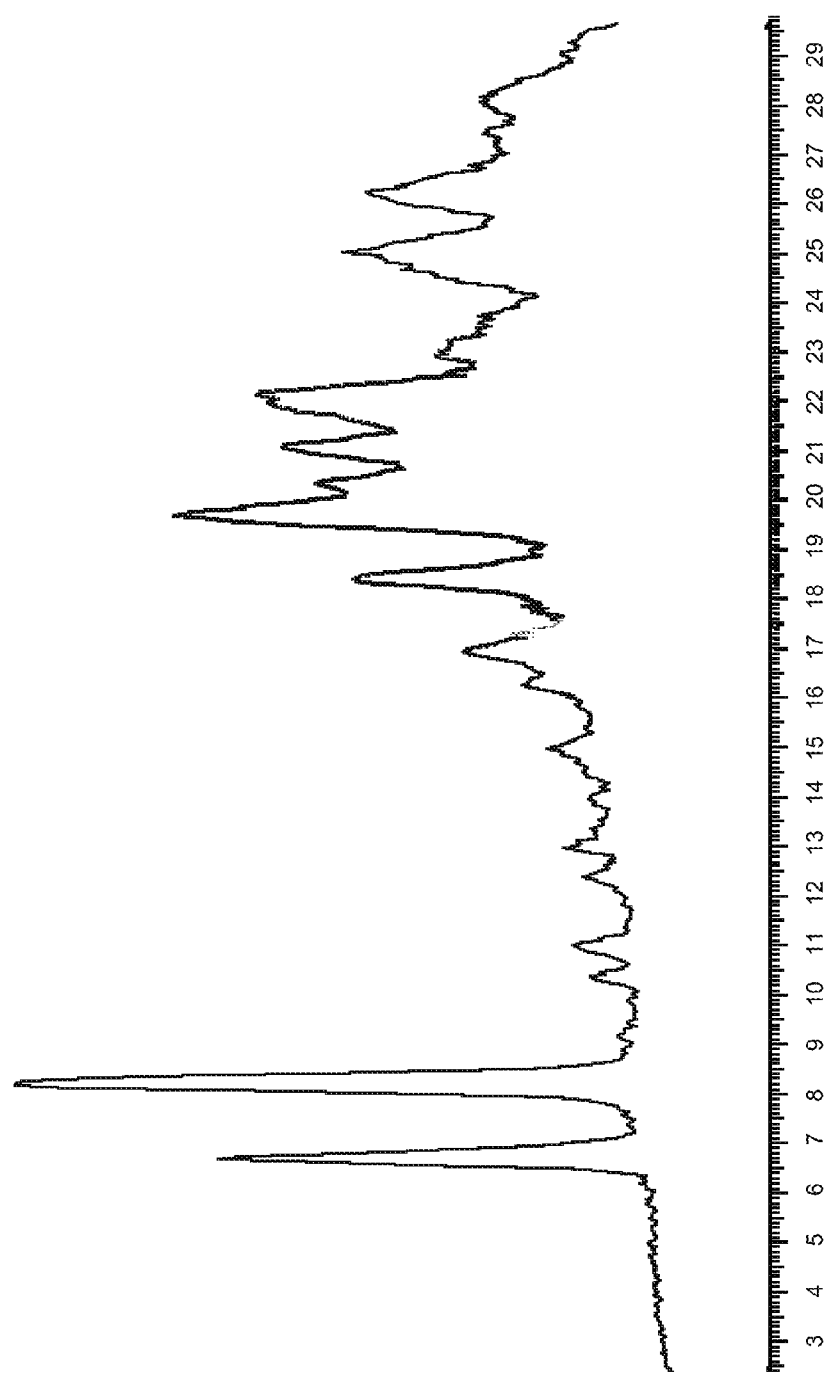
FIG. 2 illustrates an XRPD pattern of Polymorph Form B of Compound 2.

In some embodiments, provided herein is a crystalline Form B of Compound 2 having (1b) an XRPD pattern substantially similar to the one set forth in FIG. 2.

In some embodiments, provided herein is a crystalline Form B of Compound 2 having (2b) an XRPD pattern with peaks at about 6.6°2-Theta, at about 8.1°2-Theta, at about 19.7°2-Theta, at about 21.0°2-Theta, at about 21.9°2-Theta, and at about 22.1°2-Theta.

In some embodiments, provided herein is a crystalline Form B of Compound 2 having (3b) an X-ray powder diffraction (XRPD) pattern substantially similar to an XRPD pattern for crystals of Compound 2 obtained from methyl tert-butyl ether (MTBE) or isopropanol.

In some embodiments, provided herein is a crystalline Form B of Compound 2 having (4b) at least one endotherm and at least one exotherm observed by differential scanning calorimetry (DSC).

Figure 11:
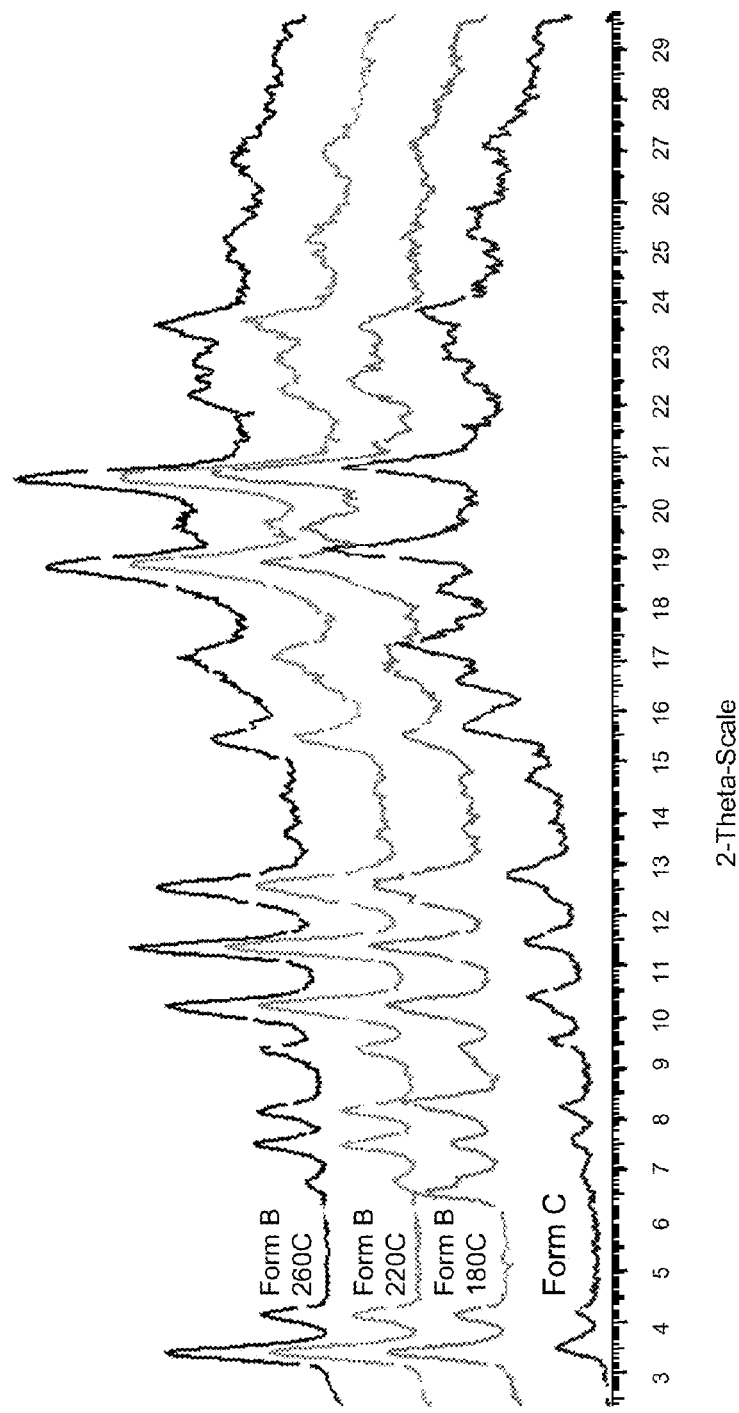
FIG. 11 illustrates a comparison of the XRPD patterns of Polymorph Form B of Compound 2 at 180° C., 220° C. and 260° C. with the XRPD pattern of Polymorph Form C.

In some embodiments, provided herein is a crystalline Form B of Compound 2 having (5b) a phase change to a second crystalline form when heated above about 180° C., wherein the second crystalline form that is formed above about 180° C. is characterized by an XRPD pattern substantially similar to any one of the XRPD patterns set forth in FIG. 11.

In some embodiments, provided herein is a crystalline Form B of Compound 2 having the property of being (6b) hygroscopic.

In some embodiments, provided herein is a crystalline Form B of Compound 2 having (7b) loss of crystallinity after a full sorption/desorption cycle of a GVS experiment.

In some embodiments, Form B is crystallized from MTBE or isopropanol. In some embodiments, Form B is crystallized from isopropanol. In some embodiments, Form B is obtained from MTBE solutions wherein a protic co-solvent (e.g. water or ethanol) is present during the crystal formation (whether by a crystallization, solid-to-solid transformation or crystalline inter-conversion). In some embodiments, Form B is obtained by crystal formation from a protic solvent such as, but not limited to, isopropanol. In some embodiments, Form B is converted to Form C by removal (dehydration) of protic solvents from the form B crystals.

Polymorph Form C

In some embodiments, crystalline Compound 2 is in polymorph Form C. Polymorph Form C of Compound 2 has at least one property selected from:
(1c) an X-ray powder diffraction (XRPD) pattern substantially similar to the one set forth in FIG. 1;
(2c) an XRPD pattern with peaks at about 17.2°2-Theta, at about 18.4°2-Theta, at about 19.1°2-Theta, at about 20.8°2-Theta, and at about 23.8°2-Theta;
(3c) a single melting point at about 290° C. to about 295° C.;
(4c) a DSC or a TGA substantially similar to the ones set forth in FIG. 15;

(5c) physical and chemical stability (at 5° C., 25° C./60% RH, and/or 40° C./75% RH for at least one month);
(6c) non-hygroscopicity;
(7c) IR spectrum substantially similar to the one set forth in FIG. 19; and/or
(8c) an X-ray powder diffraction (XRPD) pattern substantially similar to an XRPD pattern for crystals of Compound 2 obtained from methyl tert-butyl ether (MTBE) or acetonitrile.

In certain embodiments, polymorph Form C of Compound 2 has at least two properties selected from (1c) through (8c). In certain embodiments, polymorph Form C of Compound 2 has at least three properties selected from (1c) through (8c). In certain embodiments, polymorph Form C of Compound 2 has at least four properties selected from (1c) through (8c). In certain embodiments, polymorph Form C of Compound 2 has at least five properties selected from (1c) through (8c).

In certain embodiments, polymorph Form C of Compound 2 has (1c) an X-ray powder diffraction (XRPD) pattern substantially similar to the one set forth in FIG. 1.

In certain embodiments, polymorph Form C of Compound 2 has (2c) an XRPD pattern with peaks at about 17.2°2-Theta, at about 18.4°2-Theta, at about 19.1°2-Theta, at about 20.8°2-Theta, and at about 23.8°2-Theta.

In certain embodiments, polymorph Form C of Compound 2 has (3c) a single melting point at about 290° C. to about 295° C.

Figure 15:
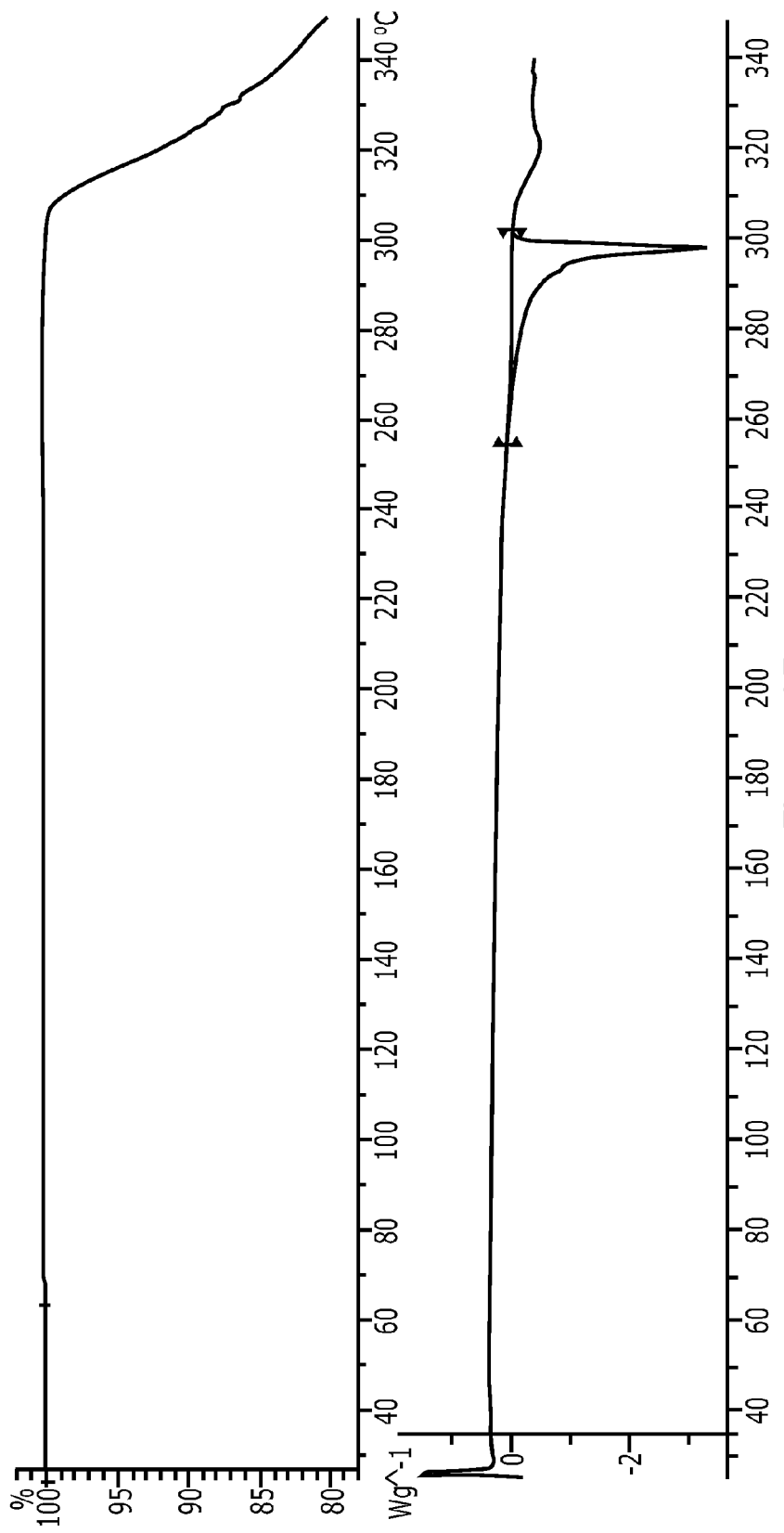
FIG. 15 illustrates a DSC (bottom) and TGA (top) trace for Polymorph Form C of Compound 2.

In certain embodiments, polymorph Form C of Compound 2 has (4c) a DSC or a TGA substantially similar to the ones set forth in FIG. 15.

In certain embodiments, polymorph Form C of Compound 2 has (5c) physical and chemical stability (at 5° C., 25° C./60% RH, and/or 40° C./75% RH for at least one month).

In certain embodiments, polymorph Form C of Compound 2 is (6c) non-hygroscopic.

Figure 19:
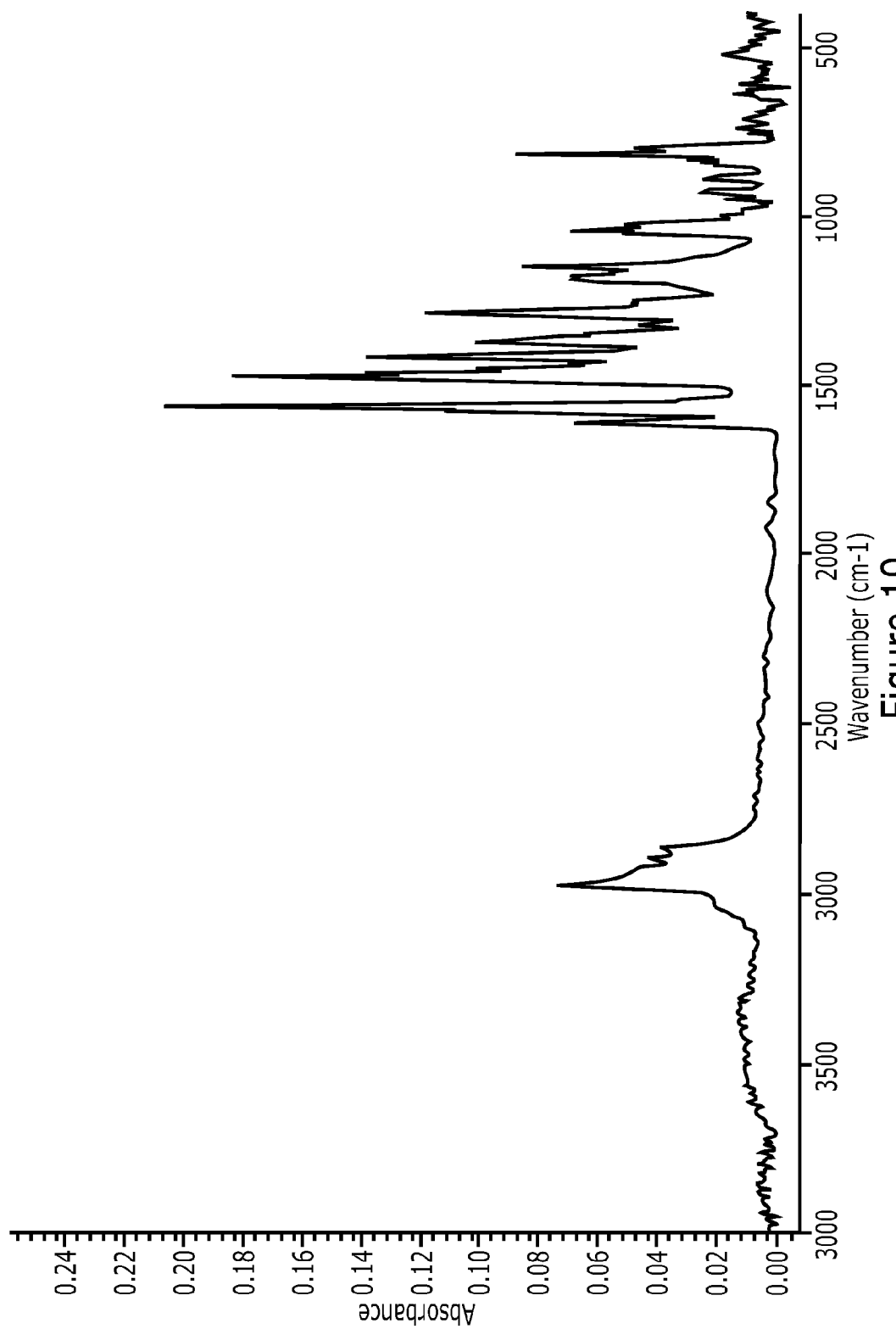
FIG. 19 illustrates an IR Spectrum for Polymorph Form C of Compound 2.

In certain embodiments, polymorph Form C of Compound 2 has (7c) IR spectrum substantially similar to the one set forth in FIG. 19.

In certain embodiments, polymorph Form C of Compound 2 has (8c) an X-ray powder diffraction (XRPD) pattern substantially similar to an XRPD pattern for crystals of Compound 2 obtained from methyl tert-butyl ether (MTBE) or acetonitrile.

In certain embodiments, polymorph Form C is formed from methyl tert-butyl ether (MTBE). In another aspect, polymorph Form C is formed from acetonitrile.

In certain embodiments, Form C is obtained by removal (dehydration) of protic solvents from the form B crystals.

As described herein, XRPD patterns are obtained in any manner, including by way of non-limiting example, (a) on a Siemens D5000 diffractometer; or (b) on a Bruker AXS C2 GADDS diffractometer. In specific embodiments, an XRPD pattern is obtained on a Siemens D5000 diffractometer using Cu Kα radiation (40 kV, 40 mA), θ-θ goniometer, divergence of V20 and receiving slits, a graphite secondary monochromator, and/or a scintillation counter. In another specific embodiment, an XRPD pattern is obtained on a Bruker AXS C2 GADDS diffractometer using Cu Kα radiation (40 kV, 40 mA), automated XYZ stage, laser video microscope for auto-sample positioning, a HiStar 2-dimensional area detector, a Göbel multilayer mirror coupled with a pinhole collimator of 0.3 mm, a beam divergence of approximately 4 mm, a θ-θ continuous scan mode, a sample detector distance of 20 cm, an effective 2θ range of 3.2°-29.7° and/or a sample exposure to the X-ray beam for about 120 seconds.

As described herein, melting points can be determined in any manner including, by way of non-limiting example, with hot stage microscopy (HSM) or differential scanning calorimetry (DSC). In specific embodiments, the hot stage microscopy is a Leica LM/DM polarized light microscope combined with a Mettler-Toledo MTFP82HT hot-stage, heating from ambient temperature at a rate of about 10° C./min to about 20° C./min. In certain embodiments, the DSC measurements are obtained in any manner including, by way of non-limiting example, (a) a TA Instrument Q1000; or (b) a Mettler DSC 823e. In specific embodiments, the TA Instrument Q1000 is calibrated for energy and temperature using certified indium, a sample of about 0.5 mg to about 3 mg, a pin-holed aluminum pan, a heat rate of about 10° C./min from 25° C. to 350° C., a nitrogen purge rate of about 50 mL/min, uses Thermal Advantage v4.6.6 as the instrument control software, and/or uses Universal Analysis v4.3A as the data analysis software. In other specific embodiments, the Mettler DSC 823e is calibrated for energy and temperature using certified indium, a sample of about 0.5 mg to about 3 mg, a pin-holed aluminum pan, a heat rate of about 10° C./min from 25° C. to 350° C., a nitrogen purge rate of about 50 mL/min, and/or uses STARe v9.01 as the instrument control and data analysis software.

Synthesis of FLAP Inhibitor

Described herein are processes for the preparation of Compound 1 and pharmaceutically acceptable salts thereof.

Synthesis of Compound 1 begins with the preparation of 2-chloromethyl-5-methyl-pyridine hydrochloride and 5-tert-butylsulfanyl-2,2-dimethyl-4-oxo-pentanoic acid alkyl ester (structure 2-4, scheme 2). Preparation of 2-chloromethyl-5-methyl-pyridine hydrochloride is outlined in Scheme 1.

Scheme 1. Synthesis of 2-Chloromethyl-5-methyl-pyridine hydrochloride

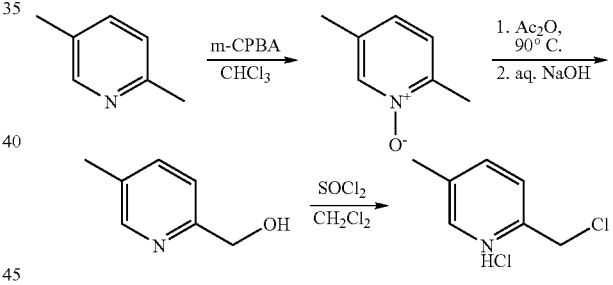

Oxidation of 2,5-dimethylpyridine provides 2,5-dimethylpyridine N-oxide. Treatment of 2,5-dimethylpyridine N-oxide with acetic anhydride followed by base, such as, sodium hydroxide, provides (5-methyl-pyridin-2-yl)-methanol. (5-Methyl-pyridin-2-yl)-methanol is then treated with thionyl chloride to provide 2-chloromethyl-5-methyl-pyridine hydrochloride.

5-tert-Butylsulfanyl-2,2-dimethyl-4-oxo-pentanoic acid alkyl ester is prepared as outlined in Scheme 2.

Scheme 2: Preparation of 5-tert-Butylsulfanyl-2,2-dimethyl-4-oxo-pentanoic acid alkyl ester

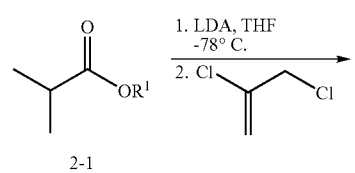

2-1

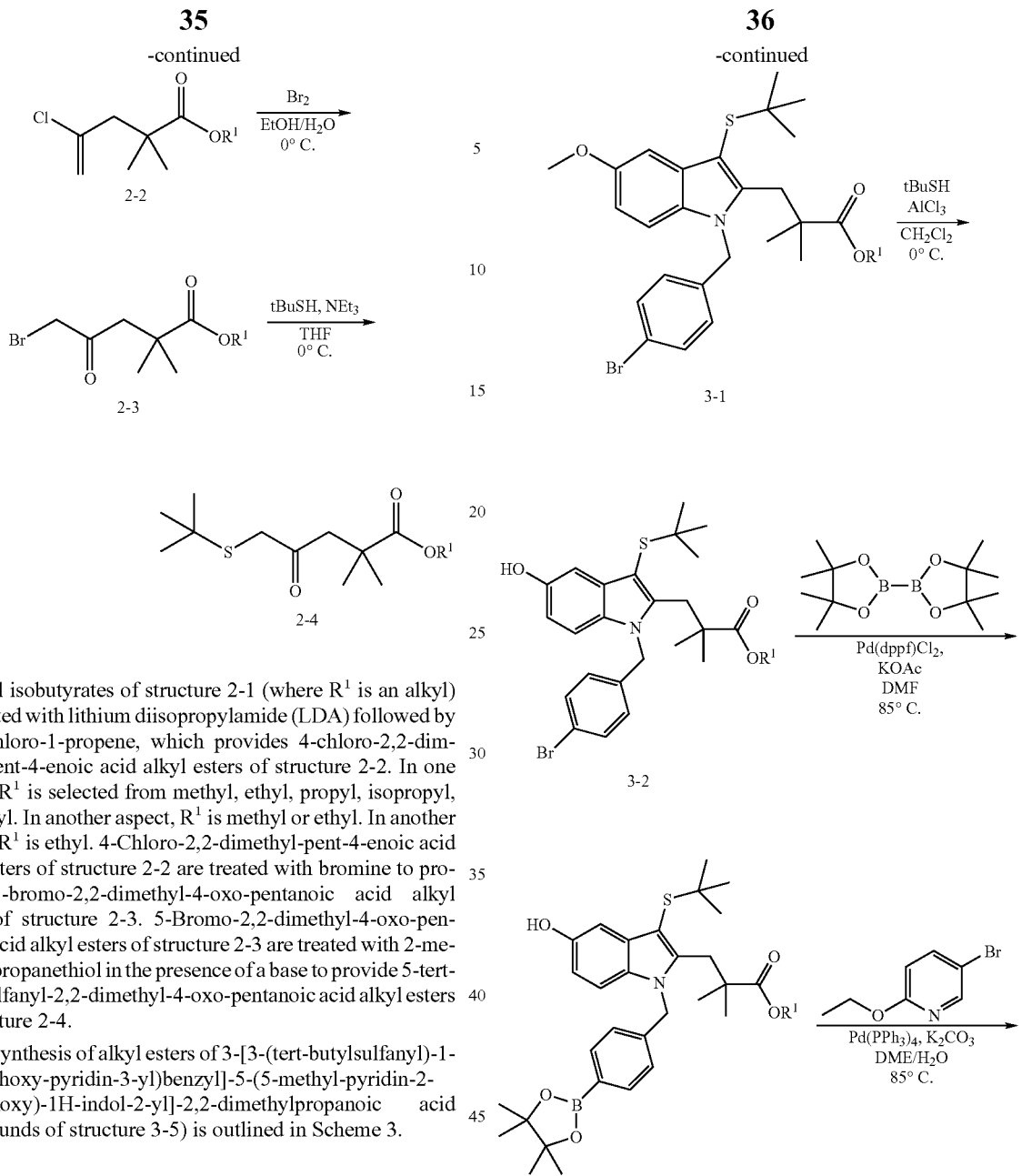

Alkyl isobutyrates of structure 2-1 (where R$^1$ is an alkyl) are treated with lithium diisopropylamide (LDA) followed by 2,3-dichloro-1-propene, which provides 4-chloro-2,2-dimethyl-pent-4-enoic acid alkyl esters of structure 2-2. In one aspect, R$^1$ is selected from methyl, ethyl, propyl, isopropyl, and butyl. In another aspect, R$^1$ is methyl or ethyl. In another aspect, R$^1$ is ethyl. 4-Chloro-2,2-dimethyl-pent-4-enoic acid alkyl esters of structure 2-2 are treated with bromine to provide 5-bromo-2,2-dimethyl-4-oxo-pentanoic acid alkyl esters of structure 2-3. 5-Bromo-2,2-dimethyl-4-oxo-pentanoic acid alkyl esters of structure 2-3 are treated with 2-methyl-2-propanethiol in the presence of a base to provide 5-tert-butylsulfanyl-2,2-dimethyl-4-oxo-pentanoic acid alkyl esters of structure 2-4.

The synthesis of alkyl esters of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropanoic acid (compounds of structure 3-5) is outlined in Scheme 3.

Scheme 3. Preparation of Alkyl Esters of Compound 1

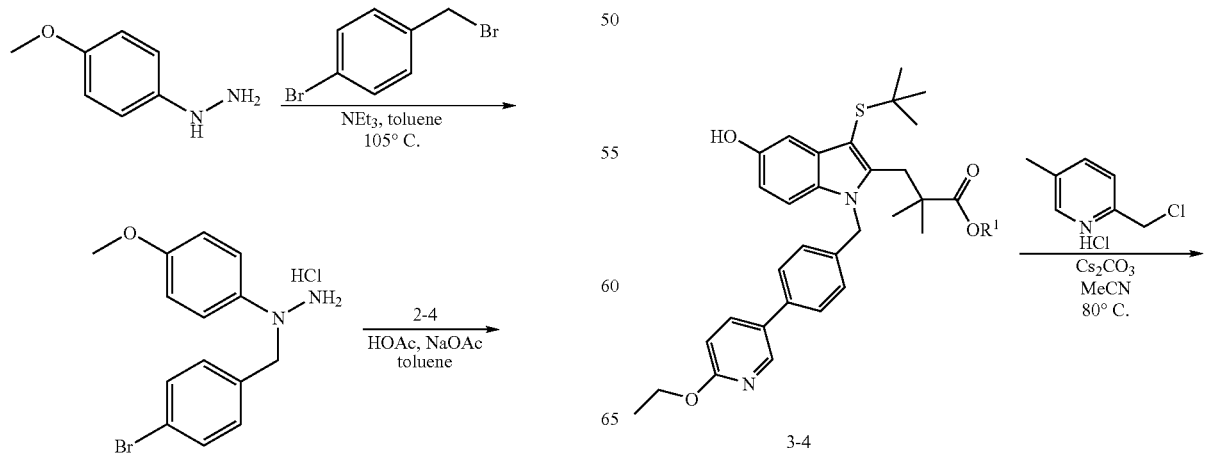

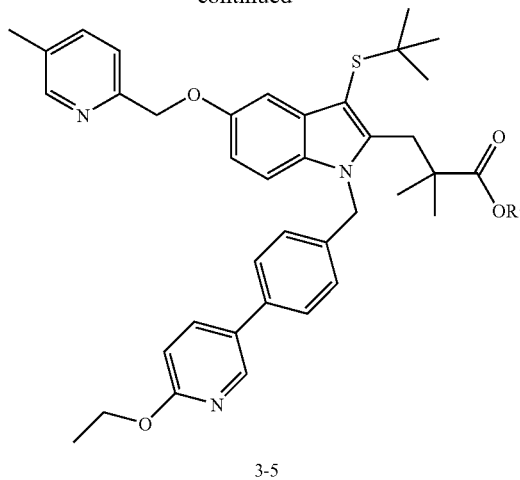

3-5

4-Methoxyphenylhydrazine hydrochloride is reacted with 4-bromobenzyl bromide in the presence of a base to provide N-(4-bromo-benzyl)-N-(4-methoxy-phenyl)-hydrazine hydrochloride. N-(4-bromo-benzyl)-N-(4-methoxy-phenyl)-hydrazine hydrochloride is reacted with 5-tert-butylsulfanyl-2,2-dimethyl-4-oxo-pentanoic acid alkyl esters of structure 2-4 (where $R^1$ is $C_1$-$C_6$ alkyl) to provide 3-[1-(4-bromo-benzyl)-3-tert-butylsulfanyl-5-methoxy-1H-indol-2-yl]-2,2-dimethyl-propionic acid alkyl esters of structure 3-1. In one aspect, $R^1$ is selected from methyl, ethyl, propyl, isopropyl, and butyl. In another aspect, $R^1$ is methyl or ethyl. In another aspect, $R^1$ is ethyl.

Demethylation of alkyl esters of structure 3-1 is carried out with 2-methyl-2-propanethiol and aluminum chloride, which provides alkyl esters of structure 3-2.

Conversion of the bromide to a boronate ester is achieved with bis(pinacolato)diboron, potassium acetate, and a palladium catalyst. In one aspect, the palladium catalyst is Pd(dppf)Cl$_2$. Alkyl esters of structure 3-3 are then coupled with 5-bromo-2-ethoxypyridine under Suzuki mediated coupling conditions to provide alkyl esters of structure 3-4. In one aspect, the Suzuki mediated coupling conditions include an inorganic base and a palladium catalyst. In one aspect, the Suzuki mediated coupling conditions include potassium carbonate and tetrakis(triphenylphosphine)palladium.

Bases used in palladium mediated reactions include, but are not limited to, cesium carbonate, triethylamine, diisopropylethylamine, 1,2,2,6,6-pentamethylpiperidine, tributylamine, sodium carbonate, potassium carbonate, sodium acetate, potassium acetate, and potassium phosphate.

Alkyl esters of structure 3-4 are then treated with a base followed by 2-chloro-5-methylpyridine hydrochloride to provide compounds of structure 3-5. In one aspect, the base is cesium carbonate.

In some embodiments, compounds of structure 3-5 are treated with a purifying means for reducing the amount of palladium to less than about 20 ppm. In one aspect, the purifying means for reducing the amount of palladium comprises thiol derivatized silica gel.

In one aspect, compounds of structure 3-5 are isolated before hydrolysis of the ester. In another aspect, compounds of structure 3-5 are not isolated before hydrolysis of the ester. In one aspect, isolating compounds of structure 3-5 comprises a means for reducing residual palladium. In one aspect, means for reducing residual palladium comprises activated carbon. In yet a further embodiment, the activated carbon is DARCO® KB-G, DARCO® KB-WJ. In other embodiments, means for reducing residual palladium comprises derivatized silica gel. In another embodiment, means for reducing residual palladium comprises thiol derivatized silica gel.

In one aspect, compounds of structure 3-5 are converted via a two-step procedure to Compound 2 as outlined in Scheme 4.

Scheme 4. Hydrolysis and Salt Formation

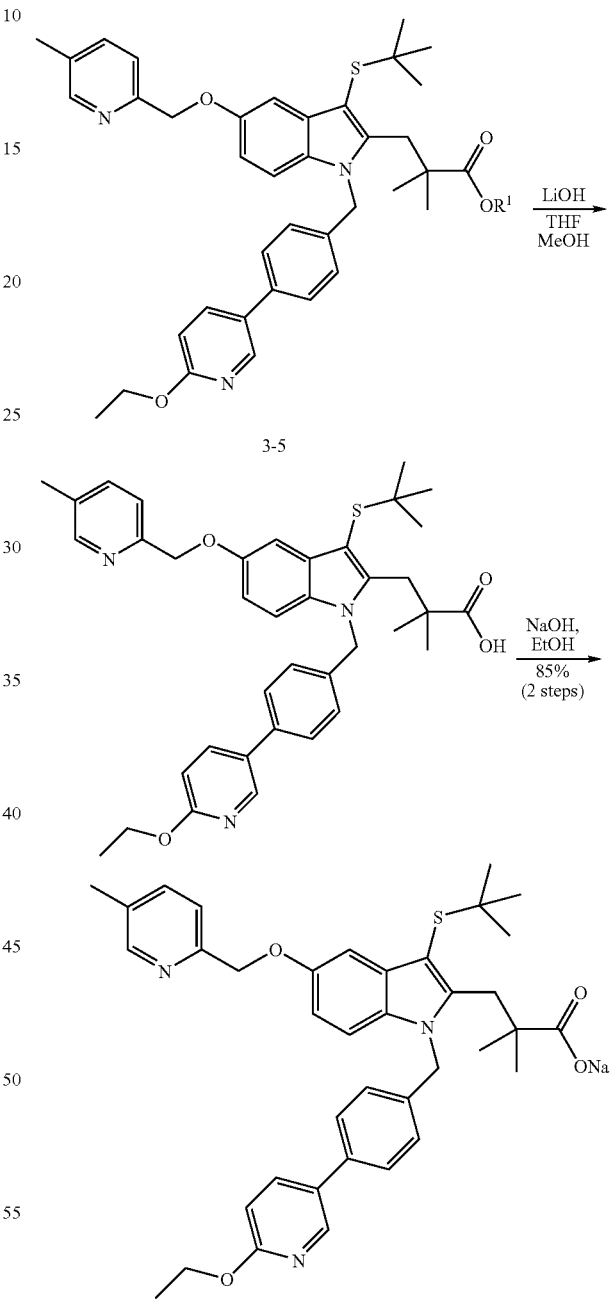

Hydrolysis of alkyl esters of structure 3-5 with LiOH in a suitable solvent provides, after pH adjustment to form the carboxylic acid, Compound 1. Compound 1 is then treated with sodium hydroxide in ethanol to furnish Compound 2.

In one aspect, Compound 2 is prepared from compounds of structure 3-5 in high yield, high purity by performing a one-step hydrolysis and salt forming reaction. In one aspect, alkyl esters of structure 3-5 are converted to Compound 2 in a high yielding one-step procedure as outlined in Scheme 5.

Scheme 5. One-Step Hydrolysis and Salt Formation

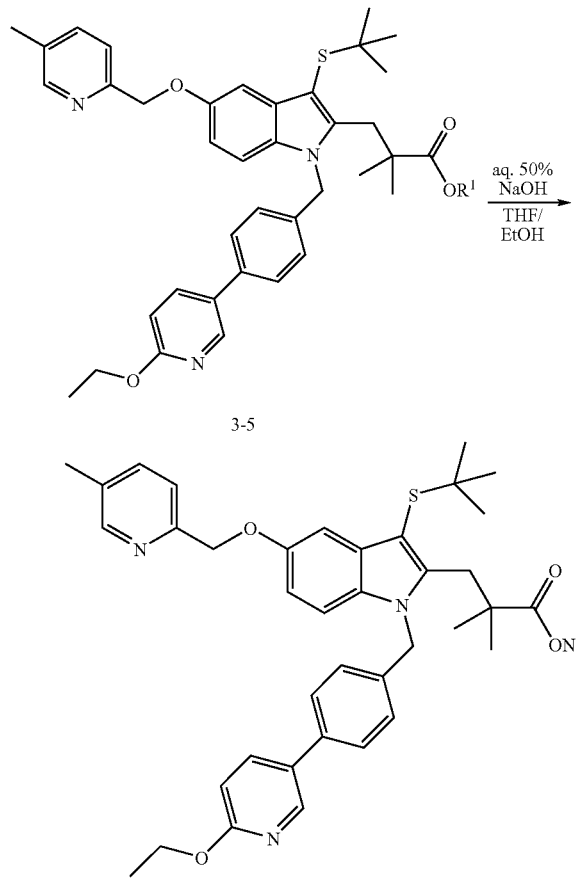

Treatment of alkyl esters of structure 3-5 in a suitable solvent with a 50% aqueous sodium hydroxide solution results in the formation of Compound 2. In one aspect, the reaction is heated.

In one aspect, Compound 2 is formed (whether by a crystallization, solid-to-solid transformation or crystalline interconversion) or precipitated from a Class 3 solvent. In one aspect, Compound 2 is formed or precipitated from methyl tert-butyl ether (MTBE). In one aspect, Compound 2 is crystallized from methyl tert-butyl ether (MTBE).

In one aspect, described herein is a crystalline form of Compound 2 solvated with a Class 3 solvent. In one aspect, the Class 3 solvent is selected from ethyl acetate, isopropyl acetate, methyl tert-butyl ether, heptane, isopropanol, and ethanol. In one aspect, the crystalline form of Compound 2 is solvated with MTBE. In one aspect, the crystalline form of Compound 2 is solvated with methyl tert-butyl ether and water.

In some embodiments, Compound 1 is treated with potassium hydroxide in a solvent to form potassium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate.

In some embodiments, Compound 1 is treated with lithium hydroxide in a solvent to form lithium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate.

In some embodiments, Compound 1 is treated with calcium hydroxide in a solvent to form the calcium salt of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropanoic acid.

In some embodiments, Compound 1 is treated with dicyclohexylamine in a solvent to form the corresponding salt.

In some embodiments, Compound 1 is treated with N-methyl-D-glucamine in a solvent to form the corresponding salt.

In some embodiments, Compound 1 is treated with tris (hydroxymethyl)methylamine in a solvent to form the corresponding salt.

In some embodiments, Compound 1 is treated with arginine in a solvent to form the corresponding salt.

In some embodiments, Compound 1 is treated with lysine in a solvent to form the corresponding salt.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

An "alkyl" group refers to an aliphatic hydrocarbon group. The alkyl moiety is branched, straight chain, or cyclic. The alkyl group may be designated as "$C_1$-$C_6$ alkyl". In one aspect, an alkyl is selected from methyl, ethyl, propyl, isopropyl, butyl, isobutyl, tert-butyl, pentyl, neopentyl, hexyl, ethenyl, propenyl, allyl, butenyl, cyclopropyl, cyclobutyl, cyclopentyl, cyclohexyl, and the like.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc) (ICH guidances, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "cardiovascular disease," as used herein refers to diseases affecting the heart or blood vessels or both, including but not limited to: arrhythmia; atherosclerosis and its sequelae; angina; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term "ocular disease" as used herein, refers to diseases which affect the eye or eyes and potentially the surrounding tissues as well. Ocular disease includes, but is not limited to, ocular inflammation, conjunctivitis, retinitis, scleritis, uveitis, allergic conjuctivitis, vernal conjunctivitis, pappillary conjunctivitis, and uveoretinitis.

The term "pain" as used herein, refers to acute or chronic pain which may be central or peripheral pain. Pain includes, but is not limited to nociceptive pain, neuropathic pain, inflammatory pain and non-inflammatory pain, for example, peripheral neuropathic pain.

The term "skin disease", as used herein, includes but is not limited to eczema, psoriasis, skin disease, neurodermatitis, pruritis, exfoliative dermatitis, allergic dermatitis, pemphigus and hypersensitivity reactions.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study The terms "co-administration" or the like, as used herein, are meant to encompass administration of the selected therapeutic agents to a single patient, and are intended to include treatment regimens in which the agents are administered by the same or different route of administration or at the same or different time.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "leukotriene-driven mediators," as used herein, refers to molecules able to be produced in a patient that results from excessive production of leukotriene stimulation of cells, such as, by way of example only, $LTB_4$, $LTC_4$, $LTE_4$, cysteinyl leuktorienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (I1-6), C-reactive protein (CRP), and serum amyloid A protein (SAA).

The term "leukotriene-related mediators," as used herein, refers to molecules able to be produced in a patient that result from excessive production of leukotriene stimulation of cells, such as, by way of example only, $LTB_4$, $LTC_4$, $LTE_4$, cysteinyl leuktorienes, monocyte inflammatory protein (MIP-1α), interleukin-8 (IL-8), interleukin-4 (IL-4), interleukin-13 (IL-13), monocyte chemoattractant protein (MCP-1), soluble intracellular adhesion molecule (sICAM; soluble ICAM), myeloperoxidase (MPO), eosinophil peroxidase (EPO), and general inflammation molecules such as interleukin-6 (I1-6), C-reactive protein (CRP), and serum amyloid A protein (SAA).

The term "leukotriene-dependent", as used herein, refers to conditions or disorders that would not occur, or would not occur to the same extent, in the absence of one or more leukotrienes.

The term "leukotriene-mediated", as used herein, refers to conditions or disorders that occur in the absence of leukotrienes but also occur in the presence of one or more leukotrienes.

The term "leukotriene-responsive patient," as used herein, refers to a patient who has been identified by either genotyping of FLAP haplotypes, or genotyping of one or more other genes in the leukotriene pathway and/or, by phenotyping of patients either by previous positive clinical response to another leukotriene modulator, including, by way of example only, zileuton, montelukast, pranlukast, zafirlukast, and/or by their profile of leukotriene-driven mediators that indicate excessive leukotriene stimulation of inflammatory cells, as likely to respond favorably to leukotriene modulator therapy.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized (biotransformed). The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases (UGT) catalyze the transfer of an activated glucuronic-acid molecule to aromatic alcohols, aliphatic alcohols, carboxylic acids, amines and free sulphydryl groups (e.g. conjugation reactions). Further information on metabolism is available in The Pharmacological Basis of Therapeutics, 9th Edition, McGraw-Hill (1996). In one embodiment, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "prodrug", as used herein, refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be Compound 1 which is administered as an ester ("the prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "subject" or "patient" encompasses mammals. In one aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

"Bioavailability" refers to the percentage of the weight of Compound 1, or a pharmaceutically acceptable salt and/or solvate thereof, dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which Compound 1, or a pharmaceutically acceptable salt and/or solvate thereof, is absorbed into the general circulation when the pharmaceutical composition is taken orally as compared to intravenous injection.

"Blood plasma concentration" refers to the concentration Compound 1, in the plasma component of blood of a mammal. It is understood that the plasma concentration of Compound 1 may vary significantly between subjects, due to variability with respect to metabolism and/or interactions with other therapeutic agents. In one aspect, the blood plasma concentration of Compound 1 varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of Compound 1 varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

A "measurable serum concentration" or "measurable plasma concentration" describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

"Treat" or "treatment" as used herein refers to any treatment of a disorder or disease, such as preventing the disorder or disease from occurring in a subject predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder either prophylactically and/or therapeutically. Thus, as used herein, the term "treat" is used synonymously with the term "prevent."

"Purifying means for reducing the amount of palladium" or "means for reducing residual palladium" (or a similarly worded phrase) refers to means used for reducing the amount of palladium in samples comprising active pharmaceutical ingredients in order to meet palladium specification guidelines. ("Guideline on the Specification Limits for Residues of Metal Catalysts" European Medicines Agency *Pre-authorisation Evaluation of Medicines for Human Use*, London, January 2007, Doc. Ref. CPMP/SWP/QWP/4446/00 corr.). In one aspect, reducing the amount of palladium includes, but is not limited to, treatment with solid trimercaptotriazine (TMT), polystyrene-bound TMT, mercapto-porous polystyrene-bound TMT, polystyrene-bound ethylenediamine, activated carbon, glass bead sponges, Smopex™, silica bound scavengers, thiol-derivatized silica gel, N-acetylcysteine, n-Bu₃P, crystallization, extraction, 1-cysteine, n-Bu₃P/lactic acid. Garrett et al., Adv. Synth. Catal. 2004, 346, 889-900). In one aspect, activated carbon includes but is not limited to DARCO® KB-G, DARCO® KB-WJ. In one aspect silica bound scavengers include but are not limited to

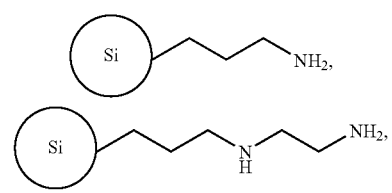

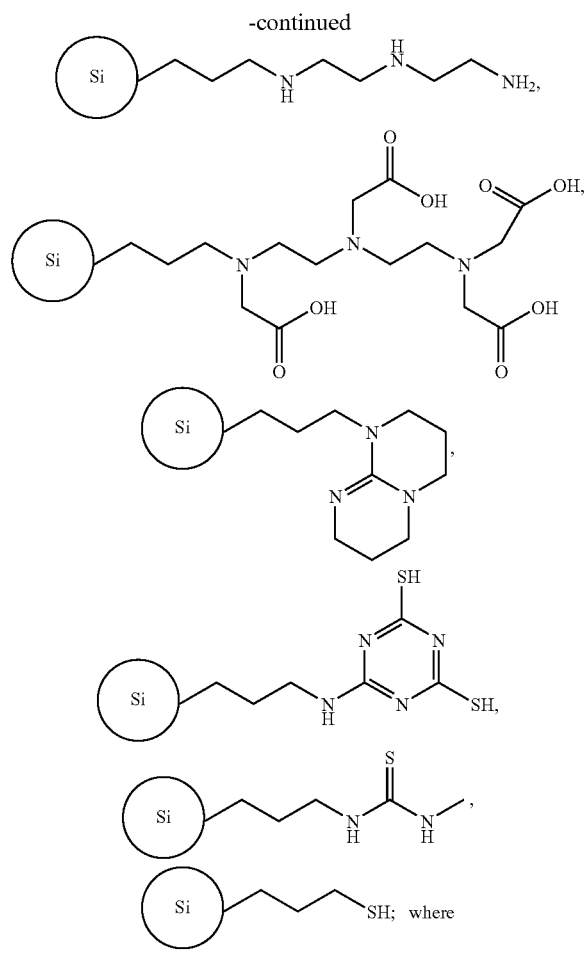

Ⓢⁱ denotes silica gel.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising salts of Compound 1 comprise an organic solvent(s). In some embodiments, compositions comprising salts of Compound 1 comprise a residual amount of an organic solvent(s). In some embodiments, compositions comprising salts of Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In one aspect, described are compositions comprising a polymorph of a salt of Compound 1. In one aspect, the polymorph is amorphous, semi-crystalline, or crystalline. In one aspect, the polymorph is crystalline. In another aspect, the polymorph is amorphous.

In one aspect, described are compositions comprising crystalline form of a salt of Compound 1. In one aspect, described are compositions comprising crystalline form of Compound 2.

In one aspect, described are compositions comprising amorphous form of a salt of Compound 1. In one aspect, described are compositions comprising amorphous form of Compound 2.

In one aspect, the compositions comprising a salt of Compound 1 include a detectable amount of an organic solvent. In some embodiments, the salt of Compound 1 is a sodium salt. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In yet a further embodiment, the Class 3 solvent is selected from ethyl acetate, isopropyl acetate, tert-butylmethylether, heptane, isopropanol, and ethanol. In other embodiments the organic solvent is selected from isopropanol, acetonitrile, ethanol, propylene glycol, and methylcellulose in water.

In one aspect, the salt of Compound 1 is a sodium salt, potassium salt, lithium salt, calcium salt, ammonium salt, protonated dicyclohexylamine salt, protonated N-methyl-D-glucamine salt, protonated tris(hydroxymethyl)methylamine salt, arginine salt, or lysine salt. In one aspect, the salt of Compound 1 is a sodium salt.

In other embodiments are compositions comprising Compound 2, wherein the composition comprises a detectable amount of solvent that is less than about 1%, wherein the solvent is selected from 1,2-dimethoxyethane, acetonitrile, ethyl acetate, tetrahydrofuran, methanol, ethanol, heptane, and 2-propanol. In a further embodiment are compositions comprising Compound 2, wherein the composition comprises a detectable amount of solvent which is less than about 5000 ppm. In yet a further embodiment are compositions comprising Compound 2, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

For oral administration, Compound 1, or a pharmaceutically acceptably salt thereof (e.g. Compound 2), are formulated by combining the active compound with pharmaceutically acceptable carriers or excipients. Such carriers enable Compound 1, or a pharmaceutically acceptably salt thereof (e.g. Compound 2) to be formulated as tablets, powders, pills, dragees, capsules, liquids, gels, syrups, elixirs, slurries, suspensions and the like, for oral ingestion by a patient to be treated.

The pharmaceutical compositions will include at least one pharmaceutically acceptable carrier, diluent or excipient and Compound 1 as an active ingredient in free-acid or free-base form, or in a pharmaceutically acceptable salt form.

The oral solid dosage formulations described herein include particles of Compound 1, or a pharmaceutically acceptable salt thereof (e.g. Compound 2) in crystalline form, amorphous form, semi-crystalline form, semi-amorphous form, or mixtures thereof. In one aspect, the oral solid dosage formulations described herein include crystalline particles of Compound 2. In one aspect, the oral solid dosage formulations described herein include crystalline particles of Compound 1 (free acid). In one aspect, the oral solid dosage formulations described herein include amorphous particles of Compound 1 (free acid).

The pharmaceutical compositions described herein include: (a) Compound 1, or a pharmaceutically acceptable salt thereof (e.g. Compound 2); and one or more of the following: (b) binders; (c) disintegrants; (d) fillers (diluents); (e) lubricants; (f) glidants (flow enhancers); (g) compression aids; (h) colors; (i) sweeteners; (j) preservatives; (k) suspensing/dispersing agents; (l) film formers/coatings; (m) flavors; (o) printing inks.

In one aspect, pharmaceutical compositions described herein include one or more of the following in addition to Compound 1, or a pharmaceutically acceptable salt thereof (e.g. Compound 2): (a) magnesium stearate; (b) lactose; (c) microcrystalline cellulose; (d) silicified microcrystalline cellulose; (e) mannitol; (f) starch (corn); (g) silicon dioxide; (h) titanium dioxide; (i) stearic acid; (j) sodium starch glycolate; (k) Gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, extended release formulations, inhaled powder, inhaled dispersion, IV formulations.

In some embodiments, formulations provide a therapeutically effective amount of Compound 1, or a pharmaceutically acceptable salt thereof (e.g. Compound 2), enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of Compound 1, or a pharmaceutically acceptable salt thereof (e.g. Compound 2) enabling once-a-day administration.

In certain embodiments, the effective amount of Compound 1, or a pharmaceutically acceptable salt thereof (e.g. Compound 2) is about 1 mg to about 5 g per dose, about 10 mg to about 2 g per dose, about 10 mg to about 1 g per dose, about 10 mg to about 1 g per dose, about 10 mg to about 0.5 g per dose, or about 10 mg to about 0.4 g per dose. In some embodiments, the effective amount of Compound 1, or a pharmaceutically acceptable salt thereof (e.g. Compound 2) is about 1 mg to about 5 g per day, about 10 mg to about 2 g per day, about 10 mg to about 1 g per day, about 10 mg to about 0.6 g per day, about 10 mg to about 0.5 g per day, or about 10 mg to about 0.4 g per day.

In one embodiment, the effective amount of Compound 1, or a pharmaceutically acceptable salt thereof (e.g. Compound 2) is about 5 mg per dose, about 10 mg per dose, about 50 mg per dose, about 150 mg per dose, about 300 mg per dose, about 450 mg per dose, about 600 mg per dose, or about 1000 mg per dose.

In one aspect, oral pharmaceutical solutions include about 10 mg/ml to about 50 mg/ml of Compound 1, or a pharmaceutically acceptable salt thereof (e.g. Compound 2). In one aspect, oral pharmaceutical solutions include about 10 mg/ml to about 40 mg/ml, about 10 mg/ml to about 30 mg/ml, or about 10 mg/ml to about 20 mg/ml of Compound 1, or a pharmaceutically acceptable salt thereof (e.g. Compound 2). In one aspect, oral pharmaceutical solutions include about 10 mg/ml of Compound 1, or a pharmaceutically acceptable salt thereof (e.g. Compound 2).

In one embodiment, pediatric oral pharmaceutical solutions include about 1 mg/ml to about 20 mg/ml of Compound 1, or a pharmaceutically acceptable salt thereof (e.g. Compound 2). In one embodiment, pediatric oral pharmaceutical solutions include about 1 mg/ml to about 15 mg/ml, or about 5 mg/ml to about 15 mg/ml of Compound 1, or a pharmaceutically acceptable salt thereof (e.g. Compound 2). In some embodiments, pediatric oral pharmaceutical solutions include about 10 mg/ml of Compound 1, or a pharmaceutically acceptable salt thereof (e.g. Compound 2).

In one aspect, immediate release tablets include about 5% w/w to about 50% w/w of Compound 1, or a pharmaceutically acceptable salt thereof (e.g. Compound 2). In some embodiments, immediate release tablets include about 5% w/w to about 40% w/w, or about 10% w/w to about 40% w/w of Compound 1, or a pharmaceutically acceptable salt thereof (e.g. Compound 2). In some embodiments, immediate release tablets include about 5% w/w, about 10% w/w, about 15% w/w, about 20% w/w, about 25% w/w, about 30% w/w, about 33% w/w, about 35% w/w, about 40% w/w of Compound 1, or a pharmaceutically acceptable salt thereof (e.g. Compound 2).

In one aspect, immediate release capsules include about 1.25% w/w to about 50% w/w of Compound 1, or a pharmaceutically acceptable salt thereof (e.g. Compound 2). In some embodiments, immediate release capsules include about 5% w/w to about 40% w/w, about 10% w/w to about 30% w/w, of Compound 1, or a pharmaceutically acceptable salt thereof (e.g. Compound 2). In some embodiments, immediate release capsules include about 5% w/w, about 10% w/w, about 15% w/w, about 20% w/w, about 25% w/w, or about 30% w/w of Compound 1, or a pharmaceutically acceptable salt thereof (e.g. Compound 2).

In one embodiment, Compound 1, or a pharmaceutically acceptable salt thereof (e.g. Compound 2) is formulated into an immediate release form that provides for once-a-day administration. Generally speaking, one will desire to administer an amount of Compound 1, or a pharmaceutically acceptable salt thereof (e.g. Compound 2) that is effective to achieve a plasma level commensurate with the concentrations found to be effective in vivo for a period of time effective to elicit a therapeutic effect.

Binders impart cohesive qualities. In one aspect, solid oral dosage forms include about 2% w/w to about 10% w/w of binder. In some embodiments, solid oral dosage forms include about 5% w/w of binder. In some embodiments, solid oral dosage forms include about 2% w/w to about 25% w/w of binder. In some embodiments, solid oral dosage forms include about 5% w/w to about 25% w/w of binder. In some embodiments, solid oral dosage forms include about 18% w/w of binder.

In one aspect, the binder is hypromellose (e.g., Methocel E5). In another aspect, the binder is povidone, or starch.

Carrier materials include any excipients in pharmaceutics and should be selected on the basis of compatibility with Compound 1, or a pharmaceutically acceptable salt thereof (e.g. Compound 2) and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

Dispersing agents, and/or viscosity modulating agents include materials that control the diffusion and homogeneity of a drug through liquid media or a granulation method or blend method. In some embodiments, these agents also facilitate the effectiveness of a coating or eroding matrix.

Diluents increase bulk of the composition to facilitate compression or create sufficient bulk for homogenous blend for capsule filling.

The term "disintegrate" includes both the dissolution and dispersion of the dosage form when contacted with gastrointestinal fluid. "Disintegration agents or disintegrants" facilitate the breakup or disintegration of a substance.

In one aspect, the disintegrant is croscarmellose sodium. In another aspect, the disintegrant is sodium starch glycolate or crospovidone.

In one aspect, solid oral dosage forms include up to 15% w/w of disintegrant. In some embodiments, solid oral dosage forms include about 0.5% w/w to about 10% w/w of disintegrant. In some embodiments, solid oral dosage forms include about 0.5% w/w to about 5% w/w of disintegrant.

Filling agents include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In one aspect, the filler is lactose (e.g. monohydrate). In another aspect, the filler is mannitol, or dicalcium phosphate. In another aspect, the filler is mannitol, microcrystalline cellulose, dicalcium phosphate or sorbitol.

Gastrointestinal fluid is the fluid of stomach secretions of a subject or the saliva of a subject after oral administration of a composition described herein, or the equivalent thereof. An "equivalent of stomach secretion" includes, e.g., an in vitro fluid having similar content and/or pH as stomach secretions such as a 1% sodium dodecyl sulfate solution or 0.1N HCl solution in water. In addition, simulated intestinal fluid (USP) is an aqueous phosphate buffer system at pH 6.8.

Lubricants and glidants are compounds that prevent, reduce or inhibit adhesion or friction of materials. In one aspect, solid oral dosage forms include about 0.25% w/w to about 2.5% w/w of lubricant. In another aspect solid oral dosage forms include about 0.5% w/w to about 1.5% w/w of lubricant.

In some embodiments, the solid dosage forms described herein are in the form of a tablet, (including an immediate release tablet, an extended release tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages. In some embodiments, the pharmaceutical formulation is administered in two, or three, or four tablets.

In some embodiments, solid dosage forms, e.g., tablets, effervescent tablets, and capsules, are prepared by mixing Compound 1, or a pharmaceutically acceptable salt thereof (e.g. Compound 2) with one or more pharmaceutical excipients to form a bulk blend composition. When referring to these bulk blend compositions as homogeneous, it is meant that the Compound 1, or a pharmaceutically acceptable salt thereof (e.g. Compound 2) particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein include the Compound 1, or a pharmaceutically acceptable salt thereof (e.g. Compound 2) compositions described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

Compound 1, or a pharmaceutically acceptable salt thereof (e.g. Compound 2) is rapidly absorbed in the upper gastrointestinal tract, and thus there is a strong correlation between the rate of dissolution and bioavailability. Thus, it is important to optimize the rate of dissolution in biological matrices in order to enhance in vivo absorption. In order to release the Compound 1, or a pharmaceutically acceptable salt thereof (e.g. Compound 2) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step.

In general, binder levels of 20-70% are used in powder-filled gelatin capsule formulations. Binder usage level in tablet formulations varies whether direct compression, wet granulation, roller compaction, or usage of other excipients such as fillers which itself acts as moderate binder.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 3% of the tablet weight. In other embodiments, the compressed tablets include one or more excipients.

In certain embodiments, provided herein are tablets with a hardness of about 5 to about 20 Kp, or about 5 to about 15 Kp or about 8-12 Kp. In further or alternative embodiments, provided herein are tablets with a friability of less than 1%.

In one embodiment, a capsule is prepared, e.g., by placing the bulk blend formulation described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating. In some embodiments, the therapeutic dose is split into multiple (e.g., two, three, or four) capsules. In some embodiments, the entire dose of the formulation is delivered in a capsule form.

In one aspect, Compound 1, or a pharmaceutically acceptable salt thereof (e.g. Compound 2) and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the Compound 1, or a pharmaceutically acceptable salt thereof (e.g. Compound 2) formulation into the gastrointestinal fluid.

In other embodiments a powder comprising the Compound 1, or a pharmaceutically acceptable salt thereof (e.g. Compound 2) formulations described herein are formulated to include one or more pharmaceutical excipients and flavors. Such a powder is prepared, for example, by mixing the Compound 1, or a pharmaceutically acceptable salt thereof (e.g. Compound 2) formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

Wet granulation is one of the oldest method of granule preparation. The individual steps in the wet granulation process of tablet preparation include milling and sieving of the ingredients, dry powder mixing, wet massing, granulation, drying and final grinding. In various embodiments, the composition is added to the other excipients of the pharmaceutical formulation after they have been wet granulated.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the formulation is dry granulated with other excipients in the pharmaceutical formulation. In other embodiments, the formulation is added to other excipients of the pharmaceutical formulation after they have been dry granulated.

In some embodiments, pharmaceutical formulations are provided comprising Compound 1, or a pharmaceutically acceptable salt thereof (e.g. Compound 2) and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of Compound 1, or a pharmaceutically acceptable salt thereof (e.g. Compound 2) at any point throughout the suspension (USP Chapter 905).

Liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including Compound 1, or a pharmaceutically acceptable salt thereof (e.g. Compound 2), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent.

In one embodiment, the aqueous suspensions and dispersions described herein remain in a homogenous state, as defined above by USP Chapter 905, for at least 4 hours. The homogeneity should be determined by a sampling method consistent with regard to determining homogeneity of the entire composition. In one embodiment, an aqueous suspension is re-suspended into a homogenous suspension by physical agitation lasting less than 1 minute. In another embodiment, an aqueous suspension is re-suspended into a homogenous suspension by physical agitation lasting less than 45 seconds. In yet another embodiment, an aqueous suspension is re-suspended into a homogenous suspension by physical agitation lasting less than 30 seconds. In still another embodiment, no agitation is necessary to maintain a homogeneous aqueous dispersion.

In one embodiment, the aqueous suspensions, solutions or dispersions described herein include Compound 1, or a pharmaceutically acceptable salt thereof (e.g. Compound 2) at a concentration of about 5 mg/ml to about 50 mg/ml of solution.

In some embodiments, the aqueous suspensions, solutions or dispersions described herein include Compound 1, or a pharmaceutically acceptable salt thereof (e.g. Compound 2) at a concentration of about 5 mg/ml to about 30 mg/ml of solution.

In some embodiments, the aqueous suspensions, solutions or dispersions described herein include Compound 1, or a pharmaceutically acceptable salt thereof (e.g. Compound 2) at a concentration of about 10 mg/ml of solution.

The aqueous dispersions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447, 4,596,795, 4,755,386, and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, in soft capsules, the active compounds are dissolved or suspended in suitable liquids, such as fatty oils, liquid paraffin, or liquid polyethylene glycols. In addition, in one embodiment, stabilizers are added. All formulations for oral administration should be in dosages suitable for such administration.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is aqueous.

In one embodiment, the aqueous suspension also contains one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, pharmaceutical compositions also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous suspension compositions are packaged in single-dose non-reclosable containers. Alternatively, multiple-dose reclosable containers are used, in which case it is typical to include a preservative in the composition.

Pharmacokinetic Analysis

In one embodiment, any standard pharmacokinetic protocol is used to determine blood plasma concentration profile in humans following administration of a formulation described herein (that include Compound 1, or a pharmaceutically acceptable salt thereof (e.g. Compound 2)), and thereby establish whether that formulation meets the pharmacokinetic criteria set out herein. For example, a randomized single-dose crossover study is performed using a group of healthy adult human subjects. The number of subjects is sufficient to provide adequate control of variation in a statistical analysis, and is typically about 10 or greater, although for certain purposes a smaller group suffices. Each subject receives administration at time zero a single dose of a formulation of Compound 1, or a pharmaceutically acceptable salt thereof (e.g. Compound 2) (e.g., a dose containing about 10 mg, about 25 mg, about 50 mg, about 150 mg, about 300 mg, about 450 mg, about 600 mg, or about 1000 mg of Compound 1, or a pharmaceutically acceptable salt thereof (e.g. Compound 2)), normally at around 8 am following an overnight fast. The subjects continue to fast and remain in an upright position for about 2 hours after administration of the formulation. Blood samples are collected from each subject prior to administration (e.g., 15 minutes) and at several intervals after administration. In certain instances, several samples are taken within the first hour and taken less frequently thereafter. Illustratively, blood samples are collected at 0 (pre-dose), 0.25, 0.5, 1, 2, 3, 4, 6, 8, 12, and 16 hours after administration and, 24, 36, 48, 60 and 72 hours after administration. If the same subjects are to be used for study of a second test formulation, a period of at least 10 days should elapse before administration of the second formulation. Plasma is separated from the blood samples by centrifugation and the separated plasma is analyzed for Compound 1 by a validated high performance liquid chromatography/tandem weight spectrometry (LC/APCI-MS/MS) procedure such as, for example, Ramu et al., *Journal of Chromatography B*, 751 (2001) 49-59).

Any formulation giving the desired pharmacokinetic profile is suitable for administration according to the present methods.

In some embodiments, a pharmaceutical composition or formulation provided herein provides a $C_{max}$ (peak plasma concentration) of less than about 20 µM, less than about 15 µM, less than about 10 µM, or less than about 5 µM of a Compound 1.

In some embodiments, a pharmaceutical composition or formulation provided herein reduces urinary $LTE_4$ levels by at least 50% at 24 hours, at least 60% at 24 hours, at least 70% at 24 hours, at least 80% at 24 hours or at least 90% at 24 hours. In some embodiments, a pharmaceutical composition or formulation provided herein reduces blood $LTB_4$ levels by at least 50% at 8 hours, at least 60% at 8 hours, at least 70% at 8 hours, at least 80% at 8 hours or at least 90% at 8 hours. In some embodiments, a pharmaceutical composition or formulation described herein reduces blood $LTB_4$ levels by at least 5% at 24 hours, at least 10% at 24 hours, at least 20% at 24 hours, or at least 30% at 24 hours.

In some embodiments, a pharmaceutical composition or formulation provided herein provides a $T_{max}$ (time to peak blood plasma concentration) of Compound 1 of less than about 5 hours, less than about 4 hours, less than about 3 hours, or about 2 hours.

In some embodiments, a pharmaceutical composition or formulation provided herein provides an $AUC_{0-24}$ (area under the plasma concentration-time curve) of less than about 150 hr·µM, less than about 120 hr·µM, less than about 110 hr·µM, less than about 100 hr·µM, less than about 90 hr·µM, less than about 50 hr·µM, less than about 25 hr·µM.

Methods of Dosing and Treatment Regimens

In one embodiment, the compositions containing Compound 1, or a pharmaceutically acceptable salt thereof (e.g. Compound 2), described herein is administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, compositions containing Compound 1, or a pharmaceutically acceptable salt thereof (e.g. Compound 2), described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In specific embodiments, chronic administration is utilized in certain instances wherein the patient's condition does not improve and upon the doctor's discretion. In certain embodiments, chronic administration includes administration for an extended period of time, including, e.g., throughout the duration of the patient's life in order to ameliorate or otherwise control or limit the symptoms of the patient's disease or condition.

In some embodiments, administration of the compounds, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, the compounds, compositions or therapies described herein are administered in at least one priming dose, followed by at least one maintenance dose. In certain embodiments, a priming dose of the agent(s) is administered until the symptoms of the disorder, disease or condition treated have been reduced (e.g., to a satisfactory level). Upon reduction, a maintenance dose of the compounds, compositions or therapies described herein is administered if desired or if necessary. In some embodiments, the maintenance dose comprises administration of the agent(s) described herein in an amount sufficient to at least partially maintain the reduction achieved by administration of the priming dose. In various embodiments, the maintenance dose, compared to the priming dose, includes a decrease in dosage and/or frequency of administration of the agent or one or more of the agents administered in the method. In certain embodiments, however, intermittent treatment with increased frequency and/or dosage amounts may be necessary upon any recurrence of symptoms.

In certain embodiments, the amount of a given agent that corresponds to a priming or maintenance amount varies depending upon factors including, by way of non-limiting example, the specific agent(s) utilized, the disease condition and its severity, the identity (e.g., weight) of the subject or host in need of treatment, and/or the route of administration. In various embodiments, the desired dose is conveniently presented in a single dose or in divided doses administered simultaneously (or over a short period of time) or at appropriate intervals, for example as two, three, four or more sub-doses per day.

In some embodiments, the pharmaceutical compositions described herein are in unit dosage forms suitable for single administration of precise dosage amounts. In unit dosage form, the formulation is divided into unit doses containing appropriate quantities of the active drug. In one embodiment, the unit dosage is in the form of a package containing discrete quantities of the formulation. Non-limiting examples are packaged tablets or capsules, and powders in vials or ampoules. In one embodiment, aqueous suspension compositions are packaged in single-dose non-reclosable containers. Alternatively, multiple-dose reclosable containers are used, in which case it is typical to include a preservative in the composition.

Leukotriene-Dependent or Leukotriene Mediated Diseases or Conditions

In accordance with one aspect, compositions and methods described herein include compositions and methods for treating, preventing, reversing, halting or slowing the progression of leukotriene-dependent or leukotriene mediated diseases or conditions once it becomes clinically evident, or treating the symptoms associated with or related to leukotriene-dependent or leukotriene mediated diseases or conditions, by administering to the subject Compound 1, or a pharmaceutically acceptable salt thereof (e.g. Compound 2), or pharmaceutical composition or medicament thereof. In one embodiment, the subject already has a leukotriene-dependent or leukotriene mediated disease or condition at the time of administration, or be at risk of developing a leukotriene-dependent or leukotriene mediated disease or condition (e.g., those symptoms described in the medical literature for such diseases).

In one embodiment, the activity of 5-lipoxygenase activating protein in a mammal is directly or indirectly modulated by the administration of (at least once) an effective amount of Compound 1, or a pharmaceutically acceptable salt thereof (e.g. Compound 2), to a mammal. Such modulation includes, but is not limited to, reducing and/or inhibiting the activity of 5-lipoxygenase activating protein. In addition, in one embodiment, the activity of leukotrienes in a mammal is directly or indirectly modulated, including reducing and/or inhibiting, by the administration of (at least once) an effective amount of Compound 1, or a pharmaceutically acceptable salt thereof (e.g. Compound 2) to a mammal. Such modulation includes, but is not limited to, reducing and/or inhibiting the activity of 5-lipoxygenase activating protein.

The prevention and/or treatment of leukotriene-dependent or leukotriene mediated diseases or conditions comprises administering to a mammal at least once an effective amount of Compound 1, or a pharmaceutically acceptable salt thereof (e.g. Compound 2). By way of example, the prevention and/or treatment of inflammation diseases or conditions comprises administering to a mammal at least once an effective amount of Compound 1, or a pharmaceutically acceptable salt thereof (e.g. Compound 2). Leukotriene-dependent or leukotriene mediated diseases or conditions that is treated by a method comprising administering to a mammal at least once an effective amount of Compound 1, or a pharmaceutically acceptable salt thereof (e.g. Compound 2), include, but are not limited to, inflammatory diseases and disorders, cardiovascular disease and disorders, and respiratory diseases and disorders. In various embodiments, the leukotriene-dependent or leukotriene mediated diseases or conditions described herein are dependent or mediated alone or in part and directly or indirectly by one or more leukotrienes (e.g., $LTE_4$, $LTB_4$).

In certain embodiments, the effective amount of Compound 1, or a pharmaceutically acceptable salt thereof (e.g. Compound 2) is about 1 mg to about 5 g per dose, about 5 mg to about 2 g per dose, about 10 mg to about 1 g per dose, about 10 mg to about 1 g per dose, about 10 mg to about 0.5 g per dose, or about 10 mg to about 0.4 g per dose. In some embodiments, the effective amount of Compound 1, or a pharmaceutically acceptable salt thereof (e.g. Compound 2) is about 1 mg to about 5 g per day, about 10 mg to about 2 g per day, about 10 mg to about 1 g per day, about 10 mg to about 0.6 g per day, about 10 mg to about 0.5 g per day, or about 10 mg to about 0.4 g per day.

In one embodiment, the effective amount of Compound 1, or a pharmaceutically acceptable salt thereof (e.g. Compound 2) is about 10 mg per dose, about 50 mg per dose, about 150 mg per dose, about 300 mg per dose, about 450 mg per dose, about 600 mg per dose, or about 1000 mg per dose.

By way of example only, included in the prevention/treatment methods described herein are methods for treating and/or preventing respiratory diseases comprising administering to the mammal at least once an effective amount of Compound 1, or a pharmaceutically acceptable salt thereof (e.g. Compound 2). By way of example the respiratory disease is asthma. In addition, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vasomotor rhinitis, vascular responses, endotoxin shock, fibrogenesis, pulmonary fibrosis, allergic diseases, chronic inflammation, and adult respiratory distress syndrome.

By way of example only, included in such treatment methods are methods for preventing and/or treating chronic obstructive pulmonary disease comprising administering to the mammal at least once an effective amount of Compound 1, or a pharmaceutically acceptable salt thereof (e.g. Compound 2). In addition, chronic obstructive pulmonary disease includes, but is not limited to, chronic bronchitis or emphysema, pulmonary hypertension, interstitial lung fibrosis and/or airway inflammation and cystic fibrosis.

By way of example only, included in such treatment methods are methods for preventing and/or treating increased mucosal secretion and/or edema in a disease or condition comprising administering to the mammal at least once an effective amount of Compound 1, or a pharmaceutically acceptable salt thereof (e.g. Compound 2).

By way of example only, included in the prevention/treatment methods described herein are methods for preventing and/or treating eosinophil and/or basophil and/or dendritic cell and/or neutrophil and/or monocyte recruitment comprising administering at least once to the mammal an effective amount of Compound 1, or a pharmaceutically acceptable salt thereof (e.g. Compound 2).

By way of example only, included in the prevention/treatment methods described herein are methods for preventing and/or treating ocular disease comprising administering at least once to the mammal an effective amount of Compound 1, or a pharmaceutically acceptable salt thereof (e.g. Compound 2). In another aspect included in the prevention/treatment methods described herein are methods for preventing ocular inflammation, allergic conjunctivitis, vernal keratoconjunctivitis, and papillary conjunctivitis comprising administering at least once to the mammal an effective amount of Compound 1, or a pharmaceutically acceptable salt thereof (e.g. Compound 2).

By way of example only, included in the prevention/treatment methods described herein are methods for preventing and/or treating exercise-induced bronchoconstriction comprising administering at least once to the mammal an effective amount of Compound 1, or a pharmaceutically acceptable salt thereof (e.g. Compound 2).

By way of example only, included in the prevention/treatment methods described herein are methods for preventing and/or treating cardiovascular disease comprising administering at least once to the mammal an effective amount of Compound 1, or a pharmaceutically acceptable salt thereof (e.g. Compound 2).

By way of example only, included in the prevention/treatment methods described herein are methods for preventing and/or treating NSAID-induced gastric lesions comprising administering at least once to the mammal an effective amount of Compound 1, or a pharmaceutically acceptable salt thereof (e.g. Compound 2).

By way of example only, included in the prevention/treatment methods described herein are methods for preventing and/or treating pain comprising administering at least once to the mammal an effective amount of Compound 1, or a pharmaceutically acceptable salt thereof (e.g. Compound 2).

By way of example only, included in the prevention/treatment methods described herein are methods for preventing and/or treating skin disease comprising administering at least once to the mammal an effective amount of Compound 1, or a pharmaceutically acceptable salt thereof (e.g. Compound 2).

Combination Therapies

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the compounds are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

In one embodiment, it is understood that the dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in one embodiment, the dosage regimen actually employed varies widely and therefore deviates from the dosage regimens set forth herein. In certain embodiments, prevention and/or treatment of a leukotriene-dependent or leukotriene mediated disease or condition with a combination of Compound 1, or a pharmaceutically acceptable salt thereof (e.g. Compound 2) and a second agent allows for the effective amount of Compound 1, or a pharmaceutically acceptable salt thereof (e.g. Compound 2) to be decreased.

The formulations described herein are administered and dosed in accordance with good medical practice, taking into account the clinical condition of the individual patient, the method of administration, scheduling of administration, and other factors known to medical practitioners.

Contemplated pharmaceutical compositions provide a therapeutically effective amount of Compound 1, or a pharmaceutically acceptable salt thereof (e.g. Compound 2) enabling, for example, once-a-day, twice-a-day, three times a day, etc. administration. In one aspect, pharmaceutical compositions provide an effective amount of Compound 1, or a pharmaceutically acceptable salt thereof (e.g. Compound 2) enabling once-a-day dosing.

In certain instances, it is appropriate to administer Compound 1, or a pharmaceutically acceptable salt thereof (e.g. Compound 2) in combination with another therapeutic agent.

In specific embodiments, in a treatment for asthma involving administration of Compound 1, or a pharmaceutically acceptable salt thereof (e.g. Compound 2), increased therapeutic benefit results by also providing the patient with other therapeutic agents or therapies for asthma. In various embodiments, administration to an individual of Compound 1, or a pharmaceutically acceptable salt thereof (e.g. Compound 2) in combination with a second agent provides the individual with, e.g., an additive or synergistic benefit.

Therapeutically-effective dosages vary when the drugs are used in treatment combinations. Determination of therapeutically-effective dosages of drugs and other agents when used in combination treatment regimens is achieved in any manner. For example, the use of metronomic dosing, i.e., providing more frequent, lower doses in order to minimize toxic side effects can be utilized. In certain instances, the combination therapy allows for either or both of the Compound 1, or a pharmaceutically acceptable salt thereof (e.g. Compound 2)

and the second agent to have a therapeutically effective amount that is lower than would be obtained when administering either agent alone.

A combination treatment regimen encompasses, by way of non-limiting example, treatment regimens in which administration of Compound 1, or a pharmaceutically acceptable salt thereof (e.g. Compound 2) is initiated prior to, during, or after treatment with a second agent, and continues until any time during treatment with the second agent or after termination of treatment with the second agent. It also includes treatments in which Compound 1, or a pharmaceutically acceptable salt thereof (e.g. Compound 2) and the second agent being used in combination are administered simultaneously or at different times and/or at decreasing or increasing intervals during the treatment period. Combination treatment further includes periodic treatments that start and stop at various times to assist with the clinical management of the patient.

In accordance with some aspects, any of the pharmaceutical compositions disclosed herein are used to treat respiratory diseases, e.g. asthma, and/or to induce bronchodilation in a subject. In one embodiment, pharmaceutical compositions disclosed herein are used to treat a subject suffering from a vascular inflammation-driven disorder, such as but not limited to coronary artery disease, atherosclerosis, stroke, peripheral arterial disease, aortic aneurysm, myocardial infarction.

In certain embodiments, combination therapies described herein are used as part of a specific treatment regimen intended to provide a beneficial effect from the co-action of a FLAP inhibitor, e.g Compound 1, or a pharmaceutically acceptable salt thereof (e.g. Compound 2), and a concurrent treatment. It is understood that in certain embodiments, the dosage regimen to treat, prevent, or ameliorate the condition(s) for which relief is sought, is modified, in one embodiment, in accordance with a variety of factors. These factors include, by way of non-limiting example, the type of respiratory disorder and the type of bronchodilation from which the subject suffers, as well as the age, weight, sex, diet, and/or medical condition of the subject. Thus, in some embodiments, the dosage regimen employed, varies and/or deviates from the dosage regimens set forth herein.

In certain combination therapies described herein, dosages of the co-administered compounds vary depending on, by way of non-limiting example, the type of co-drug employed, on the specific drug employed, and/or on the disease or condition being treated.

In any case, the multiple therapeutic agents (one of which is Compound 1, or a pharmaceutically acceptable salt thereof (e.g. Compound 2)) are administered either in any order, including, e.g., simultaneously. If administration is simultaneous, the multiple therapeutic agents are provided, in various embodiments, in a single, unified form, or in multiple forms (by way of example only, either as a single pill or as two separate pills). In various embodiments, one of the therapeutic agents is given in multiple doses, or both are given as multiple doses. In certain embodiments wherein administration of the multiple agents is not simultaneous, the timing between administration of the multiple agents is of any acceptable range including, e.g., from more than zero weeks to less than four weeks. In some embodiments, the combination methods, compositions and formulations include Compound 1, or a pharmaceutically acceptable salt thereof (e.g. Compound 2), a second agent and a third agent. In further embodiments, additional agents are also utilized.

Compound 1, or a pharmaceutically acceptable salt thereof (e.g. Compound 2), and combination therapies thereof, in one embodiment, are administered before, during or after the occurrence of a disease or condition, and the timing of administering the composition containing a compound vary. In certain embodiments, Compound 1, or a pharmaceutically acceptable salt thereof (e.g. Compound 2) (either alone or in a combination) is used as a prophylactic. In certain embodiments, prophylactic treatment involves continuous administered of the agent(s) to subjects with a propensity to develop conditions or diseases in order to prevent the occurrence of the disease or condition. In certain embodiments, the agents and/or compositions described herein are administered to a subject during or as soon as possible after the onset of the symptoms. In some embodiment, the administration of the agents or compositions described herein is initiated within the first 48 hours of the onset of the symptoms, within the first 6 hours of the onset of the symptoms, or within 3 hours of the onset of the symptoms. In certain embodiments, the initial administration is via oral administration, such as, for example, a pill, a capsule, a tablet, a solution, a suspension, and the like, or combination thereof. In certain embodiments, Compound 1, or a pharmaceutically acceptable salt thereof (e.g. Compound 2) is administered as soon as is practicable after the onset of a disease or condition is detected or suspected, and for a length of time necessary for the treatment of the disease. In certain embodiments, administration of the agents, formulations or compositions described herein is for a length of time necessary for the treatment of disease.

In certain embodiments, provided herein are combinations therapies that combine treatment with Compound 1, or a pharmaceutically acceptable salt thereof (e.g. Compound 2), with treatment with an inhibitor of leukotriene synthesis or with a leukotriene receptor antagonist. In various embodiments, the inhibitors of leukotriene synthesis or the leukotriene receptor antagonist, act at the same or other points in the leukotriene synthesis pathway. In specific embodiments, these types of combination therapies are used for treating leukotriene-dependent or leukotriene mediated diseases or conditions.

In additional embodiments, provided herein are therapies which combine administration of Compound 1, or a pharmaceutically acceptable salt thereof (e.g. Compound 2) with the administration of an anti-inflammatory agent. In specific embodiments, such therapies are used in the treatment of leukotriene-dependent or leukotriene mediated diseases or conditions.

Agents to Treat Respiratory Diseases or Conditions

In certain embodiment, provided herein are methods for the treatment of leukotriene-dependent or leukotriene mediated conditions or diseases by administering to a patient Compound 1, or a pharmaceutically acceptable salt thereof (e.g. Compound 2) and another therapeutic agent that is used in the treatment of respiratory conditions or disorders, such as, but not limited to asthma. In some embodiments, provided herein are compositions, and methods of administering such compositions, comprising Compound 1, or a pharmaceutically acceptable salt thereof (e.g. Compound 2) and a therapeutic agent useful for treating respiratory conditions. Therapeutic agents useful for treating respiratory conditions and disorders, include, by way of non-limiting example: glucocorticoids, such as, ciclesonide, beclomethasone dipropionate, budesonide, flunisolide, fluticasone propionate, fluticasone furoate, mometasone furoate, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamines, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, olapatidine and azelastine; an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, indacaterol and bambuterol.

In one aspect, Compound 1, or a pharmaceutically acceptable salt thereof (e.g. Compound 2) is used in combination with one or more other therapeutic agents or the pharmaceutical compositions of Compound 1, or a pharmaceutically acceptable salt thereof (e.g. Compound 2) include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, or antihistamines. In one case, antiinfective agents include antibiotics and/or antivirals. In a further aspect, a combination comprising Compound 1, or a pharmaceutically acceptable salt thereof (e.g. Compound 2) includes one or more other therapeutically active agent, where the one or more other therapeutically active agents are selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment encompasses combinations comprising Compound 1, or a pharmaceutically acceptable salt thereof (e.g. Compound 2) together with a $\beta_2$-adrenoreceptor agonist, and/or an anticholinergic, and/or a PDE-4 inhibitor, and/or an antihistamine. Another embodiment encompasses combinations comprising Compound 1, or a pharmaceutically acceptable salt thereof (e.g. Compound 2) together with a corticosteroid or NSAID.

One embodiment encompasses combinations comprising one or two other therapeutic agents, one of which is Compound 1, or a pharmaceutically acceptable salt thereof (e.g. Compound 2).

In one aspect, the other therapeutic ingredient(s) will be used in the form of salts (e.g. as alkali metal or amine salts or as acid addition salts), or prodrugs (such as esters (e.g. alkyl esters)), or as solvates (e.g. hydrates). In one aspect, if appropriate, the therapeutic ingredients will be used in optically pure form. In another aspect, if appropriate, the therapeutic ingredients will be used in racemic form.

Examples of $\beta_2$-adrenoreceptor agonists include salmeterol (as a racemate or a single enantiomer such as the R-enantiomer), salbutamol (as a racemate or a single enantiomer such as the R-enantiomer), formoterol (as a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

Other $\beta_2$-adrenoreceptor agonists include those described in WO02/066422, WO02/070490, WO02/076933, WO03/024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include: 3-(4-{[6-({(2R)-2-hydroxy-2-[4-hydroxy-3-(hydroxymethyl)phenyl]ethyl}amino)hexyl]oxy}butyl)benzenesulfonamide; 3-(3-{[7-({(2R)-2-hydroxy-2-[4-hydroxy-3-hydroxymethyl)phenyl]ethyl}-amino)heptyl]oxy}propyl)benzenesulfonamide; 4-{(1R)-2-[(6-{2-[(2,6-dichlorobenzyl)oxy]ethoxy}hexyl)amino]-1-hydroxyethyl}-2-(hydroxymethyl)phenol; 4-{(1R)-2-[(6-{4-[3-(cyclopentylsulfonyl)phenyl]butoxy}hexyl)amino]-1-hydroxyethyl}-2-(hydroxymethyl)phenol; N-[2-hydroxyl-5-[(1R)-1-hydroxy-2-[[2-4-[[(2R)-2-hydroxy-2-phenylethyl]amino]phenyl]ethyl]amino]ethyl]phenyl]formamide; N-2 {2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

In one aspect, the $\beta_2$-adrenoreceptor agonist is in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Examples of corticosteroids include oral and inhaled corticosteroids and their pro-drugs that have anti-inflammatory activity. Examples of corticosteroids include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-1'-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Further examples of corticosteroids include those described in WO 02/088167, WO 02/100879, WO 02/12265, WO 02/12266, WO 05/005451, WO 05/005452, WO 06/072599 and WO 06/072600.

Non-steroidal compounds having glucocorticoid agonism that may possess selectivity for transrepression over transactivation and that may be useful in combination therapy include those covered in the following published patent applications and patents: WO 03/082827, WO 98/54159, WO 04/005229, WO 04/009017, WO 04/018429, WO 03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000334, WO07/054294, WO07/122165, WO07/144327 and WO08/074814.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO 93/13055, WO 98/30537, WO 02/50021, WO 95/34534 and WO 99/62875. Examples of CCR3 inhibitors include, but are not limited to those disclosed in WO 02/26722.

In one embodiment, Compound 1, or a pharmaceutically acceptable salt thereof (e.g. Compound 2) is combined with or administered in combination with a phosphodiesterase 4 (PDE4) inhibitor, especially in the case of a formulation adapted for inhalation. The PDE4-specific inhibitor useful in this aspect is any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO 99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO 99/47505, the disclosure of which is hereby incorporated by reference) from Byk-Gulden; Pumafentrine, (−)-p-[(4aR*, 10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO 04/024728, WO 04/056823 and WO 04/103998.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide), oxitropium (for example, as the bromide) and tiotropium (for example, as the bromide). Also of interest are revatropate (for example, as the hydrobromide) and LAS-34273 which is disclosed in WO01/04118. Exemplary compounds for oral administration include pirenzepine, darifenacin (hydrobromide), oxybutynin, terodiline, tolterodine, tolterodine tartrate, otilonium (for example, as the bromide), trospium chloride, solifenacin, and solifenacin succinate.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide; (3-endo)-3-(2,2-diphenylethenyl)-8,8-dimethyl-8-azoniabicyclo[3.2.1]octane bromide; (3-endo)-3-(2,2-diphenylethenyl)-8,8-dimethyl-8-azoniabicyclo[3.2.1]octane 4-methylbenzenesulfonate; (3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example: (endo)-3-(2-methoxy-2,2-di-thiophen-2-yl-ethyl)-8,8-dimethyl-8-azonia-bicyclo[3.2.1]octane iodide; 3-((endo)-8-methyl-8-aza-bicyclo[3.2.1]oct-3-yl)-2,2-diphenyl-propionitrile; (endo)-8-methyl-3-(2,2,2-triphenyl-ethyl)-8-aza-bicyclo[3.2.1]octane; 3-((endo)-8-methyl-8-aza-bicyclo[3.2.1]oct-3-yl)-2,2-diphenyl-propionamide; 3-((endo)-8-methyl-8-aza-bicyclo[3.2.1]oct-3-yl)-2,2-diphenyl-propionic acid; (endo)-3-(2-cyano-2,2-diphenyl-ethyl)-8,8-dimethyl-8-azonia-bicyclo[3.2.1]octane iodide; (endo)-3-(2-cyano-2,2-diphenyl-ethyl)-8,8-dimethyl-8-azonia-bicyclo[3.2.1]octane bromide; 3-((endo)-8-methyl-8-aza-bicyclo[3.2.1]oct-3-yl)-2,2-diphenyl-propan-1-ol; N-benzyl-3-((endo)-8-methyl-8-aza-bicyclo[3.2.1]oct-3-yl)-2,2-diphenyl-propionamide; (endo)-3-(2-carbamoyl-2,2-diphenyl-ethyl)-8,8-dimethyl-8-azonia-bicyclo[3.2.1]octane iodide; 1-benzyl-3-[3-((endo)-8-methyl-8-aza-bicyclo[3.2.1]oct-3-yl)-2,2-diphenyl-propyl]-urea; 1-ethyl-3-[3-((endo)-8-methyl-8-aza-bicyclo[3.2.1]oct-3-yl)-2,2-diphenyl-propyl]-urea; N-[3-((endo)-8-methyl-8-aza-bicyclo[3.2.1]oct-3-yl)-2,2-diphenyl-propyl]-acetamide; N-[3-((endo)-8-methyl-8-aza-bicyclo[3.2.1]oct-3-yl)-2,2- diphenyl-propyl]-benzamide; 3-((endo)-8-methyl-8-aza-bicyclo[3.2.1]oct-3-yl)-2,2-di-thiophen-2-yl-propionitrile; (endo)-3-(2-cyano-2,2-di-thiophen-2-yl-ethyl)-8,8-dimethyl-8-azonia-bicyclo[3.2.1]octane iodide; N-[3-((endo)-8-methyl-8-aza-bicyclo[3.2.1]oct-3-yl)-2,2-diphenyl-propyl]-benzenesulfonamide; [3-((endo)-8-methyl-8-aza-bicyclo[3.2.1]oct-3-yl)-2,2-diphenyl-propyl]-urea; N-[3-((endo)-8-methyl-8-aza-bicyclo[3.2.1]oct-3-yl)-2,2-diphenyl-propyl]-methanesulfonamide; and/or (endo)-3-{2,2-diphenyl-3-[(1-phenyl-methanoyl)-amino]-propyl}-8,8-dimethyl-8-azonia-bicyclo[3.2.1]octane bromide.

Further compounds include: (endo)-3-(2-methoxy-2,2-di-thiophen-2-yl-ethyl)-8,8-dimethyl-8-azonia-bicyclo[3.2.1]octane iodide; (endo)-3-(2-cyano-2,2-diphenyl-ethyl)-8,8-dimethyl-8-azonia-bicyclo[3.2.1]octane iodide; (endo)-3-(2-cyano-2,2-diphenyl-ethyl)-8,8-dimethyl-8-azonia-bicyclo[3.2.1]octane bromide; (endo)-3-(2-carbamoyl-2,2-diphenyl-ethyl)-8,8-dimethyl-8-azonia-bicyclo[3.2.1]octane iodide; (endo)-3-(2-cyano-2,2-di-thiophen-2-yl-ethyl)-8,8-dimethyl-8-azonia-bicyclo[3.2.1]octane iodide; and/or (endo)-3-{2,2-diphenyl-3-[(1-phenyl-methanoyl)-amino]-propyl}-8,8-dimethyl-8-azonia-bicyclo[3.2.1]octane bromide.

In one embodiment, Compound 1, or a pharmaceutically acceptable salt thereof (e.g. Compound 2) is combined with or administered in combination with an H1 antagonist. Examples of H1 antagonists include, but are not limited to, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly azelastine, cetirizine, levocetirizine, efletirizine and fexofenadine.

In another embodiment, Compound 1, or a pharmaceutically acceptable salt thereof (e.g. Compound 2) is combined with or administered in combination with an H3 antagonist (and/or inverse agonist). Examples of H3 antagonists include, for example, those compounds disclosed in WO 2004/035556, WO 2006/045416, WO 2006/090142, WO 2006/125665, WO 2007/009739 and WO2007/009741.

In another embodiment, Compound 1, or a pharmaceutically acceptable salt thereof (e.g. Compound 2) is combined with or administered in combination with an H1/H3 dual antagonist (and/or inverse agonist). Examples of H1/H3 dual antagonists include, for example, those compounds disclosed in WO 2004/035556, WO 2007/071691, WO 2007/122156 and WO 2007/135081.

In a further embodiment, Compound 1, or a pharmaceutically acceptable salt thereof (e.g. Compound 2) is combined with or administered in combination with an H1/H3 dual antagonist selected from 3-(4-{[4-(4-{[3-(3,3-dimethyl-1-piperidinyl)propyl]oxy}phenyl)-1-piperidinyl]carbonyl}-1-naphthalenyl) propanoic acid and 4-[(4-chlorophenyl)methyl]-2-({(2R)-1-[4-(4-{[3-(hexahydro-1H-azepin-1-yl)propyl]oxy}phenyl)butyl]-2-pyrrolidinyl}methyl)-1(2H)-phthalazinone. Other histamine receptor antagonists include antagonists (and/or inverse agonists) of the H4 receptor, for example, the compounds disclosed in Jablonowski et al., *J. Med. Chem.* 46:3957-3960 (2003).

In another aspect, provided herein is a combination comprising Compound 1, or a pharmaceutically acceptable salt thereof (e.g. Compound 2) together with a PDE4 inhibitor.

In another aspect, provided herein is a combination comprising Compound 1, or a pharmaceutically acceptable salt thereof (e.g. Compound 2) together with a $\beta_2$-adrenoreceptor agonist.

In another aspect, provided herein is a combination comprising Compound 1, or a pharmaceutically acceptable salt thereof (e.g. Compound 2) together with a corticosteroid.

In another aspect, provided herein is a combination comprising Compound 1, or a pharmaceutically acceptable salt thereof (e.g. Compound 2) together with another non-steroidal GR agonist.

In another aspect, provided herein is a combination comprising Compound 1, or a pharmaceutically acceptable salt thereof (e.g. Compound 2) together with an anticholinergic.

In another aspect, provided herein is a combination comprising Compound 1, or a pharmaceutically acceptable salt thereof (e.g. Compound 2) together with an antihistamine.

In another aspect, provided herein is a combination comprising Compound 1, or a pharmaceutically acceptable salt thereof (e.g. Compound 2) together with a PDE4 inhibitor and a $\beta_2$-adrenoreceptor agonist.

In another aspect, provided herein is a combination comprising Compound 1, or a pharmaceutically acceptable salt thereof (e.g. Compound 2) together with an anticholinergic and a PDE-4 inhibitor.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

In another aspect, provided herein is a pharmaceutical composition comprising Compound 1, or a pharmaceutically acceptable salt thereof (e.g. Compound 2) together with a PDE4 inhibitor.

In another aspect, provided herein is a pharmaceutical composition comprising Compound 1, or a pharmaceutically acceptable salt thereof (e.g. Compound 2) together with a $\beta_2$-adrenoreceptor agonist.

In another aspect, provided herein is a pharmaceutical composition comprising Compound 1, or a pharmaceutically acceptable salt thereof (e.g. Compound 2) together with a corticosteroid.

In another aspect, provided herein is a pharmaceutical composition comprising Compound 1, or a pharmaceutically acceptable salt thereof (e.g. Compound 2) together with another non-steroidal GR agonist.

In another aspect, provided herein is a pharmaceutical composition comprising Compound 1, or a pharmaceutically acceptable salt thereof (e.g. Compound 2) together with an anticholinergic.

In another aspect, provided herein is a pharmaceutical composition comprising Compound 1, or a pharmaceutically acceptable salt thereof (e.g. Compound 2) together with an antihistamine.

In another aspect, provided herein is a pharmaceutical composition comprising Compound 1, or a pharmaceutically acceptable salt thereof (e.g. Compound 2) together with a PDE4 inhibitor and a $\beta_2$-adrenoreceptor agonist.

In another aspect, provided herein is a pharmaceutical composition comprising Compound 1, or a pharmaceutically acceptable salt thereof (e.g. Compound 2) together with an anticholinergic and a PDE4 inhibitor.

In certain aspects, Compound 1, or a pharmaceutically acceptable salt thereof (e.g. Compound 2) is combined with or administered in combination with one or more agents used to treat used to treat asthma, including, but not limited to: combination Inhalers (fluticasone propionate and salmeterol xinafoate (e.g. Advair), budesonide and formoterol fumarate (e.g. Symbicort) and indacaterol and mometasone furoate); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, Compound 1, or a pharmaceutically acceptable salt thereof (e.g. Compound 2) is combined with or administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionic acid is combined with or administered in combination with one or more agents used to treat chronic obstructive pulmonary disease (COPD), including, but not limited to: anticholinergics-ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, Compound 1, or a pharmaceutically acceptable salt thereof (e.g. Compound 2) is combined with or administered to a patient in combination with norastemizole. In one embodiment, Compound 1, or a pharmaceutically acceptable salt thereof (e.g. Compound 2) is combined with or administered to a patient in combination with loratadine. In one embodiment, Compound 1, or a pharmaceutically acceptable salt thereof (e.g. Compound 2) is combined with or administered to a patient in combination with desloratadine. In one embodiment, Compound 1, or a pharmaceutically acceptable salt thereof (e.g. Compound 2) is combined with or administered to a patient in combination with terfenadine.

In one embodiment, Compound 1, or a pharmaceutically acceptable salt thereof (e.g. Compound 2) is combined with or administered to a patient in combination with cetirizine. In one embodiment, Compound 1, or a pharmaceutically acceptable salt thereof (e.g. Compound 2) is combined with or administered to a patient in combination with (−)-cetirizine. In one embodiment, Compound 1, or a pharmaceutically acceptable salt thereof (e.g. Compound 2) is combined with or administered to a patient in combination with (+)-cetirizine.

In one embodiment, Compound 1, or a pharmaceutically acceptable salt thereof (e.g. Compound 2) is combined with or administered to a patient in combination with inhaled corticosteroids.

In one embodiment, Compound 1, or a pharmaceutically acceptable salt thereof (e.g. Compound 2) is combined with or administered to a patient in combination with beta2-adrenergic receptor agonists. In one embodiment, Compound 1, or a pharmaceutically acceptable salt thereof (e.g. Compound 2) is combined with or administered to a patient in combination with short acting beta2-adrenergic receptor agonists. In one embodiment, Compound 1, or a pharmaceutically acceptable salt thereof (e.g. Compound 2) is combined with or administered to a patient in combination with long-acting beta2-adrenergic receptor agonists.

In any of the compositions, combinations, methods of treating or combination methods of treating described herein Compound 2 is used. In more specific embodiments, Compound 2 is in Form C. In other specific embodiments, Compound 2 is in either Phase A or Solvated Form B.

In any of the compositions, combinations, methods of treating or combination methods of treating described herein Compound 1 (free acid) is used. In more specific embodiments, Compound 1 is in crystalline form. In other specific embodiments, Compound 1 is in amorphous phase.

In some embodiments described herein, methods for treatment of leukotriene-dependent or leukotriene mediated conditions or diseases includes administering to a patient Compound 1, or a pharmaceutically acceptable salt thereof (e.g. Compound 2) in combination with leukotriene receptor antagonists including, but are not limited to, $CysLT_1/CysLT_2$ dual receptor antagonists, and $CysLT_1$ receptor anatagonists. $CysLT_1/CysLT_2$ dual receptor antagonists include, but are not limited to, BAY u9773, Cuthbert et al EP 00791576 (published 27 Aug. 1997), DUO-LT (Galczenski et al, D38, Poster F4 presented at American Thoracic Society, May 2002) and Tsuji et al, *Org. Biomol. Chem.*, 1, 3139-3141, 2003. In one embodiment, for a particular patient, the most appropriate formulation or method of use of such combination treatments depends on the type of leukotriene-dependent or leukotriene mediated disorder, the time period in which Compound 1, or a pharmaceutically acceptable salt thereof (e.g. Compound 2)

acts to treat the disorder and the time period in which the $CysLT_1/CysLT_2$ dual receptor antagonist acts to inhibit CysLT receptor activity. By way of example only, such combination treatments are used for treating a patient suffering from a respiratory disorder.

In another embodiment described herein, methods for treatment of leukotriene-dependent or leukotriene mediated conditions or diseases includes administered to a patient compounds, pharmaceutical compositions, or medicaments described herein in combination with a $CysLT_1$ receptor antagonist. $CysLT_1$ receptor antagonists include, but are not limited to, zafirlukast, montelukast, prankulast, and derivatives or analogs thereof. In one embodiment, such combinations are used to treat leukotriene-dependent or leukotriene mediated disorder, including respiratory disorders.

In one embodiment, the co-administration of Compound 1, or a pharmaceutically acceptable salt thereof (e.g. Compound 2) with a $CysLT_1$ receptor antagonist or a dual $CysLT_1/CysLT_2$ receptor antagonist has therapeutic benefit over and above the benefit derived from the administration of either Compound 1, or a pharmaceutically acceptable salt thereof (e.g. Compound 2) or a $CysLT_1R$ antagonist alone. In the case that substantial inhibition of leukotriene production has undesired effects, partial inhibition of this pathway through the amelioration of the effects of the proinflammatory $LTB_4$ and cysteinyl leukotrienes combined with the block of the $CysLT_1$ receptor and/or dual $CysLT_1/CysLT_2$ receptor block affords substantial therapeutic benefits, particularly for respiratory diseases.

In some embodiment described herein, are methods for treatment of leukotriene-dependent or leukotriene mediated conditions or diseases include administering to a patient Compound 1, or a pharmaceutically acceptable salt thereof (e.g. Compound 2) in combination with an anti-inflammatory agent. In certain embodiments, provided herein are compositions comprising and methods of administering compositions comprising Compound 1, or a pharmaceutically acceptable salt thereof (e.g. Compound 2), and an anti-inflammatory agent. Anti-inflammatory agents include, by way of non-limiting example, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Corticosteroids do not directly inhibit leukotriene production, therefore co-dosing with steroids, in one embodiment, provide additional anti-inflammatory benefit.

In another embodiment described herein, methods for treatment of leukotriene-dependent or leukotriene mediated conditions or diseases include administering to a patient Compound 1, or a pharmaceutically acceptable salt thereof (e.g. Compound 2) in combination with an anti-inflammatory agent including, but not limited to poly-unsaturated fatty acids (PUFAs) such as docosahexanoic acid (DHA), eicosapentanoic acid (EPA) and alpha-linolenic acid (ALA).

In certain embodiments, the leukotriene-dependent or leukotriene mediated condition or disease, e.g., a respiratory disease, involves eosinophilic, basophilic, and/or mast cell inflammation. In specific embodiments, the eosinophilic, basophilic, and/or mast cell inflammation is pulmonary inflammation. In more specific embodiments, the pulmonary inflammation is the result of a chronic inflammatory condition. In still more specific embodiments, the chronic inflammatory disease is characterized by pulmonary inflammation and airway hyperresponsiveness, e.g., asthma. Furthermore, leukotriene-dependent or leukotriene mediated condition or disease is asthma, wherein leukotrienes may be released from mast cells, eosinophils, and/or basophils. In certain embodiments, the leukotrienes are involved in contraction of airway smooth muscle, an increase in vascular permeability and mucus secretions, and have been reported to attract and activate inflammatory cells in the airways of asthmatics. Thus, in certain embodiment described herein, the methods for treatment of respiratory diseases include administering to a patient Compound 1, or a pharmaceutically acceptable salt thereof (e.g. Compound 2) either alone or in combination with an anti-inflammatory agent.

In another embodiment described herein, methods for treatment of leukotriene-dependent or leukotriene mediated conditions or diseases include administering to a patient Compound 1, or a pharmaceutically acceptable salt thereof (e.g. Compound 2) in combination with NSAIDs and NO-donors or NSAIDs and proton-pump inhibitors. In further embodiments, provided herein are compositions comprising such agents and methods of administering such compositions.

UGT Inhibitors

In one embodiment, Compound 1, or a pharmaceutically acceptable salt thereof (e.g. Compound 2) is combined with or administered in combination with one or more agents that are inhibitors of UDP-glucuronosyltransferase (UGT). UGT inhibitors include those described in U.S. 2003/0215462; U.S. 2004/0014648. In some embodiments, co-administration of a UGT inhibitor allows for lower doses of Compound 1, or a pharmaceutically acceptable salt thereof (e.g. Compound 2) to be administered.

Diagnostic Methods for Patient Identification

The screening of "leukotriene-responsive patients" which are selected for treatment with Compound 1, or a pharmaceutically acceptable salt thereof (e.g. Compound 2), or pharmaceutical compositions or medicaments described herein, is accomplished using techniques and methods described herein. Such techniques and methods include, by way of example, evaluation of gene haplotypes (genotype analysis), monitoring/measurement of biomarkers (phenotype analysis), monitoring/measurement of functional markers (phenotype analysis), which indicate patient response to modulators of the leukotriene pathway, or any combination thereof.

Genotype Analysis: FLAP Polymorphisms

Human FLAP has been purified and cloned and is an 18 kilodalton membrane-bound protein which is most highly expressed in human neutrophils. The FLAP gene is located at 13q12 and the gene has been linked to increased risk for both myocardial infarction and stroke in several populations. A number of polymorphisms and haplotypes in the gene encoding FLAP have been identified in individuals (U.S. Patent Application 2005113408; Sayers, Clin. Exp. Allergy, 33(8): 1103-10, 2003; Kedda, et al., Clin. Exp. Allergy, 35(3):332-8, 2005). In some cases polymorphisms in certain genes have been demonstrated to correlate with responsiveness to given therapies. Therefore, in one embodiment, patients who are under consideration for treatment with Compound 1, or a pharmaceutically acceptable salt thereof (e.g. Compound 2), or drug combinations that include Compound 1, or a pharmaceutically acceptable salt thereof (e.g. Compound 2), are screened for potential responsiveness to treatment based on their FLAP polymorphisms, or haplotypes (see also WO 99/052942, herein incorparated by reference).

Additionally, polymorphisms in any of the synthetic or signaling genes dedicated to the leukotriene pathway could result in a patient who is more responsive or less responsive to leukotriene modulator therapy (either FLAP or 5-LO inhibitor or leukotriene receptor antagonists). The genes dedicated to the leukotriene pathway are 5-lipoxygenase, 5-lipoxygenase-activating protein, $LTA_4$ hydrolase, $LTC_4$ synthase, $LTB_4$ receptor 1 ($BLT_1$), $LTB_4$ receptor 2 ($BLT_2$), cysteinyl leukotriene receptor 1 ($CysLT_1R$), cysteinyl leukotriene receptor 2 ($CysLT_2R$). For example, the 5-LO gene has been linked to aspirin intolerant asthma and airway hyperresponsiveness (Choi J H et al. Hum Genet. 114:337-344 (2004); Kim, S H et al. Allergy 60:760-765 (2005). Genetic variants in the promoter region of 5-LO have been shown to predict clinical responses to a 5-LO inhibitor in asthmatics (Drazen et al, Nature Genetics, 22, p 168-170, (1999). The $LTC_4$ synthase gene has been linked to atopy and asthma (Moissidis I et al. Genet Med 7:406-410 (2005). The $CysLT_2$ receptor has been linked to asthma and atopy (Thompson M D et al. Pharmacogenetics 13:641-649 (2003); Pillai S G et al. Pharmacogenetics 14:627-633 (2004); Park J S et al. Pharmacogenet Genomics 15:483-492 (2005); Fukai H et al. Pharmacogenetics 14:683-690 (2004). Any polymorphisms in any leukotriene pathway gene or combination of polymorphisms or haplotypes may result in altered sensitivity of the patient to therapy aimed at reducing the pathological effects of leukotrienes. In one embodiment, selection of patients who best respond to the leukotriene modulator therapies described herein is based, in part, on knowledge of polymorphisms in the leukotriene pathway genes and also knowledge of the expression of leukotriene-driven mediators. In one embodiment, patient selection is made on the basis of leukotriene pathway genotype alone, phenotype alone (biomarkers or functional markers) or any combination of genotype and phenotype.

Several variants of the FLAP gene have been reported to correlate with the incidence of myocardial infarction in patients (Hakonarson, JAMA, 293(18):2245-56, 2005), plus FLAP gene markers reportedly associated with the risk for developing asthma have been described in U.S. Pat. No. 6,531,279. Methods for identifying FLAP sequence variants are described, e.g., in U.S. Publication No. 2005/0113408, and in U.S. Pat. No. 6,531,279, incorporated herein by reference herein in their entirety.

In one embodiment, detecting haplotypes is accomplished by methods for detecting sequences at polymorphic sites, and therefore patients are selected using genotype selection of FLAP, 5-LO or other leukotriene pathway gene polymorphisms. In one embodiment, the presence or absence of a leukotriene pathway gene polymorphism or haplotype is determined by various methods, including, for example, using enzymatic amplification, restriction fragment length polymorphism analysis, nucleic acid sequencing, electrophoretic analysis of nucleic acid from the individual, or any combination thereof. In certain embodiments, determination of a SNP or haplotype identifies patients who will respond to, or gain benefit from, treatment with a FLAP inhibitor. By way of example, methods of diagnosing a susceptibility to myocardial infarction or stroke in an individual, comprises determining the presence or absence of certain single nucleotide polymorphisms (SNPs) or of certain haplotypes, wherein the presence of the SNP or the haplotype is diagnostic of susceptibility to myocardial infarction or stroke.

Phenotype Analysis: Biomarkers

In one embodiment, patients who are under consideration for treatment with Compound 1, or a pharmaceutically acceptable salt thereof (e.g. Compound 2), or drug combinations thereof, are screened for potential responsiveness to treatment based on leukotriene-driven inflammatory biomarker phenotypes.

In one embodiment, patient screening based on leukotriene-driven inflammatory biomarker phenotypes is used as an alternative to, or it is complimentary with, patient screening by leukotriene pathway gene haplotype detection. The term "biomarker" as used herein refers to a characteristic which is measured and evaluated as an indicator of normal biological processes, pathological processes, or pharmacological responses to therapeutic intervention. Thus a biomarker is any substance, structure or process which is measured in the body, or its products, and which influences or predicts the incidence of outcome or disease. Biomarkers are classified into markers of exposure, effect, and susceptibility. Biomarkers are physiologic endpoints, by way of example blood pressure, or they are analytical endpoints, by way of example, blood glucose, or cholesterol concentrations. Techniques, used to monitor and/or measure biomarkers include, but are not limited to, NMR, LC-MS, LC-MS/MS, GC-MS, GC-MS/MS, HPLC-MS, HPLC-MS/MS, FT-MS, FT-MS/MS, ICP-MS, ICP-MS/MS, peptide/protein sequencing, nucleic acid sequencing, electrophoresis techniques, immuno-assays, immuno-blotting, in-situ hybridization, fluorescence in-situ hybridization, PCR, radio-immuno assays, and enzyme-immuno assays. Single nucleotide polymorphisms (SNPs) have also been useful for the identification of biomarkers for propensity to certain diseases and also susceptibility or responsiveness to drugs such as chemotherapeutic agents and antiviral agents. In one embodiment, these techniques, or any combination thereof, are used to screen patients for leukotriene-dependent or leukotriene mediated diseases or conditions, wherein such patients are beneficially treated with Compound 1, or a pharmaceutically acceptable salt thereof (e.g. Compound 2), or drug combinations described herein.

By way of example only, patients are selected for treatment with Compound 1, or a pharmaceutically acceptable salt thereof (e.g. Compound 2), or drug combinations described herein by screening for enhanced inflammatory blood biomarkers such as, but not limited to, stimulated $LTB_4$, $LTC_4$, $LTE_4$, myeloperoxidase (MPO), eosinophil peroxidase (EPO), C-reactive protein (CRP), soluble intracellular adhesion molecule (sICAM), monocyte chemoattractant protein (MCP-1), monocyte inflammatory protein (MIP-1α), interleukin-6 (IL-6), the TH2 T cell activators interleukin 4 (IL-4), and 13 (IL-13) and other inflammatory cytokines. In certain embodiments, patients with inflammatory respiratory diseases, including but not limited to, asthma and COPD, are selected as those most likely to be responsive to leukotriene synthesis inhibition using Compound 1, or a pharmaceutically acceptable salt thereof (e.g. Compound 2), by using a panel of leukotriene driven inflammatory biomarkers.

Phenotype Analysis: Functional Markers

In one embodiment, patients who are under consideration for treatment with Compound 1, or a pharmaceutically acceptable salt thereof (e.g. Compound 2), or drug combinations described herein, are screened for response to known modulators of the leukotriene pathway. In one embodiment, patient screening by evaluation of functional markers as indicators of a patient's response to known modulators of the leukotriene pathway are used as an alternative to, or it is complimentary with, patient screening by leukotriene pathway gene haplotype detection (genotype analysis) and/or monitoring/measurement of leukotriene-driven inflammatory biomarker phenotypes. Functional markers include, but are not limited to, any physical characteristics associated with a leukotriene dependent condition or disease, or knowledge of current or past drug treatment regimens.

By way of example only, the evaluation of lung volume and/or function are used as a functional marker for leukotriene-dependent or leukotriene mediated diseases or conditions, such as respiratory diseases. In one embodiment, lung function tests are used to screen patients, with such leukotriene-dependent or leukotriene mediated diseases or conditions, for treatment using Compound 1, or a pharmaceutically acceptable salt thereof (e.g. Compound 2), or pharmaceutical compositions or medicaments thereof. Such tests include, but are not limited to, evaluation of lung volumes and capacities, such as tidal volume, inspiratory reserve volume, expiratory reserve volume, residual volume, inspiratory capacity, functional residual capacity, vital capacity, total lung capacity, respiratory minute volume, alveolar ventilation, timed vital capacity, and ventilatory capacity. Method of measurement of lung volumes and capacities include, but are not limited to, maximum expiratory flow volume curve, forced expiratory volume in 1 sec. (FEV1), peak expiratory flow rate. In addition, other lung function tests used as functional markers for patient evaluation described herein include, but are not limited to, respiratory muscle power, maximum inspiratory pressure, maximum expiratory pressure, transdiaphragmatic pressure, distribution of ventilation, single breath nitrogen test, pulmonary nitrogen washout, and gas transfer.

Additionally, the knowledge of a patients past or current treatment regimen is used as a functional marker to assist in screening patients for treatment of leukotriene dependent conditions or diseases using Compound 1, or a pharmaceutically acceptable salt thereof (e.g. Compound 2), or pharmaceutical compositions or medicaments thereof. By way of example only, such treatment regimens include past or current treatment using zileuton, montelukast, pranlukast, zafirlukast.

Also, patients who are under consideration for treatment with Compound 1, or a pharmaceutically acceptable salt thereof (e.g. Compound 2), or drug combinations described herein, are screened for functional markers which include, but are not limited to, reduced eosinophil and/or basophil, and/or neutrophil, and/or monocyte and/or dendritic cell and/or lymphocyte recruitment, decreased mucosal secretion, decreased mucosal edema, and/or increased bronchodilation.

In certain embodiments, a patient sample is analyzed for leukotriene gene haplotypes, by way of example only, FLAP haplotypes, and the information obtained identifies a patient in need of treatment using various treatment methods. Such treatment methods include, but are not limited to, administering a therapeutic effective amount of Compound 1, or a pharmaceutically acceptable salt thereof (e.g. Compound 2), or pharmaceutical composition or medicament thereof, alone or in combination with a therapeutic effective amount of a leukotriene receptor antagonist (by way of example, $CysLT_1$/$CysLT_2$ antagonist or $CysLT_1$ antagonist). In other embodiments a patient sample is analyzed for leukotriene gene haplotypes, by way of example only, FLAP haplotypes, and/or phenotype biomarkers, and/or phenotype functional marker responses to leukotriene modifying agents. In one embodiment, the patient is then treated using various treatment methods. Such treatment methods include, but are not limited to, administering a therapeutic effective amount of Compound 1, or a pharmaceutically acceptable salt thereof (e.g. Compound 2), or pharmaceutical composition or medicament thereof, alone or in combination with a therapeutic effective amount of a leukotriene receptor antagonist (by way of example, $CysLT_1$/$CysLT_2$ antagonist or $CysLT_1$ antagonist), or another anti-inflammatory agent. In still other embodiments a patient sample is analyzed for leukotriene gene haplotypes, by way of example only, FLAP haplotypes, and phenotype biomarkers, and phenotype functional marker responses to leukotriene modifying agents. In one embodiment, the patient is then treated using various treatment methods. Such treatment methods include, but are not limited to, administering a therapeutic effective amount of a FLAP inhibitor, or pharmaceutical composition or medicament which includes a FLAP inhibitor, administering a therapeutic effective amount of a FLAP inhibitor, or pharmaceutical composition or medicament which includes a FLAP inhibitor, in combination with a therapeutic effective amount of a leukotriene receptor antagonist (by way of example, $CysLT_1$/$CysLT_2$ antagonist or $CysLT_1$ antagonist), or administering a therapeutic effective amount of a FLAP inhibitor, or pharmaceutical composition or medicament which includes a FLAP inhibitor, in combination with a therapeutic effective amount of another anti-inflammatory agent.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of FLAP, or in which FLAP is a mediator or contributor to the symptoms or cause.

For example, the container(s) include Compound 1, or a pharmaceutically acceptable salt thereof (e.g. Compound 2), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

It is to be understood that as used herein, pharmaceutical compositions described as comprising a pharmaceutically acceptable salt described herein, e.g., liquid solutions, encompass pharmaceutical compositions comprising the associated and/or disassociated forms of the salt. Thus, for example, a pharmaceutical composition described herein comprising an aqueous solution of Compound 2 encompasses a composition comprising a population of sodium cations and a population of 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionate anions.

EXAMPLES

| Abbreviations | |
|---|---|
| AUC | area under the curve |
| $CO_2$ | carbon dioxide |
| $Cs_2CO_3$ | cesium carbonate |
| DME | dimethoxyethane |
| DMF | dimethylformamide |
| DMSO | dimethylsulphoxide |
| dppf | diphenylphosphinoferrocene |
| DSC | Differential scanning calorimetry |
| DTT | dithiothreitol |
| $Et_3N$ | triethylamine |
| ECG | Electrocardiography |
| EDTA | ethylenediaminetetraacetic acid |
| eq | equivalent(s) |
| EtOAc | ethylacetate |
| EtOH | ethanol |
| HCl | hydrochloric acid |
| $H_2O$ | water |
| HPLC | high performance liquid chromatography |
| ICP-AES | Inductively coupled plasma atomic emission spectroscopy |

-continued

| Abbreviations | |
|---|---|
| KOH | potassium hydroxide |
| LCMS | liquid chromatogrpahy mass spectrometry |
| MeOH | methanol |
| MTBE | methyl tert-butyl ether |
| $MgSO_4$ | magnesium sulfate |
| NaOH | sodium hydroxide |
| $Na_2CO_3$ | sodium carbonate |
| NMR | nuclear magnetic resonance |
| ppm | parts per million |
| PD | pharmacodynamics |
| PK | pharmacokinetics |
| RH | Relative humidity |
| SD | Standard deviation |
| THF | tetrahydrofuran |
| TGA | Thermogravimetric Analysis |
| TLC | Thin layer chromatography |
| TRIS | Tromethamine |
| V/W | Volume/weight |

The following ingredients, formulations, processes and procedures for practicing the methods disclosed herein correspond to that described above. The procedures below describe with particularity illustrative, non-limiting embodiment of formulations that include a Compound 1, or a pharmaceutically acceptable salt and/or solvate thereof, and pharmacokinetic profiles and pharmacodynamic effects thereof. By way of example only, Compound 1 is optionally prepared as outlined in US 2007/0105866, or as outlined herein.

Example 1

Synthesis of Compound 1, Esters, Solvates, Salts, and Polymorphs Thereof

Step 1: Synthesis of 2-Chloromethyl-5-methyl-pyridine hydrochloride

Step 1-1: Synthesis of 2,5-Dimethyl-pyridine 1-oxide

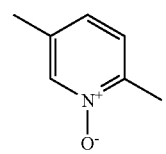

2,5-Lutidine (1419 g) was dissolved in chloroform (13.5 L) and cooled to below 10° C. m-Chloroperoxybenzoic acid (70%, 3354.21 g) was added portion-wise to maintain the temperature at below 10° C., and then the reaction was warmed to room temperature and stirred overnight. Once no starting material was seen by tlc analysis, the mixture was cooled to 10° C. and quenched with aqueous 20% sodium hydroxide (2.5 L to 3 L) dropwise while maintaining a temperature below 20° C., which resulted in the formation of a very thick suspension. The mixture was stirred for 30 minutes and then allowed to separate. Water (5 L) was added, the organic layer was separated, and the aqueous layer was extracted twice with chloroform (4 L). The combined organic layers were washed with aqueous 1% sodium hydroxide, followed by aqueous 1N hydrochloric acid, and then concentrated under vacuum to give the desired product (1365 g).

Step 1-2: Synthesis of
(5-Methyl-pyridin-2-yl)-methanol

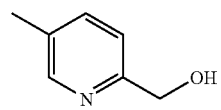

To acetic anhydride (1.61 L) at 90° C. was added 2,5-dimethyl-pyridine 1-oxide (1000 g) dropwise over 3 hours, maintaining a temperature between 90-100° C. The reaction was stirred at 90° C. for 1.5 hours, and then cooled with stirring overnight. The mixture was slowly poured into aqueous 25% sodium hydroxide (3 L) over 4 hours, and then dichloromethane (8 L) and water (8 L) were added, and the mixture was allowed to separate for 2 days. The aqueous layer was separated and extracted separately with dichloromethane and ethyl acetate, and the combined organic layers were concentrated to dryness. The crude material was applied to the top of a pad of silica (~1 kg) and eluted with ethyl acetate until no product was observed in the eluant. The filtrate was concentrated under vacuum to give the desired product (320 g).

Step 1-3: Synthesis of
2-Chloromethyl-5-methyl-pyridine hydrochloride

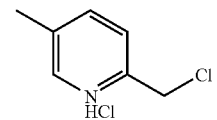

To (5-methyl-pyridin-2-yl)-methanol (310 g) in dichloromethane (1.2 L) was added thionyl chloride (200 mL) dropwise over 1.5 hours. The reaction was stirred for 2 hours, and then concentrated under vacuum. Ethyl acetate (1 L) was added, and the mixture was again concentrated to dryness. Additional ethyl acetate (1.5 L) was added, and the suspension was stirred for 30 minutes and then filtered to isolate the desired product as a solid, which was dried under nitrogen.

Step 2: Synthesis of
5-tert-Butylsulfanyl-2,2-dimethyl-4-oxo-pentanoic acid ethyl ester Step 2-1: Synthesis of
4-Chloro-2,2-dimethyl-pent-4-enoic acid ethyl ester

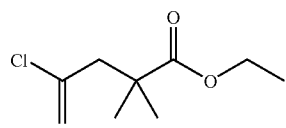

Diisopropylamine (1.25 eq) was added to a reaction flask containing tetrahydrofuran (10.0-fold, V/W of ethyl isobutyrate) under nitrogen. The mixture was cooled to less than −70° C., and n-butyllithium (2.7M; 1.14 eq) was added to the reaction mixture while the temperature was maintained at less than −65° C. The reaction mixture was slowly warmed to room temperature and then stirred for 2 hours under nitrogen. The reaction mixture was then cooled to less than −70° C., and ethyl isobutyrate (1.0 eq) was added, followed by 2,3-dichloro-1-propene (1.09 eq), while the temperature was maintained at less than −70° C. The reaction was allowed to warm to room temperature and stirred overnight under nitrogen. The reaction was then quenched with ice water (10.0-fold, V/W of starting material), and the pH adjusted to pH 7 with aqueous 6M hydrochloric acid. The organic layer was separated, washed twice with brine, and dried over sodium sulfate. The solvent was removed in vacuo and the product was taken on to the next step without further purification.

Step 2-2: Synthesis of
5-Bromo-2,2-dimethyl-4-oxo-pentanoic acid ethyl ester

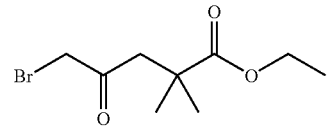

4-Chloro-2,2-dimethyl-pent-4-enoic acid ethyl ester (1.0 eq) was added to a reaction flask containing ethanol (4.4-fold, V/W of starting material) and water (3.2-fold, V/W of starting material) under nitrogen. The reaction mixture was cooled to less than 0° C., and bromine (1.02 eq) was added to the reaction mixture while the temperature was maintained at less than 0° C. After agitating for 2 hours, the reaction was checked for completion by NMR analysis. Since no starting material was seen by NMR analysis, the reaction was diluted with cold water (10.0-fold, V/W of starting material) and stirred for 5-10 minutes. The organic layer (on the bottom) was separated, with the aqueous layer was extracted with dichloromethane until no product was seen in the aqueous layer. The combined organic layers were then washed with aqueous 5% sodium carbonate (6-fold, V/W of starting material) and brine (3.0-fold, V/W of starting material). The organic layer was dried over sodium sulfate and concentrated in vacuo to give the desired product.

Step 2-3: Synthesis of
5-tert-Butylsulfanyl-2,2-dimethyl-4-oxo-pentanoic acid ethyl ester

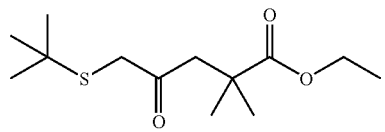 [SMILES: CCOC(=O)C(C)(C)CC(=O)CSC(C)(C)C]

To a reaction flask containing tetrahydrofuran (5.0-fold, V/W of starting material) was added 5-bromo-2,2-dimethyl-4-oxo-pentanoic acid ethyl ester (1.0 eq) under nitrogen. The mixture was cooled to a temperature of −5-0° C., and a solution of 2-methyl-2-propanethiol (1.2 eq) and triethylamine (1.25 eq) was added while maintaining the temperature below 0° C. The reaction was stirred at room temperature for 25 hours, and then hexane (3.0-fold, V/W of starting material)

was slowly added. After agitating for 30 minutes, the solid material was removed by filtration and washed with 50% ethyl acetate/hexane solution. The filtrate was concentrated under reduced pressure to give the desired product, which was taken on to the next step without further purification.

Step 3: Synthesis of Compound 1 and Salts Thereof

Step 3-1: Synthesis of N-(4-Bromo-benzyl)-N-(4-methoxy-phenyl)-hydrazine Hydrochloride

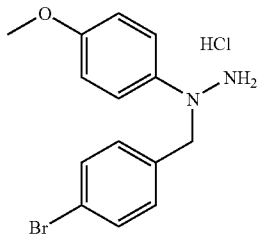 [SMILES: COc1ccc(N(N)Cc2ccc(Br)cc2)cc1 ; Cl]

4-Methoxyphenylhydrazine hydrochloride (1.0 eq) was added to a reaction flask containing toluene (16.5-fold, V/W of starting material) under $N_2$. 4-Bromobenzyl bromide (1.05 eq) and triethylamine (2.1 eq) were added, and the mixture was heated to 100-105° C. and stirred for 3 hours. The reaction was then cooled to room temperature and checked by analytical thin layer chromatography (tlc) for completion. Since no starting material was seen by tlc analysis, the reaction was diluted with ethyl acetate (10.0-fold, V/W of starting material) and agitated for 1.5 hours. The mixture was filtered to collect the solid product, which was subsequently washed with toluene and dried under vacuum at 60-65° C. Ethyl acetate (10.0-fold, V/W of starting material) was then added to the product and the mixture was agitated well. The pH of the solution was adjusted to pH 2 with saturated hydrochloric acid/ethyl acetate solution and further agitated for 1 hour. The solid was then collected by filtration, washed with cold ethyl acetate, and air dried. The product was taken on to the next step without further purification.

Step 3-2: Synthesis of 3-[1-(4-Bromo-benzyl)-3-tert-butylsulfanyl-5-methoxy-1H-indol-2-yl]-2,2-dimethyl-propionic acid ethyl ester

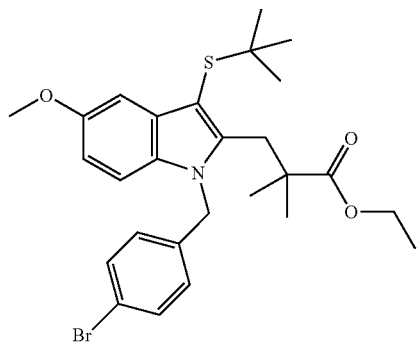 [SMILES: CCOC(=O)C(C)(C)Cc1c(SC(C)(C)C)c2cc(OC)ccc2n1Cc1ccc(Br)cc1]

N-(4-Bromo-benzyl)-N-(4-methoxy-phenyl)-hydrazine hydrochloride (1.0 eq) was added to a reaction flask containing toluene (10.0-fold, V/W of starting material) under nitrogen. Acetic acid (5.0-fold, V/W of starting material) was added, followed by 5-tert-butylsulfanyl-2,2-dimethyl-4-oxo-pentanoic acid ethyl ester (1.05 eq) and sodium acetate (2.3 eq), and the reaction mixture was stirred at room temperature for 4 days. Cold water (15.0-fold, V/W of starting material) was then added to the reaction, and the mixture was agitated for 30 minutes. The organic layer was separated, and the aqueous layer was extracted with toluene (2.0-fold, V/W of starting material) to recover additional product. The combined organic layers were washed with water and brine, dried over sodium sulfate, and concentrated under reduced pressure. A slurry of the crude material was made in methanol (5.0-fold, V/W of starting material), and the mixture was cooled to 0-5° C. for 4 hours. The solid was collected by filtration and washed with cold methanol, and the isolated material was dried under reduced pressure at 28-30° C.

Step 3-3: Synthesis of 3-[1-(4-Bromo-benzyl)-3-tert-butylsulfanyl-5-hydroxy-1H-indol-2-yl]-2,2-dimethyl-propionic acid ethyl ester

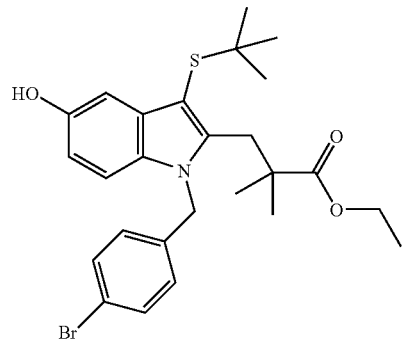 [SMILES: CCOC(=O)C(C)(C)Cc1c(SC(C)(C)C)c2cc(O)ccc2n1Cc1ccc(Br)cc1]

To a reaction vessel containing dichloromethane (3.3-fold, V/W of starting material) was added 3-[1-(4-bromo-benzyl)-3-tert-butylsulfanyl-5-methoxy-1H-indol-2-yl]-2,2-dimethyl-propionic acid ethyl ester (1.0 eq) under nitrogen. 2-Methyl-2-propanethiol (7.80 eq) was added to the mixture, and the reaction was cooled to a temperature of −5-0° C. While maintaining the reaction mixture at less than 0° C., aluminum chloride (3.30 eq) was added portion-wise, and the reaction was stirred at 0-5° C. for 2 hours. Once no starting material was seen by tlc analysis (5% ethyl acetate/hexanes), the reaction was warmed to room temperature and quenched with ice-water (6.5-fold, V/W of starting material). The mixture was acidified to pH 2 with aqueous 2.0M hydrochloric acid, and the organic layer was separated. The aqueous layer was extracted with dichlormethane to recover remaining product, and the combined organic layers were washed successively with aqueous 1.0M hydrochloric acid, water, and brine, and concentrated in vacuo. Ethyl acetate (1.0-fold, V/W of starting material) was added to the crude material, and the mixture was heated until all the product was in solution. The flask was gradually cooled to 0-2° C., and hexane (11.0-fold, V/W of starting material) was slowly added. The mixture was agitated for 2 hours, and the precipitate was isolated by filtration and dried under vacuum to give the desired product.

Step 3-4: Synthesis of 3-{3-tert-Butylsulfanyl-5-hydroxy-1-[4-(4,4,5,5-tetramethyl-[1,3,2]dioxaborolan-2-yl)-benzyl]-1H-indol-2-yl}-2,2-dimethyl-propionic acid ethyl ester

Step 3-5: Synthesis of 3-{3-tert-Butylsulfanyl-1-[4-(6-ethoxy-pyridin-3-yl)-benzyl]-5-hydroxy-1H-indol-2-yl}-2,2-dimethyl-propionic acid ethyl ester

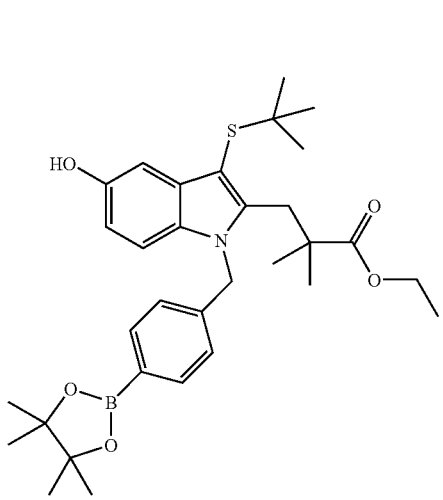 [SMILES: CCOC(=O)C(C)(C)Cc1c(SC(C)(C)C)c2cc(O)ccc2n1Cc1ccc(B2OC(C)(C)C(C)(C)O2)cc1]

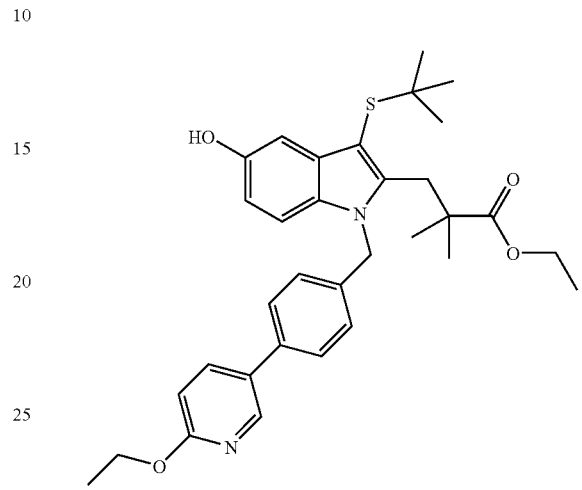

3-[1-(4-Bromo-benzyl)-3-tert-butylsulfanyl-5-hydroxy-1H-indol-2-yl]-2,2-dimethyl-propionic acid ethyl ester (1.0 eq), bis(pinacolato)diboron (1.10 eq), and potassium acetate (3.0 eq) were dissolved in dimethylformamide (10.0-fold, V/W of starting material) under nitrogen. The solution was sparged with nitrogen for 30 minutes with stirring, and then Pd(dppf)Cl$_2$ (0.057 eq) was added, and the mixture was sparged with nitrogen for an additional 15 minutes with stirring. The reaction was then heated to 80-85° C. under nitrogen for 2 hours. Once no starting material was seen by tlc analysis (7% ethyl acetate/hexanes), the reaction was cooled to room temperature and diluted with water (12.0-fold, V/W of starting material). The mixture was extracted with methyl tert-butyl ether until no product was observed in the aqueous layer. The combined organic layers were washed twice with water (10.0-fold, V/W of starting material) and once with brine (6.0-fold, V/W of starting material), dried over sodium sulfate, and then filtered through a pad of silica (2.0-fold, V/W of starting material, prewashed with methyl tert-butyl ether). The pad of silica was washed with methyl tert-butyl ether until no product was observed in the filtrate, and the solvent was removed in vacuo to give the crude material. The solid was dissolved in ethyl acetate (0.85-fold, V/W of starting material) and stirred for 30 minutes, and then cooled to 0-2° C. Hexane (10.0-fold, V/W of starting material) was slowly added over 30 minutes, and the suspension was stirred for an additional 3 hours at 0-2° C. The precipitate was isolated by filtration, washed with 50% ethyl acetate/hexanes, and dried under vacuum at 30-35° C. to give the desired product.

To a stirring mixture of dimethoxyethane (16.5 L) and water (6.6 L) in a 50 L reaction flask under nitrogen was added 3-{3-tert-butylsulfanyl-5-hydroxy-1-[4-(4,4,5,5-tetramethyl-[1,3,2]dioxaborolan-2-yl)-benzyl]-1H-indol-2-yl}-2,2-dimethyl-propionic acid ethyl ester (1652.19 g), 5-bromo-2-ethoxypyridine (650.30 g), and potassium carbonate (605.03 g). The mixture was sparged with nitrogen for 30 minutes to remove dissolved oxygen gas, and then tetrakis (triphenylphosphine)palladium(0) (59.15 g) was added, and the reaction mixture was heated to 65-85° C. over 2 hours and stirred at 65-85° C. under nitrogen for 19 hours. Once no starting material was seen by tlc analysis, the reaction was cooled to 40° C. and water (6.6 L) was added. Ethyl acetate (6.6 L) was added, and the mixture was agitated for 20 minutes and then allowed to separate over 1.5 hours. The aqueous layer was separated, and additional water (6.6 L) was added to the organic layer. The mixture was agitated for 2 minutes and then allowed to separate over 1 hour, with additional ethyl acetate (1.4 L) added to facilitate phase separation. The aqueous layer was separated, and the two aqueous layers were combined. Ethyl acetate (5.0 L) was added to the combined aqueous layer, and the mixture was agitated for 3 minutes and allowed to separate over 2 minutes. The aqueous layer was separated, and the two organic layers were combined and treated with activated carbon, Novit Neutral (446.43 g). The mixture was stirred for 17 hours at room temperature, and then filtered through a 1-2" pad of Celite. The reaction flask was rinsed twice with ethyl acetate (1.25 L) and filtered through the pad of Celite, and the filtrate was concentrated to give the crude material. Methyl tert-butyl ether (8.2 L) was added to the solids, and the mixture was agitated for 1.5 hours and filtered. The flask was rinsed with methyl tert-butyl ether (1 L) three times and then filtered through the filter cake. The Step 3-6: Synthesis of 3-[3-tert-Butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester

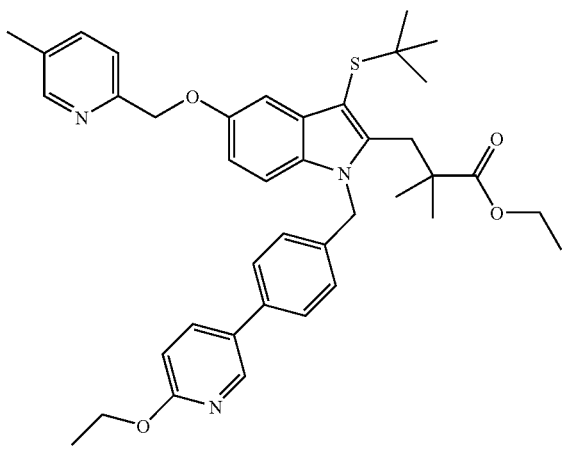 [SMILES: CCOC(=O)C(C)(C)Cc1c(SC(C)(C)C)c2cc(OCc3ccc(C)cn3)ccc2n1Cc1ccc(-c2ccc(OCC)nc2)cc1]

3-{3-tert-Butylsulfanyl-1-[4-(6-ethoxy-pyridin-3-yl)-benzyl]-5-hydroxy-1H-indol-2-yl}-2,2-dimethyl-propionic acid ethyl ester (1313.2 g) was dissolved in acetonitrile (20.0 L) in a 50 L reaction flask under nitrogen, and the mixture was stirred and heated to 30-40° C. Cesium carbonate (2118.67 g) was added, followed by 2-chloro-5-methylpyridine hydrochloride (497.17 g), and the temperature was increased to 70-80° C. over 2 hours. After heating at 70-80° C. for 4 hours, no starting material was seen by tlc analysis, and the mixture was cooled to 55° C. and concentrated. The residue was dissolved in dichloromethane (2 L) and water (2 L) and transferred to a flask containing dichloromethane (4 L) and water (4 L). The original flask was rinsed twice with dichloromethane (2 L) and water (2 L), and the combined material was then diluted with an additional 3 L of dichloromethane and 6 L water to a total volume of 13 L of dichloromethane and 16 L of water. The mixture was agitated for 10 minutes and allowed to separate over 10 minutes. The organic layer was separated, and additional dichloromethane (9 L) was added to the aqueous layer. The mixture was agitated for 6 minutes and allowed to separate over 5 minutes. The organic layer was separated, and the two organic layers were combined and treated with activated carbon, Novit Neutral (433.07 g) and silica gel, thiol derivatized (91.17 g). The mixture was stirred for 17 hours at room temperature, and then filtered through a 1-2" pad of Celite. The flask was rinsed with dichloromethane (2.6 L) and filtered through the pad of Celite, and the filtrate was concentrated to give the crude material. Ethanol (9.2 L) was added to the solids, and the mixture was stirred slowly for 17 hours and filtered. The isolated solids were dried in a drying oven at 45° C. under vacuum for 2 days to give the desired product (1459.4 g).

isolated solids were dried in a drying oven at 25° C. under vacuum for 3 days to give the desired product (1314 g).

Synthesis of Compound 1

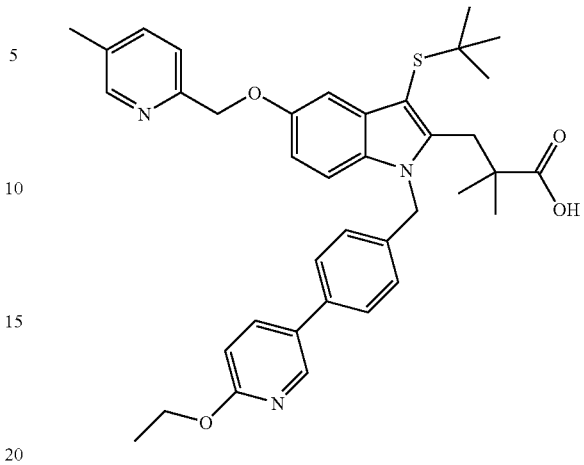

Compound 1

To 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester (313.8 g) in a mixture of tetrahydrofuran (1.8 L), methanol (600 mL) and water (600 mL) was added lithium hydroxide monohydrate (25.5 g, 0.607 mol) after which the solution was heated to 55° C. Upon completion by LCMS analysis the reaction volume was reduced by half through rotary evaporation, diluted with dichloromethane and 1N HCl (605 mL) was added to reduce the aqueous pH to approximately pH 3. The mixture was then extracted with dichloromethane (three times), the combined organic phases dried (magnesium sulfate), filtered and evaporated. The residue was triturated with 4 L of a 10:1 hexanes:ethyl acetate mixture for 12 hrs and filtered to afford Compound 1 as a colorless solid. $^1$H NMR (300 MHz, CDCl$_3$) δ 8.46 (s, 1H), 8.27 (d, 1H), 7.76 (d, 1H), 7.46-7.55 (m, 2H), 7.32 (m, 3H), 6.99 (d, 1H), 6.82 (m, 3H), 6.73 (d, 1H), 5.42 (s, 2H), 5.19 (s, 2H), 5.36 (q, 2H), 3.33 (br s, 2H), 2.34 (s, 3H), 1.40 (t, 3H), 1.26 (s, 6H), 1.21 (s, 9H).

Synthesis of Compound 2

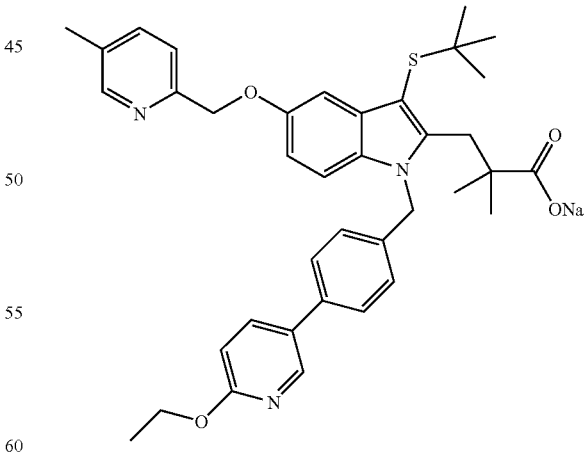

Compound 2

3-[3-tert-Butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid ethyl ester (1298.9 g) was dissolved in ethanol (5.2 L) and tetrahydrofuran (2.6 L) in a 50 L reaction flask. 50% Sodium hydroxide solution (148.48 g) was added, and the mixture was stirred and heated to 66-75°

C. over 1.5 hours. After heating at 66-75° C. for 16 hours, the reaction was analyzed by tlc to determine whether starting material was still present. 50% Sodium hydroxide solution was added in 1% increments until the reaction was complete by tlc analysis, which resulted in the addition of an additional 1.56 g of 50% aqueous sodium hydroxide solution. The reaction was then filtered through a 90 mm 1 micron filter membrane, and the filtrate was concentrated to give the product (1344.3 g).

Example 2

Polymorph Control of Compound 2

Methyl tert-butyl ether (10.6 L) was filtered through a 1 micron filter membrane into a 50 L reaction flask. Compound 2 (1324.3 g) was added, and the mixture was heated to 53-55° C. for 5 hours with stirring. The solids were then isolated by filtration and dried under vacuum at room temperature for 5 days to give the product (1161.4 g) as Form C.

Polymorphs of Compound 2

Compound 2 is a white to off-white crystalline powder with pKa values of 3.45, 4.71, and 5.82 and a log PO/W of 5.9. At least three polymorphic forms have been characterized, which are labeled as amorphous Phase A, crystalline Solvated Form B and crystalline Form C (desolvated). Form C is physically and chemically stable, crystalline, non-hygroscopic, and desolvated. In one aspect, Polymorph Solvated Form B and Polymorph Form C are obtained by solid to solid transformation from methyl tert-butyl ether (MTBE).

Amphorous Phase A.

Amphorous Phase A is chemically stable, amorphous and hygroscopic. Hygroscopicity was assessed by GVS, and the amorphous material adsorbed more than 20% of water at 90% RH. The TGA (thermogravimetric analysis) for the amorphous material showed a weight loss of 4.6% at low temperatures and the DSC experiment showed a phase change to the more stable crystalline form.

Solvated Form B:

Solvated Form B is crystalline, solvated with methyl tert-butyl ether and water, and is physically and chemically stable. The melting point range for Solvated Form B is 130-170° C. The DSC for Solvated Form B showed a phase change to a more stable form. Solvated Form B converts to Form C upon heating. GVS (gravimetric vapor sorption) experiments show that Solvated Form B is a hygroscopic material, taking up to more than 30% of water at 90% RH after a full sorption/desorption cycle.

Solvated Form B is obtained from methyl tert-butyl ether solutions wherein a protic co-solvent (such as for example water or ethanol) is also present during the transformation event. In one aspect, the protic co-solvent is present in the methyl tert-butyl ether solvent. In other aspects, the protic co-solvent is carried forward from the hydrolysis reaction (i.e. hydrolysis of the ester).

Solvated Form B is also obtained as follows: Amorphous Phase A (50 mg) was dissolved in 200 µl of isopropyl alcohol with controlled heating. The resulting solution was left to cool down to room temperature, with crystals forming after about an hour. Both the XRPD (X-ray powder diffraction) pattern and the DSC (differential scanning calorimetry) thermogram of the isolated crystals matched that of crystalline form B.

Polymorph Form C

Polymorph Form C is physically and chemically stable (5° C., 25° C./60% RH (relative humidity) and 40° C./75% RH for at least one month), crystalline and desolvated. The melting point range for Form C is 295-300° C. By dynamic vapor sorption analysis, Form C reversibly adsorbed <9% water at 90% relative humidity and is, therefore, considered to be nonhygroscopic. Form C did not show any weight loss in the TGA prior to degradation and only a melt in the DSC thermogram.

Form C is obtained by ensuring removal (dehydration) of any protic co-solvents during the isolation from methyl tert-butyl ether. The use of a re-suspension of the crude final material along with heating in anhydrous methyl tert-butyl ether is intended to ensure that protic solvents are removed (thereby pushing the crystal form to form C).

In the event that Solvated Form B is formed during the final crystallization event, Solvated Form B can be converted to Form C through the suspension/heating in anhydrous methyl tert-butyl ether (with the crystalline inter-conversion presumably proceeding through a process of dehydration).

Oral dosing in rats of both amorphous phase A and polymorph Form C provided equivalent plasma exposures.

A number of other solvents were examined in order to explore other crystal formation or precipitation conditions. The procedure consisted of dissolving 50 mg of material (amorphous batch) in the corresponding solvent system, assisted by controlled heating. The samples were then left to cool down to room temperature. If the produced no solids after cooling, the solvent was left to evaporate slowly. These results are summarized in the Table 1 below.

TABLE 1

Solvent Systems used For Crystal Formation

| Solvent System | Volume of Solvent System | Comments |
| --- | --- | --- |
| Methanol | 200 µl | Amorphous formed by evaporation of solvent |
| Ethanol | 200 µl | Amorphous formed by evaporation of solvent |
| Isopropanol | 200 µl | Crystalline material; XRPD correlates to Form B |
| Dimethylsulfoxide | 200 µl | Crystalline material |
| methanol/water | 200 µl | Very fine particles |
| ethanol/water | 200 µl | Very fine particles |
| isopropanol/water | 200 µl | Very fine particles |
| Acetone/water | 200 µl | amorphous |
| Acetonitrile | 200 µl | Crystalline material formed by evaporation of solvent; XRPD correlates to Form C |
| acetonitrile/water | 200 µl | amorphous formed by evapouration of solvent |

Crystals obtained from acetonitrile have an XRPD pattern which correlates with the XRPD pattern of Form C. The crystals obtained from isopropanol or dimethylsulfoxide showed different crystalline patterns. The crystals obtained from isopropanol have an XRPD pattern which correlates with the XRPD pattern for Form B. The DSC thermograms for both materials also match.

Example 3

Amorphous potassium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-propionate Compound 1 (1.03 g, 1.62 mmol) was suspended in ethanol (20 mL) to which 1N potassium hydroxide (1.62 mL, 1.62 mmol) was added and the solution stirred for 1 hour. The solvent was then evaporated and the residue dissolved in water, frozen rapidly and lyophilized until dry.

Example 4

Amorphous 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethyl-proprionic acid choline salt Compound 1 (1.05 g, 1.64 mmol) was dissolved in ethanol (20 mL) to which a 20% (by weight) solution of choline hydroxide (0.97 mL, 1.64 mmol) was added and the suspension stirred for 1 hour. The solvent was evaporated and the residue dissolved in water, frozen rapidly and lyophilized until dry.

Example 5

Ion Chromatography (IC)

Data were collected on a Metrohm 861 Advanced Compact IC using IC Net software v2.3. Samples were prepared as 1000 ppm stocks in water. Where sample solubility was low, a suitable solvent such as dimethylsulfoxide was used. Samples were diluted to 50 ppm or 100 ppm with an appropriate solvent prior to testing. Quantification was achieved by comparison with standard solutions of known concentration of the ion being analysed.

TABLE 2

Ion Chromatography (IC) conditions

| Type of method | Cation exchange |
|---|---|
| Column: | Metrosep C 2 – 250 (4.0 × 250 mm) |
| Column Temperature (° C.): | Ambient |
| Injection (µl): | 20 |
| Detection: | Conductivity detector |
| Flow Rate (ml · min$^{-1}$): | 1.0 |
| Eluent: | 4.0 mM Tartaric acid, 0.75 mM Dipicolinic acid in water |

The stoichiometry of the sodium salts was determined by ion chromatography to be about 1:1.

Example 6

Thermodynamic Aqueous Solubility by HPLC

Aqueous solubility was determined by suspending sufficient compound in water to give a maximum final concentration of ≥10 mg.ml$^{-1}$ of the parent free-form of the compound. The suspension was equilibrated at 25° C. for 24 hours then the pH was measured. The suspension was then filtered through a glass fibre C filter into a 96 well plate. The filtrate was then diluted by a factor of 101. Quantitation was by HPLC with reference to a standard solution of approximately 0.1 mg.ml$^{-1}$ in DMSO. Different volumes of the standard, diluted and undiluted sample solutions were injected. The solubility was calculated using the peak areas determined by integration of the peak found at the same retention time as the principal peak in the standard injection.

The HPLC protocol is set forth in Table 3.

TABLE 3

Experimental conditions for Thermodynamic Aqueous Solubility by HPLC

| Type of method: | Reverse phase with gradient elution | | |
|---|---|---|---|
| Column: | Phenomenex Luna, C18 (2) 5 µm 50 × 4.6 mm | | |
| Column Temperature (° C.): | 25 | | |
| Standard Injections (µl): | 1, 2, 3, 5, 7, 10 | | |
| Test Injections (µl): | 1, 2, 3, 10, 20, 50 | | |
| Detection: Wavelength, Bandwidth (nm): | 260, 80 | | |
| Flow Rate (ml · min$^{-1}$): | 2 | | |
| Phase A: | 0.1% TFA in water | | |
| Phase B: | 0.085% TFA in acetonitrile | | |
| Timetable: | Time (min) | % Phase A | % Phase B |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

The results of the determination of the thermodynamic solubility of the three samples are shown in Table 4.

TABLE 4

Results of aqueous solubility determination

| Sample | Compound 2 Phase A | Compound 2 Form C |
|---|---|---|
| Appearance of mixture after equilibration for 24 hours | Suspension | Solution |
| pH of unfiltered saturated solution | 9.14 | 9.57 |
| Concentration of filtrate (as mg/mL of free base) | >10 | >10 |

The solubility in water for both batches of Compound 2 is greater than 10 mg.ml$^{-1}$. The pH of the unfiltered saturated solution is above 9 for both materials.

Example 7

Solubility vs. pH

A study of solubility of Compound 2 at different values of pH was carried out. Suspensions were made up in 0.15M sodium chloride (aqueous) and the pH adjusted to the appropriate value with either diluted hydrochloric acid or sodium hydroxide, to ensure that different salt forms with different solubilities are not produced in solution. The suspension was then allowed to equilibrate for 2 h, and the pH was checked and re-adjusted if required.

The pH of the resultant solution was measured, and the solubility was calculated by HPLC-UV assay of the compound concentration in solution.

TABLE 5

Solubility of Compound 2 at different values of pH

| pH | Concentration (mg/ml) |
|---|---|
| 1.1 | 0.026 |
| 3.8 | <0.0001 |
| 6.9 | 0.0007 |
| 9.0 | 3.5 |
| 9.8 | >10 |
| 11.2 | >10 |

Aqueous solubility shows the lowest values at about pH 3-7. In this range of pH the compound is present in its neutral form. When the pH is very acidic (pH 1-2) the mildly basic groups can be protonated, and so the solubility increases slightly, although possibly not as much as expected. At basic pH (pH>8) solubility starts increasing markedly, to reach its peak at pH greater than 10, when only the corresponding sodium carboxylate is present in the solution.

Example 8

Solubility Profile in Common Organic Solvents

Table 6 provides solubility data for Compound 2 in various organic solvents.

TABLE 6

Solubility Profile in Common Organic Solvents

| Solvent | Solubility, mg/mL at 25° C. |
|---|---|
| Isopropanol | 0.2 |
| Acetonitrile | <0.01 |
| Ethanol | 109 |
| 0.5% Methylcellulose/Water | 10 |
| Methanol | 129 |

Compound 2 is very soluble in methanol and ethanol and sparingly soluble in acetonitrile and isopropanol.

Example 9

X-Ray Powder Diffraction (XRPD) Pattern Determination

X-Ray powder diffraction patterns were collected on a Siemens D5000 or Bruker AXS C2 GADDS diffractometer.

X-Ray powder diffraction patters collected on a Siemens D5000 use Cu Kα radiation (40 kV, 40 mA), θ-θ goniometer, divergence of V20 and receiving slits, a graphite secondary monochromator, and a scintillation counter. The instrument was performance checked using a certified Corundum standard (NIST 1976). Samples run under ambient conditions were prepared as flat plate specimens. Approximately 35 mg of sample was gently packed into a cavity cut into polished, zero-background (510) silicon wafer. The sample was rotated in its own plane during analysis. The details of the data collection are: (1) angular range: 2 to 42°2θ; step size: 0.05°2θ; collection time 4 s/step.

X-Ray powder diffraction patterns obtained on a Bruker AXS C2 GADDS diffractometer use Cu Kα radiation (40 kV, 40 mA), automated XYZ stage, laser video microscope for auto-sample positioning and a HiStar 2-dimentional area detector. X-ray optics consists of a single Göbel multilayer mirror coupled with a pinhole collimator of 0.3 mm. The beam divergence, i.e., the effective size of the X-ray beam on a sample of Compound 2 was approximately 4 mm. A θ-θ continuous scan mode was employed with a sample-detector distance of 20 cm which gives an effective 2θ range of 3.2°-29.7°. Typically the sample was exposed to the X-ray beam for 120 seconds. Samples run under ambient conditions were mounted as flat plate specimens. Approximately 1-2 mg of sample was lightly pressed on a glass slide to obtain a flat surface. Samples run under non-ambient conditions were mounted on a silicon wafer with heat-conducting compound. The sample was then heated to the appropriate temperature at about 10° C./min and subsequently held isothermally for about 1 minute before data collection was initiated.

The X-Ray powder diffraction pattern for Polymorph Form C is displayed in FIG. 1 and characteristic peaks were tabulated in Table 7.

TABLE 7

XRPD pattern peak data for Polymorph Form C:

| Angle 2-Theta ° | Intensity % |
|---|---|
| 15.6 | 42.7 |
| 16.6 | 43.3 |
| 17.2 | 69 |
| 17.8 | 42.6 |
| 18.4 | 49.2 |
| 19.1 | 100 |
| 19.8 | 40.5 |
| 20.8 | 91.6 |
| 23.1 | 47.8 |
| 23.8 | 59.2 |

The X-Ray powder diffraction pattern for Polymorph Form B is displayed in FIG. 2 and characteristic peaks were tabulated in Table 8.

TABLE 8

XRPD pattern peak data for Polymorph Form B:

| Angle 2-Theta ° | Intensity % |
|---|---|
| 6.6 | 68.5 |
| 8.1 | 100 |
| 19.7 | 65.1 |
| 20.3 | 42.2 |
| 21.0 | 47.4 |
| 21.9 | 49.6 |
| 22.1 | 51.4 |
| 25.0 | 38.9 |

Figure 4:
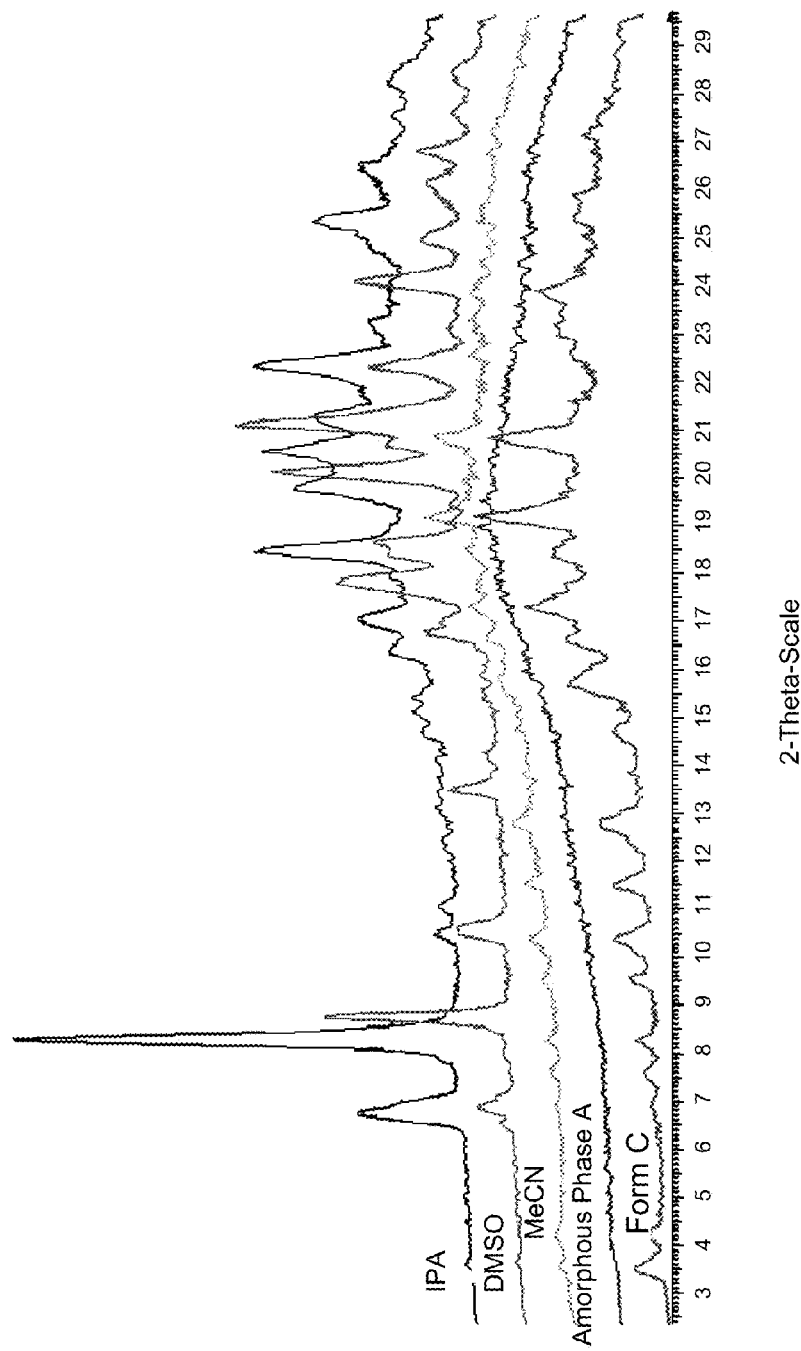
FIG. 4 illustrates a comparison of XRPD patterns of Compound 2 in which crystal formation (whether by a crystallization, solid-to-solid transformation or crystalline inter-conversion) or precipitation occurred in various solvents.

XRPD patterns of crystals obtained from isopropanol (IPA), dimethylsulfoxide (DMSO) and acetonitrile (MeCN) are shown in FIG. 4. Crystals obtained from acetonitrile have an XRPD pattern which correlates with polymorph Form C. The crystals obtained from isopropanol or dimethylsulfoxide showed different crystalline patterns. The crystals obtained from isopropanol have an XRPD pattern which correlates with the XRPD pattern for polymorph Form B. The DSC thermograms for both materials also match.

Variable Temperature XRPD

Figure 8:
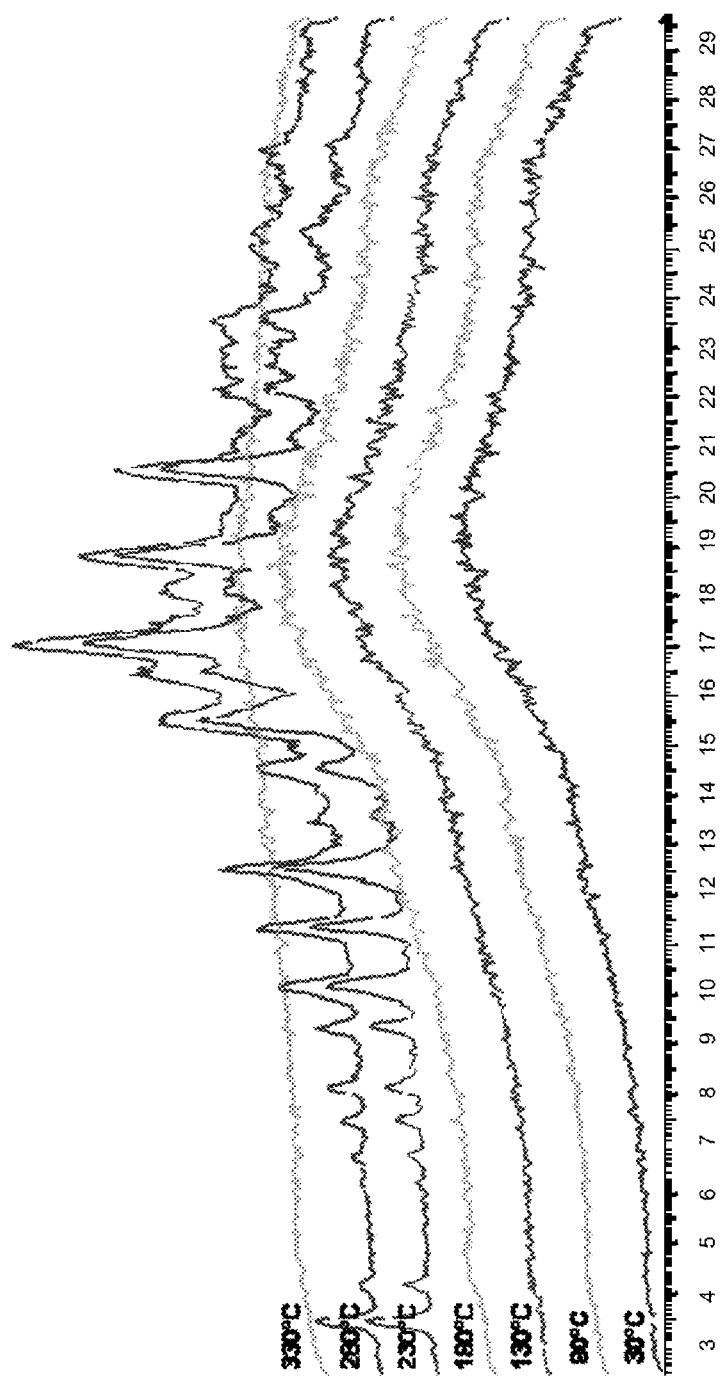
FIG. 8 illustrates a variable temperature XRPD patterns of Amorphous Phase A of Compound 2.

To investigate the possibility of a phase change occurring with the amorphous material when heated, VT-XRPD was conducted. The temperatures at which the XRPD patterns were collected were chosen based on the events observed in the DSC experiment. FIG. 8 shows the variable temperature XRPD for Amorphous Phase A. The material remains amorphous at temperatures below 180° C. However, at higher temperatures, the material shows a crystalline pattern until it melts, when it becomes amorphous again.

FIG. 9 shows a comparison of XRPD of Amorphous Phase A at high temperatures with XRPD of Form C. The new crystalline pattern for Amorphous Phase A at 230° C. and 280° C. matches the one for Form C. The differences in the shift of the peaks may be due to a difference in the lattice of the crystal due to thermal expansion.

Based on the observations from the DSC thermogram (see below), an investigation into whether a phase change from Form B to Form C was occurring was investigated using VT-XRPD experiments.

Figure 10:
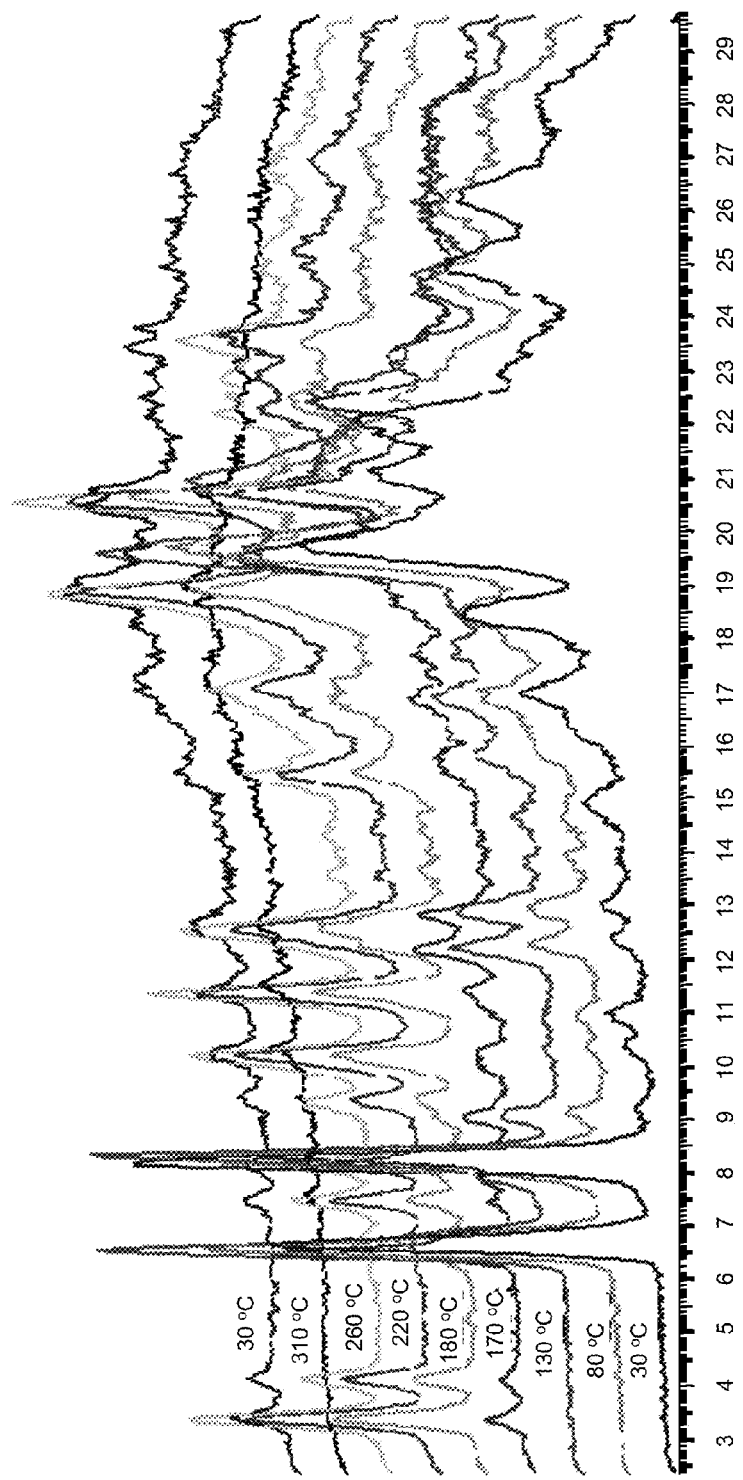
FIG. 10 illustrates a variable temperature XRPD patterns of Polymorph Form B of Compound 2.

FIG. 10 shows the VT-XRPD of polymorph Form B. Form B is stable at low temperatures. Between 130 and 170° C., a phase change starts occurring. This new crystalline form is stable until it melts at around 300° C. Then, on cooling, the material re-crystallises to produce Form C albeit with lower crystallinity, most likely due to some decomposition occurring.

FIG. 11. shows the comparison of the VT-XRPD for Form B with Form C. Form B transforms to Form C upon heating. At 180° C., there is still a mixture of 2 forms, and only above this temperature is there only one form (Form C). This is consistent with the observations extracted from the DSC thermogram for Form B.

Example 10

One Week Stability at 40° C. & 75% RH

Figure 5:
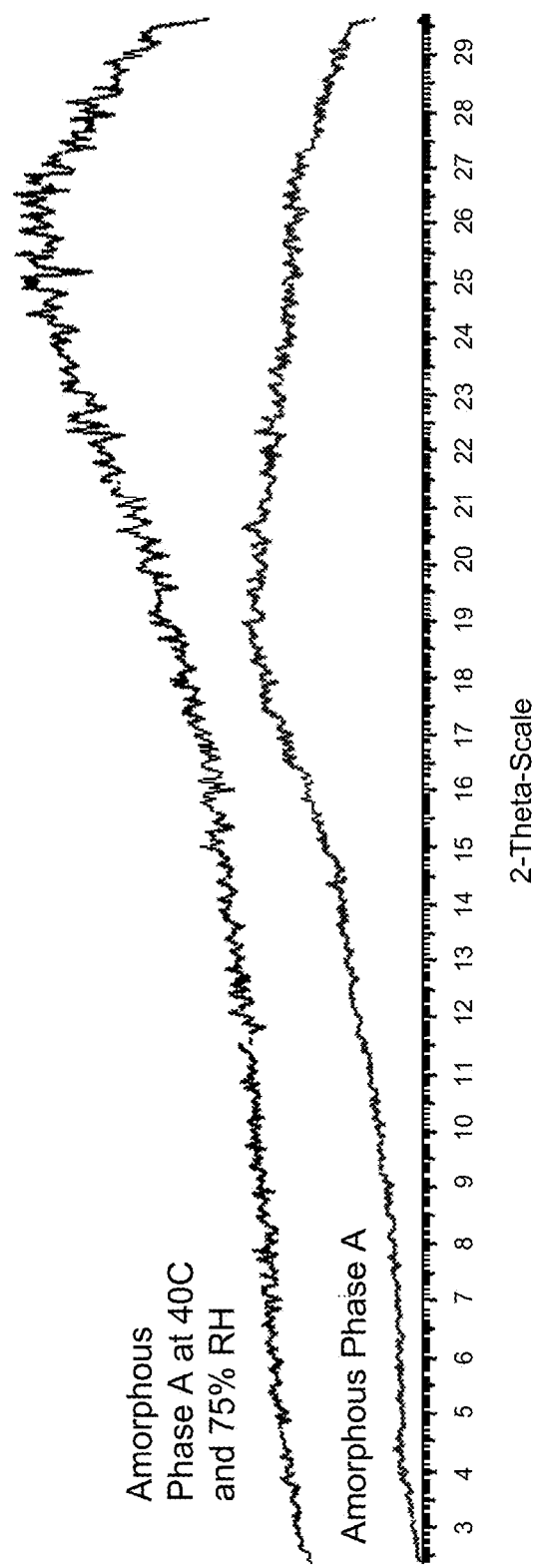
FIG. 5 illustrates a comparison of the XRPD patterns of Amorphous Phase A of Compound 2 before and after one week at 40° C. and 75% relative humidity.

One week stability study of Amorphous Phase A at 40° C. and 75% RH is shown in FIG. 5. Amorphous Phase A remains amorphous after a week in the humidity chamber, indicating that no phase change has occurred to a hydrate or otherwise.

Figure 7:
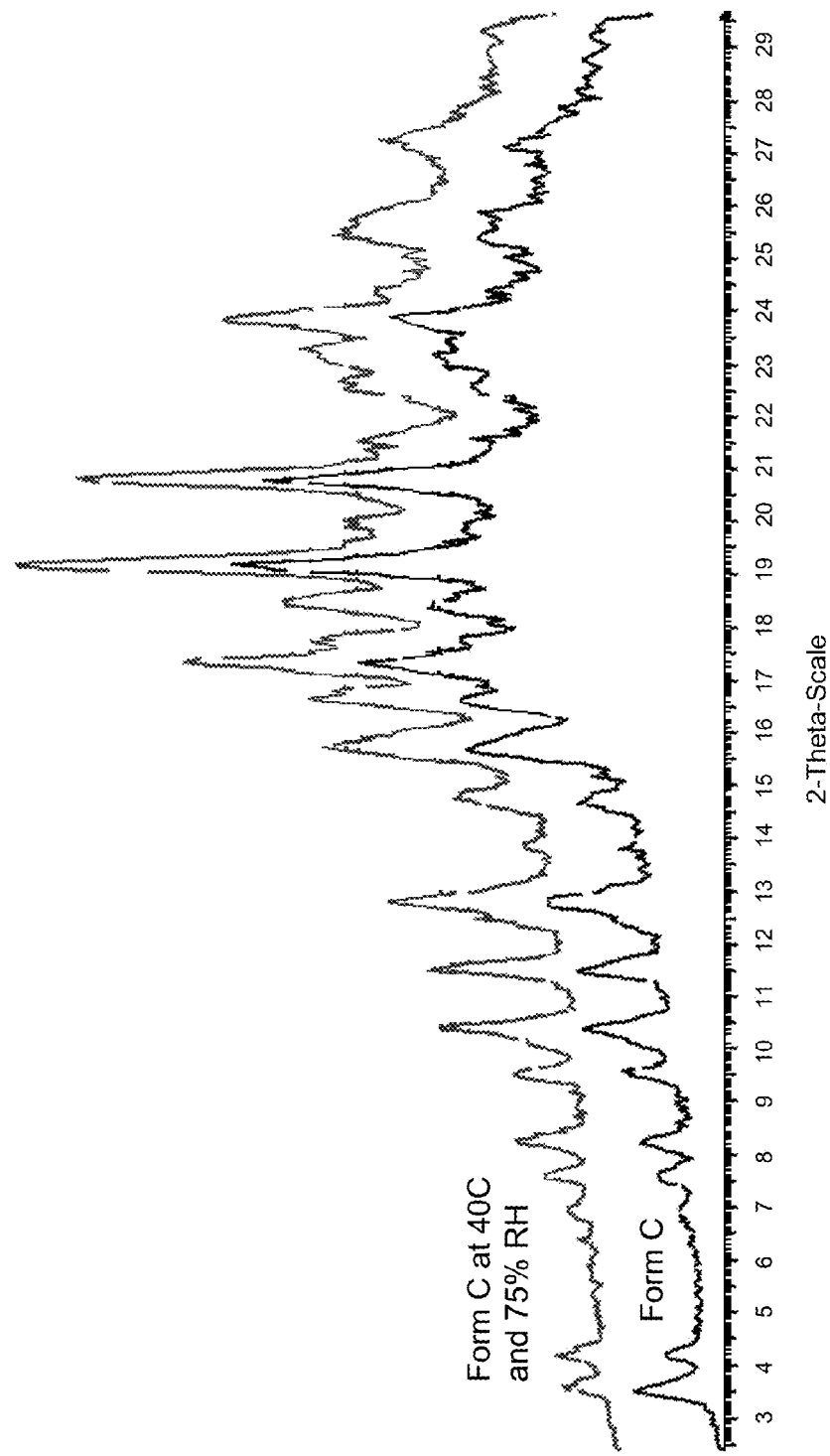
FIG. 7 illustrates a comparison of the XRPD patterns of Polymorph Form C of Compound 2 before and after one week at 40° C. and 75% relative humidity.

One week stability study of polymorph Form C at 40° C. and 75% RH is shown in FIG. 7. The crystalline pattern for polymorph Form C remains unchanged after a week in the humidity chamber.

Example 11

Differential Scanning Calorimetry (DSC) and Thermo-Gravimetric Analysis (TGA)

DSC data were collected on a TA Instruments Q1000 or a Mettler DSC 823e. DSC data were collected on a TA Instruments Q1000 equipped with a 50 position auto-sampler. The instrument was calibrated for energy and temperature calibration using certified indium. Typically 0.5-3 mg of each sample, in a pin-holed aluminium pan, was heated at 10° C.min$^{-1}$ from 25° C. to 350° C. A nitrogen purge at 50 ml.min$^{-1}$ was maintained over the sample. The instrument control software was Thermal Advantage v4.6.6 and the data were analysed using Universal Analysis v4.3A.

DSC data were collected on a Mettler DSC 823e equipped with a 50 position auto-sampler. The instrument was calibrated for energy and temperature using certified indium. Typically 0.5-3 mg of each sample, in a pin-holed aluminium pan, was heated at 10° C.min$^{-1}$ from 25° C. to 350° C. A nitrogen purge at 50 ml.min$^{-1}$ was maintained over the sample. The instrument control and data analysis software was STARe v9.01.

TGA data were collected on a Mettler TGA/SDTA 851e equipped with a 34 position auto-sampler. The instrument was temperature calibrated using certified indium. Typically 5-30 mg of each sample was loaded onto a pre-weighed aluminium crucible and was heated at 110° C.min$^{-1}$ from ambient temperature to 350° C. A nitrogen purge at 50 ml.min$^{-1}$ was maintained over the sample. The instrument control and data analysis software was STARe v9.01.

Amorphous Phase A

FIG. 12 shows the TGA (top) and DSC (bottom) thermograms for Amorphous Phase A. Amorphous Phase A shows a weight loss of 4.6% at low temperatures. The compound is otherwise stable up to temperatures above 300° C. In the DSC, three endothermic events are observed and one exothermic phase change. The first event, occurring at 35° C. is associated with the weight loss observed in the TGA. There is another small endotherm at 126° C. followed by an exotherm at 212° C., which likely corresponds to a phase change of the material. The compound then melts at 295° C. These observations are consistent with what was observed by hot-stage microscopy. The DSC experiment showed a phase change to the more stable crystalline form. This point was later confirmed by variable temperature XRPD experiments, and it was further illustrated by hot-stage microscopy.

Figure 13:
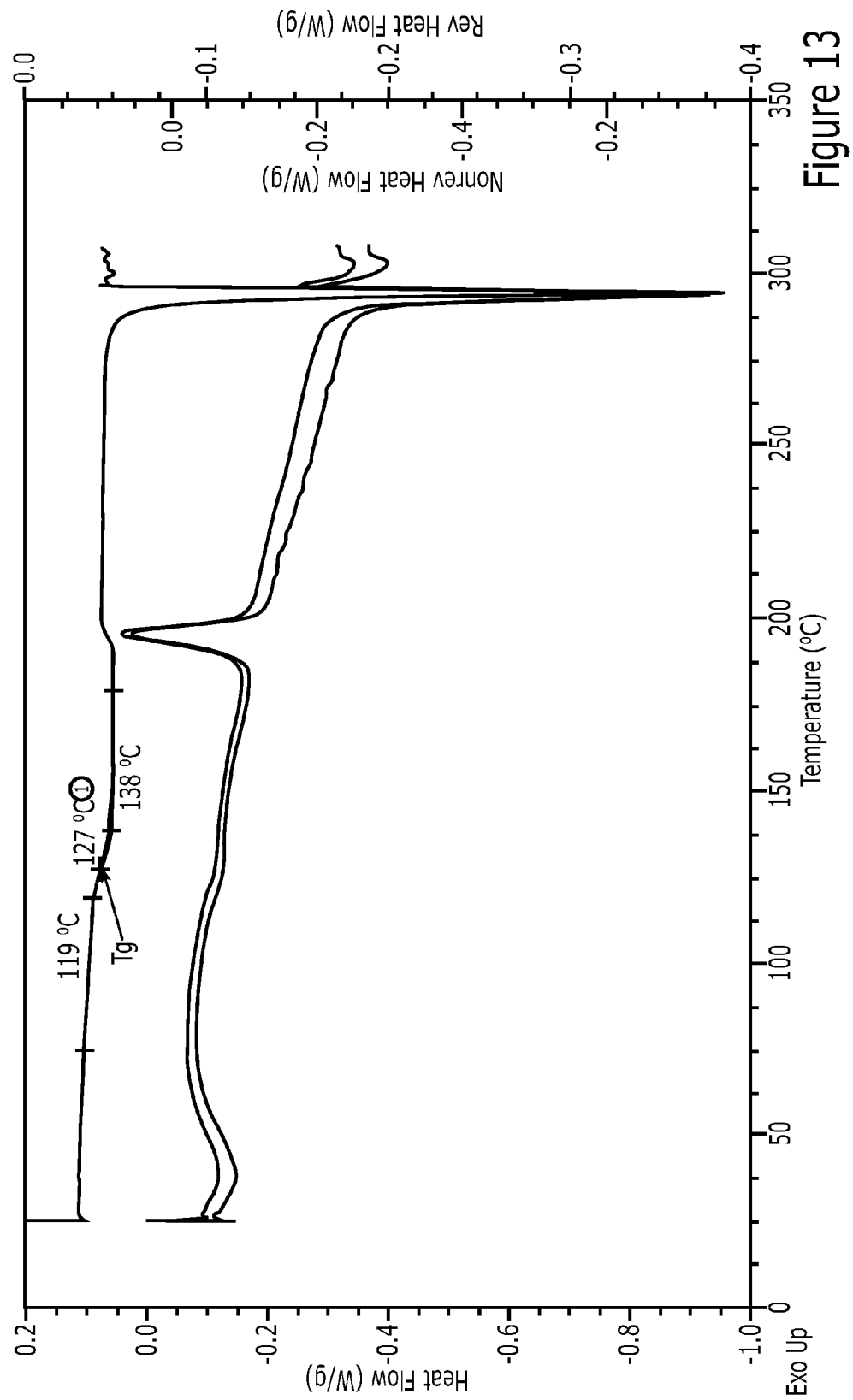
FIG. 13 illustrates a modified DSC (bottom) and TGA (top) trace for Amorphous Phase A of Compound 2.

FIG. 13 shows a modulated DSC thermogram for Amorphous Phase A. In order to measure the glass transition temperature of the amorphous form, a modulated DSC experiment was carried out. $T_g$ was estimated to be 127° C. (coincidental with the weak endotherm observed in the standard DSC experiment). Another step in the thermogram (phase change) is observed and the corresponding melt. These two events also correlate with the ones observed in the standard DSC experiment.

Polymorph Form B

Figure 14:
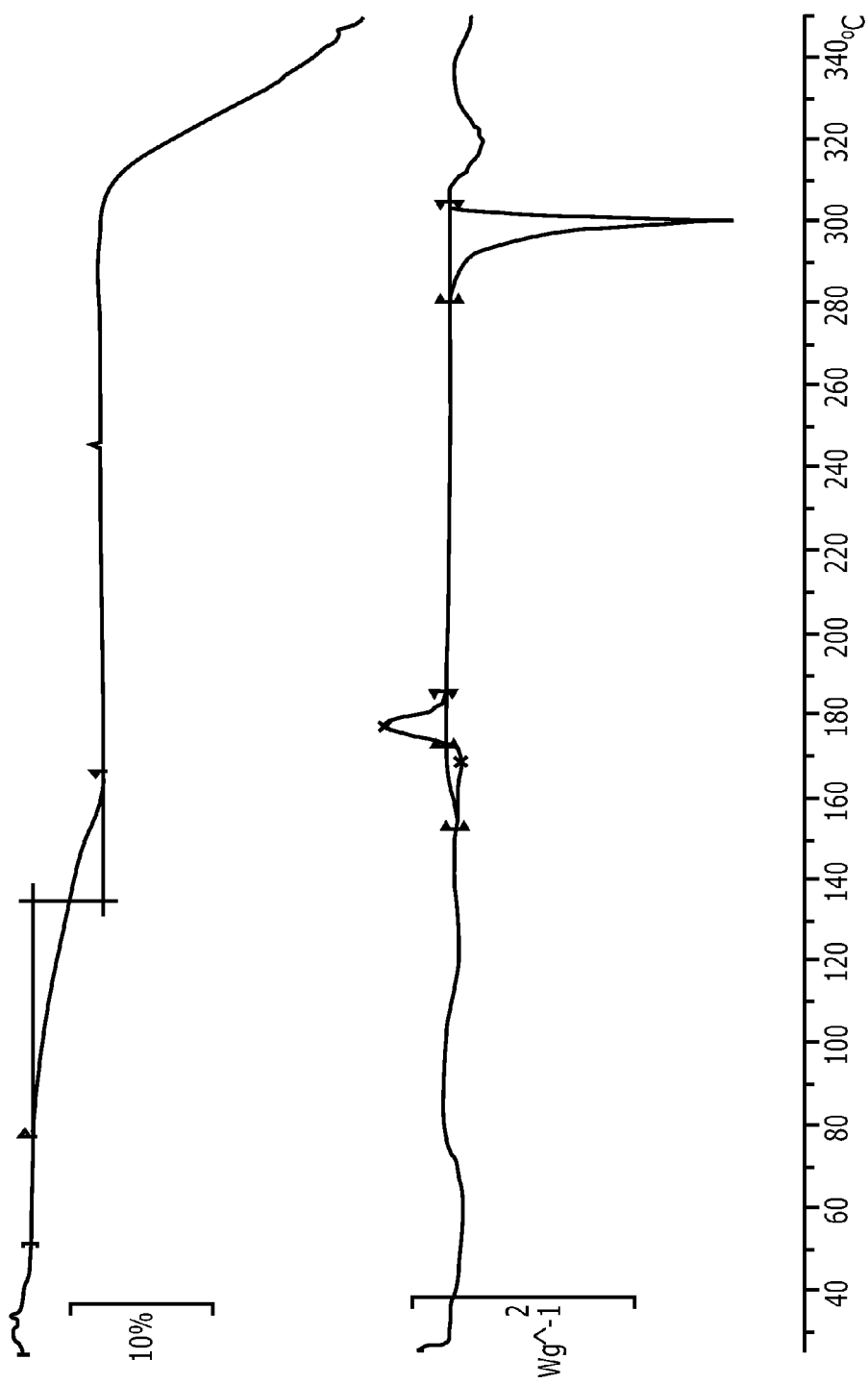
FIG. 14 illustrates a DSC (bottom) and TGA (top) trace for Polymorph Form B of Compound 2.

FIG. 14 shows the results of TGA (top) and DSC (bottom) experiments for polymorph Form B. There is a weight loss of 4.8% between 80 and 160° C. This could be due to process solvent or to the desolvation of a solvate. Being such a hygroscopic material, the presence of moisture cannot be ruled out. After this, the weight remains constant until the temperature is above 310° C., when decomposition starts. There are some fluctuations on the baseline of the DSC which correlate with the weight losses observed in the TGA. Three more significant events can also be observed. Firstly, a weak endotherm (onset at 158° C.) immediately followed by an exotherm (onset at 173° C.), a phase change and re-crystallisation to a new form. There is also an endothermic event at 297° C., which correlates with the melt of the previous crystalline batch.

Polymorph Form C

FIG. 15 shows TGA (top) and DSC (bottom) thermograms for polymorph Form C. No significant weight loss is observed in the TGA experiment for polymorph Form C. The compound starts decomposing at temperatures above 300° C. No events are observed in the DSC thermogram other than a melt at 295° C.

Example 12

Polarised Light Microscopy (PLM)

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a X false-colour filter.

Polarised light microscopy showed very clear differences between Amorphous Phase A and polymorph Form C. Amorphous Phase A shows no birefringence at all, which is consistent with the amorphous character of this material. Particles of this material come in different shapes and sizes. Form C appears as clusters of needles of about 40 μm in diameter. There are, however, some amorphous particles, although the crystalline material constitutes the bulk of this batch.

Example 13

Hot Stage Microscopy (HSM)

Hot Stage Microscopy was carried out using a Leica LM/DM polarised light microscope combined with a Mettler-Toledo MTFP82HT hot-stage and a digital video camera for image capture. A small amount of each sample was placed onto a glass slide with individual particles separated as well as possible The sample was viewed with appropriate magnification and partially polarised light, coupled to a λ false-colour filter, whilst being heated from ambient temperature typically at 10-20° C.min$^{-1}$.

The hot-stage microscopy experiment showed that the amorphous material (Amorphous Phase A) undergoes a phase change upon heating. Amorphous Phase A starts melting at around 155° C.; at 200° C. a re-crystallisation occurs. The new crystals start melting at around 288° C. and by 295° C. the material has melted and starts decomposing.

Form C only shows a single major event. The particles start melting at temperatures just above 290° C. and by 295° C. all of them have melted, and start decomposing.

Example 14

Gravimetric Vapour Sorption (GVS)

Sorption isotherms were obtained using a Hiden IGASorp moisture sorption analyser, controlled by CFRSorp software. The sample temperature was maintained at 25° C. by a Huber re-circulating water bath. The humidity was controlled by mixing streams of dry and wet nitrogen, with a total flow rate of 250 ml. min$^{-1}$. The relative humidity was measured by a calibrated Vaisala RH probe (dynamic range of 0-95% RH), located near the sample. The weight change, (mass relaxation) of the sample as a function of % RH was constantly monitored by the microbalance (accuracy ±0.001 mg).

Typically 10-20 mg of sample was placed in a tared mesh stainless steel basket under ambient conditions. The sample was loaded and unloaded at 40% RH and 25° C. (typical room conditions).

A moisture sorption isotherm was performed as outlined below (2 scans giving 1 complete cycle). The standard isotherm was performed at 25° C. at 10% RH intervals over a 0-90% RH range.

TABLE 9

Gravimetric Vapour Sorption (GVS) Experimental conditions

| Parameters | Values |
|---|---|
| Adsorption - Scan 1 | 40-90 |
| Desorption/Adsorption - Scan 2 | 85 - Dry, Dry - 40 |
| Intervals (% RH) | 10 |
| Number of Scans | 2 |
| Flow rate (ml · min$^{-1}$) | 250 |

TABLE 9-continued

Gravimetric Vapour Sorption (GVS) Experimental conditions

| Parameters | Values |
|---|---|
| Temperature (° C.) | 25 |
| Stability (° C. · min$^{-1}$) | 0.05 |
| Minimum Sorption Time (hours) | 1 |
| Maximum Sorption Time (hours) | 4 |
| Mode | AF2 |
| Accuracy (%) | 98 |

The software uses a least squares minimisation procedure together with a model of the mass relaxation, to predict an asymptotic value. The measured mass relaxation value must be within 5% of that predicted by the software, before the next % RH value is selected. The minimum equilibration time was set to 1 hour and the maximum to 4 hours.

Amorphous Phase A

Figure 16:
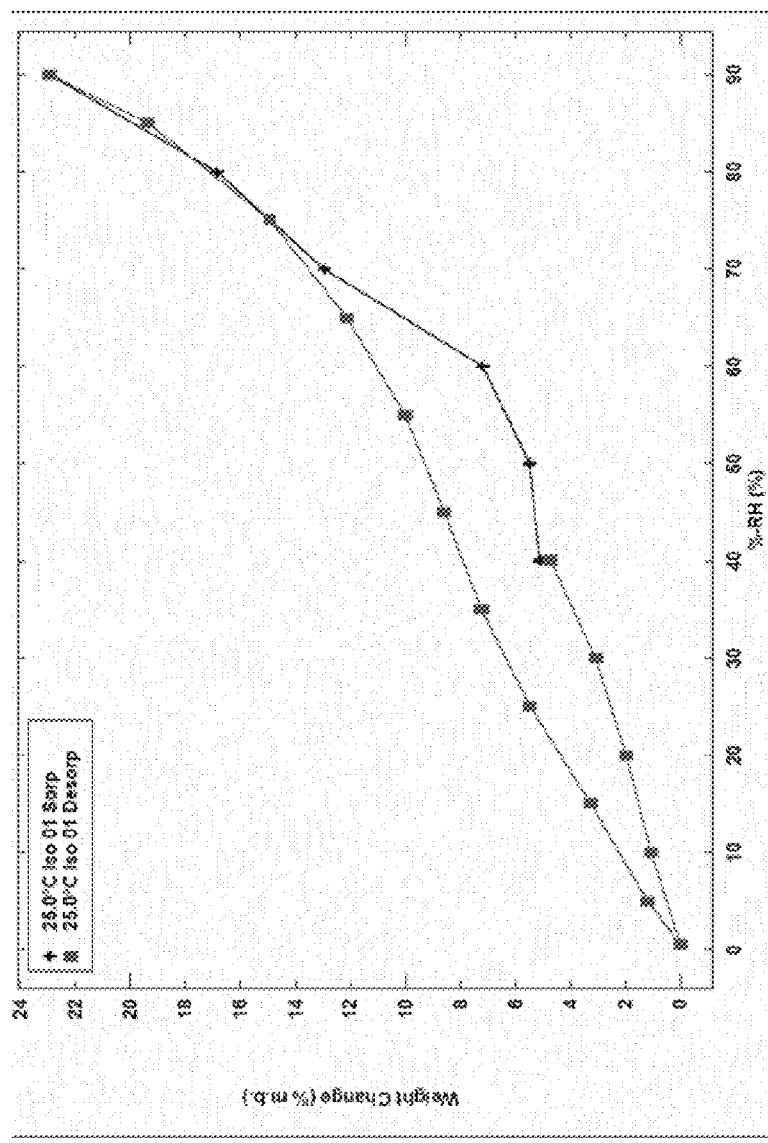
FIG. 16 illustrates a GVS diagram for Amorphous Phase A of Compound 2.

FIG. 16 shows the GVS diagram for Amorphous Phase A. Amorphous Phase A is a hygroscopic material, taking up to more than 22% of water at 90% RH after a full sorption/desorption cycle. No changes were observed in the XRPD patterns for Amorphous Phase A after the GVS experiment.

Polymorph Form B

Figure 6:
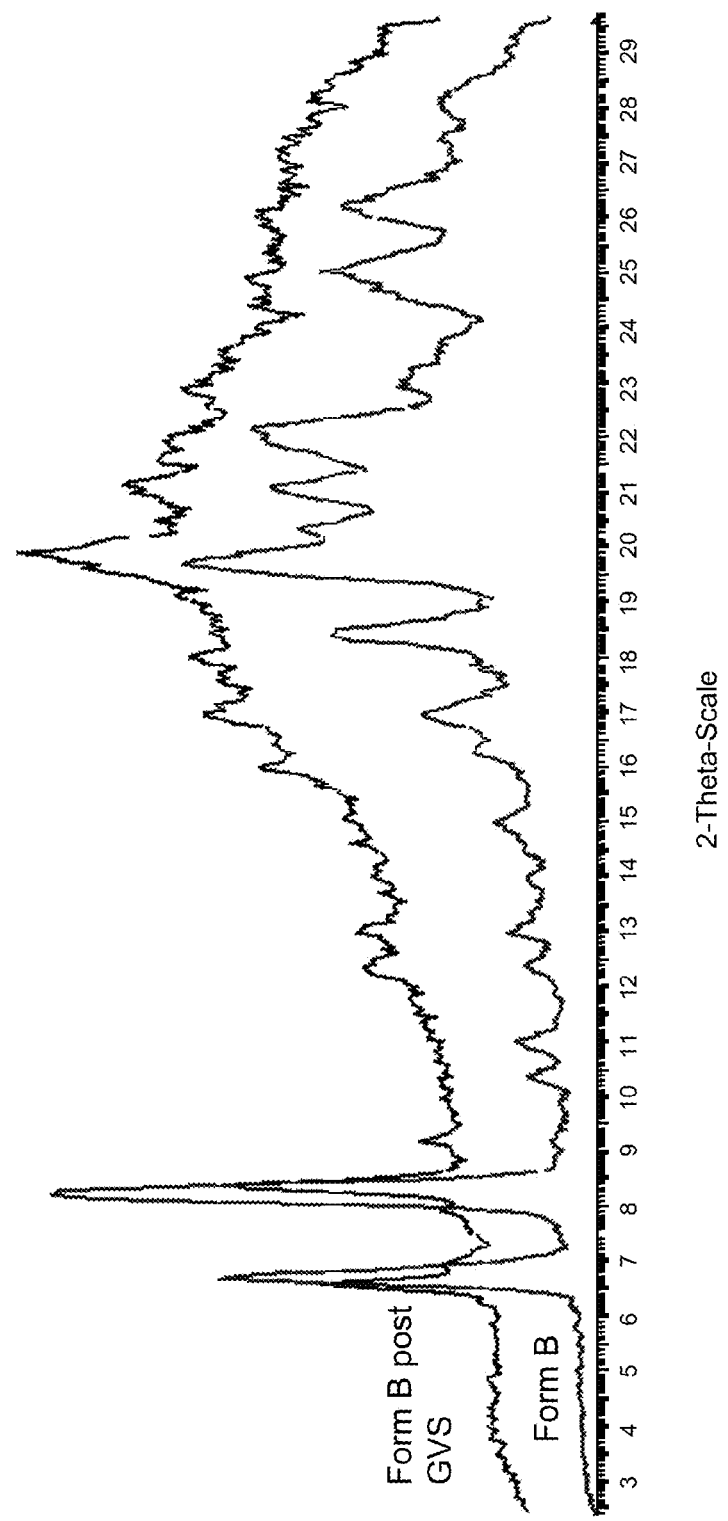
FIG. 6 illustrates a comparison of the XRPD patterns of Polymorph Form B of Compound 2 before and after GVS experiments.
Figure 17:
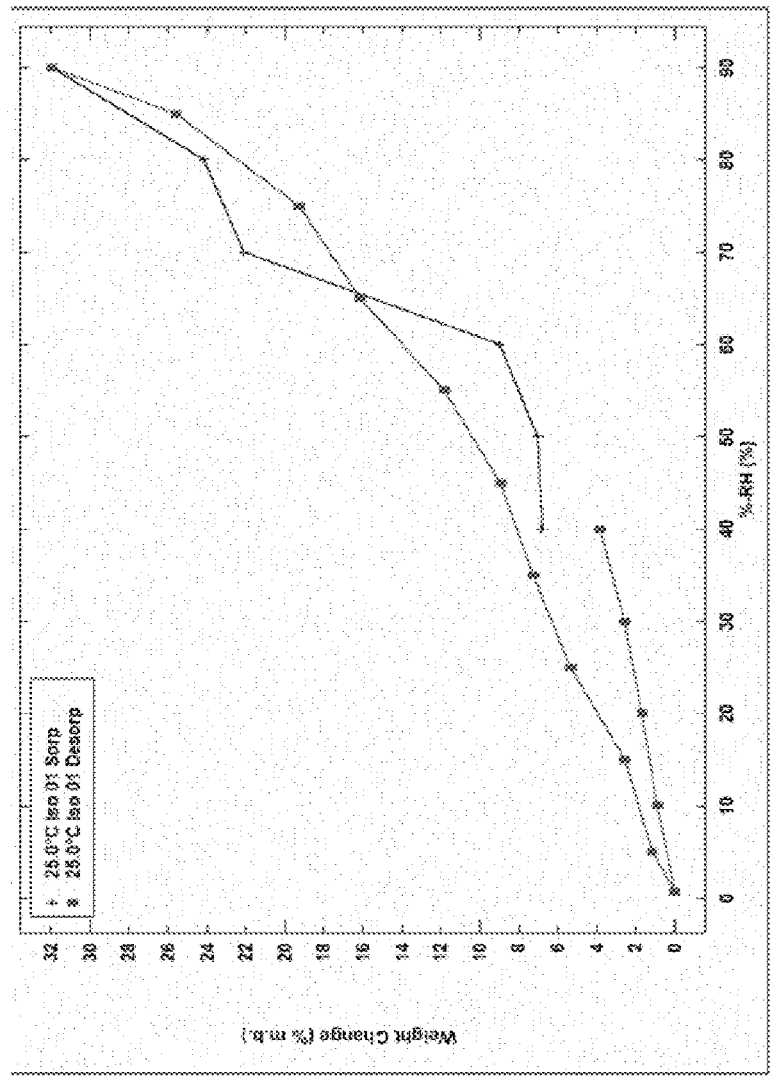
FIG. 17 illustrates a GVS diagram for Polymorph Form B of Compound 2.

FIG. 17 shows the GVS diagram for polymorph Form B. Polymorph Form B is a hygroscopic material, taking up to more than 30% of water at 90% RH after a full sorption/desorption cycle. It is even more hygroscopic than the amorphous material. The analysis of the material by XRPD (see FIG. 6), after the full sorption/desorption cycle shows that it becomes almost totally amorphous, although some peaks from the original form can be identified.

Polymorph Form C

Figure 18:
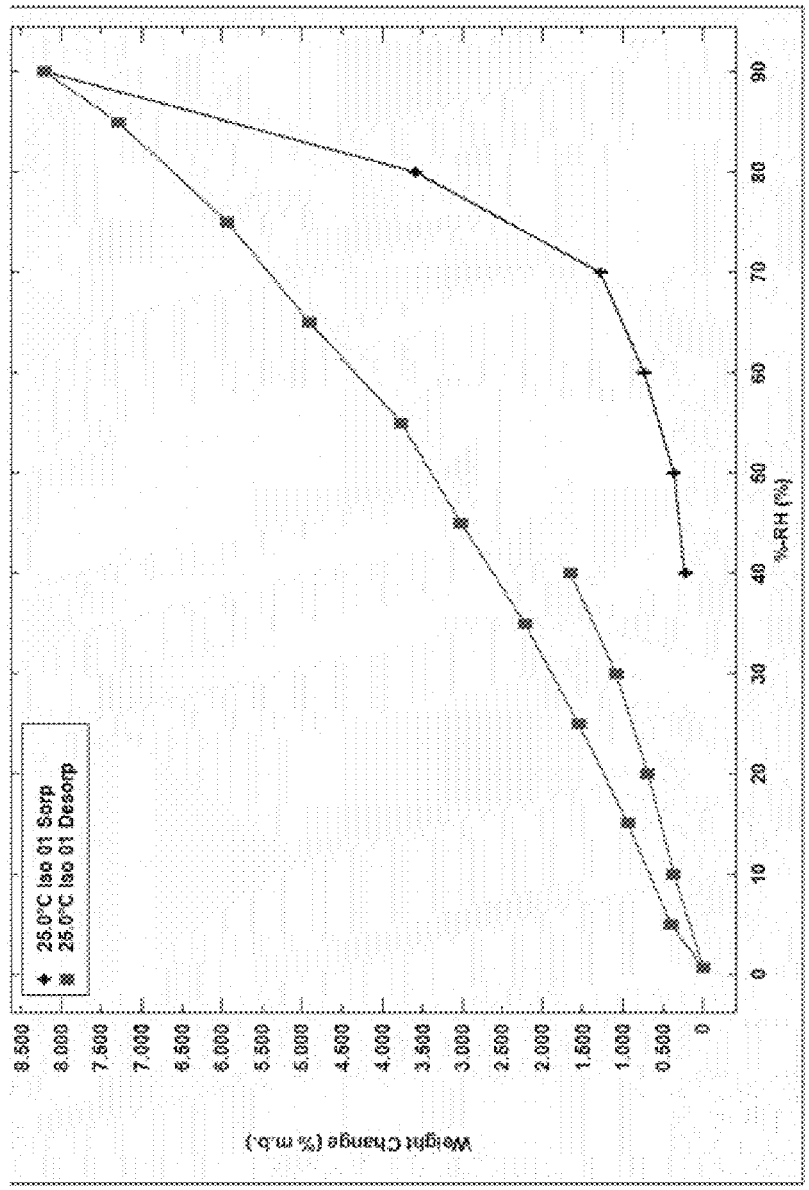
FIG. 18 illustrates a GVS diagram for Polymorph Form C of Compound 2.

FIG. 18 shows the GVS diagram for Form C. The crystalline form, polymorph Form C, is significantly less hygroscopic than the amorphous material, taken up to only 8.2% of water at 90% RH. No changes were observed in the XRPD patterns for polymorph Form C after the GVS experiment.

Example 15

Water Determination by Karl Fischer (KF)

The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and duplicate determinations were made.

The content of water in the amorphous material (Amorphous Phase A) was determined to be about 5.1% by Coulometric Karl Fisher analysis. This result could explain the weight loss of 4.6% observed in the TGA experiment.

The content of water in polymorph Form C was determined to be less than 1% by Coulometric Karl Fisher analysis. The content of water in polymorph Form C was determined to be a detectable amount that is less than 1% by Coulometric Karl Fisher analysis. The content of water in polymorph Form C was determined to be about 0.54%, about 0.56%, or about 0.85% by Coulometric Karl Fisher analysis.

Example 16

Chemical Purity Determination by HPLC

Purity analysis was performed on an Agilent HP 1100 series system equipped with a diode array detector and using ChemStation software vB.02.01-SR1.

The stability indicating method used for the determination of Compound 1 content and content of drug-related impurities is a gradient reversed phase HPLC method utilizing a Waters 150×4.6 mm 3.5 μm C8 column for separation. The mobile phase is a binary gradient starting with 70% mobile Phase A (0.1% trifluoroacetic acid in water) changing to 30% mobile Phase A. Mobile Phase B consists of 0.1% trifluoroacetic acid in acetonitrile. The sample for analysis is dissolved at a nominal concentration of 0.2 mg/mL in Methanol, and the injection volume for the separation is 10 μl. Detection of the Compound 1 and its related substances is by UV at a wavelength of 260 nm.

The specificity, accuracy, linearity (range), precision (system and method), and stability indicating ability of the method were investigated during the method validation process. The results indicate the method to be linear from a concentration of 0.02 mg/mL (10% of nominal) to 0.30 mg/mL (120% of nominal). The accuracy of the method was established by injecting samples prepared at 80%, 100%, and 120% of the nominal concentration of 0.2 mg/mL. The results from the accuracy study showed all recoveries to be within 80-120% of theoretical.

The stability indicating ability of the method was investigated by injecting samples of Compound 2 forcibly degraded under conditions of acid (0.1N hydrochloric acid), base (0.1N sodium hydroxide), oxidation (10% hydrogen peroxide), and high intensity light (ICH Photostability conditions II). Samples were degraded by a minimum of 10%. No degradant peaks were found to interfere with the main Compound 1 band in the HPLC chromatograms. Therefore, the method demonstrated adequate specificity for use as a stability indicating method.

The results of the method validation show the method to be suitable for use in release testing and stability testing of Compound 1, or pharmaceutically acceptable salts and/or solvates thereof.

Some related impurities in samples containing Compound 2 include, but are not limited to, the following:

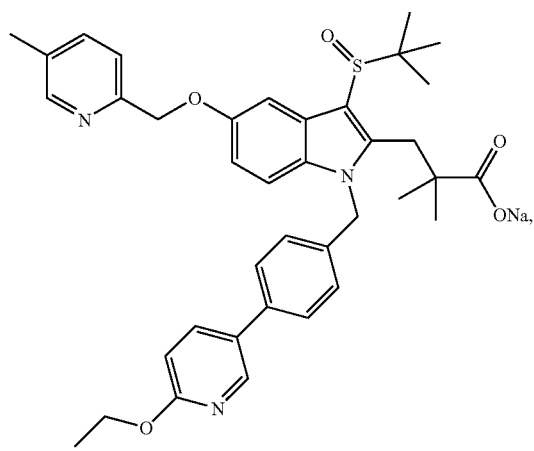

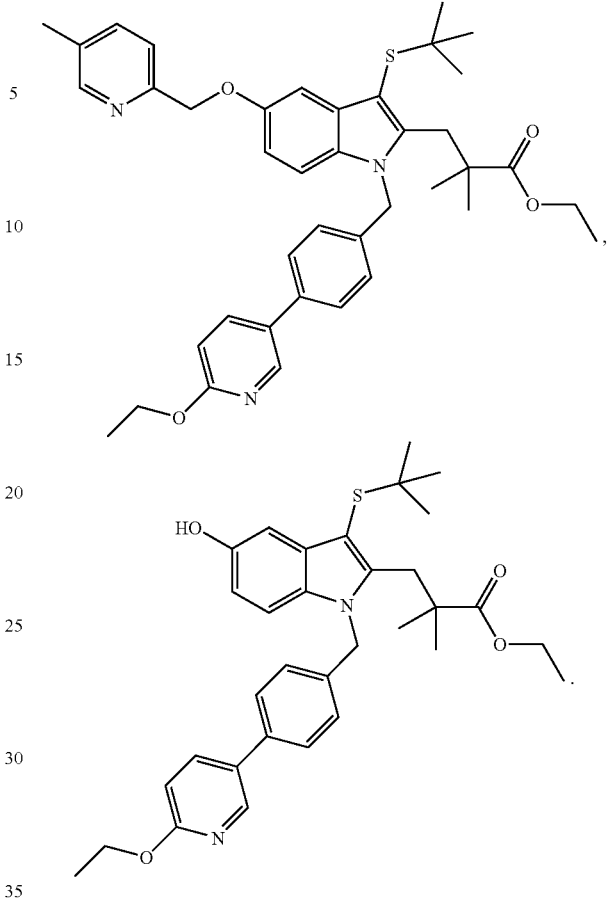

The total amount of impurities (based on HPLC area) is less than 4%, less than 3.5%, less than 3%, less than 2.5%, less than 2%, less than 1.5%, less than 1%, or less than 0.5%.

A sample of Compound 2 described herein has a purity (based on HPLC area) greater than 95%, greater than 96%, greater than 97%, greater than 98%, greater than 98.2%, greater than 98.98%, greater than 99%, or greater than 99.5%.

Residual Solvents

The test for Residual Solvents is performed to detect trace amounts of solvents used in the synthesis that may be present in the API. The analysis is performed via headspace or direct injection analysis using a gas chromatograph equipped with a flame ionization detector (FID). All residual solvents used in the synthesis are capable of being detected by this method.

Potential residual solvents include ethanol, acetonitrile, dichloromethane, methyl-tert-butyl-ether (MTBE), ethyl acetate, tetrahydrofurna, 1,2-dimethoxyethane.

TABLE 10

| Residual Solvents by GC Headspace | |
|---|---|
| Residual Solvent | Amount (ppm) |
| 1,2-dimethoxyethane | ≤100 ppm |
| Ethyl acetate | ≤410 ppm |
| THF | ≤720 ppm |
| dichloromethane | ≤600 ppm |
| ethanol | ≤5000 ppm |
| MTBE | ≤5000 ppm |

Example 17

Heavy Metals (Pd) by ICP-AES

Trace palladium (Pd) resulting from the use of catalytic amounts of Pd in the synthesis is assayed by inductively coupled plasma atomic emission spectrometry (ICP-AES). Pd content by ICP-AES is a detectable amount of palladium that is less than about 20 ppm. Pd content by ICP-AES is less than about 20 ppm. Pd content by ICP-AES is a detectable amount of palladium that is less than about 20 ppm, less than about 15 ppm, less than about 10 ppm, less than about 9 ppm, less than about 8 ppm, less than about 7 ppm, less than about 6 ppm, or less than about 5 ppm. Pd content by ICP-AES is less than about 20 ppm, less than about 15 ppm, less than about 10 ppm, less than about 9 ppm, less than about 8 ppm, less than about 7 ppm, less than about 6 ppm, or less than about 5 ppm. Pd content by ICP-AES is about 10 ppm, about 6 ppm, about 5 ppm, about 4 ppm, about 3 ppm, about 2 ppm, or about 1 ppm. In one aspect, samples or pharmaceutical compositions do not include a detectable amount of palladium.

Example 18

Heavy Metals (as Lead)

This test is performed according to USP<231> Method II.

Example 19

IR Spectroscopy of Form C

A Nicolet Model 510M-O infrared spectrophotometer equipped with a Harrick internal reflectance nanosampler was used. A small portion of the sample was placed on the internal reflectance nanosampler and a background corrected spectrum from 400 cm$^{-1}$ to 4000 cm$^{-1}$ was collected.

TABLE 11

Infrared Vibrational Assignments for Form C

| Wavenumber (cm-1) | Vibrational Assignment |
|---|---|
| 2968, 2935, 2893, 2866 | Aliphatic C—H stretch |
| 1604 | Aromatic ring breathing |
| 1563 | CO2—, asymmetric stretch |
| 1369 | CO2—, symmetric stretch |
| 1414 (1473) | Aromatic ring breathing |
| 1285 | C—O—C stretch, alkyl-aryl ether |
| 815, 796 | C—H out of plane deformation, p-substituted benzene or pyridine |

Example 20

FLAP Binding Assays

Compound 2 was examined for its ability to bind human FLAP using a membrane-binding assay. The affinity of Compound 2 for human FLAP was assessed using membranes from human polymorphonuclear leukocytes and tritiated leukotriene synthesis inhibitor, $^3$H-3-[5-(pyrid-2-ylmethoxy)-3-tert-butylthio-1-benzyl-indol-2-yl]-2,2-dimethylpropionic acid, as a ligand. A non-limiting example of such a FLAP binding assay is as follows:

Packed human polymorphonuclear cell pellets (1.8×109 cells) (Biological Speciality Corporation) were resuspended, lysed and 100,000 g membranes prepared as described (Charleson et al. *Mol. Pharmacol*, 41, 873-879, 1992). 100,000 g pelleted membranes were resuspended in Tris-Tween assay buffer (100 mM Tris HCl pH 7.4, 140 mM NaCl, 2 mM EDTA, 0.5 mM DTT, 5% glycerol, 0.05% Tween 20) to yield a protein concentration of 50-100 μg/mL. 10 μL membrane suspension was added to 96 well Millipore plate, 78 μL Tris-Tween buffer, 10 μL $^3$H 3-[5-(pyrid-2-ylmethoxy)-3-tert-butylthio-1-benzyl-indol-2-yl]-2,2-dimethylpropionic acid (or $^{125}$I MK591 derivative Eggler et al, *J. Labelled Compounds and Radiopharmaceuticals*, 1994, vXXXIV, 1147)) to ~30,000 cpm, 2 μL inhibitor and incubated for 30 minutes at room temperature. 100 μL ice-cold washed buffer was added to the incubation mixture. Plates were then filtered and washed 3× with 200 μL ice cold Tris-Tween buffer, scintillation bottoms sealed, 100 μL scintillant added, shaken for 15 minutes then counted in a TopCount. Specific binding was determined as defined as total radioactive binding minus non-specific binding in the presence of 10 μM 3-[5-(pyrid-2-ylmethoxy)-3-tert-butylthio-1-benzyl-indol-2-yl]-2,2-dimethylpropionic acid. IC$_{50}$ values were determined using Graphpad prism analysis of drug titration curves. Compound 2 inhibited radioligand binding dose-dependently with a mean IC$_{50}$ of 2.9±1.0 nM. The results are set forth in Table 12.

TABLE 12

Inhibition of FLAP Radioligand Binding IC$_{50}$ (nM)

| Test 1 | Test 2 | Test 3 | Test 4 | Test 5 | Test 6 | Test 7 | Test 8 |
|---|---|---|---|---|---|---|---|
| 4.9 | 2.1 | 2.9 | 2.8 | 4.1 | 1.8 | 2.1 | 2.2 |

IC$_{50}$: 2.9 ± 1.0 nM

Example 21

Human Blood LTB$_4$ Inhibition Assay

Compound 2 was evaluated for its ability to inhibit production of LTB$_4$ after ionophore stimulation in washed human leukocytes and in human and rat whole blood. A non-limiting example of such a human blood LTB$_4$ inhibition assay is as follows: Blood was drawn from consenting human volunteers into heparinized tubes and 125 μL aliquots added to wells containing 2.5 μL 50% dimethylsulfoxide (vehicle) or 2.5 μL drug in 50% dimethylsulfoxide. Samples were incubated for 15 minutes at 37° C. 2 μL calcium ionophore A23817 (from a 50 mM dimethylsulfoxide stock diluted just prior to the assay in Hanks balanced salt solution (Invitrogen)) to 1.25 mM) was added, solutions mixed and incubated for 30 minutes at 37° C. Samples were centrifuged at 1,000 rpm (~200×g) for 10 minutes at 4° C., plasma removed and a 1:100 dilution assayed for LTB$_4$ concentration using ELISA (Assay Designs). Drug concentrations to achieve 50% inhibition (IC50's) of vehicle LTB$_4$ were determined by nonlinear regression (Graphpad Prism) of % inhibition versus log drug concentration. The results from the human leukocytes assay are set forth in Table 13.

TABLE 13

Inhibition of LTB$_4$ in Washed Human Leukocytes
Inhibitor Concentration (nM)

|  | Test 1 | Test 2 | Test 3 | Test 4 |
|---|---|---|---|---|
| IC$_{50}$ | 0.49 | 0.87 | 0.22 | 0.17 |
| IC$_{90}$ | 0.77 | 1.03 | 0.46 | 0.41 |

IC$_{50}$: 0.44 ± 0.28 nM

The results from the human whole blood assay are set forth in Table 14.

TABLE 14

Inhibition of LTB$_4$ in Human Whole Blood
Inhibitory Concentration (μM)

|  | Test 1 | Test 2 | Test 3 | Test 4 | Test 5 | Test 6 | Test 7 | Test 8 |
|---|---|---|---|---|---|---|---|---|
| IC$_{50}$ | 0.552 | 0.645 | 0.563 | 0.410 | 0.642 | 0.482 | 0.310 | 0.444 |
|  |  |  | IC$_{50}$: 0.506 ± 0.109 μM |  |  |  |  |  |
| IC$_{90}$ | 3.44 | 1.22 | 1.55 | 0.81 | 1.05 | 0.79 | 0.36 | 1.24 |
|  |  |  | IC$_{90}$: 1.31 ± 0.87 μM |  |  |  |  |  |

The results from the rat whole blood assay are set forth in Table 15.

TABLE 15

Inhibition of LTB$_4$ in Rat Whole Blood
Inhibitory Concentration (μM)

|  | Test 1 | Test 2 | Test 3 | Test 4 | Test 5 |
|---|---|---|---|---|---|
| IC$_{50}$ | 0.302 | 0.160 | 0.380 | 0.212 | 0.141 |
|  |  | IC$_{50}$: 0.239 ± 0.090 μM |  |  |  |
| IC$_{90}$ | 6.00 | 0.351 | 0.705 | 0.688 | 0.422 |
|  |  | IC$_{90}$: 1.63 ± 2.19 μM |  |  |  |

Example 22

Identification of Metabolic Pathways

The metabolic profile of Compound 2 was investigated using: (1) rat, dog, monkey, and human hepatic microsomes; (2) rat and human hepatocytes; and (3) bile collected from Sprague-Dawley rats after oral dosing.

In vitro microsomal incubations generates hydroxylated metabolites, which include:
a) hydroxylated 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid (M1); b) 3-[3-tert-butylsulfinyl-1-[4-(6-ethoxy-pyridin-3-yl)-benzyl]-5-(5-methyl-pyridin-2-ylmethoxy)-1H-indol-2-yl]-2,2-dimethyl-propionic acid (M2); and c) 3-[3-tert-butylsulfanyl-1-[4-(6-ethoxy-pyridin-3-yl)-benzyl]-5-(5-methyl-N-oxy-pyridin-2-ylmethoxy)-1H-indol-2-yl]-2,2-dimethyl-propionic acid (M3).

In vitro hepatocyte incubations forms metabolites, which include:
a) 3-[3-tert-butylsulfinyl-1-[4-(6-ethoxy-pyridin-3-yl)-benzyl]-5-(5-methyl-pyridin-2-ylmethoxy)-1H-indol-2-yl]-2,2-dimethyl-propionic acid (M2); b) 3-[3-tert-butylsulfanyl-1-[4-(6-ethoxy-pyridin-3-yl)-benzyl]-5-(5-methyl-N-oxy-pyridin-2-ylmethoxy)-1H-indol-2-yl]-2,2-dimethyl-propionic acid (M3) and c) the acyl gluconuride of 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid (M4).

Metabolites identified in bile collected from Sprague-Dawley rats after oral dosing include:
a) 3-[3-tert-butylsulfanyl-1-[4-(6-hydroxy-pyridin-3-yl)-benzyl]-5-(5-methyl-pyridin-2-ylmethoxy)-1H-indol-2-yl]-2,2-dimethyl-propionic acid (M5); b) a hydroxylated metabolite where hydroxylation occurs at the phenyl-pyridine moiety; and c) glucuronidation metabolite that was also hydroxylated.

Rat, dog, monkey, and human microsomes or rat and human hepatocytes revealed similar profiles.

Example 23

Extracellular Cytochrome P450 Inhibition

To investigate whether Compound 2 would likely cause any drug-drug interactions, microsomes were incubated test substrates, which were known to be metabolized by CYP enzymes, with or without Compound 2.

Specific aspects of the incubation conditions for each assay (e.g., protein concentration, incubation time, etc.) are defined in Walsky & Obach, 2004 (Walsky, R. L., and Obach, R. S. Validated assays for human Cytochrome P450 activities. Drug Met. Disp. 32:647-660, 2004.)

In general, microsomes at protein concentrations as defined in Tables 1a and 1b were mixed with buffer (100 mM potassium dihydrogen phosphate, pH 7.4), magnesium chloride (3.3 mM) and substrate, and were kept on ice. Aliquots of this mixture (89 μL) were delivered to each well of a 96-well polypropylene plate which contained an aliquot of inhibitor (1 μL). Final solvent concentrations were 1% (v/v) or less. Incubations were commenced with the addition of 10 μL β-NADPH (10 mM stock) to a final volume of 100 μL. Incubations were terminated by the addition of 1.5-2× acetonitrile containing internal standard (buspirone or CJ-13,610). Samples were centrifuged, and supernatant was transferred for LC-MS analysis.

The results are presented in Table 16.

TABLE 16

Lack of Extracellular Cytochrome P450 Inhibition

| Cytochrome P450 Enzyme | CYP Reaction | Compound 2 IC$_{50}$ (μM) | Inhibitor Control (IC$_{50}$ (μM)) |
|---|---|---|---|
| 3A4 | testosterone 6β-hydroxylation | >40 | Ketoconazole (0.01) |
| 3A4 | midazolam 1-hydroxylation | >50 | Ketoconazole (0.01) |
| 2C9 | diclofenac 4'-hydroxylation | >50 | Sulfaphenazole (0.13) |
| 2C19 | mephenytoin 4'-hydroxylation | >40 | (−)-N-3-benzyl-phenobarbital (2.8) |

TABLE 16-continued

Lack of Extracellular Cytochrome P450 Inhibition

| Cytochrome P450 Enzyme | CYP Reaction | Compound 2 IC$_{50}$ (μM) | Inhibitor Control (IC$_{50}$ (μM)) |
|---|---|---|---|
| 2D6 | dextromethorphan O-demethylation | >50 | Quinidine (0.01) |
| 1A2 | phenacetin O-deethylation | >40 | Furafylline (1.90) |

Compound 2 was not an inhibitor of P450 (CYP) enzymes according to conversion of substrates to known metabolites with and without Compound 2 in the incubation. No apparent inhibition is observed at concentrations up to and exceeding 40 μM for CYP3A4, 1A2, 2C9, 2C19, and 2D6 enzymes.

Example 24

Lack of Cellular Cytochrome P450 Induction

Figure 20:
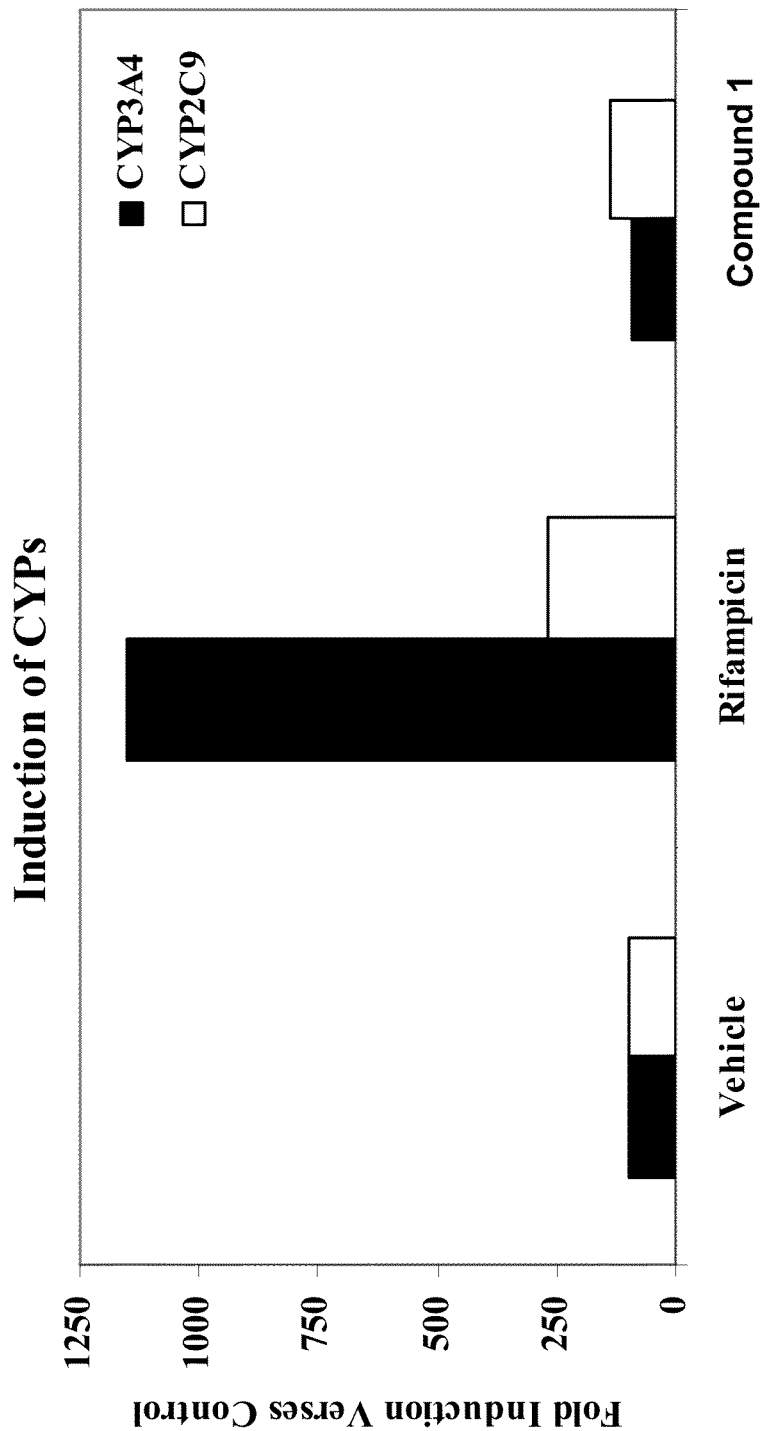
FIG. 20 illustrates results of experiments conducted to evaluate CYP induction of Compound 2.

Compound 2 was not an inducer of P450 CYP3A4 or CYP2C9 in cryopreserved human hepatocytes, according to conversion of substrates to known metabolites with and without Compound 2 in the incubation. Briefly, cryopreserved human hepatocytes thawed and plated according to the manufacturer's instructions (In Vitro Technologies, Gathersburg, Md.). The cells were warmed and then poured into pre-warmed InVitroGRO CP medium, gently resuspended, and then the cells were counted using Trypan Blue exclusion. Cells were then diluted to $0.7 \times 10^{-6}$ viable cells/ml with CP medium. Each well received 0.2 ml of the viable cell mixture. The plate was gently shaken to disperse the cells evenly in the well, and the plate was incubated at 37° C., 5% carbon dioxide. At 24 hrs, medium was replaced with fresh CP medium. After 48 hrs, CP medium is replaced with HI medium containing Compound 2 tested at 10M, and the positive control, rifampicin was tested at 25 M. Medium was replaced with fresh medium plus test article 24 hrs later. At 48 hrs, midazolam (50 μM) and diclofenac (50 μM) were incubated in 0.15 mL of K—H buffer for 4 hrs. Reactions were terminated with addition of 0.15 mL of acetonitrile containing internal standard (buspirone), material centrifuged, and supernatants were transferred for LC-MS analysis. No apparent induction was observed for CYP3A4 and CYP2C9 when tested at 10 μM (U.S. FDA Guidance for Industry, "Drug Interaction Studies—Study Design, Data Analysis, and Implications for Dosing and Labeling", September 2006). In contrast, rifampicin, a therapeutic agent known to induce CYP3A4 and CYP2C9, induced CYP3A4 11-fold and 2C9 2.5-fold. FIG. 20 illustrates the lack of CYP3A4 and 2C9 induction by Compound 2.

Example 25

Plasma Binding

Compound 2 (10 μM) was highly bound in rat, dog, monkey and human plasma. Experiments were performed using equilibrium dialysis. Table 17 summarizes such binding.

TABLE 17

Plasma Binding Protein

| Species | % Bound |
|---|---|
| Rat (mixed breeds) | 99.8 |
| Dog (mixed breeds) | 99.7 |
| Monkey (cynomologus) | 99.7 |
| Human | 99.5 |

Example 26

Liver Weight Change in Mice

Significant liver weight increases were not evident in female CD-1 mice after oral administration of Compound 2 for 4 days at 250 mg/kg/day when compared with vehicle control (n=6/group, Table 11). Liver weight was not altered significantly (5% as compared to vehicle control) and necropsy revealed no gross abnormalities. In contrast, zileuton (250 mg/kg/day) significantly increased liver weight (31.0% as compared to vehicle control; P<0.05). Compound 2, zileuton and acetaminophen (APAP) were prepared as uniform suspensions in 0.5% methyl cellulose vehicle and administered in a volume of 10 ml/kg of body weight. Mice (6/group) received either vehicle, Compound 2 (250 mg/kg), zileuton (250 mg/kg) or APAP (250 mg/kg) daily for 4 days. Twenty-four hours following the final drug administration mice were placed into an enclosed Plexiglas chamber and exposed to $CO_2$ for a period of 30-60 seconds or until breathing ceased. They were then removed subject to cervical dislocation and blood taken via a cardiac puncture. Mice were next placed in a supine position and a midline incision made. All organs were inspected and the livers removed by careful dissection. Liver weights were recorded as well as any gross abnormalities.

TABLE 18

Liver Weight After Repeat Dosing

| Substance | Liver weight (% body weight) |
|---|---|
| Vehicle | 1.2 ± 0.1 (4.2) |
| Compound 2 | 1.2 ± 0.1 (4.4) |
| Zileuton | 1.6 ± 0.2 (5.5) |

Pharmaceutical Compositions

Pharmaceutical compositions that include Compound 1, including pharmaceutically acceptable salts and/or pharmaceutically acceptable solvates thereof include a variety of forms. In one aspect, pharmaceutical compositions were in the form of oral dosage forms. In one aspect, the oral dosage forms were formulated as: oral solutions, oral suspensions, tablets, pills, or capsules.

Example 27

Oral Solutions/Suspensions

In one embodiment, oral aqueous solutions suitable for human use were prepared for oral administration. In one embodiment, oral aqueous solutions were prepared prior to administration.

In certain embodiments, Compound 2 was formulated into solutions suitable for oral administration to a mammal.

Compound 2, anhydrouse sodium carbonate ($Na_2CO_3$), absolute ethanol, Syrpalta™ (Humco), Simple syrup (Humco), and 70% sorbitol solution (Humco) were used for all formulations shown below. Values of pH reported were estimated based on pH indicating strips. Compound 1 was observed in certain solvent systems to be sparingly soluble below pH values of about 9-10. Accordingly, provided in certain embodiments herein were formulations having a pH above about 9, above about 10 or of about 10. In certain embodiments, the formulation was buffered at a pH of about 10. All formulations prepared were sonicated for about 10 minutes. The formulations prepared were set forth in Table 19.

TABLE 19

Liquid Formulations

| Vehicle | Approximate pH | Drug amount (mg/mL) | Results |
|---|---|---|---|
| 0.5% Methylcellulose | | 3.33 | Suspension |
| 0.010 M sodium carbonate buffer | 10 | 10 | Clear solution |
| 0.010 M sodium carbonate buffer, 2% v/v ethanol and 0.05% splenda | 10 | 10 | Clear solution |
| 0.010 M sodium carbonate buffer, 5% v/v Ethanol and 0.05% splenda | 10 | ~10 | Some undissolved solid remains |
| 0.010 M sodium carbonate buffer, 1% v/v Lutrol and 0.05% splenda | 10 | ~10 | Clear solution |
| 0.010 M sodium carbonate buffer, 5% v/v Simple syrup | 10 | 10 | Some undissolved solid remains |

Clear solutions remain clear after being stored for 24 hours at about 2° C. to about 8° C.

Administration of the solutions outlined in Table 19 to male Spargue-Dawley rats resulted $T_{max}$ of less than or equal to about 2 hrs, which indicates that Compound 2 was rapidly absorbed in the stomach and upper gastrointestinal tract.

An example of an immediate release paediatric formulation is presented in Table 20 and 21.

TABLE 20

Oral Suspension Formulation (10 mg/ml - 1.0% w/v)

| Ingredients | % w/v | Function |
|---|---|---|
| Compound 1 | 1.00 | Active |
| Avicel CL611 | 3.0 | Thixotropic Gelling Agent |
| Sodium lauryl sulphate | 0.20 | Wetting agent |
| Sodium citrate | 0.10 | Buffering agent |
| Citric acid | 0.15 | Buffering agent |
| Glycerol | 5.00 | Humectant/co-solvent |
| Sorbitol 70% Solution | 40.0 | Bulk Solvent |
| Propylene glycol | 5.0 | Co-solvent |
| Propyl parabens | 0.2 | Preservative |
| Butyl parabens | 0.06 | Preservative |
| Sucrolose | 0.005 | Sweetener |
| Natural Grape | 0.02 | Flavour |
| FD&C Yellow No. 6 | 0.009 | Colourant |
| Purified Water | qs 100.00 | Solvent |

TABLE 21

Oral Solution Formulation (10 mg/ml - 1.0% w/v)

| Ingredients | % w/v | Function |
|---|---|---|
| Compound 1 | 1.00 | Active |
| Lutrol/Polysorbate 80 | 5.0 | Solubilizing agent |
| Sodium citrate | 0.10 | Buffering agent |
| Citric acid | 0.15 | Buffering agent |
| Glycerol | 5.00 | Humectant/co-solvent |
| Sorbitol 70% Solution | 40.0 | Bulk Solvent |
| Propylene glycol | 5.0 | Co-solvent |
| Propyl parabens | 0.2 | Preservative |
| Butyl parabens | 0.06 | Preservative |
| Sucrolose | 0.05 | Sweetener |
| Natural Grape | 0.02 | Flavour |
| FD&C Yellow No. 6 | 0.009 | Colorant |
| Purified Water | qs 100.00 | Solvent |

An example of an oral re-constituted granules formulation is presented in Table 22.

TABLE 22

Oral Re-constituted Granules Formulation 10 mg/ml (granules produced by wet granulation method)

| Ingredients | mg/ml | Function |
|---|---|---|
| Compound 1 | 50.00 | Active |
| Sucrose | 2250.00 | Granulating agent |
| Povidone | 13.00 | Binder |
| Sucrolose | 6.75 | Sweetener |
| Explotab | 100.00 | disintegrant |
| Natural Grape | 25.00 | Flavour |
| Xanthum Gum | 50.00 | Suspending agent |
| Magnesium lauryl sulphate | 100.0 | Soluble lubricant |
| Unit Dose | 2.595 g | — |

An example of a dispersable tablet formulation is presented in Table 23.

TABLE 23

Dispersible Tablet Formulation

| Ingredients | mg/tablet | Function |
|---|---|---|
| Compound 1 | 50.00 | Active |
| Avicel PH102 | 150.00 | Granulating Agent |
| Crospovidone | 25.0 | Disintegrant |
| Mannitol | 65.85 | Diluent |

TABLE 23-continued

Dispersible Tablet Formulation

| Ingredients | mg/tablet | Function |
|---|---|---|
| Explotab | 6.0 | Super disintegrant |
| Sucrolose | 0.15 | Sweetener |
| Magnesium lauryl sulphate | 3.0 | Soluble lubricant |
| Total Tablet weight | 300.00 | — |

Example 28

Immediate Release Tablets

Tablets were prepared with the components set forth in Table 24.

TABLE 24

Components of IR Tablets

| Component | % (w/w) | mg/tablet |
|---|---|---|
| Compound 2 | 15 | 50 |
| Silicified microcrystalline cellulose | 45 | 150 |
| Mannitol | 34 | 113.3 |
| Crospovidone | 5 | 16.7 |
| Magnesium stearate | 1 | 3.3 |
| Total | 100 | 333.3 |

All components except magnesium stearate were weighed out into a stainless steel container. The powder mixture was passed through a 70-mesh sieve into another SS container. The sieved powder was then transferred to a V-blender with an intensifying bar: (Peterson-Kelly Blend Master 17425102Q) and mixed for 30 min. Magnesium stearate was then added into the V-blender and mixed for another 1 minute. The powder blend was collected in a plastic bottle with screw cap. Certain lots were made using a Colton 4-station rotary tablet press with a 10 mm dia round-shaped B-tooling. Other lots were made using a Piccola 10-station rotary tablet press with a new set of 10 mm dia round-shaped B-tooling. The tablets were compressed to hardness=8-12 Kp with an average weight of 333.3±10 mg. The tablet weight and hardness were checked randomly during compression. The defect tablets including "caking", "chipping", "sticking to punch", "off weight" were removed and the total number of tablets yield was calculated. The tablets were stored in a HDPE bottle without desiccant.

Disintegration: Tablet disintegration tests were performed using a USP disentegration apparatus with a Di-water medium, a temperature of 37° C.+/−2° C. at a rate of 29-32 cycles/minute. The average disintegration time measured was 75 seconds with a standard deviation of 7 seconds.

Friability: 20 tablets were placed in a No. 10 sieve and a soft brush was used to remove loose dust. The weight of the tablets was recorded. The tablets were then placed into a drum of a USP friability apparatus and rotated 100 times at 25 rpm. The tablets were taken out of the drum and any loose dust was removed with a soft brush. The total weight of the tablets was recorded again to calculate percentage weight loss. The weight loss was about 0.17%.

Hardness: Tablet hardness measurements were performed with a Schleuniger Model 2E/106 tablet tester. The average hardness determined was 8.5 Kp with a standard deviation of 0.8.

Dissolution: The dissolution tests on 6 tablets were performed using USP dissolution apparatus with the following conditions:

| Medium: | 1% sodium dodecyl sulfate in di-water, pH 7.0 |
|---|---|
| Volume: | 500 mL |
| Temperature: | 37° C. |
| USP method: | USP Type I, Basket |
| Speed: | 100 rpm |

The dissolution profile is set forth in Table 25 (n=6), as measured by HPLC.

TABLE 25

Tablet Dissolution

| Time (min) | Release (% label claim) | STDEV |
|---|---|---|
| 0 | 0 | 0 |
| 10 | 92.2 | 20.5 |
| 20 | 98.7 | 7.7 |
| 30 | 101.2 | 3.3 |
| 45 | 101.3 | 3.0 |
| 60 | 101.6 | 3.0 |
| 120 | 101.5 | 2.5 |

Stability: Tables 26-30 illustrate the results of stability testing performed on the tablets.

TABLE 26

Hardness (n = 3)

| Storage Condition | Initial Avg (KP) | STDEV | 1 month Avg (KP) | STDEV | 3 months Avg (KP) | STDEV |
|---|---|---|---|---|---|---|
| 25° C./60% RH | 8.5 | 0.8 | 14.1 | 4.8 | 17.0 | 1.8 |
| 40° C./75% RH |  |  | 6.4 | 2.2 | 5.9 | 0.2 |

TABLE 27

Assay by HPLC (n = 3)

| Storage Condition | Initial mg/tablet[1] | 1 month mg/tablet[1] | 3 months mg/tablet[1] |
|---|---|---|---|
| 25° C./60% RH | 47.4 ± 0.7 | 51.5 | 52.4 |
| 40° C./75% RH |  | 51.6 | 53.4 |

[1]Normalized to 333.3 mg/tablet based on actual weight of each tablet

TABLE 28

% Label Claim (n = 3)

| Storage Condition | Initial % label claim (50 mg) | 1 month % label claim (50 mg) | 3 months % label claim (50 mg) |
|---|---|---|---|
| 25° C./60% RH | 94.8 ± 1.8 | 102.9 ± 0.6 | 104.9 ± 1.1 |
| 40° C./75% RH |  | 103.1 ± 0.9 | 106.7 ± 1.1 |

TABLE 29

Purity % by HPLC (n = 3)

| Storage Condition | Initial % purity | 1 month % purity | 3 months % purity |
|---|---|---|---|
| 25° C./60% RH | 98.7 ± 0.0 | 99.7 ± 0.0 | 99.6 ± 0.0 |
| 40° C./75% RH |  | 99.3 ± 0.0 | 99.5 ± 0.0 |

TABLE 30

Dissolution Tests (n = 6)

| Time (min) | Initial % of release | STDEV | 1 month @ 25° C./60% RH % of release | STDEV | 1 month @ 40° C./75% RH % of release | STDEV | 3 months @ 25° C./60% RH % of release | STDEV | 3 months @ 40° C.75% RH % of release | STDEV |
|---|---|---|---|---|---|---|---|---|---|---|
| 0 | 0.0 | 0 | 0.0 | 0 | 0.0 | 0 | 0.0 | 0 | 0.0 | 0 |
| 10 | 90.8 | 20.5 | 93.7 | 7.6 | 98.5 | 2.4 | 91.5 | 17.6 | 98.0 | 2.8 |
| 20 | 97.2 | 7.7 | 99.0 | 6.8 | 98.1 | 1.9 | 101.2 | 2.0 | 97.9 | 1.5 |
| 30 | 99.8 | 3.3 | 99.4 | 6.8 | 98.7 | 2.4 | 100.7 | 1.4 | 98.5 | 1.3 |
| 45 | 99.8 | 3.0 | 99.5 | 6.8 | 99.2 | 2.2 | 99.4 | 0.9 | 99.3 | 1.3 |
| 60 | 100.2 | 3.0 | 99.4 | 7.2 | 100.0 | 2.2 | 100.4 | 1.1 | 98.9 | 1.1 |
| 120 | 100.0 | 2.5 | 100.0 | 7.7 | 100.0 | 2.1 | 100.0 | 1.4 | 100.0 | 1.9 |

In another aspect, provided herein is an immediate release (IR) tablet formulation as described in Table 31 and 32. Manufacturing process will typically be granulation (dry, wet or melt) or direct compression. Example given below is for 50 mg tablets.

TABLE 31

Components of IR Tablets

| Ingredient (material) | Function | Range | Example (% w/w) | Example (mg) |
|---|---|---|---|---|
| Compound 1 | Active | 5% to 50% | 33.3% | 50.00 |
| Hypromellose (e.g., Methocel E5) | Binder | 2% to 10% | 5.0 | 7.50 |
| Croscarmellose sodium | Disintegrant | 0% to 15% | 1.5 | 2.25 |
| Microcrystalline cellulose (e.g., Avicel PH101) | Compression Aid and Filler | 5% to 50% | 20.0 | 30.00 |
| Lactose (e.g. monohydrate) | Filler | 10% to 75% | 37.9 (qs) | 56.875 |
| Croscarmellose sodium (extragranular)[1] | Disintegrant | 0% to 15% | 1.5 | 2.25 |
| Magnesium stearate (extragranular) | Lubricant | 0.25% to 2.5% | 0.75 | 1.125 |
| Total | Tablet weight range: 100 mg to 500 mg | | 100 | 150 |

[1] The disintegrant can be intragranular, extragranular or split between both

TABLE 32

Components of IR Tablets

| Ingredient (material) | Function | Range | Example (% w/w) | Example (mg) |
|---|---|---|---|---|
| Compound 1 | Active | 5% to 50% | 33.3% | 50.00 |
| PEG6000 | Binder | 2% to 25% | 18.0 | 7.50 |
| Lactose (e.g. monohydrate) | Filler | 10% to 75% | 44.7 | 56.875 |
| Croscarmellose sodium (extragranular) | Disintegrant | 0% to 15% | 3.0 | 2.25 |
| Magnesium stearate (extragranular) | Lubricant | 0.25% to 2.5% | 1.0 | 1.125 |
| Total | Tablet weight range: 100 mg to 500 mg | | 100 | 150 |

In yet another embodiment, provided herein are immediate release capsule formulations. Examples of immediate release capsule formulations include those described in Tables 33 and 34.

TABLE 33

Components of Immediate Release Capsules

| Ingredient (material) | Function | Range | Example (% w/w) | Example (mg) |
|---|---|---|---|---|
| Compound 1 | Active | 1.25% to 50% | 20.0 | 50.00 |
| Polyethylene Glycol (e.g., PEG 3350) | vehicle | 98.75% to 50% | 79.0% | 197.50 |
| BHT | Anti-oxidant | 0% to 5% | 1.0 | 2.50 |
| Total | Tablet weight range: 100 mg to 500 mg | | 100 | 250 |

TABLE 34

Components of Immediate Release Capsules

| Ingredient (material) | Function | Range | Example (% w/w) | Example (mg) |
|---|---|---|---|---|
| Compound 1 | Active | 1.25% to 50% | 20.0 | 50.00 |
| Gelucire (e.g. Gelucire 44/14) | vehicle | 98.75% to 50% | 79.0% | 197.50 |
| BHT | Anti-oxidant | 0% to 5% | 1.0 | 2.50 |
| Total | Tablet weight range: 100 mg to 500 mg | | 100 | 250 |

Example 30

Single Dose Kinetics

Compound 2 was investigated in fasted and fed female beagle dogs as a suspension and as a 50 mg immediate release (IR) pill. The results are shown in Table 35.

TABLE 35

| Single-Dose Pharmacokinetics Beagle Dogs | | | | | |
|---|---|---|---|---|---|
| Species | | | Dog | | |
| Route | IV | Oral | Oral | Oral | Oral |
| Vehicle | 4:1 PEG400:Water | 0.5% Methylcellulose | 0.5% Methylcellulose | 50 mg Pill | 50 mg Pill |
| Dose | 0.67 mg/kg | 5 mg/kg | 5 mg/kg | 6.5 mg/kg | 6.5 mg/kg |
| Fasted/Fed | Fasted | Fasted | Fed | Fasted | Fed |
| Sex | f | f | f | f | f |
| $T_{max}$ (hr) | 0.017 | 2 | 1.3 | 2 | 1.7 |
| $C_{max}$ (µg/mL) | 11.98 | 12.4 | 3.7 | 7.6 | 3.2 |
| $t_{1/2}$ (hr) | 13 | NA | NA | NA | NA |
| $AUC_{0-\infty}$ (µg · h/mL) | 17.6 | 67.8 | 24.3 | 41 | 14.4 |
| $AUC_{dose-adjusted}$ | 26.3 | 13.6 | 4.9 | 6.3 | 2.2 |
| $CL_p$ (mL/min/kg) | 0.6 | NA | NA | NA | NA |
| $Vd_{SS}$ (L/kg) | 0.2 | NA | NA | NA | NA |
| F % | 100 | 52 | 19 | 24 | 8.4 |

Data are group means. Half-life was calculated from terminal portion of the curve.
AUC = area under plasma concentration-time curve;
$C_{max}$ = peak plasma concentration;
$Cl_p$ = systemic plasma clearance;
F % = bioavailability calculated from $AUC_{0-\infty}$;
iv = intravenous;
NA = not applicable;
NC = not calculated;
$t_{1/2}$ = terminal half-life;
$T_{max}$ = time to peak plasma concentration;
$Vd_{ss}$ = volume of distribution at steady state;
f = female beagle dog Administration of the oral suspension to female beagle dogs that were fasted or fed, Compound 2 shows a decrease in bioavailability (F) and dose-adjusted AUC (52% and 19%; 26 and 13.6 µg·hr/mL, respectively) in the fed animals. The IR pill also shows an approximate 30% reduction in oral bioavailability and dose-adjusted AUC when compared to the oral suspension in the fasted or fed comparator dogs. Compound 2 has a slight decrease in oral absorption in the presence of food and the IR pill form.

Example 31

Phase I Study

This is a phase 1, Single-Center, Double-Blind Study of Compound 2 in healthy volunteers.

Objective: To assess: (1) the safety and tolerability of single and multiple doses of Compound 2 following oral administration; and (2) the pharmacokinetics (PK) of Compound 2 after single and multiple doses; and (3) the effects of Compound 2 on pharmacodynamic (PD) markers: whole blood ionophore-stimulated leukotriene $LTB_4$ and urinary $LTE_4$ production.

Study Design: Single center, double-blind, randomized, placebo-controlled, single ascending dose followed by multiple ascending dose study.

Sample Size: (1) Single Dose Phase: eight (8) subjects (6 active, 2 placebo) per dose level; up to 5 dose levels are planned (a total of 40 subjects if all 5 dose levels are completed); and (2) Multiple Dose Phase: eight (8) subjects (6 active, 2 placebo) per dose level; up to 4 dose levels are planned (a total of 32 subjects if all 4 dose levels are completed).

Formulations: Compound 2 was supplied as an oral powder for reconstitution. Placebo solution matched. Compound 2 (10 mg/mL) is prepared in an aqueous solution comprising 1% (w/w) Lutrol L-44 (Poloxamer 124) and 99% (w/w) aqueous sodium carbonate buffer (0.010 M, pH9-10), and with sucralose (as a sweetener, concentration of about 5 mg/100 mL). The placebo differed only in the absence of the active.

Dosage and Dose Progression: (1) Single Dose Phase: placebo; and Compound 2 doses; (2) Multiple Dose Phase: placebo; and Compound 2 doses per day for eleven (11) days. The following dosing cohorts were used:

TABLE 36

| Dosing Cohorts | | |
|---|---|---|
| Cohort | Single Dose Phase | Multiple Dose Phase |
| 1 | 50 mg | — |
| 2 | 150 mg | — |
| 3 | 300 mg | — |
| 4 | 600 mg | — |
| 5 | 1000 mg | — |
| 6 | — | 150 mg |
| 7 | — | 450 mg |
| 8 | — | 50 mg |
| 9 | — | 10 mg |

Routes of Administration: All doses were administered orally with approximately 100 mL of water rinse. Subjects were fasted for at least 8 hours prior to dosing and for 2 hours after dosing. For BID dosing in the Multiple Dose Phase, when applicable, subjects were fasted for at least 2 hours prior to the second daily dose.

Study Procedures:

Plasma concentrations of Compound 1 were determined using a validated LC/MS method. Whole blood ionophore-stimulated leukotriene $LTB_4$ and urinary $LTE_4$ production were assayed by ELISA and mass spectrometry, respectively.

Screening Visit Procedures: The following examinations and assessments were performed within 21 days (3 weeks) prior to study drug administration to determine whether the subject satisfies inclusion and exclusion criteria. Those subjects not fulfilling all inclusion and exclusion criteria were not enrolled in the study. Screening visit procedures are as follows: subjects must report to the investigational site in the morning, before breakfast, following at least an 8-hour overnight fast; review and sign the consent document; informed consent must be obtained before performing any study-related procedures, including screening procedures; collect medical history; measure height and weight; perform physical examination and record vital signs (including blood pressure, heart rate (pulse), respiratory rate, and body temperature); perform a standard 12-lead ECG; record concomitant medication; obtain fasting blood samples for hematology determinations; obtain fasting blood samples for serum chemistry, including serum HCG (female subjects only); perform viral screen for HIV, HCV and HBsAg; obtain fasting urine samples for urinalysis and urine drug screen.

Procedures for Evening Prior to Day 1: Subjects must report to the investigational site at approximately 3:00 PM in the afternoon prior to Day 1 study drug administration. No food is permitted after 10:00 PM (may have a standardized snack prior to 10:00 PM). The visit procedures are as follows: confirm continued eligibility; obtain updated medical history; record updated concomitant medication; record vital signs (including blood pressure, heart rate (pulse), respiratory rate, and body temperature); conduct a repeat urine drug screen; collect urine for baseline (pre-dose) $LTE_4$; perform serum HCG pregnancy testing (female subjects only).

Day 1 Procedures: Record pre-dose vital signs. Obtain pre-dose fasting blood samples for hematology determinations. Obtain pre-dose fasting blood samples for serum chemistry determinations. Obtain pre-dose blood samples (5 mL EDTA and 4 mL heparinized) for baseline PK and $LTB_4$. Collect 'spot' urine prior to study drug administration for baseline (pre-dose) LTE4. Administer study drug. Record vital signs 1, 2, 4 and 12 hours after study drug administration. Record AEs. Record concomitant medication. Perform a standard 12-lead ECG 2-4 hours after study drug administration. Collect blood samples (5 mL EDTA) for PK of Compound 2 at 0.25, 0.5, 1, 2, 3, 4, 6, 8, 12, and 16 hours. Collect blood samples (4 mL heparinized) for $LTB_4$ at 0.5, 1, 2, 3, 4, 6, 8, and 12 hours. Collect urine for $LTE_4$ for the following separate intervals: 0-3, 3-6, 6-9, and 9-12 hours, and a spot urine at 16 hours. For twice daily dosing group (if conducted): administer study drug 12 hours ±30 minutes after prior dose, preceded by ≥2 hours fast.

Day 2 Procedures (24→up to 48 hours post dosing): For All Subjects (Note: No study drug will be administered to Single Dose Phase subjects): Record pre-dose vital signs (24 hours after $1^{st}$ study drug administration). Obtain pre-dose fasting blood samples for hematology determinations. Obtain pre-dose fasting blood samples for serum chemistry determinations. Record AEs. Record concomitant medication. Collect blood samples (5 mL EDTA) for PK of Compound 2 at 24 and 36 hours after the first study drug administration. Collect blood samples (4 mL heparinized) for $LTB_4$ at 24 hours after the first study drug administration. Collect 'spot' urine sample for $LTE_4$ at 24 and 36 hours after first study drug administration. For Multiple Dose Phase subjects: Administer study drug. Record vitals signs 2 and 12 hours after study drug administration. For twice daily dosing group (if conducted): administer study drug 12 hours ±30 minutes after prior dose, preceded by ≥2 hours fast.

Day 3 Procedures (≥48 hours post dosing): For All Subjects (Note: No study drug will be administered to Single Dose Phase subjects): Record AEs. Record concomitant medication. Collect blood samples (5 mL EDTA) for PK of Compound 2 at 48 and 60 hours after the first study drug administration. Collect 'spot' urine sample for $LTE_4$ at 48 hours after first study drug administration. Single Dose subjects only: collect blood samples (4 mL heparanized) for $LTB_4$ at 48 hours after the first study drug administration. For Multiple Dose Phase subjects: Collect blood samples (5 mL EDTA) for PK of Compound 2 at 1, 2, 3, 4, and 6 hours. Record pre-dose vital signs. Administer study drug. Record vitals signs 2 and 12 hours after study drug administration. For twice daily dosing group (if conducted): administer study drug 12 hours ±30 minutes after prior dose, preceded by ≥2 hours fast.

Days 4-10 Procedures: For Single Dose Phase subjects on Day 4: Refer to End of Study Procedures. For Multiple Dose Phase subjects: Record pre-dose vital signs. Collect 'spot' urine sample for $LTE_4$ at 72 hours after the first study drug administration. Collect daily pre-dose fasting blood samples (5 mL EDTA) for PK of Compound 2. Perform a standard 12-lead ECG 2-4 hours after study drug administration on Day 5. Obtain pre-dose fasting blood samples for hematology determinations on Days 5 and 7. Obtain pre-dose fasting blood samples for serum chemistry determinations on Days 5 and 7. Administer study drug daily. Record vital signs 2 and 12 hours after study drug administration. Record AEs. Record concomitant medication. For twice daily dosing group (if conducted): administer study drug 12 hours ±30 minutes after prior dose, preceded by ≥2 hours fast.

Day 11 Procedures: Record pre-dose vital signs. Obtain pre-dose fasting blood samples for hematology determinations. Obtain pre-dose fasting blood samples for serum chemistry determinations. Obtain pre-dose blood samples (5 mL EDTA and 4 mL heparinized) for PK and $LTB_4$. Collect pre-dose urine for LTE4. Administer study drug (last dose of drug). Record vital signs 2 and 12 hours after study drug administration. Record AEs. Record concomitant medication. Perform a standard 12-lead ECG 2-4 hours after study drug administration. Collect blood samples (5 mL EDTA) for PK of Compound 2 at 0.25, 0.5, 1, 2, 3, 4, 6, 8, 12, and 16 hours. Collect blood samples (4 mL heparinized) for $LTB_4$ at 0.5, 1, 2, 3, 4, 6, 8, and 12, hours. Collect urine for $LTE_4$ for the following separate intervals: 0-3, 3-6, 6-9, and 9-12 hours, and a 'spot' urine at 16 hours after study drug administration.

Day 12 Procedures (24→up to 48 hours post last dose): Record vital signs 24 hours after Day 11 study drug administration. Record AEs. Record concomitant medication. Collect blood sample (5 mL EDTA) for PK of Compound 2 at 24 and 36 hours after Day 11 study drug administration. Collect blood sample (4 mL heparinized) for $LTB_4$ at 24 hours after Day 11 study drug administration. Collect 'spot' urine sample for $LTE_4$ at 24 and 36 hours after Day 11 study drug administration.

Day 13 Procedures: Collect blood sample (5 mL EDTA) for PK of Compound 2 at 48, and 60 hours after Day 11 study drug administration. Collect blood sample (4 mL heparinized) for $LTB_4$ at 48 hours after Day 11 study drug administration. Collect 'spot' urine sample for $LTE_4$ at 48 hours after Day 11 study drug administration.

End-of-Study Procedures (≥72 hours after last study drug administration): Conduct a physical exam and record vital signs (including blood pressure, heart rate (pulse), respiratory rate, and body temperature). Obtain fasting blood samples for hematology determinations. Obtain fasting blood samples for serum chemistry determinations. Obtain 'spot' fasting urine samples for urinalysis. Collect blood sample (5 mL EDTA) for PK of Compound 2 at 72 hours after study drug administration. Collect blood sample (4 mL heparinized) for $LTB_4$ at 72 hours after Day 11 study drug administration. Collect blood sample (4 mL heparinized) for $LTB_4$ at 72 hours after Day 1 study drug administration (Single Dose Phase only). Collect 'spot' urine sample for $LTE_4$ at 72 hours after study drug administration. Perform a standard 12-lead ECG. Record AEs. Record concomitant medication.

Procedural Time Windows: The following time windows are utilized in this study. Unless stated otherwise, there are windows of ±15 minutes for study specified assessments. For safety laboratory assessments (fasting hematology and serum chemistry), the window is ±4 hours of the specified time points. For urine spot checks, the window is ±30 minutes of the specified time points.

Volume of Blood Collected: The following is the estimated volume of blood collected during the Single and the Multiple Dose Phases of the study. If BID dosing is explored in the Multiple Dose Phase, the volume of blood collected for the PK and PD assessments is less than amount stated in Table 37 below.

TABLE 37

Blood Volume Collected

| | Single Dose Phase | | | Multiple Dose Phase | | |
|---|---|---|---|---|---|---|
| | Labs | PK | PD | Labs | PK | PD |
| | 40 | 80 | 48 | 70 | 215 | 88 |
| Total | 168 mL | | | 373 mL | | |

Analysis of Samples: Concentrations of Compound 1 was determined in plasma samples collected from subjects. Similarly, concentrations of $LTB_4$ in plasma and urinary LTE4 were determined in blood and urine samples collected.

Figure 21:
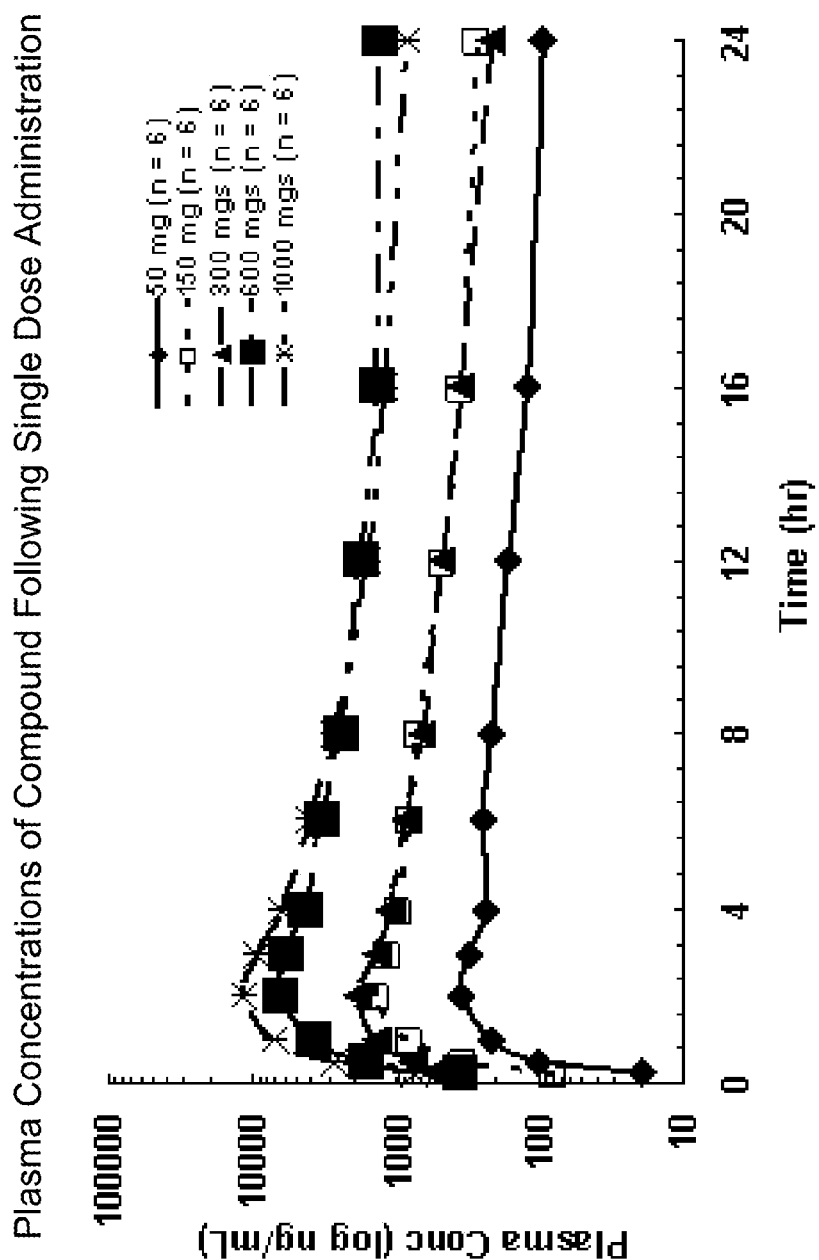
FIG. 21 illustrates pharmacokinetic properties of a single dose and multiple dose of an aqueous solution of Compound 2.

The pK results from the single dose study are presented in Table 38 and FIG. 21.

TABLE 38

Single Dose Pharmacokinetic data using oral solutions.

| Dose of Active | $T_{max}$ (hr) AVE ± SD | $C_{max}$ (mM) AVE ± SD | $t_{1/2}$ (hr) AVE ± SD | $AUC_{0-24}$ (hr*mM) AVE ± SD |
|---|---|---|---|---|
| 50 mg | 2.2 ± 0.4 | 0.57 ± 0.3 | 12.8 ± 2.9 | 6.5 ± 2.2 |
| 150 mg | 2.3 ± 0.5 | 2.2 ± 0.5 | 11.1 ± 2.8 | 21.7 ± 6.1 |
| 300 mg | 2.7 ± 1.5 | 3.0 ± 1.5 | 9.8 ± 2.5 | 23.6 ± 5.9 |
| 600 mg | 2.3 ± 0.5 | 11.2 ± 7.0 | 14.1 ± 6.8 | 90 ± 50 |
| 1000 mg | 2 ± 0 | 18.2 ± 7.6 | 8.3 ± 1.1 | 110 ± 49 |

Figure 22:
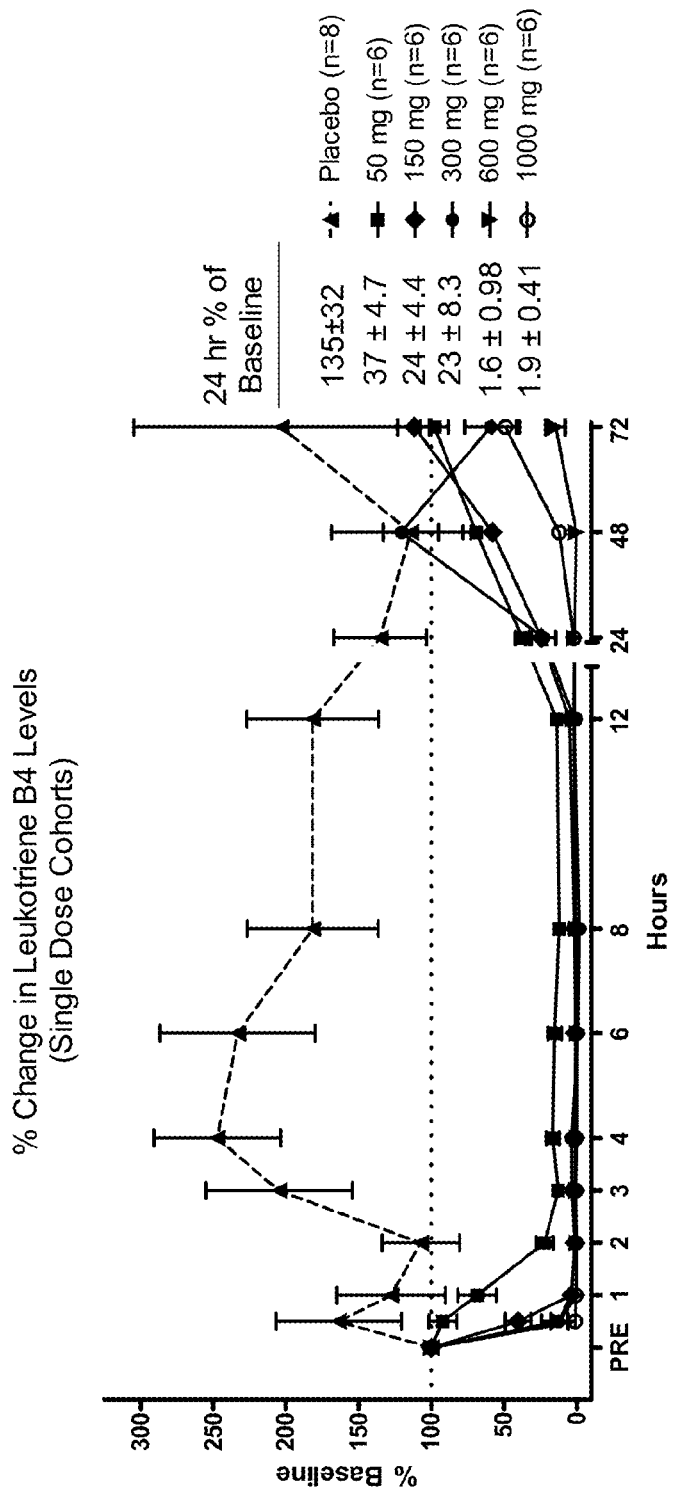
FIG. 22 illustrates pharmacodynamic properties (blood $LTB_4$ levels) of single dose administrations of an aqueous solution of Compound 2.
Figure 23:
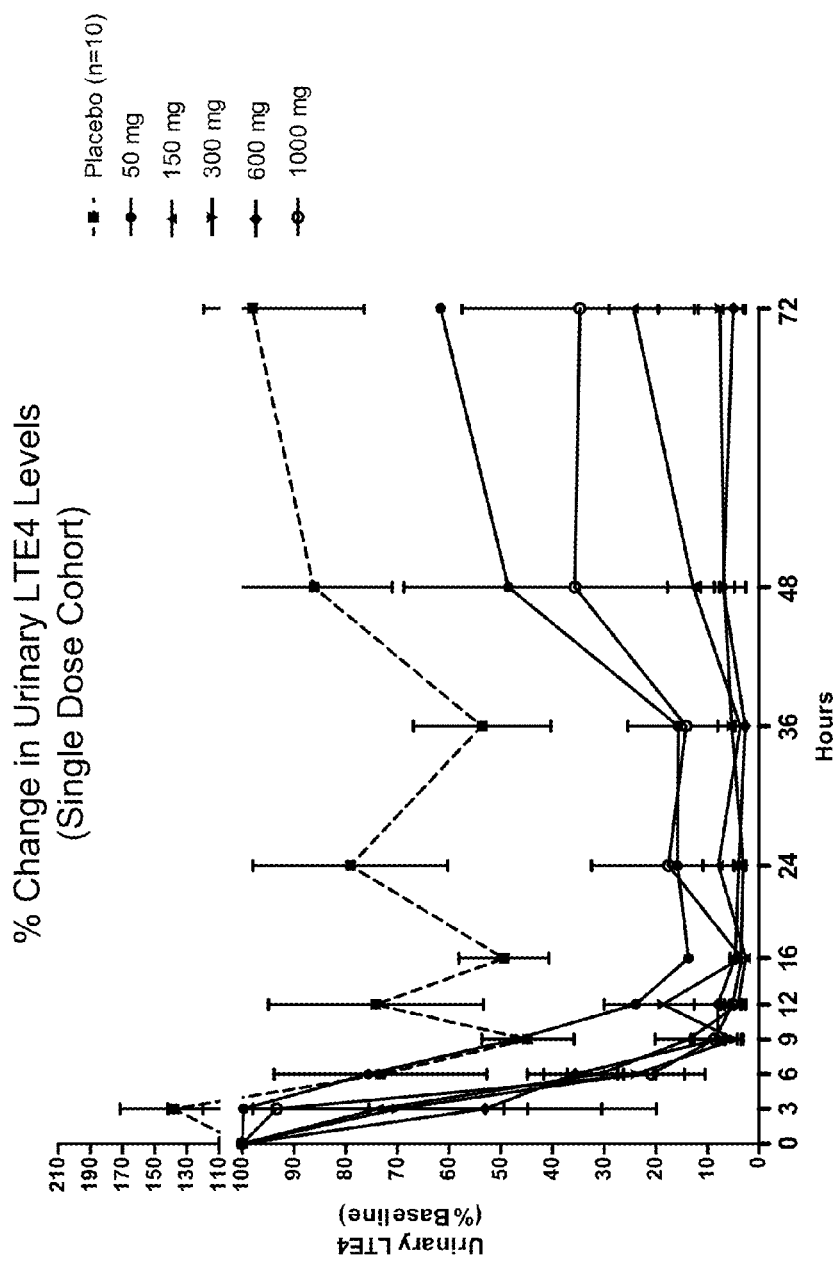
FIG. 23 illustrates pharmacodynamic properties (urinary $LTE_4$ levels) of single dose administration of aqueous solutions of Compound 2.

The pharmacodynamic properties after the single doses are administered (blood $LTB_4$ levels; urinary $LTE_4$ levels) are presented in FIGS. 22 and 23 and Table 39.

TABLE 39

Single Dose $LTB_4$ data using oral solutions.

| Dose of Active | $LTB_4$ level at t = 24 hrs. (% of baseline) |
|---|---|
| Placebo | 135 ± 32 |
| 50 mg | 37 ± 4.7 |
| 150 mg | 24 ± 4.4 |
| 300 mg | 23 ± 8.3 |
| 600 mg | 1.6 ± 0.98 |
| 1000 mg | 1.9 ± 0.41 |

The pharmacodynamic properties after the single doses and multiple doses are administered (blood $LTB_4$ levels; urinary $LTE_4$ levels) are presented in Table 40 and Table 41.

TABLE 41

PD Parameters for $LTB_4$ During Treatment With Compound 2

| Study part | Day | Treatment | $E_{max}$ (%) | $T_{max}$ (h) | $t_{E>50\%}$* (h) | $t_{E>90\%}$ (h) | $EC_{50}$ (ng/mL) | $EC_{90}$ (ng/mL) |
|---|---|---|---|---|---|---|---|---|
| Single dose part | 1 | placebo | 7.2 | .00 | | | | |
| | | 50 mg | 87.9 | 8.00 | 32.2 | 0.0 | | |
| | | 150 mg | 98.8 | 6.00 | 41.9 | 14.2 | | |
| | | 300 mg | 102.0 | 8.00 | 30# | 16.1 | | |
| | | 600 mg | 100.3 | 6.00 | >71.7 | 67.2 | | |
| | | 1000 mg | 99.6 | 6.00 | >71.7 | 42.6 | | |
| | | Single dose total | | | | | 90 | 342 |
| Multiple dose part | 1 | placebo | 25.0 | 1.00 | | | | |
| | | 10 mg | 60.8 | 12.00 | 17.5 | 0.0 | | |
| | | 50 mg | 89.6 | 4.00 | >23.3 | 0.0 | | |
| | | 150 mg | 98.5 | 3.00 | >23.4 | 15.1 | | |
| | | 450 mg | 97.6 | 3.00 | >23.7 | 17.4 | | |
| | | Multiple dose total | | | | | 51 | 296 |
| | 11 | placebo | −6.4 | 48.00 | | | | |
| | | 10 mg | 74.4 | 12.00 | 27.4 | 0.0 | | |
| | | 50 mg | 97.9 | 4.00 | 42.4 | 10.0 | | |
| | | 150 mg | 99.7 | 2.00 | >72.0 | 52.4 | | |
| | | 450 mg | 100.6 | 2.00 | >72.0 | 50.4 | | |

TABLE 41-continued

PD Parameters for LTB$_4$ During Treatment With Compound 2

| Study part | Day | Treatment | E$_{max}$ (%) | T$_{max}$ (h) | t$_{E>50\%}$* (h) | t$_{E>90\%}$ (h) | EC$_{50}$ (ng/mL) | EC$_{90}$ (ng/mL) |
|---|---|---|---|---|---|---|---|---|
| | | Multiple dose total | | | | | 52 | 308 |

= estimated
EC$_{50}$ is the concentration at which 50% inhibition was reached;
EC$_{90}$ is the concentration at which 90% inhibition was reached;
E$_{max}$ is maximum inhibition;
t$_{E>50\%}$ is time above 50% LTB4 inhibition;
t$_{E>90\%}$ is time above 90% LTB4 inhibition;
T$_{max}$ is time to reach Emax.

TABLE 42

PD Parameters for LTE$_4$ During Treatment With Compound 2

| Study part | Day | Treatment | Emax (%) | Tmax (h) |
|---|---|---|---|---|
| Single dose part | 1 | placebo | 55.26 | 9.00 |
| | | 50 mg | 86.31 | 16.00 |
| | | 150 mg | 97.39 | 16.00 |
| | | 300 mg | 96.96 | 24.00 |
| | | 600 mg | 96.05 | 24.00 |
| | | 1000 mg | 96.61 | 16.00 |
| Multiple dose part | 1 | placebo | 32.49 | 12.00 |
| | | 10 mg | 54.10 | 24.00 |
| | | 50 mg | 94.02 | 16.00 |
| | | 150 mg | 98.29 | 24.00 |
| | | 450 mg | 85.65 | 24.00 |
| | 11 | placebo | 37.23 | 6.00 |
| | | 10 mg | 88.63 | 12.00 |
| | | 50 mg | 97.67 | 9.00 |
| | | 150 mg | 97.46 | 24.00 |
| | | 450 mg | 98.37 | 12.00 |

Multiple dose pharmacokinetic data are set forth in Table 42.

TABLE 42

Multiple Dose Pharmacokinetic data using oral solutions

| | 10 mg | | 50 mg | | 150 mg | | 450 mg | |
|---|---|---|---|---|---|---|---|---|
| | Day 1 | Day 11 | Day 1 | Day 11 | Day 1 | Day 11 | Day 1 | Day 11 |
| Tmax (hr) | 4.0 ± 3.1 | 10 ± 6.9 | 4.2 ± 3.0 | 3.2 ± 2.0 | 2.3 ± 0.8 | 2 ± 0 | 2 ± 0 | 2 ± 0 |
| Cmax (mM) | 0.07 ± 0.01 | 0.13 ± 0.05 | 0.6 ± 0.2 | 0.9 ± 0.1 | 1.4 ± 0.7 | 3.0 ± 1.2 | 7.3 ± 6.0 | 9.3 ± 5.4 |
| t½ (hr) | 32 ± 23 | 50 ± 41 | 19 ± 10 | 25 ± 11 | 16 ± 7.7 | 19 ± 13 | 12 ± 4 | 14 ± 4 |
| AUClast (hr * mM) | 1.1 ± 0.2 | 2.4 ± 1.1 | 8.3 ± 2.9 | 13.5 ± 3.4 | 16 ± 6.8 | 33 ± 16 | 57 ± 39 | 76 ± 33 |

Values are Average ± Standard deviation.

Single and multiple doses of Compound 2 markedly inhibited ex vivo ionophore-stimulated LTB$_4$ formation in whole blood, with a mean maximum inhibition of 61% to 102% across the dose range studied.

Single and multiple doses of Compound 2 markedly inhibited urinary LTE$_4$ excretion, with a mean maximum inhibition of 54% to 98% across the dose range studied.

On average, T$_{max}$ was between 2 h and 12 h for inhibition of ionophore-stimulated LTB$_4$ formation and between 9 h and 24 h for inhibition of LTE4.

There was a relationship between Compound 1 plasma concentrations and the inhibition of ionophore-stimulated LTB$_4$ production for the dose range studied, with an EC$_{50}$ value of approximately 70 ng/mL and an EC$_{90}$ of approximately 320 ng/mL.

Complete inhibition of ionophore-stimulated LTB$_4$ production was reached at a Compound 1 plasma concentration of roughly 1000-1500 ng/mL.

Figure 24:
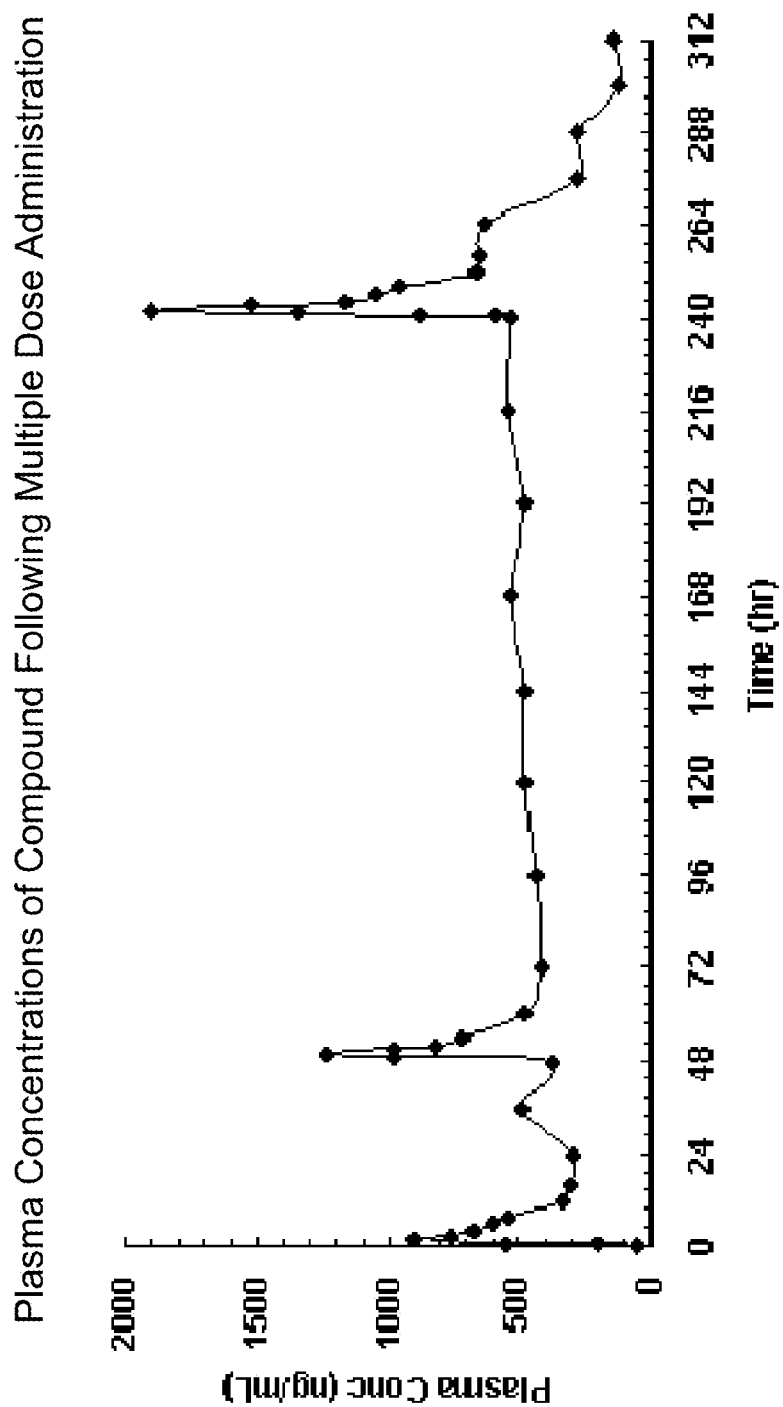
FIG. 24 illustrates plasma concentrations of Compound 1 observed in the 150 mg multiple dose cohort after administration of Compound 2.

FIG. 24 illustrates the plasma concentrations of Compound 1 observed in the 150 mg multiple dose cohort. On days 3-9, the plasma concentration is measured pre-dose.

Figure 25:
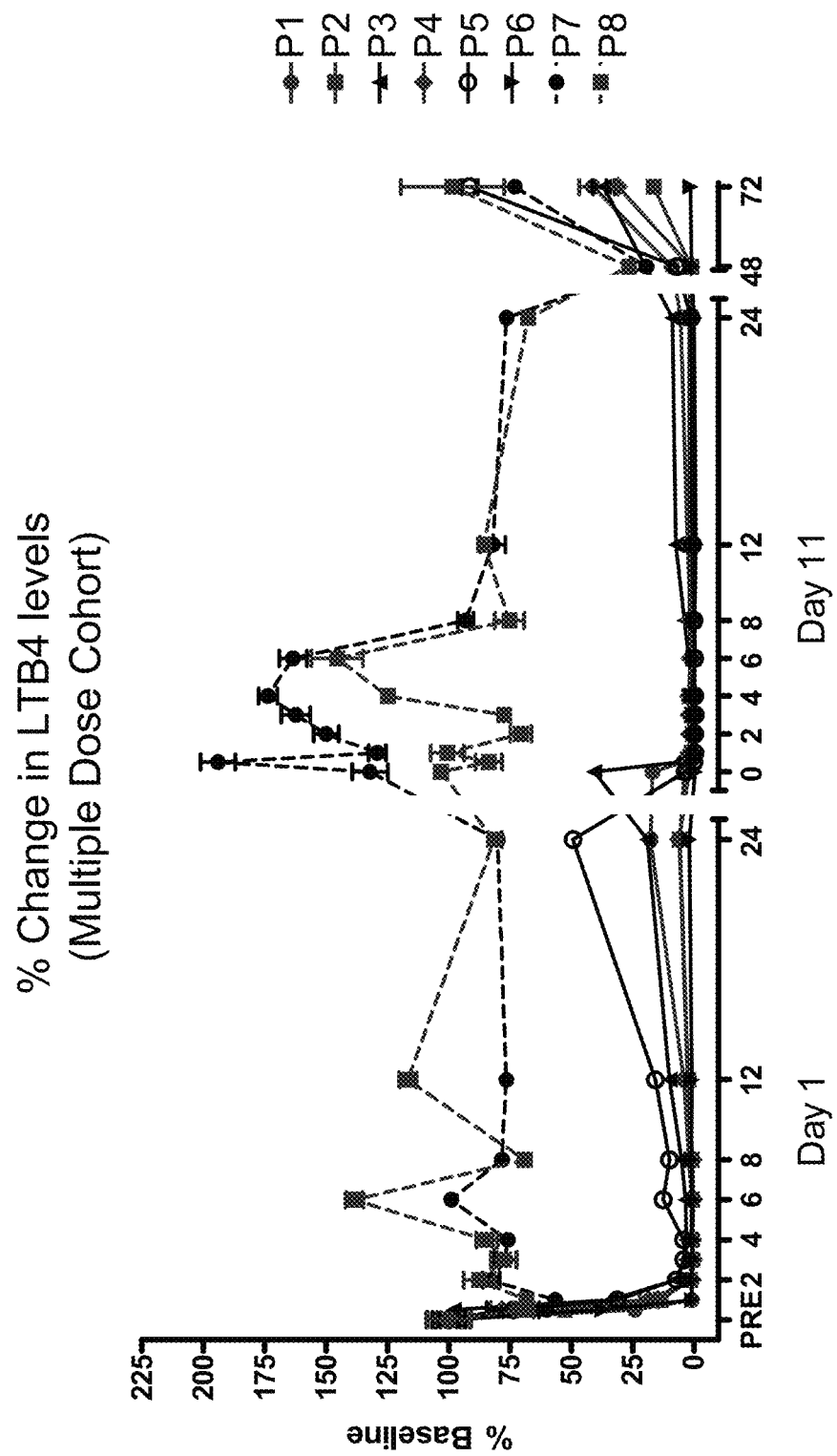
FIG. 25 illustrates pharmacodynamic properties (blood $LTB_4$ levels) of multiple dose administrations of an aqueous solution of Compound 2.

FIG. 25 illustrates the inhibition of ionophore-stimulated LTB$_4$ formation from blood observed in the 150 mg multiple dose cohort. P1, P2, P3, P4, P5, P6, P7, and P8 refer to humans in the 150 mg multiple dose cohort. P1 and P2 were controls did not receive Compound 2.

Pharmacokinetic measurements of Compound 2 includes measurement of the protonated form (Compound 1).

The foregoing clinical trial has shown that Compound 1, or a pharmaceutically acceptable salt thereof (e.g. Compound 2), lowers ionophore-stimulated LTB$_4$ formation from blood and LTE$_4$ levels in humans. LTB$_4$ and cysteinyl leukotrienes (LTC$_4$, LTD$_4$ and LTE$_4$) are leukotrienes that are elevated in humans with leukotriene-dependent or leukotriene mediated conditions or diseases. Lowering leukotriene levels in humans with leukotriene-dependent or leukotriene mediated conditions or diseases provides benefit in the condition or disease. The foregoing clinical trial has shown that Compound 1, or a pharmaceutically acceptable salt thereof (e.g. Compound 2) is useful in the treatment or prevention of leukotriene-dependent or leukotriene mediated conditions or diseases.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline polymorphic Form C of sodium 3-[3-(tert-butylsulfanyl)-1-[4-(6-ethoxy-pyridin-3-yl)benzyl]-5-(5-methyl-pyridin-2-yl-methoxy)-1H-indol-2-yl]-2,2-dimethylpropionate:

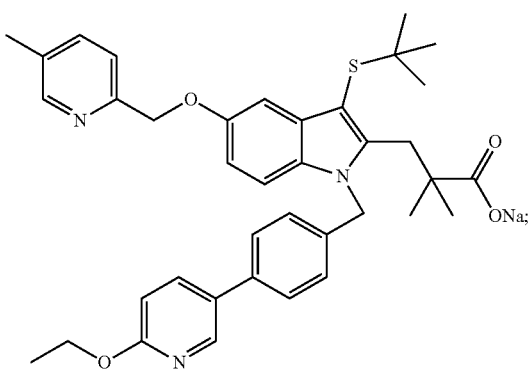

Compound 2 having an X-ray powder diffraction spectrum with peaks comprising the 2-theta values listed below, obtained with a diffractometer using copper Kα-radiation;

| Angle 2-Theta° | Intensity % |
|---|---|
| 15.6 | 42.7 |
| 16.6 | 43.3 |
| 17.2 | 69 |
| 17.8 | 42.6 |
| 18.4 | 49.2 |
| 19.1 | 100 |
| 19.8 | 40.5 |
| 20.8 | 91.6 |
| 23.1 | 47.8 |
| 23.8 | 59.2. |

2. The crystalline polymorphic Form C according to claim 1 having a single melting point at about 290° C. to about 295° C. as measured by differential scanning calorimetry (DSC).

3. The crystalline polymorphic Form C according to claim 1 having a differential scanning calorimetry (DSC) thermogram or a thermo-gravimetric analysis (TGA) thermogram substantially similar to the ones set forth in FIG. 15.

4. The crystalline polymorphic Form C according to claim 1 having physical and chemical stability (at 5° C., 25° C./60% relative humidity (RH), and/or 40° C./75% RH for at least one month in a humidity chamber).

5. The crystalline polymorphic Form C according to claim 1 having an infrared (IR) spectrum substantially similar to the one set forth in FIG. 19.

6. The crystalline polymorphic Form C according to claim 1 having an X-ray powder diffraction (XRPD) pattern substantially similar to an XRPD pattern obtained for crystals of Compound 2 obtained from methyl tert-butyl ether (MTBE) or acetonitrile.

7. The crystalline polymorphic Form C according to claim 1, wherein the Crystalline Form C is desolvated.

\* \* \* \* \*